US008598355B2

(12) United States Patent
Nozawa et al.

(10) Patent No.: US 8,598,355 B2
(45) Date of Patent: Dec. 3, 2013

(54) AMIDE COMPOUND

(75) Inventors: Eisuke Nozawa, Tokyo (JP); Ryotaro Ibuka, Tokyo (JP); Kazuhiro Ikegai, Tokyo (JP); Keisuke Matsuura, Tokyo (JP); Tatsuya Zenkoh, Tokyo (JP); Ryushi Seo, Tokyo (JP); Susumu Watanuki, Tokyo (JP); Michihito Kageyama, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 256 days.

(21) Appl. No.: 12/992,388

(22) PCT Filed: May 12, 2009

(86) PCT No.: PCT/JP2009/058821

§ 371 (c)(1),
(2), (4) Date: Nov. 12, 2010

(87) PCT Pub. No.: WO2009/139373

PCT Pub. Date: Nov. 19, 2009

(65) Prior Publication Data

US 2011/0144153 A1 Jun. 16, 2011

(30) Foreign Application Priority Data

May 14, 2008 (JP) ................................ 2008-127424

(51) Int. Cl.
*C07D 215/38* (2006.01)

(52) U.S. Cl.
USPC ......................................... 546/159; 514/373

(58) Field of Classification Search
USPC ......................................... 546/159; 514/373
See application file for complete search history.

(56) References Cited

U.S. PATENT DOCUMENTS

| | | | | |
|---|---|---|---|---|
| 6,346,532 | B1 | 2/2002 | Maruyama et al. | |
| 6,348,480 | B1 | 2/2002 | Kubota et al. | |
| 6,903,125 | B2 | 6/2005 | Kontani et al. | |
| 7,238,714 | B2 | 7/2007 | Nakao et al. | |
| 7,417,068 | B2 | 8/2008 | Clark et al. | |
| 7,491,748 | B2 | 2/2009 | Tani et al. | |
| 7,534,914 | B2 | 5/2009 | Koike et al. | |
| 7,569,602 | B2 | 8/2009 | Clark et al. | |
| 7,705,035 | B2 | 4/2010 | Boyd et al. | |
| 7,786,161 | B2 | 8/2010 | Tani et al. | |
| 7,968,578 | B2 * | 6/2011 | Boyd et al. ................... | 514/373 |
| 2004/0092569 | A1 | 5/2004 | Demaine et al. | |
| 2005/0065188 | A1 | 3/2005 | Nakao et al. | |
| 2005/0124676 | A1 | 6/2005 | Clark et al. | |
| 2005/0250818 | A1 | 11/2005 | Koike et al. | |
| 2005/0267170 | A1 | 12/2005 | Koike et al. | |
| 2006/0194836 | A1 | 8/2006 | Honda et al. | |
| 2007/0142638 | A1 | 6/2007 | Hattori et al. | |
| 2008/0167377 | A1 | 7/2008 | Gaiba et al. | |
| 2008/0306117 | A1 | 12/2008 | Clark et al. | |
| 2009/0036495 | A1 | 2/2009 | Audoly | |
| 2009/0105321 | A1 | 4/2009 | Boyd et al. | |
| 2009/0163558 | A1 | 6/2009 | Koike et al. | |
| 2009/0247596 | A1 | 10/2009 | Blouin et al. | |
| 2009/0253756 | A1 | 10/2009 | Boyd et al. | |
| 2009/0318518 | A1 | 12/2009 | Boyd et al. | |
| 2010/0022650 | A1 | 1/2010 | Gaiba et al. | |
| 2010/0216803 | A1 | 8/2010 | Zenkoh et al. | |
| 2011/0028463 | A1 * | 2/2011 | Nozawa et al. ............ | 514/230.5 |

FOREIGN PATENT DOCUMENTS

| | | | |
|---|---|---|---|
| CN | 1218045 | | 6/1999 |
| CN | 1218046 | | 6/1999 |
| CN | 1832930 | | 9/2006 |
| EP | 1 602 647 | A1 | 12/2005 |
| EP | 2 172 447 | A1 | 4/2010 |
| JP | 5-45790 | | 2/1993 |
| JP | 2002-501502 | | 1/2002 |
| JP | 2002-145840 | | 5/2002 |
| JP | 2005-232149 | | 9/2005 |
| JP | 2007 504210 | | 3/2007 |
| JP | 2007 508364 | | 4/2007 |
| JP | 2007 533723 | | 11/2007 |
| JP | 2007 536366 | | 12/2007 |
| JP | 2007 536367 | | 12/2007 |
| RU | 2285527 | | 6/2005 |
| WO | WO 98/49152 | A1 | 11/1998 |
| WO | WO 02/50031 | A1 | 6/2002 |
| WO | 03 016254 | | 2/2003 |
| WO | WO 03/086371 | A2 | 10/2003 |
| WO | WO 2005/021508 | A1 | 3/2005 |

(Continued)

OTHER PUBLICATIONS

Extended European Search Report issued May 10, 2012 in patent application No. 09746580.1.
Australian Office Action Issued Jul. 9, 2012 in Patent Application No. 2009247262.
Office Action issued Aug. 3, 2012 in Indonesian Patent Application No. W-00 2010 03906 with English language translation.
International Search Report issued Jun. 30, 2009 in PCT/JP09/058821 filed May 12, 2009.
Notice of Allowance issued Oct. 23, 2012 in Russian Application No. 2010150911/04 (With English Translation).

(Continued)

*Primary Examiner* — D M Seaman
(74) *Attorney, Agent, or Firm* — Oblon, Spivak, McClelland, Maier & Neustadt, L.L.P.

(57) ABSTRACT

[Problems] A compound, which is useful as an active ingredient of a pharmaceutical composition, for example, a pharmaceutical composition for treating chronic renal failure and/or diabetic nephropathy, is provided.
[Solving Means] The present inventors have conducted extensive studies on a compound having an EP4 receptor antagonistic activity, and confirmed that the amide compound of the present invention has an EP4 receptor antagonistic activity, thereby completing the present invention. The amide compound of the present invention has an EP4 receptor antagonistic activity, and can be used as an active ingredient of a pharmaceutical composition for preventing and/or treating various EP4-related diseases, for example, chronic renal failure and/or diabetic nephropathy, and the like.

10 Claims, No Drawings

(56) References Cited

FOREIGN PATENT DOCUMENTS

| | | | |
|---|---|---|---|
| WO | 2005/037812 | | 4/2005 |
| WO | 2005 061475 | | 7/2005 |
| WO | 2005/102389 | * | 11/2005 |
| WO | WO 2005/102389 | A2 | 11/2005 |
| WO | WO 2005/105723 | A1 | 11/2005 |
| WO | WO 2005/105732 | A1 | 11/2005 |
| WO | WO 2005/105733 | A1 | 11/2005 |
| WO | 2007 121578 | | 11/2007 |
| WO | 2007 143825 | | 12/2007 |
| WO | 2008 017164 | | 2/2008 |
| WO | 2008 071736 | | 6/2008 |
| WO | 2008 104055 | | 9/2008 |
| WO | 2008 123207 | | 10/2008 |
| WO | 2009 005076 | | 1/2009 |
| WO | 2009 056582 | | 5/2009 |

OTHER PUBLICATIONS

Extended Search Report issued May 8, 2012 in European Application No. 12151731.2.

Extended European Search Report issued Jul. 21, 2011, in Patent Application No. 08790794.5.

Peter Igarashi et. al., "Genetics and Pathogenesis of Polycystic Kidney Disease", Journal of the American Society of Nephrology, 2002, American Society of Nephrology, vol. 13, pp. 2384-2398.

Katalin Susztak et. al., "Glucose-Induced Reactive Oxygen Species Cause Apoptosis of Podocytes and Podocyte Depletion at the Onset of Diabetic Nephropathy", Diabetes, 2006, American Diabetes Association, vol. 55, pp. 225-233.

Bertrand L. Jaber et. al., "Progression of chronic kidney disease: can it be prevented or arrested?", The American Journal of Medicine, 2005, Elsevier, vol. 118, pp. 1323-1330.

Combined Taiwanese Office Action and Search Report Issued Dec. 24, 2012 in Patent Application No. 098115967 (with English translation).

Office Action issued Jun. 25, 2013, in Japanese Patent Application No. 2010-511978 (with English Translation).

Office Action issued Feb. 27, 2013 in Chinese Patent Application No. 200980117392.7(with English Translation).

Office Action issued May 15, 2013 in Japanese Patent Application No. 2009-521644 (with English Translation).

Office Action issued Jun. 11, 2013 in European Patent Application No. 12 151 731.2.

Office Action issued Sep. 11, 2013, in Chinese Patent Application No. 200980117392.7 (with English Translation).

Office Action issued Sep. 3, 2013, in Taiwanese Patent Application No. 098115967 (with English Translation).

* cited by examiner

AMIDE COMPOUND

CROSS REFERENCES TO RELATED APPLICATIONS

This application is a 371 of International Patent Application No. PCT/JP2009/058821, filed on May 12, 2009, and claims priority to Japanese Patent Application No. 2008-127424, filed on May 14, 2008.

TECHNICAL FIELD

The present invention relates to an amide compound which is useful as an active ingredient of a pharmaceutical composition, for example, a pharmaceutical composition for treating chronic renal failure and/or diabetic nephropathy.

BACKGROUND ART

Prostaglandin E2 (hereinafter referred to as "PGE2") is known as one of the metabolites in an arachidonic acid cascade. The PGE2 exhibits various activities, for example, a pain inducing and increasing action, a pro-inflammatory action, an anti-inflammatory action, an uterine contractile action, a digestive peristalsis promoting action, an awaking action, a gastric acid secretion inhibiting action, a hypotensive action, a platelet aggregation inhibition action, a bone resorption-promoting action, an angiogenic action, and the like.

There exist four subtypes, EP1, EP2, EP3, and EP4, for the PGE2 receptors, which have a wide distribution in various tissues. The activation of the EP1 receptor is believed to cause the increase in intracellular $Ca^{2+}$. The EP3 receptor is one of the receptors having different routes for second-messenger systems. The activation of the EP2 and EP4 receptors is believed to cause the activation of adenylate cyclase, and thus to increase the intracellular cAMP level. In particular, it is believed that the EP4 receptor is related to relaxation of smooth muscles, promotion or inhibition of an inflammatory reaction, lymphocyte differentiation, hypertrophy or proliferation of mesangial cells, secretion of gastrointestinal mucus, and the like.

An inhibitor of a PGE2 receptor, that is, a PGE2 antagonist has a binding activity to the PGE2 receptor. That is, the PGE2 antagonist exhibits a PGE2 antagonistic activity or a PGE2 inhibitory activity. Accordingly, the PGE2 antagonist is expected to be a drug for treating diseases caused by PGE2. Among these, the EP4 receptor antagonist is expected to be an agent for treating EP4-related diseases, for example, renal disease, inflammatory diseases, various pains, and the like, in human and animals. In addition, the antagonist selective to the EP4 receptor is preferred from the viewpoint that it can avoid the side-effects based on the subtypes of other EP1, EP2, and EP3.

As an EP4 receptor antagonist, a compound represented by the following formula is known (Patent Document 1).

[Chem. 1]

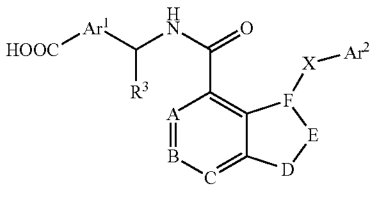

(For the symbols in the formula, refer to this publication.)

Further, as an EP4 receptor ligand, a compound represented by the following formula is known (Patent Document 2).

[Chem. 2]

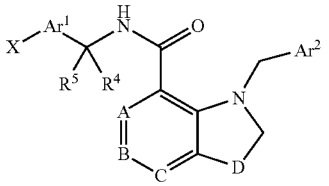

(For the symbols in the formula, refer to this publication.)

Further, as an EP4 receptor antagonist, a compound represented by the following formula is known (Patent Document 3). In this connection, this document was published after the priority date of the present application.

[Chem. 3]

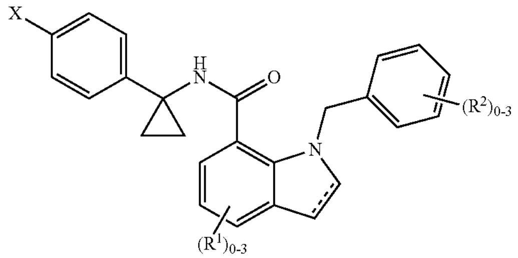

(For the symbols in the formula, refer to this publication.)

Further, as an EP4 receptor antagonist, a compound represented by the following formula is known (Patent Document 4).

[Chem. 4]

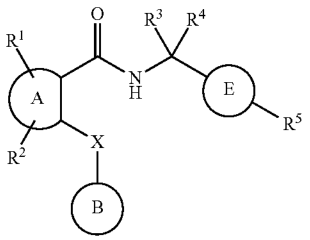

(For the symbols in the formula, refer to this publication.)

Further, as an EP4 receptor antagonist, a compound represented by the following formula is known (Patent Document 5).

[Chem. 5]

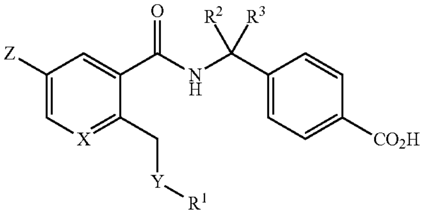

(For the symbols in the formula, refer to this publication.)

Further, as an EP4 receptor antagonist, a compound represented by the following formula is known (Patent Document 6).

[Chem. 6]

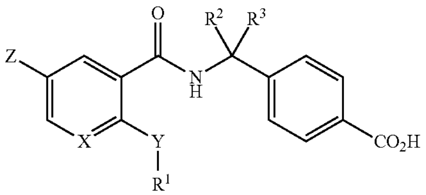

(For the symbols in the formula, refer to this publication.)

Further, as EP4 receptor ligands, compounds represented by the following formulae are known (Patent Document 7).

[Chem. 7]

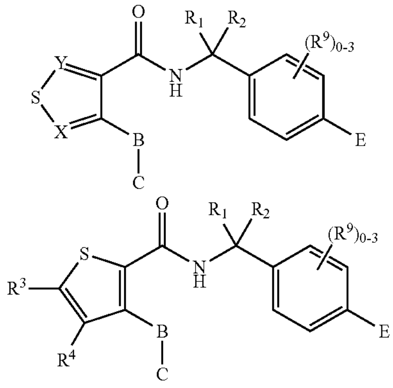

(For the symbols in the formulae, refer to this publication.)

Further, as an EP3 and/or EP4 receptor antagonist, a compound represented by the following formula is known (Patent Document 8).

[Chem. 8]

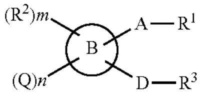

(For the symbols in the formula, refer to this publication.)

Further, as an EP4 receptor blocker, a compound represented by the following formula is known (Patent Document 9).

[Chem. 9]

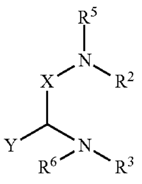

(For the symbols in the formula, refer to this publication.)

Further, as an EP4 receptor antagonist, a compound represented by the following formula is known (Patent Document 10). In this connection, this document was published after the priority date of the present application.

[Chem. 10]

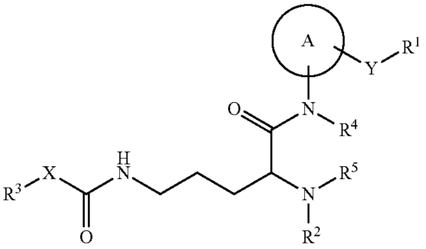

(For the symbols in the formula, refer to this publication.)

Further, as an EP4 receptor antagonist, a compound represented by the following formula is known (Patent Document 11). In this connection, this document was published after the priority date of the present application.

[Chem. 11]

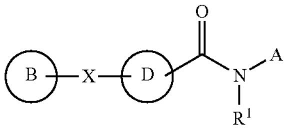

(For the symbols in the formula, refer to this publication.)

RELATED ART DOCUMENTS

Patent Documents

Patent Document 1: Pamphlet of International Publication No. WO 2007/121578

Patent Document 2: Pamphlet of International Publication No. WO 2007/143825

Patent Document 3: Pamphlet of International Publication No. WO 2008/104055

Patent Document 4: Pamphlet of International Publication No. WO 2005/021508

Patent Document 5: Pamphlet of International Publication No. WO 2005/105732

Patent Document 6: Pamphlet of International Publication No. WO 2005/105733

Patent Document 7: Pamphlet of International Publication No. WO 2008/017164

Patent Document 8: Pamphlet of International Publication No. WO 03/016254

Patent Document 9: Pamphlet of International Publication No. WO 2005/061475

Patent Document 10: Pamphlet of International Publication No. WO 2008/123207

Patent Document 11: Pamphlet of International Publication No. WO 2009/005076

SUMMARY OF THE INVENTION

Problems that the Invention is to Solve

A compound which is useful as an active ingredient of a pharmaceutical composition, for example, a pharmaceutical composition for treating chronic renal failure and/or diabetic nephropathy is provided.

Means for Solving the Problems

The present inventors have conducted extensive studies on a compound having an EP4 receptor antagonistic activity, and have found that a compound of the formula (I) exhibits excellent effectiveness, thereby completing the present invention.

That is, the present invention is related to the compound of the formula (I) or a salt thereof, and a pharmaceutical composition comprising the compound of the formula (I) or a salt thereof and a pharmaceutically acceptable excipient.

[Chem. 12]

(I)

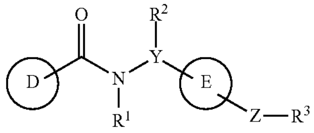

(wherein

Ring D is a group of the formula (II), the formula (III), the formula (IV), the formula (V), or the formula (VI),

[Chem. 13]

(II)

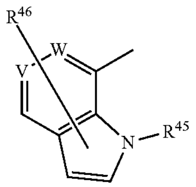

(III)

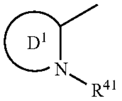

(IV)

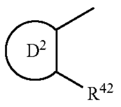

(V)

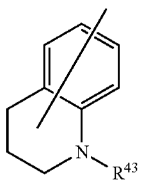

-continued (VI)

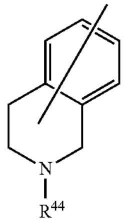

Ring $D^1$ is a monocyclic or bicyclic nitrogen-containing hetero ring which may be substituted with phenyl, Ring $D^2$ is aryl, a hetero ring, or $C_{3-10}$ cycloalkyl, $R^{41}$, $R^{42}$, $R^{43}$ and $R^{44}$ are the same as or different from each other, and are each —$X^2$—$B^4$, $R^{45}$ is —$X^1$—$B^5$, $R^{46}$ is —H, halogen, $C_{1-6}$ alkyl which may be substituted with one or more halogens, or —O—$C_{1-6}$ alkyl, V and W are the same as or different from each other, and are CH or N, provided that there is no case where V and W are N at the same time, $X^1$ is a bond, $C_{1-6}$ alkylene, ($C_{1-6}$ alkylene)-CONH—, ($C_{1-6}$ alkylene)-O—, ($C_{1-6}$ alkylene)-O—($C_{1-6}$ alkylene), or $C_{2-6}$ alkenylene, $X^2$ is a bond, $C_{1-6}$ alkylene, ($C_{1-6}$ alkylene)-CONH—, ($C_{1-6}$ alkylene)-O—, ($C_{1-6}$ alkylene)-O—($C_{1-6}$ alkylene), $C_{2-6}$ alkenylene, —O—, —S—, —NH—, —N($C_{1-6}$ alkylene)-, —N($C_{1-6}$ alkylene)-($C_{1-6}$ alkylene), or —O—($C_{1-6}$ alkylene), $B^4$ is aryl, a hetero ring, or $C_{3-10}$ cycloalkyl, each of which may be substituted with the same or different 1 to 5 groups selected from $R^4$, $R^4$ is a group consisting of halogen, —OH, —O—($C_{1-6}$ alkyl), —O—($C_{1-6}$ alkylene)-O—($C_{1-6}$ alkyl), aryl which may be substituted, a hetero ring which may be substituted, ($C_{1-6}$ alkylene)-aryl, ($C_{1-6}$ alkylene)-hetero ring, —O—($C_{1-6}$ alkylene)-aryl, and —O—($C_{1-6}$ alkylene)-hetero ring, $B^5$ represents (i) a bicyclic hetero ring which may be substituted with one or more groups selected from the group consisting of halogen and $C_{1-6}$ alkyl, or (ii) monocyclic aryl, a monocyclic hetero ring, or $C_{3-10}$ monocyclic cycloalkyl, each of which is substituted with the same or different 1 to 5 groups selected from $R^5$, $R^5$ is a group consisting of halogen, —OH, —O—($C_{1-6}$ alkyl), —O—($C_{1-6}$ alkylene)-O—($C_{1-6}$ alkyl), aryl which may be substituted, a hetero ring which may be substituted, ($C_{1-6}$ alkylene)-aryl, ($C_{1-6}$ alkylene)-hetero ring, —O—($C_{1-6}$ alkylene)-aryl, and —O—($C_{1-6}$ alkylene)-hetero ring: provided that when $X^1$ is a bond, methylene, or ethylene, Y is CH, $R^2$ is methyl, Ring E is phenylene, Z is a bond, and $R^3$ is —$CO_2H$; $R^5$ is a group consisting of —OH, —O—($C_{1-6}$ alkyl), —O—($C_{1-6}$ alkylene)-O—($C_{1-6}$ alkyl), aryl which may be substituted, a hetero ring which may be substituted, ($C_{1-6}$ alkylene)-aryl, ($C_{1-6}$ alkylene)-hetero ring, —O—($C_{1-6}$ alkylene)-aryl, and —O—($C_{1-6}$ alkylene)-hetero ring, Ring E is phenylene or $C_{5-7}$ cycloalkanediyl, $R^1$ and $R^2$ are the same as or different from each other, and are H or $C_{1-6}$ alkyl, provided that when $R^5$ is a bicyclic hetero ring which may be substituted, $R^2$ is —H, Y is CH or N, Z is a bond or $C_{1-6}$ alkylene, and $R^3$ is —$CO_2H$ or a biological equivalent thereof, provided that when Ring D is phenyl which may be substituted or pyridyl which may be substituted, Y is CH, and Z is a bond, $R^3$ represents a group other than —$CO_2H$, tetrazolyl, and sulfonamide).

In this connection, unless otherwise specifically described, when a symbol in a chemical formula in the present specification is used in other chemical formulae, the symbol represents the same meaning.

Furthermore, the present invention relates to a pharmaceutical composition for preventing or treating chronic renal failure and/or diabetic nephropathy, which contains the compound of the formula (I) or a salt thereof. In this connection, this pharmaceutical composition includes an agent for preventing or treating chronic renal failure and/or diabetic nephropathy, which contains the compound of the formula (I) or a salt thereof.

Furthermore, the present invention relates to use of the compound of the formula (I) or a salt thereof for the manufacture of a pharmaceutical composition for preventing or treating chronic renal failure and/or diabetic nephropathy, the compound of the formula (I) or a salt thereof for use in the prevention and treatment of chronic renal failure and/or diabetic nephropathy, and a method for preventing or treating chronic renal failure and/or diabetic nephropathy, comprising administering an effective amount of the compound of the formula (I) or a salt thereof to a subject. In this connection, the "subject" is a human or a non-human animal in need of the prevention or treatment, and in a certain embodiment, is a human in need of the prevention or treatment.

Effects of the Invention

The compound of the formula (I) or a salt thereof has an EP4 receptor antagonistic activity, and can be used as an active ingredient of a pharmaceutical composition for preventing and/or treating chronic renal failure and/or diabetic nephropathy.

MODE FOR CARRYING OUT THE INVENTION

Hereinbelow, the present invention will be described in detail.

In the present specification, the "alkyl" includes linear alkyl and branched alkyl. Thus, the $C_{1-6}$ alkyl is a linear or branched alkyl having 1 to 6 carbon atoms, and specifically, for example, methyl, ethyl, n-propyl, isopropyl, n-butyl, isobutyl, sec-butyl, tert-butyl, n-pentyl, n-hexyl, or the like. In a certain embodiment, it is methyl, ethyl, n-propyl, or isopropyl, in a further embodiment, methyl, or ethyl, and in yet another embodiment, methyl.

The "alkylene" is a divalent group formed by removing any one of the hydrogen atoms of the "alkyl" above. Thus, the $C_{1-6}$ alkylene is a linear or branched alkylene having 1 to 6 carbon atoms, and specifically, for example, methylene, ethylene, trimethylene, or the like, and in a further embodiment, methylene.

The "alkenylene" is a divalent group in which any one or more single bonds in the "alkylene" above are double bonds, and thus, the $C_{2-6}$ alkenylene is linear or branched alkenylene having 2 to 6 carbon atoms, and specifically, for example, vinylene, propenylene, isopropenylene, or the like, and in a further embodiment, vinylene.

The "halogen" means F, Cl, Br, or I.

Thus, the "$C_{1-6}$ alkyl which may be substituted with one or more halogens" is, in addition to $C_{1-6}$ alkyl which is not substituted with halogen, $C_{1-6}$ alkyl which is substituted with one or more halogens which are the same or different, and specifically, for example, trifluoromethyl, fluoromethyl, difluoromethyl, 2-fluoroethyl, 3-fluoropropyl, or the like.

The "cycloalkyl" is a saturated hydrocarbon ring group, which may be bridged or may be condensed with a benzene ring. Thus, the $C_{3-10}$ cycloalkyl is a saturated carbon ring having 3 to 10 carbon atoms, and specifically, for example, cyclopropyl, cyclobutyl, cyclopentyl, cyclohexyl, cycloheptyl, cyclooctyl, cyclodecanyl, norbornyl, bicyclo[2.2.2]octyl, adamantyl, indanyl, 1,2,3,4-tetrahydronaphthyl, or the like. In a certain embodiment, it is $C_{3-6}$ cycloalkyl, and in yet another embodiment, $C_{5-6}$ cycloalkyl. The "monocyclic cycloalkyl" means a monocyclic saturated hydrocarbon ring group, and thus, the $C_{3-10}$ monocyclic cycloalkyl is specifically, for example, cyclopropyl, cyclobutyl, cyclopentyl, cyclohexyl, or the like. The "cycloalkanediyl" is a divalent group formed by removing any one of the hydrogen atoms of the "cycloalkyl" above. Thus, the $C_{5-7}$ cycloalkanediyl is specifically, for example, cyclopentane-1,3-diyl, cyclohexane-1,3-diyl, cyclohexane-1,4-diyl, cycloheptane-1,3-diyl, or cycloheptane-1,4-diyl, and in a certain embodiment, cyclohexane-1,4-diyl.

The "aryl" is a $C_{6-14}$ mono- to tricyclic aromatic hydrocarbon ring group, and includes a partially hydrogenated ring group thereof. It is specifically, for example, phenyl, naphthyl, tetrahydronaphthyl, indanyl, indenyl, or the like. In a certain embodiment, it is phenyl or naphthyl, and in a further embodiment, phenyl. The "monocyclic aryl" means a monocyclic aromatic hydrocarbon ring group, and specifically, for example, phenyl.

The "hetero ring" means a ring group containing i) a monocyclic 3- to 8-membered ring containing 1 to 4 hetero atoms selected from oxygen, sulfur, and nitrogen, and in a certain embodiment, a 5- to 7-membered hetero ring, and ii) a bi- to tricyclic hetero ring containing 1 to 5 hetero atoms selected from oxygen, sulfur, and nitrogen, which is formed by condensation of the monocyclic hetero ring and one or two selected from a monocyclic hetero ring, a benzene ring, $C_{5-8}$ cycloalkane, and $C_{5-8}$ cycloalkene. The ring atom, sulfur or nitrogen, may be oxidized to form an oxide or a dioxide.

Examples of the "hetero ring" include the following groups.

(1) Monocyclic Saturated Hetero Ring Group i) those containing 1 to 4 nitrogen atoms, specifically azepanyl, diazepanyl, aziridinyl, azetidinyl, pyrrolidinyl, imidazolidinyl, piperidinyl, pyrazolidinyl, piperazinyl, and the like;

ii) those containing 1 to 3 nitrogen atoms and 1 to 2 sulfur atoms and/or 1 to 2 oxygen atoms, specifically a thiomorpholinyl, thiazolidinyl, isothiazolidinyl, oxazolidinyl, morpholinyl, and the like;

iii) those containing 1 to 2 sulfur atoms, specifically tetrahydrothiinyl and the like;

iv) those containing 1 to 2 sulfur atoms and 1 to 2 oxygen atoms, specifically oxathiolane and the like; and v) those containing 1 to 2 oxygen atoms, specifically oxiranyl, dioxolanyl, oxolanyl, tetrahydropyranyl, 1,4-dioxanyl, and the like;

(2) Monocyclic Unsaturated Hetero Ring Group i) those containing 1 to 4 nitrogen atoms, specifically pyrrolyl, imidazolyl, pyrazolyl, pyridyl, dihydropyridyl, pyrimidinyl, pyrazinyl, pyridazinyl, triazolyl, tetrazolyl, dihydrotriazinyl, azepinyl, and the like;

ii) those containing 1 to 3 nitrogen atoms and 1 to 2 sulfur atoms and/or 1 to 2 oxygen atoms, specifically thiazolyl, isothiazolyl, thiadiazolyl, dihydrothiazinyl, oxazolyl, isoxazolyl, oxadiazolyl, oxadinyl, and the like;

iii) those containing 1 to 2 sulfur atoms, specifically thienyl, thiepinyl, dihydrodithiinyl, dihydrodithionyl, and the like;

iv) those containing 1 to 2 sulfur atoms and 1 to 2 oxygen atoms, specifically dihydrooxathiinyl and the like; and v) those containing 1 to 2 oxygen atoms, specifically furyl, pyranyl, oxepinyl, dioxolyl, and the like;

(3) Condensed Polycyclic Saturated Hetero Ring Group i) those containing 1 to 5 nitrogen atoms, specifically quinuclidine, 7-azabicyclo[2.2.1]heptyl, 3-azabicyclo[3.2.2]nonanyl, and the like;

ii) those containing 1 to 4 nitrogen atoms, and 1 to 3 sulfur atoms and/or 1 to 3 oxygen atoms, specifically trithiadiazaindenyldioxoloimidazolidinyl and the like; and iii) those containing 1 to 3 sulfur atoms and/or 1 to 3 oxygen atoms, specifically 2,6-dioxabicyclo[3.2.2]oct-7-yl and the like;

(4) Condensed Polycyclic Unsaturated Hetero Ring Group i) those containing 1 to 5 nitrogen atoms, specifically indolyl, isoindolyl, indolinyl, indolidinyl, benzimidazolyl, quinolyl, tetrahydroquinolyl, isoquinolyl, tetrahydroisoquinolyl, indazolyl, imidazopyridyl, benzotriazolyl, tetrazolopyridazinyl, carbazolyl, quinoxalinyl, dihydroindazolyl, benzopyrimidinyl, naphthyridinyl, quinazolinyl, cinnolinyl, and the like;

ii) those containing 1 to 4 nitrogen atoms, and 1 to 3 sulfur atoms and/or 1 to 3 oxygen atoms, specifically benzothiazolyl, dihydrobenzothiazolyl, benzothiadiazolyl, imidazothiazolyl, imidazothiadiazolyl, benzoxazolyl, benzoxadiazolyl, and the like;

iii) those containing 1 to 3 sulfur atoms, specifically benzothienyl, benzodithiinyl, and the like;

iv) those containing 1 to 3 sulfur atoms and 1 to 3 oxygen atoms, specifically benzoxathiinyl, phenoxadinyl, and the like; and v) those containing 1 to 3 oxygen atoms, specifically benzodioxolyl, benzofuranyl, isobenzofuranyl, chromenyl, benzodihydrofuranyl, and the like.

The "nitrogen-containing hetero ring" means, among the aforementioned hetero rings, a ring group selected from i) and ii) of (1), i) and ii) of (2), i) and ii) of (3), and i) and ii) of (4), and the like. In a certain embodiment, it is a ring group having a bond on the nitrogen atom constituting the ring.

Specific examples of the "monocyclic or bicyclic nitrogen-containing hetero ring" in Ring $D^1$ include pyrrole, pyrrolofuran, pyrrolothiophene, indole, benzimidazole, indazole, and 4,5,6,7-tetrahydroindole.

Specific examples of the "hetero ring" in Ring $D^2$ include benzothiophene, 4,5,6,7-tetrahydrobenzothiophene, and pyridine.

Specific examples of the "hetero ring" in $B^4$ include quinolyl, isoquinolyl, oxazole, thiazole, and indole.

Specific examples of the "hetero ring" in $R^4$ include pyridine, thiazole, oxazole, and imidazole.

Specific examples of the "bicyclic hetero ring" in $B^5$ include quinoline, isoquinoline, benzofuran, benzothiophene, benzoxazole, benzothiazole, indole, quinoxaline, naphthylidine, quinazoline, cinnoline, and benzimidazole. In a further embodiment, the examples include quinoline, isoquinoline, benzofuran, benzothiophene, benzoxazole, and benzothiazole.

Specific examples of the "monocyclic hetero ring" in $B^5$ include thiazole, oxazole, pyridine, thiophene, furan, pyrrole, imidazole, triazole, oxadiazole, thiadiazole, pyrazine, pyrimidine, pyridazine, piperidine, pyrrolidine, azepan, tetrahydropyran, tetrahydrothiopyran, and piperazine. In a further embodiment, the examples include thiazole, oxazole, pyridine, thiophene, piperidine, and tetrahydropyran.

Specific examples of the "hetero ring" in $R^5$ include piperidine, piperazine, morpholine, thiomorpholine, pyridine, thiazole, oxazole, and imidazole. In a further embodiment, the examples include piperidine.

Further, the ring above is described as the name of the ring itself, or a monovalent ring thereof, but if necessary, it may be a monolvalent, divalent, or higher valent ring group formed by removing hydrogen atom(s) at an arbitrary position.

The "$—CO_2H$ or a biological equivalent thereof" means $—CO_2H$, or another atom or atom group which has an electronic or steric configuration equivalent to $—CO_2H$, can release acidic protons, and has common biological properties. Examples thereof include $—CO_2H$, hydroxamic acid ($—CO—NH—OH$, $—CO—NH—O—C_{1-6}$ alkyl), sulfonamide ($—NH—SO_2—C_{1-6}$ alkyl), acylcyanamide ($—CO—NH—CN$), acyl sulfonamide ($—CO—NH—SO_2—C_{1-6}$ alkyl), $—SO_2—NH—CO—C_{1-6}$ alkyl, or tetrazolyl, oxadiazolonyl, oxadiazolethionyl, oxathiadiazolyl, thiadiazolonyl, triazolethionyl, hydroxyisoxazolyl, and the like, in a further embodiment, the examples include $—CO_2H$, acyl sulfonamide ($—CO—NH—SO_2—C_{1-6}$ alkyl), hydroxamic acid ($—CO—NH—OH$, $—CO—NH—O—C_{1-6}$ alkyl), and tetrazolyl, and in yet another embodiment, the examples include $—CO_2H$. Further, $C_{1-6}$ alkyl in the biological equivalent of $—CO_2H$ may be substituted with —OH or $—O—C_{1-6}$ alkyl.

In the present specification, the expression "may be substituted" means unsubstituted or substituted with the same or different 1 to 5 substituents. In this connection, when there is a plurality of substituents, these substituents may be the same as or different from each other.

Examples of the acceptable substituent in "aryl which may be substituted" and the "hetero ring which may be substituted" in $R^4$ and $R^5$ include halogen, $C_{1-6}$ alkyl which may be substituted with one or more halogens, $—O—(C_{1-6}$ alkyl which may be substituted with one or more halogens), and —OH.

Further, $R^{46}$ in the formula (II) is a substituent which substitutes the hydrogen atoms on the atom constituting the ring, and for example, when V or W represents CH, the hydrogen atom of the CH may be substituted with $R^{46}$. Thus, the expression "V or W is CH" means a case where the hydrogen atom is substituted with $R^{46}$, that is, V or W may be $C(—R^{46})$.

Certain embodiments of the compound of the formula (I) or a salt thereof are presented below.

(1) A compound or a salt thereof, in which Ring D is a group of the formula (II).

(2) The compound or a salt thereof, in which $R^{46}$ is —H, fluoro, chloro, methyl, or trifluoromethyl. In another embodiment, the compound or a salt thereof, in which $R^{46}$ is fluoro, chloro, methyl, or trifluoromethyl. In yet another embodiment, the compound or a salt thereof, in which $R^{46}$ is trifluoromethyl. In yet another embodiment, the compound or a salt thereof, in which $R^{46}$ is substituted on the atom constituting the ring represented by V or W (that is, $R^{46}$ is substituted at the 5- or 6-position of the indole). In yet another embodiment, the compound or a salt thereof, in which $R^{46}$ is substituted on the atom constituting the ring represented by V (that is, $R^{46}$ is substituted at the 5-position of the indole). In yet another embodiment, the compound or a salt thereof, in which $R^{46}$ is fluoro, chloro, methyl, or trifluoromethyl substituted on the atom constituting the ring represented by V. In yet another embodiment, the compound or a salt thereof, in which $R^{46}$ is trifluoromethyl substituted on the atom constituting the ring represented by V.

(3) The compound or a salt thereof, in which V is CH and W is CH. In another embodiment, the compound or a salt thereof, in which V is N and W is CH. In yet another embodiment, the compound or a salt thereof, in which V is CH and W is N.

(4) The compound or a salt thereof, in which $X^1$ is $C_{1-6}$ alkylene or $(C_{1-6}$ alkylene)-O—. In another embodiment, the compound or a salt thereof, in which $X^1$ is methylene. In yet another embodiment, the compound or a salt thereof, in which $X^1$ is $—CH_2CH_2—O—$.

(5) The compound or a salt thereof, in which $B^5$ is a bicyclic hetero ring which may be substituted with one or more groups selected from the group consisting of halogen and $C_{1-6}$ alkyl. In another embodiment, the compound or a salt thereof, in which $B^5$ is quinolyl, isoquinolyl, benzofuryl, or benzothienyl, each of which may be substituted with one or more groups selected from the group consisting of halogen and $C_{1-6}$ alkyl. In yet another embodiment, the compound or a salt thereof, in which $B^5$ is quinolyl, isoquinolyl, benzofuryl, or benzothienyl. In yet another embodiment, the compound or a salt thereof, in which $B^5$ is quinolyl. In yet another embodiment, the compound or a salt thereof, in which $B^5$ is isoquinolyl. In yet another embodiment, the compound or a salt thereof, in which $B^5$ is benzofuryl. In yet another embodiment, the compound or a salt thereof, in which $B^5$ is benzothienyl. In yet another embodiment, the compound or a salt thereof, in which $B^5$ is quinolin-2-yl. In yet another embodiment, the compound or a salt thereof, in which $B^5$ is quinolin-3-yl. In yet another embodiment, the compound or a salt thereof, in which $B^5$ is quinolin-5-yl. In yet another embodiment, the compound or a salt thereof, in which $B^5$ is quinolin-6-yl. In yet another embodiment, the compound or a salt thereof, in which $B^5$ is quinolin-7-yl. In yet another embodiment, the compound or a salt thereof, in which $B^5$ is quinolin-8-yl. In yet another embodiment, the compound or a salt thereof, in which $B^5$ is isoquinolin-1-yl. In yet another embodiment, the compound or a salt thereof, in which $B^5$ is isoquinolin-3-yl. In yet another embodiment, the compound or a salt thereof, in which $B^5$ is isoquinolin-5-yl. In yet another embodiment, the compound or a salt thereof, in which $B^5$ is isoquinolin-7-yl. In yet another embodiment, the compound or a salt thereof, in which $B^5$ is monocyclic aryl, a monocyclic hetero ring, or $C_{3-10}$ monocyclic cycloalkyl, each of which is substituted with group(s) selected from $R^5$. In yet another embodiment, the compound or a salt thereof, in which $B^5$ is a phenyl substituted with halogen(s). In yet another embodiment, the compound or a salt thereof, in which $B^5$ is a monocyclic hetero ring substituted with aryl. In yet another embodiment, the compound or a salt thereof, in which $B^5$ is thiazolyl substituted with phenyl. In yet another embodiment, the compound or a salt thereof, in which $B^5$ is pyridyl substituted with phenyl.

(6) The compound or a salt thereof, in which Ring E is 1,4-phenylene or cyclohexane-1,4-diyl. In another embodiment, the compound or a salt, in which Ring E is 1,4-phenylene. In yet another embodiment, the compound or a salt in which Ring E is cyclohexane-1,4-diyl.

(7) The compound or a salt thereof, in which $R^1$ is —H.

(8) The compound or a salt thereof, in which $R^2$ is —H or methyl. In another embodiment, the compound or a salt in which $R^2$ is —H.

(9) The compound or a salt thereof, in which Y is CH.

(10) The compound or a salt thereof, in which Z is a bond.

(11) The compound or a salt thereof, in which $R^3$ is $—CO_2H$. In another embodiment, the compound or a salt, in which $R^3$ is a biological equivalent of $—CO_2H$.

(12) The compound or a salt thereof which has a combination of two or more of the groups described in (1) to (11) above.

The present invention includes the compound or a salt thereof which has a combination of two or more of the groups described in (1) to (11) above, as described in (12), and as specific examples thereof, the following embodiments are also exemplified.

(13) The compound or a salt thereof, in which Ring D is a group of the formula (II).

(14) The compound or a salt thereof of (13), in which V is CH and W is CH.

(15) The compound or a salt thereof of (14), in which Ring E is 1,4-phenylene or cyclohexane-1,4-diyl, Z is a bond, and $R^3$ is $—CO_2H$.

(16) The compound or a salt thereof of (15), in which $R^1$ is —H and $R^2$ is —H or methyl.

(17) The compound or a salt thereof of (16), in which Y is CH and $R^2$ is —H.

(18) The compound or a salt thereof of (17), in which $X^1$ is $—CH_2CH_2—O—$ and $B^5$ is phenyl substituted with halogen(s).

(19) The compound or a salt thereof of (18), in which E is 1,4-phenylene.

(20) The compound or a salt thereof of (18), in which E is cyclohexane-1,4-diyl.

(21) The compound or a salt thereof of (17), in which $X^1$ is methylene.

(22) The compound or a salt thereof of (21), in which E is 1,4-phenylene.

(23) The compound or a salt thereof of (21), in which E is cyclohexane-1,4-diyl.

(24) The compound or a salt thereof of (22) or (23), in which $B^5$ is a bicyclic hetero ring which may be substituted with one or more groups selected from the group consisting of halogen and $C_{1-6}$ alkyl.

(25) The compound or a salt thereof of (24), in which $B^5$ is quinolyl, isoquinolyl, benzofuryl, or benzothienyl, each of which may be substituted with one or more groups selected from the group consisting of fluoro, chloro, and methyl.

(26) The compound or a salt thereof of (25), in which $B^5$ is quinolyl which may be substituted with fluoro(s). In another embodiment, the compound or a salt thereof of (25), in which $B^5$ is quinolin-2-yl which may be substituted with fluoro(s). In yet another embodiment, the compound or a salt thereof of (25), in which $B^5$ is quinolin-3-yl. In yet another embodiment, the compound or a salt thereof of (25), in which $B^5$ is quinolin-5-yl. In yet another embodiment, the compound or a salt thereof of (25), in which $B^5$ is quinolin-6-yl. In yet another embodiment, the compound or a salt thereof of (25), in which $B^5$ is quinolin-7-yl. In yet another embodiment, the compound or a salt thereof of (25), in which $B^5$ is quinolin-8-yl.

(27) The compound or a salt thereof of (25), in which $B^5$ is isoquinolyl. In another embodiment, the compound or a salt thereof of (25), in which $B^5$ is isoquinolin-1-yl. In yet another embodiment, the compound or a salt thereof of (25), in which $B^5$ is isoquinolin-3-yl. In yet another embodiment, the compound or a salt thereof of (25), in which $B^5$ is isoquinolin-5-yl. In yet another embodiment, the compound or a salt thereof of (25), in which $B^5$ is isoquinolin-7-yl.

(28) The compound or a salt thereof of (22) or (23), in which $B^5$ is a monocyclic hetero ring which is substituted with 1 to 5 groups selected from $R^5$, and $R^5$ is aryl.

(29) The compound or a salt thereof of (28), in which $B^5$ is thiazolyl and $R^5$ is phenyl.

(30) The compound or a salt thereof of (28), in which $B^5$ is pyridyl and $R^5$ is phenyl.

Furthermore, specific examples encompassed by the compound of the formula (I) or a salt thereof include the following examples.

4-[({[5-chloro-1-(quinolin-2-ylmethyl)-1H-indol-7-yl]carbonyl}amino)methyl]benzoic acid, trans-4-[({[5-methyl-1-(quinolin-2-ylmethyl)-1H-indol-7-yl]carbonyl}amino)methyl]cyclohexane carboxylic acid, trans-4-[({[5-fluoro-1-(quinolin-2-ylmethyl)-1H-indol-7-yl]carbonyl}amino)methyl]cyclohexane carboxylic acid, 4-[({[1-(quinolin-2-ylmethyl)-5-(trifluoromethyl)-1H-indol-7-yl]carbonyl}amino)methyl]benzoic acid, trans-4-[({[1-(quinolin-2-ylmethyl)-5-(trifluoromethyl)-1H-indol-7-yl]carbonyl}amino)methyl]cyclohexane carboxylic acid, trans-4-[({[5-chloro-1-(isoquinolin-3-ylmethyl)-1H-indol-7-yl]carbonyl}amino)methyl]cyclohexane carboxylic acid, trans-4-[({[1-(isoquinolin-3-ylmethyl)-5-(trifluoromethyl)-1H-indol-7-yl]carbonyl}amino)methyl]cyclohexane carboxylic acid, trans-4-{[({5-chloro-1-[(2-phenyl-1,3-thiazol-4-yl)methyl]-1H-indol-7-yl}carbonyl)amino]methyl}cyclohexane carboxylic acid, 4-{[({5-chloro-1-[2-(4-chlorophenoxy)ethyl]-1H-indol-7-yl}carbonyl)amino]methyl}benzoic acid, trans-4-{[({5-chloro-1-[2-(4-chlorophenoxy)ethyl]-1H-indol-7-yl}carbonyl)amino]methyl}cyclohexane carboxylic acid, 4-{[({1-[(2-phenyl-1,3-thiazol-4-yl)methyl]-5-(trifluoromethyl)-1H-indol-7-yl}carbonyl)amino]methyl}benzoic acid, trans-4-{[({1-[(2-phenyl-1,3-thiazol-4-yl)methyl]-5-(trifluoromethyl)-1H-indol-7-yl}carbonyl)amino]methyl}cyclohexane carboxylic acid, trans-4-{[({1-[(5-phenylpyridin-2-yl)methyl]-5-(trifluoromethyl)-1H-indol-7-yl}carbonyl)amino]methyl}cyclohexane carboxylic acid, 4-{[({1-[2-(4-chlorophenoxy)ethyl]-5-(trifluoromethyl)-1H-indol-7-yl}carbonyl)amino]methyl}benzoic acid, trans-4-[({[1-(isoquinolin-3-ylmethyl)-5-methyl-1H-indol-7-yl]carbonyl}amino)methyl]cyclohexane carboxylic acid, trans-4-[({[5-fluoro-1-(isoquinolin-3-ylmethyl)-1H-indol-7-yl]carbonyl}amino)methyl]cyclohexane carboxylic acid, trans-4-[({[6-fluoro-1-(isoquinolin-3-ylmethyl)-1H-indol-7-yl]carbonyl}amino)methyl]cyclohexane carboxylic acid, trans-4-[({[1-(1-benzofuran-2-ylmethyl)-5-chloro-1H-indol-7-yl]carbonyl}amino)methyl]cyclohexane carboxylic acid, trans-4-[({[1-(1-benzofuran-2-ylmethyl)-5-(trifluoromethyl)-1H-indol-7-yl]carbonyl}amino)methyl]cyclohexane carboxylic acid, trans-4-[({[(5-chloropyridin-2-yl)methyl]-5-(trifluoromethyl)-1H-indol-7-yl}carbonyl)amino]methyl}cyclohexane carboxylic acid, and trans-4-{[({1-[(5-chloro-1-benzofuran-2-yl)methyl]-5-(trifluoromethyl)-1H-indol-7-yl}carbonyl)amino]methyl}cyclohexane carboxylic acid, and salts thereof.

Furthermore, specific examples encompassed by the compound of the formula (I) or a salt thereof also include the following compounds.

4-{(1S)-1-[({1-[2-(4-chlorophenoxy)ethyl]-1H-indol-7-yl}carbonyl)amino]ethyl}benzoic acid, 4-[2-({1-[2-(4-chlorophenoxy)ethyl]-1H-indol-7-yl}carbonyl)-1-methylhydrazino]benzoic acid, trans-4-[({[5-chloro-1-(quinolin-2-ylmethyl)-1H-indol-7-yl]carbonyl}amino)methyl]cyclohexane carboxylic acid, trans-4-[({[1-(4-chlorobenzyl)-5-(trifluoromethyl)-1H-indol-7-yl]carbonyl}amino)methyl]cyclohexane carboxylic acid, trans-4-[({[1-(4-chlorobenzyl)-5-methyl-1H-indol-7-yl]carbonyl}amino)methyl]cyclohexane carboxylic acid, 4-[({[5-methyl-1-(quinolin-2-ylmethyl)-1H-indol-7-yl]carbonyl}amino)methyl]benzoic acid, 4-[({[1-(1-benzofuran-2-ylmethyl)-1H-indol-7-yl]carbonyl}amino)methyl]benzoic acid, trans-4-[({[1-(1-benzofuran-2-ylmethyl)-1H-indol-7-yl]carbonyl}amino)methyl]cyclohexane carboxylic acid, trans-4-[({[1-(1-benzothiophen-2-ylmethyl)-1H-indol-7-yl]carbonyl}amino)methyl]cyclohexane carboxylic acid, 4-[1-methyl-2-({1-[(2-phenyl-1,3-thiazol-4-yl)methyl]-1H-indol-7-yl}carbonyl)hydrazino]benzoic acid, 4-{[({5-chloro-1-[(2-phenyl-1,3-thiazol-4-yl)methyl]-1H-indol-7-yl}carbonyl)amino]methyl}benzoic acid, and salts thereof.

With regard to some of the compounds of the formula (I) or salts thereof, tautomers or geometrical isomers thereof can be existed, depending on the kinds of the substituents. In the present specification, the compound of the formula (I) or a salt thereof may be described in only one form of isomers, but the present invention includes other isomers, isolated forms of the isomers, or a mixture thereof.

Furthermore, some of the compounds of the formula (I) or salts thereof, may have asymmetric carbon atoms or asymmetries, and correspondingly, the optical isomers thereof can be existed. The present invention includes the isolated form of the optical isomer of the compound of the formula (I) or a salt thereof or a mixture thereof.

Additionally, pharmaceutically acceptable prodrugs of the compound of the formula (I) or a salt thereof are also included in the present invention. The pharmaceutically acceptable prodrug refers to a compound having a group which can be converted into an amino group, a hydroxyl group, a carboxyl group, or the like, by solvolysis or under a physiological condition. Examples of the groups for forming a prodrug include those as described in Prog. Med., 5, 2157-2161 (1985) or "Pharmaceutical Research and Development" (Hirokawa Publishing Company, 1990), vol. 7, Drug Design, 163-198.

Furthermore, the salt of the compound of the formula (I) is a pharmaceutically acceptable salt of the compound of the formula (I), and some of the compounds of the formula (I) may form an acid addition salt or a salt with a base, depending on the kinds of the substituents. Specifically, examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like, and with organic bases such as methylamine, ethylamine, ethanolamine, lysine, ornithine, and the like, salts with various amino acids such as acetyl leucine and the like or derivatives of amino acids, ammonium salts, and others.

Additionally, the present invention also includes various hydrates or solvates, and polymorphism of the compound of the formula (I) and a salt thereof. Furthermore, the present invention also includes the compounds labeled with various radioactive or non-radioactive isotopes.

(Production Processes)

The compound of the formula (I) or a salt thereof can be prepared by applying various known synthetic methods, using the characteristics based on their basic structures or the kinds of the substituents. At this time, depending on the types of the functional groups, it is in some cases effective from the viewpoint of the preparation techniques to protect the functional group with an appropriate protecting group (a group which is capable of being easily converted into the functional group), during the steps from starting materials to intermediates. Examples of the protecting group include the protective groups as described in "Greene's Protective Groups in Organic Synthesis (4th edition, 2006)", edited by P. G. M. Wuts and T. W. Greene, and the like, which may be appropriately selected and used depending on the reaction conditions. In these methods, a desired compound can be obtained by introducing the protecting group to carry out the reaction, and then, if desired, removing the protecting group.

Additionally, the prodrug of the compound of the formula (I) or a salt thereof can be prepared by introducing a specific group during the steps from starting materials to intermediates, in the same manner as for the above protecting groups, or by further carrying out the reaction using the obtained compound of the formula (I) or a salt thereof. The reaction can be carried out by applying a method known by a person skilled in the art, such as general esterification, amidation, dehydration, and the like.

Hereinbelow, typical production processes of the compound of the formula (I) will be described. Each of the production processes can also be carried out with reference to the documents appended to the description herein. In this connection, the production process of the compound of the formula (I) is not limited to the examples as shown below.

(Production Process 1)

[Chem. 14]

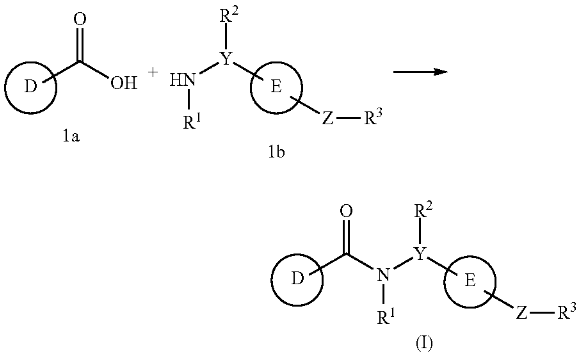

The present production process is a method for obtaining the compound of the formula (I) by reacting a compound 1a with a compound 1b.

The reaction is carried out using an equivalent amount of the compound 1a and the compound 1b or an excessive amount of either thereof, by stirring under cooling to under heating, preferably at −20° C. to 60° C., usually for 0.1 hour to 5 days, in a solvent which is inert to the reaction, in the presence of a condensing agent. Here, the solvent is not particularly limited, but examples thereof include aromatic hydrocarbons such as benzene, toluene, xylene, or the like, halogenated hydrocarbons such as dichloromethane (DCM), 1,2-dichloroethane (DCE), chloroform, or the like, ethers such as diethyl ether, tetrahydrofuran (THF), dioxane, dimethoxyethane (DME), and the like, N,N-dimethylformamide (DMF), dimethylsulfoxide (DMSO), ethyl acetate, acetonitrile, water, or a mixture thereof. As the condensing agent, 1-[bis(dimethylamino)methylene]-1H-1,2,3-triazolo[4,5-b]pyridin-1-ium-3-oxide hexafluorophosphate (HATU), 1-(3-dimethylaminopropyl)-3-ethylcarbodiimide hydrochloride (EDCI.HCl), dicyclohexylcarbodiimide (DCC), 1,1'-carbonyldiimidazole (CDI), diphenylphosphoric azide, phosphorus oxychloride, a condensing agent-carrying polystyrene resin, for example, a PS-carbodiimide (Argonaut Technologies, Inc., USA), or the like may be preferably used in some cases, but is not limited thereto. It may be preferable in some cases for the reaction to use an additive such as, for example, 1-hydroxybenzotriazole (HOBt) and the like, and it may be advantageous in some cases for the smooth progress of the reaction to carry out the reaction in the presence of, for example, an organic base such as triethylamine, N,N-diisopropylethylamine (DIPEA), N-methylmorpholine, and the like, or an inorganic base such as potassium carbonate, sodium carbonate, potassium hydroxide, and the like. Also, it is preferable to use an isocyanate-carrying polystyrene resin, for example, PS-Isocyanate (Argonaut Technologies, Inc., USA) and the like, in order to remove an excessive amine after completion of the reaction. In addition, a quaternary ammonium salt-carrying polystyrene resin, for example, MP-Carbonate (Argonaut Technologies, Inc., USA) and the like can be used, in order to remove excessive carboxylic acid and the aforementioned additives, and the like, after completion of the reaction.

Furthermore, a method, in which the compound 1a is lead into a reactive derivative thereof, and then the reactive derivative is reacted with the compound 1b, can also be used. Here, examples of the reactive derivative of the compound 1a include acid halides obtained by the reaction with a halogenating agent such as phosphorus oxychloride, thionyl chloride, and the like, mixed acid anhydrides obtained by the reaction with isobutyl chloroformate or the like, active esters obtained by condensation with HOBt or the like, and others. The reaction of these reactive derivatives and the compound 1b can be carried out under cooling to under heating, preferably at −20° C. to 60° C., in a solvent which is inert to the reaction, such as halogenated hydrocarbons, aromatic hydrocarbons, ethers, and the like.

Furthermore, by subjecting to a hydrolysis condition, the compound in which $R^3$ is a carboxylic ester can be derived to the compound of the formula (I) in which $R^3$ is a carboxylic acid can be obtained. Similarly, by subjecting the compound of the formula (I) in which $R^3$ is a substituent having a protecting group to a suitable deprotection condition, the compound of the formula (I) having a substituent from which the protecting group is removed as $R^3$ can be derived.

(Production Process 2)

[Chem. 15]

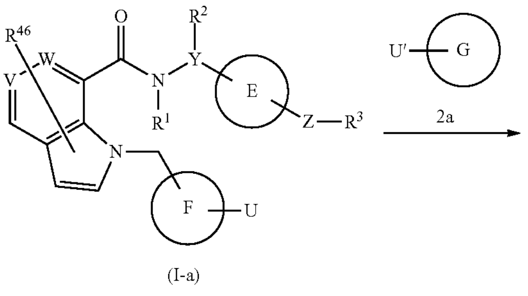

-continued

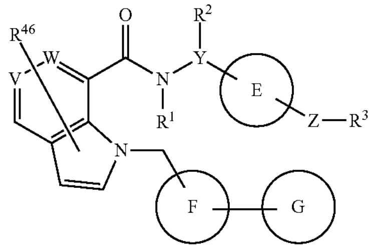

(I-b)

(In the formula, Ring F represents a monocyclic or bicyclic hetero ring or monocyclic aryl, U represents a leaving group, and U' represents —$B(OH)_2$ or —B(OL)OL'. Here, L and L' are the same as or different from each other and represent $C_{1-6}$ alkyl, or L and L' may be combined to represent $C_{2-6}$ alkylene.)

The compound (I-b) of the present invention can be obtained by a coupling reaction of the compound (I-a) and the compound 2a.

Examples of the leaving group represented by U include halogen, methanesulfonyloxy, p-toluenesulfonyloxy, and trifluoromethanesulfonyloxy groups, and the like.

This reaction is carried out using an equivalent amount of the compound (I-a) and the compound 2a or an excessive amount of either thereof, by stirring the mixture at room temperature to under heating with reflux in a solvent which is inert to the reaction, usually for 0.1 hour to 5 days, in the presence of a base and a palladium catalyst. This reaction is preferably carried out under an inert gas atmosphere. The solvent as used herein is not particularly limited, but examples thereof include aromatic hydrocarbons, ethers, halogenated hydrocarbons, alcohols such as methanol, ethanol, 2-propanol, butanol, and the like, DMF, DMSO, water, and a mixed solvent thereof. As the base, an inorganic base such as sodium carbonate, potassium carbonate, sodium hydroxide, and the like can be used. As the palladium catalyst, tetrakis(triphenylphosphine) palladium, dichlorobis(triphenylphosphine) palladium, palladium chloride-1,1'-bis (diphenylphosphino)ferrocene, or the like can be used. Further, "Metal-Catalyzed Cross-Coupling Reactions" edited by A. d. Meijere and F. Diederich, 1st Edition, VCH Publishers Inc., 1997, or "Jikken Kagaku koza (Courses in Experimental Chemistry) (5th Edition)" edited by The Chemical Society of Japan, vol. 13 (2005) (Maruzen) can be referenced to.

(Starting Material Synthesis)

Starting Material Production Process 1

[Chem. 16]

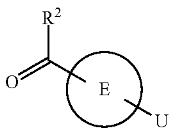

3a

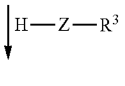

-continued

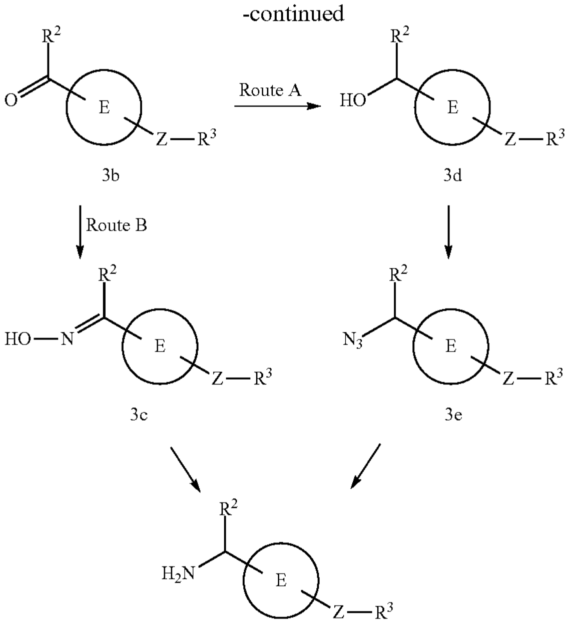

1b-1

A starting material compound 1b-1 can be prepared by using a compound 3a as a starting material, depending on the type of the substituent, by either of the route A and route B above. Route A is a method in which the compound 3b is reduced into a compound 3d, which is subjected to azidation and reduction to an amino group, thereby preparing the starting material compound 1b-1. On the other hand, Route B is a method in which the, compound 3b is subjected to oximation, followed by reduction, thereby preparing the starting material compound 1b-1.

Starting Material Production Process 2

[Chem. 17]

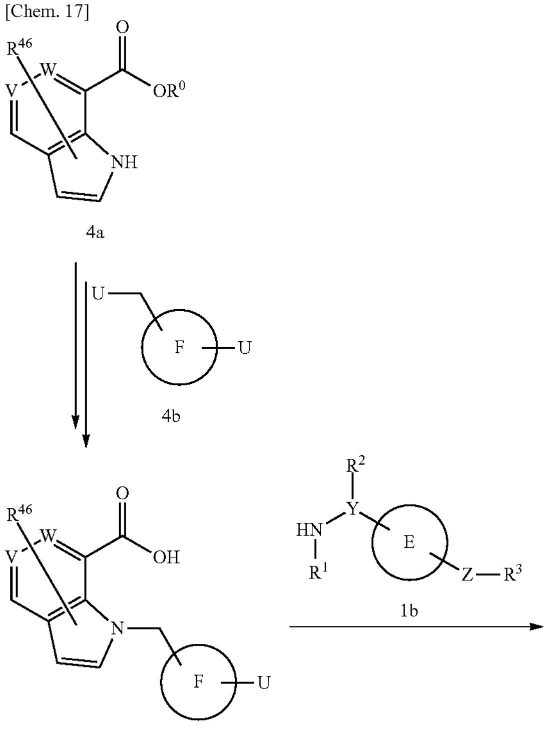

1a-1

-continued

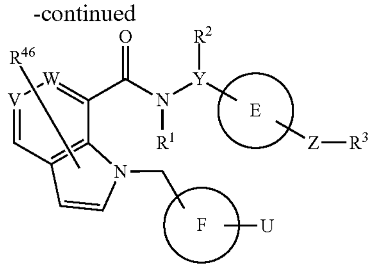

(I-a)

The compound 1a-1 can be prepared by an N-alkylation reaction and ester hydrolysis of a compound 4a and a compound 4b. The compound (I-a) can be prepared by an amidation reaction of the compound 1a-1 and the compound 1b.

The compound of the formula (I) is isolated and purified as their free compounds, salts thereof, hydrates, solvates, or polymorphic substances. The salt of the compound of the formula (I) can be prepared by subjecting to a conventional salt formation reaction.

Isolation and purification can be carried out by employing general chemical operations such as extraction, fractional crystallization, various types of fractional chromatography, and the like.

Various isomers can be prepared by selecting a suitable starting compound or separated by making use of the difference in the physicochemical properties among the isomers. For example, the optical isomers can be obtained by means of general optical resolution methods of racemic compounds (for example, by fractional crystallization introducing the compound into diastereomer salts with optically active bases or acids, chromatography using a chiral column or the like, and others), or can also be prepared from a suitable optically active starting compound.

The pharmacological activity of the compound of the formula (I) or a salt thereof was confirmed by the following test.

Test Example 1

Evaluation Test of Rat EP4 Receptor Affinity

Cell Culturing and Transfection

Using a 10 cm collagen-coated dish (Asahi Glass), HEK293 cells were cultured in D-MEM culture medium, the culture medium was removed at a confluence (90 to 100% density state) and washed with a phosphate buffer saline (PBS), and then the cells were detached with N,N,N',N'-tetrakis(carboxymethyl)ethylenediamine (EDTA). The number of the cells were counted and seeded on a 15 cm collagen-coated dish to a confluence of 70%. On the next day, to an Opti-MEM culture medium at 1.2 mL/dish was added Lipofectamine 2000 (Invitrogen) at 60 μL/dish, followed by leaving to stand at room temperature for 5 minutes. A plasmid in which rat EP4 (Sequence Number 1) had been inserted into a TA cloning site of pcDNA3.1-V5-His-topo was added thereto at 15 μg/dish. After leaving to stand at room temperature for 30 minutes, the resultant was added to the dish and cultured for 20 to 24 hours. The cell culture was carried out in a $CO_2$ incubator (37° C., 5% $CO_2$).

Preparation of Membrane Fraction

The culture medium was removed by suction, 10 mL of cooled PBS was added thereto per 15 cm dish, and the cells were scraped using a cell scraper (Sumitomo Bakelite). They were washed with cooled PBS (1,200 rpm, 4° C., 5 min), and then suspended in 6 mL of cooled 20 mM Tris-HCl (pH 7.4; Nakalai Tesque Inc., including 5 mM EDTA (Nakalai Tesque Inc.) per dish and the resultant was homogenized using a Polytron and the homogenate was centrifuged (26,000 rpm, 20 min, 4° C.). The obtained precipitate was resuspended in cooled 20 mM Tris-HCl and homogenized again using a Polytron, and the homogenate was centrifuged (26,000 rpm, 20 min, 4° C.). The obtained precipitate was resuspended in 50 mM HEPES (pH 7.5; Dojindo Laboratories) at 1 mL per dish, homogenized using a Polytron, and freeze-stored at −80° C. as a membrane fraction. At this time, a part thereof was used for the measurement of the protein concentration. Measurement of the protein concentration was carried out in duplicate using a Bio-Rad Protein assay kit (Bio-Rad Laboratories) in accordance with the appended standard Protocol.

Binding Assay

[$^3$H]PGE2 50 μL (final concentration 0.3 nM; Perkin Elmer), 100 μL (20 μg/well) of a membrane fraction prepared from the rat EP4 expression cell and 50 μL of a test compound were mixed in a 96-well microplate (Sumitomo Bakelite), incubated at room temperature for 1 hour, filtered by suction on a UniFilter-96 GF/B (Perkin Elmer) using a FilterMate Harvester (Perkin Elmer), and then washed three times with 300 μL/well of a cooled assay buffer. Dilution of [$^3$H]PGE2 and the membrane fraction was carried out using an assay buffer (50 mM HEPES, 10 mM $MgCl_2$), and dilution of the test compound and the unlabeled PGE2 was carried out using DMSO and an assay buffer. Further, in the case of the addition of a human serum albumin (HSA), dilution was carried out using an assay buffer containing 4% HSA (final concentration 1%; Sigma). The UniFilter-96 GF/B was treated preliminarily by washing twice with 200 μL/well of a cooled assay buffer. The UniFilter-96 GF/B after filtration was dried in a dryer overnight, 50 μL/well of MicroScint20 (Perkin Elmer) was added thereto, and then the radioactivity was measured using a TopCount (Perkin Elmer). For measurement of the non-specific binding, an unlabeled PGE2 (final concentration 1 μM; Cayman) was added. All of the measurements were carried out in duplicate, and the specific binding amount was determined by subtracting the non-specific binding amount from the total binding amount. The Ki value was calculated according to the general methods.

The Ki values of several compounds of the formula (I) are shown in Table 1. In the connection, Ex represents the below-described Example Compound number.

TABLE 1

| Ex | Ki (nM) |
|---|---|
| 3 | 0.76 |
| 4 | 0.82 |
| 6 | 31 |
| 23 | 0.35 |
| 32 | 12 |
| 52 | 1.8 |
| 53 | 1.4 |
| 57 | 0.85 |
| 69 | 1.4 |
| 96 | 1.7 |
| 115 | 1.0 |
| 124 | 1.4 |
| 132 | 2.6 |
| 137 | 9.1 |
| 140 | 0.61 |
| 143 | 1.0 |
| 146 | 1.8 |
| 159 | 2.1 |
| 164 | 6.3 |
| 187 | 0.75 |

TABLE 1-continued

| Ex | Ki (nM) |
|---|---|
| 188 | 1.2 |
| 206 | 1.2 |
| 207 | 1.1 |
| 208 | 1.8 |
| 209 | 1.9 |
| 210 | 1.3 |
| 211 | 1.7 |
| 212 | 2.4 |
| 213 | 2.0 |
| 214 | 2.2 |
| 215 | 2.6 |
| 216 | 16 |
| 217 | 3.0 |
| 218 | 2.9 |
| 219 | 3.3 |
| 220 | 16 |
| 222 | 2.8 |
| 223 | 3.5 |
| 224 | 2.1 |
| 225 | 2.1 |
| 226 | 2.8 |
| 227 | 1.7 |
| 228 | 2.1 |
| 229 | 3.9 |
| 231 | 1.4 |

Test Example 2

Evaluation Test of EP4 Receptor Antagonistic Activity by Measurement of cAMP Amount in Human Jurkat Cells Cell Culturing Jurkat cells (derived from human leukemia T lymphoma) were cultured with RPMI1640 (added with 10% fetal bovine serum) using a F75 flask. After proliferation to semiconfluency, indomethacin having a final concentration of 5 μM was added thereto, and the cells were further cultured for 18 hours. The cells were collected in a 15-mL Spitz tube, prepared to be $1\times10^6$ cells/mL using a Cell Banker (Mitsubishi Kagaku Iatron), and stored at −80° C. until used for assay. The cells were cultured in a $CO_2$ incubator (37° C., 5% $CO_2$).

HTRF Assay

A cAMP HiRange kit (Cisbio international) was used for cAMP measurement. A test compound, PGE2, and the cells were diluted and prepared with an assay buffer. The test compound was prepared to have a 3-fold concentration relative to the final concentration, PGE2 was prepared to be 300 nM, and the Jurkat cells frozen stored were prepared to be $1\times10^6$ cells/mL by thawing them at 37° C. To a 384-well U-bottom black microplate (Corning) were added the test compound, the cells, and PGE2 in this order in each in an amount of 5 μL, followed by shaking with a plate shaker and incubating at room temperature for 30 minutes. After incubation, 5 μL of a d2 reagent which had been diluted 0.6-fold with a lysis buffer was added to each well, followed by shaking with a plate shaker. Subsequently, 5 μL of an europium cryptate reagent which had been diluted 0.6-fold with a lysis buffer was added to each well, followed by shaking with a plate shaker and incubating at room temperature for 60 minutes under light shielding. After incubation, the fluorescence of the cryptate at 620 nm and the fluorescence of the d2 at 655 nm were measured using ARVO1420 (PerkinElmer). The cAMPs of 280, 70, 17.5, 4.38, 1.09, 0.27, and 0.068 nM were measured simultaneously for creating a standard curve. All measurements were performed in quadruplicate, and inhibitory rates were calculated by determining the cAMP amount of each test sample to the value obtained by subtracting the cAMP amount of the group without addition of PGE2 from the cAMP amount of the group with addition of PGE2 of 100 nM. $IC_{50}$ values were calculated by a Logistic regression method.

In this connection, as the "assay buffer" and "lysis buffer" above, those as shown below were used:

Assay buffer; 1×HBSS (Hanks buffered salt solution, Nissui Pharmaceutical Co., Ltd.), 20 mM HEPES (pH 7.4, Nakarai Tesque), 0.5 mM IBMX (3-isobutyl-1-methylxanthine, WAKO), 0.02% CHAPS (Sigma), 0.1% Bovine serum albumin (Sigma), 2 μM Indomethacin (Sigma)

Lysis buffer; 50 mM $NaPO_4$, 0.8 M KF, 1% Triton X-100, 0.2% Bovine serum albumin As the results of evaluation, the compounds of Example 3, Example 53, Example 57, and Example 124 showed $IC_{50}$ values of 0.11 nM, 0.094 nM, 0.037 nM, and 0.15 nM, respectively.

Test Example 3

Evaluation Test of Rat EP4 Receptor Antagonistic Activity by Measurement of cAMP Amount rEP4 cAMP HTRF Assay CHO cells in which rat EP4 had been forced to be expressed were seeded in 96-well plates at $2\times10^4$ cells/100 μL and cultured overnight. The culture medium was replaced with 2 μM Indomethacin/0.1% BSA/alpha-MEM, and further, after 60 minutes, replaced with 1 mM IBMX/2 μM Indomethacin/0.1% BSA/alpha-MEM. After 10 minutes, the test compound was added, and further, after 10 minutes, PGE2 was added at a final concentration of 100 nM. The cells were cultured and reacted in a $CO_2$ incubator (37° C., 5% $CO_2$). After 30 minutes, the culture medium was removed and 100 μL/well of 0.2% Triton X-PBS was added for lysis of the cells. The cAMP contained in this cell lysis solution was measured with a cAMP HiRange kit (Cisbio international). The cell lysis solution was disperesed at 10 μL each into a 384-well U-bottom black microplate (Corning), and a d2 reagent and an europium cryptate reagent were added in this order to each well, each in an amount of 5 μL. It was incubated at room temperature for 60 minutes under light shielding. After incubation, the fluorescence of the cryptate at 620 nm and the fluorescence of the d2 at 655 nm were measured using ARVO1420 (PerkinElmer). The cAMPs of 280, 70, 17.5, 4.38, 1.09, 0.27, and 0.068 nM were measured simultaneously for creating a standard curve. The inhibitory rates were calculated by determining the cAMP amount of each test sample to the value obtained by subtracting the cAMP amount of the group without addition of PGE2 from the cAMP amount of the group with addition of PGE2 of 100 nM. $IC_{50}$ values are calculated by a Logistic regression method.

As the results of evaluation, the compounds of Example 3, Example 53, Example 57, and Example 124 showed $IC_{50}$ values of 0.99 nM, 0.90 nM, 0.76 nM, and 1.1 nM, respectively.

Test Example 4

Evaluation Test of In Vivo Rat EP4 Receptor Antagonistic Activity

A solution of PEG 400:20% Tween 80:aqueous 1 M $NaHCO_3$ solution=1:4:5 of a test compound was orally administered to a SD rat (male, 6-week old) under non-fasting conditions, and after 1 hour, ONO-4819 was administered subcutaneously to the back of the rat. After 30 minutes, Lipopolysaccharide (LPS, 0.01 mg/kg) was administered to the tail vein without anesthesia, and after 60 minutes, 0.5 mL of heparin blood was collected from the fundus under ether anesthesia. The blood sample was centrifuged (3000 rpm, 10 minutes) to separate the plasma, and then the TNF-α concentration in the rat plasma was measured by an ELISA kit (see Hepatology Research Journal, vol. 21, 252-260, 2001). A value obtained by subtracting the TNF-α concentration of the group treated with ONO-4819 from the TNF-α concentration of the group not treated with ONO-4819 was taken as 100%, and the inhibitory rates to the value were calculated for the test compounds.

The inhibitory rates of several compounds of the formula (I) are shown in Table 2. In this connection, Ex represents the below-described Example compound number.

TABLE 2

| Ex | Inhibitory rate (%) | Dose (mg/kg) |
|---|---|---|
| 23 | 51 | 0.01 |
| 53 | 45 | 0.01 |
| 57 | 113 | 0.03 |
| 96 | 57 | 0.01 |
| 115 | 60 | 0.03 |
| 124 | 105 | 0.03 |
| 143 | 70 | 0.03 |
| 146 | 88 | 0.01 |
| 159 | 68 | 0.03 |
| 187 | 58 | 0.03 |
| 188 | 88 | 0.01 |
| 206 | 72 | 0.01 |
| 207 | 83 | 0.03 |
| 208 | 35 | 0.01 |
| 210 | 67 | 0.03 |
| 211 | 43 | 0.01 |
| 212 | 52 | 0.01 |
| 213 | 75 | 0.01 |
| 214 | 62 | 0.01 |
| 215 | 71 | 0.01 |
| 224 | 71 | 0.003 |
| 225 | 77 | 0.003 |

Test Example 5

Test to Investigate the Effect on Urine Albumin in Streptozotocin (STZ)-Induced Diabetic Rats Eight-week old male Wistar (Crj) rats were divided into groups with unbiased urinary albumin excretion (UAE) in advance, and STZ (50 mg/kg) was intravenously administered thereto. From the next day of the administration of STZ, the test compound was continuously orally administered, and urine was periodically collected in a metabolism cage for 24 hours to measure the UAE. In this way, the effect of the test compound on improvement of early nephropathy in diabetic model rats can be confirmed.

Test Example 6

Test to Investigate the Effect on the Renal Function of 5/6 Nephrectomy Chronic Renal Failure (5/6 Nx) Rats 8-Week-old Wistar male rats were used for the test. Two-thirds of the left kidney was incised under pentobarbital anesthesia, and after 1 week, the entire right kidney was extracted. After 2 weeks from extraction of 5/6 of the kidney, the protein excretion amounts in urine were measured by 24-hour urine collection in metabolic cages, and were divided into groups so that there was no difference in each group. Thereafter, over 6 to 8 weeks, 5 mL/kg of the test compound which had been suspended in 0.5% MC was administered orally. The same amounts of the solvent (0.5% MC) were administered orally to the sham group which had undergone only laparotomy and the 5/6 Nx-control group. 24-Hour urine collection was carried out every two weeks.

By measuring the protein excretion amounts in urine, plasma creatinine, plasma urea nitrogen, and creatinine clearance, the effect of the test compound on the improvement of chronic renal failure can be confirmed, and in this test, it was confirmed that compounds exhibiting effectiveness exist.

Furthermore, the selectivity of the compound of the formula (I) or a salt thereof on four subtypes of the PGE2 receptor (EP1, EP2, EP3, and EP4) was evaluated. Specifically, for the receptor of each subtype derived from the rats, inhibition of the cAMP amounts was evaluated by adding the test compounds, respectively, in the same manner as in Test Example 3. As a result, it was shown that the compound of the formula (I) or a salt thereof has a selective antagonistic activity or an EP4 receptor.

From the results of the above-described tests, it was confirmed that the compound of the formula (I) or a salt thereof has an EP4 receptor antagonistic activity, and can be used as an active ingredient of a pharmaceutical composition for preventing or treating various EP4-related diseases, and the like. Examples of the EP4-related diseases include renal diseases (for example, acute nephritis, recurrent hematuria, persistent hematuria, chronic nephritis, rapidly progressive nephritis, acute renal failure, chronic renal failure, diabetic nephropathy, Bartter's syndrome, and the like), inflammatory skin diseases (for example, sunburn, burns, eczema, dermatitis, and the like), ischemic heart diseases caused by arteriosclerosis (for example, myocardial infarction, angina, and the like), cerebrovascular disorders caused by arteriosclerosis (for example, stroke, stroke including lacunar infarction, cerebral thrombosis, cerebral hemorrhage, subarachnoid hemorrhage, cerebral infarction, and the like), peptic ulcer diseases (for example, gastric ulcer, duodenal ulcer, and the like), malignant cancer and metastasis thereof (for example, colon cancer, breast cancer, and the like), and the like, or the analogous diseases in humans and animals, and in a certain embodiment, renal diseases such as chronic renal failure, diabetic nephropathy, and the like.

Furthermore, the compound of the formula (I) or a salt thereof can be used as a compound having a diuretic action. By having a diuretic action, the compound of the formula (I) or a pharmaceutically acceptable salt thereof can be used as an agent for treating and/or preventing various types of edema (for example, cardiac edema, cerebral edema, and the like), hypertension such as malignant hypertension, and the like, a premenstrual syndrome, urinary calculus, a poor urine disease caused by an acute or chronic disease, hyperphosphatemia, and the like.

A pharmaceutical composition containing one or more kinds of the compound of the formula (I) or a salt thereof as an active ingredient can be prepared in accordance with a generally used method, using an excipient usually used in the art, that is, a pharmaceutical excipient, a pharmaceutical carrier, or the like.

The administration can be carried out in any form of oral administration via tablets, pills, capsules, granules, powders, liquid preparations, or the like; or parenteral administration via injections such as intraarticular, intravenous, or intramuscular injections, suppositories, eye drops, eye ointments, percutaneous liquid preparations, ointments, percutaneous patches, transmucosal liquid preparations, transmucosal patches, inhalations, and the like.

As the solid composition for oral administration, tablets, powders, granules, or the like are used. In such a solid composition, one or more kinds of active ingredients are mixed with at least one inert excipient. According to a conventional method, the composition may contain inert additives such as a lubricant, a disintegrator, a stabilizing agent, and a solubilizing agent. As occasion demands, the tablets or the pills may be coated with a sugar coating, or a film of a gastric or enteric material.

The liquid composition for oral administration includes pharmaceutically acceptable emulsions, solutions, suspensions, syrups, elixirs, or the like, and contains a generally used inert diluent such as purified water or ethanol. In addition to the inert diluent, this liquid composition may contain an auxiliary agent such as a solubilizing agent, a moistening agent, and a suspending agent, a sweetener, a flavor, an aroma, and an antiseptic.

The injections for parenteral administration include sterile aqueous or non-aqueous liquid preparations, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizing agent, or a solubilizing agent. These are sterilized, for example, by filtration through a bacteria retaining filter, blending of a bactericide, or irradiation. Additionally, these can also be used by preparing a sterile solid composition, and dissolving or suspending it in sterile water or a sterile solvent for injection prior to its use.

The agent for external use includes ointments, plasters, creams, jellies, cataplasms, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhalation, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate propellant, for example, a suitable gas such as chlorofluoroalkane, carbon dioxide, and the like, or other forms.

In oral administration, the daily dose is preferably from about 0.001 to 100 mg/kg, in an embodiment, from 0.1 to 30 mg/kg, and in another embodiment, from 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. Additionally, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

Although it varies depending on the administration way, dosage form, administration site, the kinds of excipient and additive, the pharmaceutical composition of the present invention includes from 0.01 to 100% by mass, in an embodiment, from 0.01 to 50% by mass, of one or more of the compound of the formula (I) or a salt thereof as an active ingredient.

The compound of the formula (I) or a salt thereof can be used in combination with various agents for treating or agents for preventing the above-described diseases for which the compound of the formula (I) or a salt thereof is considered to be effective. The combined preparation may be administered simultaneously, or separately and continuously or at a desired time interval. The preparations to be co-administered may be prepared separately, or may be a pharmaceutical composition containing various agents for treating or agents for preventing the above-described diseases for which the compound of the formula (I) or a salt thereof is considered to be effective and the compound of the formula (I) or a salt thereof.

Examples

The production processes of the compound of the formula (I) or a salt thereof will be described below in more detail based on Examples. In this connection, the present invention is not limited to the compounds described in the following Examples. Furthermore, the production processes for the starting compounds will be described in Production Examples, and the production processes for the known compounds will be described in Reference Examples. Further, the production processes for the compound of the formula (I) or a salt thereof are not limited only to the production processes of the specific Examples as below, but the compound of the formula (I) or a salt thereof can be prepared by any combination of the production processes or the methods that are apparent to a person skilled in the art.

Production Example 1

To a mixture of 5-chloro-1H-indole-7-carboxylic acid (500 mg), triphenylphosphine (1.01 g), ethanol (235 mg) and toluene (20 mL) was added dropwise diethyl azodicarboxylate (2.2 M toluene solution, 1.74 mL) at room temperature. After stirring for 2 hours at room temperature, the reaction mixture was concentrated under reduced pressure. The obtained residue was purified by silica gel column chromatography (hexane-ethyl acetate) to obtain ethyl 5-chloro-1H-indole-7-carboxylate (550 mg) as a white solid.

Production Example 2

To a mixture of ethyl 5-(1-hydroxyethyl)thiophene-2-carboxylate (1.01 g), diphenylphosphorylazide (1.67 g), and toluene (10 mL) was added 1,8-diazabicyclo[5.4.0]undec-7-ene (905 μL) under ice-cooling, followed by stirring for 30 minutes. The reaction mixture was warmed to room temperature, followed by stirring for 15 hours. The reaction liquid was washed with water and 1 M hydrochloric acid in this order, and dried over anhydrous sodium sulfate. Then, after concentration under reduced pressure, the obtained residue was purified by silica gel column chromatography (hexane-ethyl acetate) to obtain ethyl 5-(1-azidoethyl)thiophene-2-carboxylate (1.03 g) as a colorless oily substance.

Production Example 3

To a mixture of ethyl 5-(1-azidoethyl)thiophene-2-carboxylate (1.03 g), THF (20 mL), and water (4 mL) was added triphenylphosphine (2.35 g) at room temperature. This mixture was stirred at 60° C. for 3 hours. After leaving the reaction mixture to be cooled at room temperature, the mixture was concentrated under reduced pressure and azeotroped with toluene. The obtained residue was purified by silica gel column chromatography (chloroform-methanol) concentrated, and a 4 M hydrogen chloride-ethyl acetate solution (1.5 mL) was added to the obtained residue. After stirring for 3 minutes, the mixture was concentrated again under reduced pressure. Diisopropyl ether was added thereto and the precipitated white solid was collected by filtration to obtain ethyl 5-(1-aminoethyl)thiophene-2-carboxylate hydrochloride (979 mg) as a white solid.

Production Example 4

To a mixture of ethyl 1,2,3,4-tetrahydroquinoline-8-carboxylate (1.1 g) and DMF (9.0 mL) was added sodium hydride (55% dispersion in paraffin liquid, 280 mg) at 0° C., followed by stirring at room temperature for 30 minutes. To the reaction mixture was added a solution of 1-(bromoethyl)-4-chlorobenzene (1.2 g) in DMF (2.0 mL) under ice-cooling, followed by stirring at room temperature for 3 days. To the reaction mixture was added sodium hydride (55% dispersion in paraffin liquid, 280 mg), followed by stirring for 1 day. To the reaction mixture were added water and ethyl acetate, and a liquid-separation operation was carried out. The organic layer was washed with saturated brine and dried over anhydrous sodium sulfate. After filtration, the filtrate was concentrated under reduced pressure. The residue was purified by silica gel column chromatography (hexane-ethyl acetate) to obtain ethyl 1-(4-chlorobenzyl)-1,2,3,4-tetrahydroquinoline-8-carboxylate (510 mg).

Production Example 5

To a mixture of methyl 3-amino-2-hydroxybenzoate (700 mg) and THF (21 mL) was added 4-chlorophenylisothiocyanate (717 mg), followed by stirring at room temperature overnight. To the reaction mixture were sequentially added copper iodide (0.87 g) and triethylamine (641 μL), followed by stirring at 60° C. overnight. The reaction mixture was concentrated under reduced pressure and methanol was added thereto, the mixture was filtered through Celite, and the filtrate was concentrated under reduced pressure. To the residue was added ethyl acetate (20 mL), the insoluble materials were removed by filtration, and the filtrate was concentrated under reduced pressure. The residue was purified by silica gel column chromatography (hexane:ethyl acetate=2:1), and then triturated with n-hexane-ethyl acetate (10:1, 11 mL) to obtain methyl 2-[(4-chlorophenyl)amino]-1,3-benzoxazole-7-carboxylate (270 mg) as a pale yellow solid.

Production Example 6

To a mixture of methyl 1H-indole-7-carboxylate (100 mg) and DMF (1 mL) was added potassium tert-butoxide (75 mg) at room temperature, followed by stirring for 5 minutes. To the reaction mixture was added 4-(bromomethyl)benzonitrile (131 mg), followed by stirring at room temperature for 2 hours. Water was added thereto, followed by extraction with ethyl acetate. The organic layer was washed with water and saturated brine in this order, and dried over anhydrous sodium sulfate, and then the solvent was evaporated to obtain crude methyl 1-(4-cyanobenzyl)-1H-indole-7-carboxylate (211 mg). To a mixture of crude methyl 1-(4-cyanobenzyl)-1H-indole-7-carboxylate (211 mg), THF (10 mL), and methanol (5 mL) was added a 1 M aqueous sodium hydroxide solution (2.5 mL), and the obtained mixed liquid was stirred at 60° C. overnight. After leaving to be cooled to room temperature, the solvent was evaporated under reduced pressure, and to the obtained residue was added ethyl acetate, followed by extraction with water. The aqueous layer was neutralized by adding 1 M hydrochloric acid (2.5 mL), and extracted with ethyl acetate. This organic layer was dried over anhydrous sodium sulfate, and then the solvent was evaporated to obtain crude 1-(4-carbamoylbenzyl)-1H-indole-7-carboxylic acid (230 mg). To a mixture of crude 1-(4-carbamoylbenzyl)-1H-indole-7-carboxylic acid (229 mg), methyl (S)-4-[1-aminoethyl]benzoate hydrochloride (123 mg), and HOBt (23 mg) in DMF (3 mL) was added EDCI.HCl (150 μL), followed by stirring at room temperature for 3 hours. Water was added thereto, followed by extraction with ethyl acetate-diethyl ether. The organic layer was washed with water and saturated brine in this order, and dried over anhydrous sodium sulfate. After evaporating the solvent, to the obtained residue was added methanol. The precipitated solid was collected by filtration and dried to obtain methyl (S)-4-[1-({[1-(4-carbamoylbenzyl)-1H-indol-7-yl]carbonyl}amino)ethyl]benzoate (142 mg).

Production Example 7

A mixture of 1-(4-chlorobenzyl)-1,2,3,4-tetrahydroquinoline-8-carboxylic acid (310 mg), methyl 4-[(1S)-1-aminoethyl]benzoate hydrochloride (240 mg), EDCI.HCl (210 mg), HOBt (160 mg), pyridine (0.25 mL), and DMF (3.00 mL) was stirred at room temperature for 3 days. Water was added to the reaction mixture, followed by extraction with ethyl acetate. The organic layer was washed with water and saturated brine, and dried over anhydrous sodium sulfate. After filtration, the filtrate was concentrated under reduced pressure. The residue was purified by silica gel column chromatography (hexane-ethyl acetate) to obtain methyl 4-[(1S)-1-({[1-(4-chlorobenzyl)-1,2,3,4-tetrahydroquinolin-8-yl]carbonyl}amino)ethyl]benzoate (129 mg).

Production Example 8

To a mixture of methyl trans-4-acetylcyclohexane carboxylate (0.5 g) and pyridine (5.0 mL) was added hydroxylamine hydrochloride (0.57 g) under ice-cooling, followed by stirring at room temperature for 24 hours. The reaction mixture was concentrated under reduced pressure. To the residue were added ethyl acetate and a 10% aqueous citric acid solution, and the aqueous layer was extracted with ethyl acetate. The organic layer was combined, and washed with a 10% aqueous citric acid solution, a saturated aqueous sodium hydrogen carbonate solution, water, and saturated brine. The organic layer was dried over anhydrous magnesium sulfate and concentrated under reduced pressure to obtain methyl trans-4-(N-hydroxyethanimidyl)cyclohexane carboxylate (0.45 g).

Production Example 9

To a mixture of methyl trans-4-(N-hydroxyethanimidyl) cyclohexane carboxylate (0.44 g) and ethanol (8.0 mL) were added concentrated aqueous ammonia (2.0 mL) and an ethanol suspension (6.0 mL) of Raney nickel (2.0 mL), followed by stirring at room temperature for 12 hours under a hydrogen atmosphere at 3.4 atm. The reaction mixture was filtered through Celite and the filtrate was concentrated under reduced pressure. To the residue was added diethyl ether, a 4

M hydrogen chloride-dioxane solution (1.0 mL) was added thereto under ice-cooling, and the precipitated solid was collected by filtration and washed with diethyl ether to obtain methyl trans-4-(1-aminoethyl)cyclohexane carboxylate hydrochloride (0.42 g).

Production Example 10

To 5,6,7,8-tetrahydro-2H-[1]benzothieno[2,3-d][1,3]oxazine-2,4(1H)-dione (1.5 g) and potassium carbonate (1.4 g) was added DMF (15 mL), and methyl iodide (1.2 m) was added thereto under ice-cooling, followed by stirring at room temperature for 6 hours. Methyl iodide (0.61 mL) was added thereto, followed by stirring at room temperature overnight, water (15 mL) was added to the reaction mixture, and the solid was collected by filtration, washed with water, and dried under reduced pressure to obtain 1-methyl-5,6,7,8-tetrahydro-2H-[1]benzothieno[2,3-d][1,3]oxazine-2,4(1H)-dione (1.3 g).

Production Example 11

To 1-methyl-5,6,7,8-tetrahydro-2H-[1]benzothieno[2,3-d][1,3]oxazine-2,4(1H)-dione (0.50 g) was added ethanol (20 mL), and triethylamine (0.44 mL) and methyl 4-[(1S)-1-aminoethyl]benzoate hydrochloride were sequentially added, followed by heating with reflux for 18 hours. The reaction mixture was cooled to room temperature, and a 10% aqueous citric acid solution (15 mL) was added thereto. To a mixture was added ethyl acetate, followed by washing with water, and the obtained organic layer was dried over anhydrous sodium sulfate. After filtering and concentrating under reduced pressure, the residue was purified by silica gel column chromatography (hexane/ethyl acetate: 90/10-75/25) to obtain methyl 4-[(1S)-1-({[2-(methylamino)-4,5,6,7-tetrahydro-1-benzothiophen-3-yl]carbonyl}amino)ethyl]benzoate (0.42 g).

Production Example 12

To methyl 4-[(1S)-1-({[2-(methylamino)-4,5,6,7-tetrahydro-1-benzothien-3-yl]carbonyl}amino)ethyl]benzoate (0.41 g) was added 1,3-dimethyl-2-imidazolidinone (4.0 mL), and potassium carbonate (0.30 g) and 1-(bromomethyl)-4-chlorobenzene (0.34 g) were added thereto under ice-cooling, followed by stirring at 50° C. overnight. The reaction mixture was cooled to room temperature, and then water (50 mL) was added thereto, followed by extraction with ethyl acetate. The obtained organic layer was washed with brine, dried over anhydrous sodium sulfate, filtered, and then concentrated under reduced pressure. The residue was purified by silica gel column chromatography (hexane/ethyl acetate: 15/1-4/1) to obtain methyl 4-{(1S)-1-[({2-[(4-chlorobenzyl)(methyl)amino]-4,5,6,7-tetrahydro-1-benzothiophen-3-yl}carbonyl)amino]ethyl}benzoate (0.15 g).

Production Example 13

To a mixture of methyl 5-bromo-1-(4-chlorobenzyl)-1H-indole-7-carboxylic acid (300 mg), trimethylboroxin (100 mg), potassium carbonate (165 mg), and 1,4-dioxane (9 mL) was added tetrakis(triphenylphosphine) palladium (0) (46 mg) at room temperature. This mixture was stirred under heating with reflux for 15 hours. The reaction mixture was left to be cooled to room temperature, and water was added thereto, followed by extraction with ethyl acetate. The organic layer was dried over anhydrous sodium sulfate, the solvent was evaporated, and the obtained residue was purified by silica gel column chromatography (hexane-ethyl acetate) to obtain methyl 1-(4-chlorobenzyl)-5-methyl-1H-indole-7-carboxylate (60 mg).

Production Example 14

To a mixture of (3-oxo-1,3-dihydro-2-benzofuran-1-yl)(triphenyl) phosphonium bromide (5.1 g) and tetrahydrofuran (50 mL) were added potassium tert-butoxide (1.3 g) and 5-chloro-2-nitro benzoaldehyde (1.0 g) at room temperature under an argon atmosphere, followed by stirring for 5 minutes. To the reaction mixture was added water, followed by extraction with ethyl acetate. The organic layer was washed with saturated brine and dried over anhydrous sodium sulfate. After filtration, the filtrate was concentrated under reduced pressure. The residue was purified by silica gel column chromatography (hexane-ethyl acetate) to obtain 3-(5-chloro-2-nitrobenzylidene)-2-benzofuran-1(3H)-one (808 mg).

Production Example 15

A mixture of 3-(5-chloro-2-nitrobenzylidene)-2-benzofuran-1(3H)-one (808 mg), reduced iron (750 mg), ammonium chloride (72 mg), water (2.5 mL), and ethanol (25 mL) was stirred at 80° C. for 4 hours. The reaction mixture was filtered using Celite and the solvent was evaporated under reduced pressure. The residue was purified by silica gel column chromatography (hexane-ethyl acetate) to obtain 3-(2-amino-5-chlorobenzylidene)-2-benzofuran-1(3H)-one (466 mg).

Production Example 16

1-(6-Bromopyridin-3-yl)ethanone (5.00 g), propane-1,3-diylbis(diphenyl phosphine) (1.546 g), DMF (55 mL), methanol (30 mL), and triethylamine (10.5 mL) were mixed, and the inside of the reaction vessel was degassed and replaced with argon. Palladium acetate (II) (842 mg) was added thereto, and then the inside of the reaction vessel was replaced with carbon monoxide and stirred at 70° C. for 2 days. After leaving to be cooled to room temperature, the reaction mixture was diluted with a mixed liquid of diethyl ether-ethyl acetate, and washed with water and saturated brine in this order. The organic layer was dried over anhydrous sodium sulfate, then the solvent was evaporated under reduced pressure, and the obtained residue was purified by silica gel column chromatography (hexane-ethyl acetate) to obtain methyl 5-acetylpyridine-2-carboxylate (1.16 g).

Production Example 17

To a solution of 3-(2-amino-5-chlorobenzylidene)-2-benzofuran-1(3H)-one (466 mg) in ethanol (3.5 mL) was added a 1 M aqueous sodium hydroxide solution (3.4 mL) at room temperature, followed by heating with reflux for 45 minutes. The reaction mixture was acidified by adding of 1 M hydrochloric acid under ice-cooling, and stirred at room temperature for 1 hour. The resulting precipitate was separated by filtration and the filtrate was extracted with diethyl ether. The organic layer was washed with saturated brine and dried over anhydrous sodium sulfate. After filtration, the filtrate was concentrated under reduced pressure to obtain 2-(5-chloro-1H-indol-2-yl)benzoic acid (395 mg).

Production Example 18

To a mixture of 2-(5-chloro-1H-indol-2-yl)benzoic acid (217 mg), DMF (4.0 mL), and THF (1.0 mL) was added sodium hydride (55% dispersion in paraffin liquid, 77 mg) at room temperature under an argon atmosphere, followed by stirring for 5 minutes. At room temperature, methyl iodide (0.50 mL) was added thereto, followed by stirring for 12 hours. To the reaction mixture was added water, followed by extraction with ethyl acetate. The organic layer was washed with water and saturated brine, and dried over anhydrous sodium sulfate. After filtration, the filtrate was concentrated under reduced pressure to obtain methyl 2-(5-chloro-1-methyl-1H-indol-2-yl)benzoate (270 mg).

Production Example 19

To a mixture of methyl 4-propionyl benzoic acid (0.50 g) and pyridine (5.0 mL) was added hydroxylamine hydrochloride (0.54 g) under ice-cooling, followed by stirring at room temperature for 4 hours. The reaction mixture was concentrated under reduced pressure, to the residue were added ethyl acetate and a 10% aqueous citric acid solution and the aqueous layer was extracted with ethyl acetate. The organic layer was combined, and washed with a 10% aqueous citric acid solution, a saturated aqueous sodium hydrogen carbonate solution, water, and saturated brine. The organic layer was dried over anhydrous magnesium sulfate and concentrated under reduced pressure, and to the residue was added ethanol (15 mL). To the reaction mixture were added a suspension of Raney nickel (2.0 mL) in ethanol (15 mL), and concentrated aqueous ammonia (3.0 mL), followed by stirring at room temperature for 14 hours under a hydrogen atmosphere of 3 atm. The insoluble materials in the reaction mixture were separated by filtration through Celite, and the filtrate was concentrated under reduced pressure. To the residue was added diethyl ether (10 mL), and a 4 M-hydrogen chloride/dioxane solution (1.0 mL) was added thereto under ice-cooling. The precipitated crystal was collected by filtration and washed with diethyl ether to obtain methyl 4-(1-amino propyl)benzoic acid hydrochloride (0.51 g).

Production Example 20

To a mixture of methyl 5-acetylpyridine-2-carboxylate (1.00 g), THF (24 mL), and methanol (12 mL) was added sodium borohydride (110 mg), followed by stirring at room temperature for 2 hours. The mixture was concentrated under reduced pressure, and then to the obtained residue was added a saturated aqueous sodium chloride solution. After extraction with ethyl acetate, the organic layer was dried over anhydrous sodium sulfate. The solvent was evaporated and then dried under reduced pressure to obtain methyl 5-(1-hydroxyethyl)pyridine-2-carboxylate (897 mg).

Production Example 21

A mixture of methyl 5-(1-hydroxyethyl)pyridine-2-carboxylate (895 mg) and dichloromethane (10 mL) was ice-cooled, and triethylamine (1.72 mL) and methanesulfonyl chloride (765 μL) were added thereto. The mixture was stirred under ice-cooling for 3 minutes, and then stirred at room temperature for 30 minutes. To a mixture was added water, followed by extraction with chloroform. This organic layer was dried over anhydrous sodium sulfate, and then the solvent was evaporated under reduced pressure to obtain a pale yellow oily residue (1.457 g). This residue was mixed with DMF (5 mL) and sodium azide (965 mg), followed by stirring at 60° C. for 1 hour. The mixture was left to be cooled to room temperature, and water was added thereto, followed by extraction with a mixed liquid of ethyl acetate-diethyl ether. The organic layer was washed with water and saturated brine in this order, and then dried over anhydrous sodium sulfate. The solvent was evaporated under reduced pressure, and the obtained residue was purified by silica gel column chromatography (hexane-ethyl acetate) to obtain methyl 5-(1-azidoethyl)pyridine-2-carboxylate (828 mg).

Production Example 22

To a mixture of 3-hydroxy-4-methyl benzoic acid (3.0 g), potassium carbonate (10.9 g), and acetonitrile (60 mL) was added ethyl iodide (4.8 mL) under ice-cooling, followed by stirring at 60° C. overnight. Thereafter, ethyl iodide (4.8 mL) was added thereto, followed by stirring at 70° C. for 3 days. In addition, ethyl iodide (4.8 mL) and potassium carbonate (5.5 g) were added thereto, followed by stirring overnight. To the reaction mixture was added water (100 mL), followed by extraction with ethyl acetate, and the obtained organic layer was washed with saturated brine, dried over anhydrous sodium sulfate, and then concentrated under reduced pressure. The obtained residue was purified by silica gel column chromatography (ethyl acetate/hexane:5/95) to obtain ethyl 3-ethoxy-4-methylbenzoate (4.0 g).

Production Example 23

Methyl (S)-4-(1-acetamideethyl)benzoic acid (4.40 g) and concentrated sulfuric acid (15 mL) were mixed at room temperature, stirred until it became homogeneous, and then ice-cooled. To this was added dropwise a mixed liquid of fumed nitric acid (3 mL) and concentrated sulfuric acid (2 mL) over 30 minutes while the internal temperature was kept at 10° C. or lower. After completion of dropwise addition, the mixture was stirred at room temperature for 5 hours. The reaction liquid was poured into ice water, followed by stirring and then extraction with ethyl acetate. The organic layer was washed with a saturated aqueous sodium hydrogen carbonate solution, and then dried over anhydrous sodium sulfate. The solvent was evaporated under reduced pressure to obtain methyl (S)-4-(1-acetamideethyl)-3-nitro benzoate (4.83 g).

Production Example 24

Under a hydrogen atmosphere, a mixture of methyl (S)-4-(1-acetamideethyl)-3-nitro benzoate (4.83 g), ethyl acetate (30 mL), and 10% palladium/carbon (500 mg) was stirred at room temperature for 18 hours. After the reaction, the catalyst was removed by filtration and the solvent was evaporated under reduced pressure. To the obtained residue was added ethyl acetate, followed by heating with reflux. This was left to be cooled to room temperature, and then the precipitate was collected by filtration to obtain methyl (S)-3-amino-4-(1-acetamideethyl)benzoate (3.31 g).

Production Example 25

To a mixture of ethyl 3-ethoxy-4-methylbenzoate (2.0 g), N-bromosuccinimide (1.9 g) and ethyl acetate (40 mL) was added 2,2'-azobis(2-methylpropionitrile) (15 mg), followed by stirring for 14 hours under heating with reflux. The mixture was left to be cooled, hexane was added thereto, the precipitated solid was separated by filtration, and the obtained filtrate was concentrated under reduced pressure. The residue was purified by silica gel column chromatography (ethyl acetate/hexane:5/95) to obtain ethyl 4-(bromomethyl)-3-ethoxybenzoate (2.4 g).

Production Example 26

To a mixture of 4-chloro-1H-pyrrole-2-carboxylic acid (0.20 g) and DMF (2.0 mL) was added potassium tert-butoxide (0.31 g) under ice-cooling, followed by stirring at room temperature for 15 minutes. To the reaction mixture was added 1-bromomethyl-4-chlorobenzene (0.29 g) under ice-cooling, followed by stirring at room temperature for 14 hours. To the reaction mixture was added water at room temperature, followed by extraction with ethyl acetate. The organic layer was washed with water and saturated brine, dried over anhydrous magnesium sulfate, and then filtered. The filtrate was concentrated under reduced pressure, and the residue was purified by silica gel column chromatography to obtain 4-chloro-1-(4-chlorobenzyl)-1H-pyrrole-2-carboxylic acid (0.06 g).

Production Example 27

To a mixture of sodium nitrite (193 mg) and concentrated sulfuric acid (2 mL) was added dropwise a solution of methyl (S)-3-amino-4-(1-acetamideethyl)benzoate (600 mg) in acetic acid (6 mL), followed by stirring at room temperature for 30 minutes. To the ice-cooled solution of copper chloride (I) (550 mg) in concentrated hydrochloric acid (6 mL) was added dropwise the above-described reaction mixture, followed by stirring at room temperature for 5 hours. The reaction liquid was poured into ice water, followed by extraction with chloroform. The organic layer was washed with water and then dried over anhydrous sodium sulfate. The solvent was evaporated and the obtained residue was purified by silica gel column chromatography (chloroform-methanol) to obtain methyl (S)-4-(1-acetamideethyl)-3-chlorobenzoate (465 mg).

Production Example 28

To a mixture of methyl 4-formyl-3-methoxybenzoate (3.30 g) and THF (30 mL) was added dropwise methyl magnesium bromide (3 M diethyl ether solution, 3.60 mL) under ice-cooling. After dropwise addition, the mixture was stirred for 1 hour under ice-cooling. A saturated aqueous ammonium chloride solution was added thereto to stop the reaction, followed by extraction with ethyl acetate. The organic layer was washed with saturated brine, and then dried over an aqueous anhydrous sodium sulfate solution. The solvent was evaporated under reduced pressure, and the obtained residue was purified by silica gel column chromatography (hexane-ethyl acetate) to obtain methyl 4-(1-hydroxyethyl)-3-methoxybenzoate (1.92 g).

Production Example 29

To a mixture of 1-(4-bromophenyl)-1-cyclopropylmethane amine (1.08 g) and THF (10 mL) were added triethylamine (1 mL) and di-tert-butyl dicarbonate (1.25 mL), and the mixture was stirred at room temperature for 16 hours. The solvent was concentrated under reduced pressure, and the obtained residue was purified by silica gel column chromatography (hexane-ethyl acetate) to obtain tert-butyl[(4-bromophenyl)(cyclopropyl)methyl]carbamate (1.36 g).

Production Example 30

To a mixture of methyl 4-(1-hydroxyethyl)-3-methoxybenzoate (1.92 g), diphenylphosphorylazide (2.76 g), and toluene (20 mL) was added 1,8-diazabicyclo[5.4.0]undec-7-ene (1.5 mL) at room temperature, followed by stirring at room temperature for 2 days. To this mixture were added THF (10 mL), water (5 mL), and triphenylphosphine (3.0 g) at room temperature, and the mixture was stirred at 60° C. for 3 hours. The mixture was left to be cooled to room temperature, and the solvent was evaporated under reduced pressure, followed by extraction with ethyl acetate. To this organic layer was added a 1 M aqueous hydrochloric acid solution (50 mL), and a desired product was extracted in the aqueous layer. To this aqueous layer was added a 1 M aqueous sodium hydroxide solution (60 mL), and then a desired product was extracted with ethyl acetate three times. The combined organic layer was washed with saturated brine, and then dried over anhydrous sodium sulfate. The solvent was evaporated under reduced pressure, and to the obtained residue (748 mg) was added a 4 M hydrogen chloride 1,4-dioxane solution (4 mL), followed by stirring for 3 minutes and concentrating under reduced pressure. To this residue was added ethyl acetate, followed by stirring at room temperature for 10 minutes, and then the precipitate was collected by filtration to obtain methyl 4-(1-aminoethyl)-3-methoxybenzoate hydrochloride (439 mg).

Production Example 31

A mixture of methyl (S)-4-(1-acetamideethyl)-3-chlorobenzoate (464 mg) and 2 M hydrochloric acid (12 mL) was stirred at 100° C. for 2 days. After leaving to be cooled to room temperature, the mixture was concentrated under reduced pressure, further azeotroped with ethanol, and dried to obtain (S)-4-(1-aminoethyl)-3-chlorobenzoic acid hydrochloride (428 mg).

Production Example 32

To a mixture of sodium hydride (0.29 g, 55% dispersion in paraffin liquid) and DMF (10 mL) was added methyl 4H-furo[3,2-b]pyrrole-5-carboxylate (0.5 g) under ice-cooling, followed by stirring for 10 minutes and further 1-(bromomethyl)-4-chlorobenzene (0.81 g) was added thereto, followed by stirring at room temperature for 4 hours. To the reaction mixture was added a 10% aqueous citric acid solution (10 mL), followed by extraction with ethyl acetate. The organic layer was dried over anhydrous sodium sulfate and then concentrated under reduced pressure, and the residue was purified by silica gel column chromatography (hexane/ethyl acetate: 5/1-3/1) to obtain 4-(4-chlorobenzyl)-4H-furo[3,2-b]pyrrole-5-carboxylic acid (0.35 g).

Production Example 33

Methyl 4-{[(tert-butoxycarbonyl)amino](cyclopropyl)methyl}benzoate (793 mg), methanol (5 mL), and 4 M hydrogen chloride/dioxane (5 mL) were mixed, followed by stirring at room temperature for 2 hours. The solvent was evaporated under reduced pressure, and then to the residue was added ethyl acetate. The precipitated solid was collected by filtration and dried under reduced pressure to obtain methyl 4-[amino(cyclopropyl)methyl]benzoate hydrochloride (561 mg).

Production Example 34

A mixture of 7-bromo-5-methoxy-1H-indole (1.2 g) and THF (12 mL) was stirred at −78° C. under an argon atmosphere. To the reaction mixture was added dropwise an n-butyllithium n-hexane solution (1.65 M, 9.6 mL) at −50° C. or lower. The reaction mixture was stirred for 0.5 hour under ice-cooling. The reaction mixture was cooled to −78° C., and dry ice (10 g) was added thereto, followed by slowly warming to room temperature. The reaction mixture was poured into a 10% aqueous citric acid solution, followed by extraction with ethyl acetate. The organic layer was washed with saturated brine, dried over anhydrous magnesium sulfate, and filtered. The filtrate was concentrated under reduced pressure and the residue was purified by silica gel column chromatography (THF/hexane=20→60%) to obtain 5-methoxy-1H-indole-7-carboxylic acid (0.60 g).

Production Example 35

To ethyl 4-(bromomethyl)-3-ethoxybenzoate (2.4 g) was added DMF (24 mL), and sodium azide (0.54 g) was added thereto, followed by stirring at room temperature overnight. To the reaction mixture was added water (50 mL), followed by extraction with ethyl acetate, and the obtained organic layer was washed with saturated brine, dried over anhydrous sodium sulfate, and then concentrated under reduced pressure. To the residue were added THF (21 mL), and water (4.0 mL), and then added triphenylphosphine (6.6 g), followed by stirring at room temperature for 1 hour, and further at 75° C. for 1 hour. The reaction mixture was ice-cooled, adjusted to pH 2 by adding a 1 M aqueous hydrochloric acid solution, and washed with diethyl ether. The aqueous layer was neutralized with saturated aqueous sodium bicarbonate, followed by extraction with ethyl acetate. The obtained organic layer was dried over anhydrous sodium sulfate and concentrated under reduced pressure. Under ice-cooling, to the residue were added ethyl acetate (4.0 mL) and then 4 M hydrogen chloride ethyl acetate solution (4.0 mL), and the precipitated solid was collected by filtration, washed with ethyl acetate, and then dried at 60° C. under reduced pressure to obtain ethyl 4-(aminomethyl)-3-ethoxybenzoate hydrochloride (1.1 g).

Production Example 36

Under an argon atmosphere, to an ice-cooled mixture of nitrosonium tetrafluoroborate (355 mg) and dichloromethane (15 mL) was added methyl (S)-3-amino-4-(1-acetamide-ethyl)benzoate (650 mg), and the reaction mixture was stirred at room temperature for 20 hours. To this was added 1,2-dichlorobenzene (15 mL), dichloromethane was evaporated under reduced pressure and then the mixture was stirred at 160° C. for 2 hours. After cooling to room temperature, a saturated aqueous sodium hydrogen carbonate solution was added thereto, followed by extraction with chloroform.

The organic layer was dried over anhydrous sodium sulfate and then solvent was evaporated under reduced pressure. The residue was purified by silica gel column chromatography (chloroform-methanol) to obtain methyl (S)-4-(1-acetamide-ethyl)-3-fluorobenzoate (266 mg).

Production Example 37

To a mixture of methyl 4-cyano-2-methylbenzoate (3.0 g) and methanol (60 mL) was added dichlorocobalt hexahydrate (8.1 g) under ice-cooling, followed by stirring. To a mixture was slowly added sodium borohydride (3.9 g), followed by stirring at room temperature for 2 hours. Under ice-cooling, to the reaction mixture was added saturated aqueous ammonia (20 mL), followed by stirring at room temperature for 30 minutes. This solution was filtered through Celite and washed with methanol. The filtrate was concentrated under reduced pressure, and to the obtained residue was added 1 M hydrochloric acid (50 mL), followed by washing with diethyl ether. The aqueous layer was adjusted to pH 8 by adding saturated aqueous sodium bicarbonate, and further adjusted to pH 10 by adding a 1 M aqueous sodium hydroxide solution. The mixture was extracted by adding chloroform, and the organic layer was dried over anhydrous magnesium sulfate. A 4 M hydrogen chloride dioxane solution (10 mL) was added thereto, followed by concentration under reduced pressure. The solid was washed with diethyl ether, then collected by filtration, and dried at 60° C. under reduced pressure to obtain methyl 4-(aminomethyl)-3-methylbenzoate hydrochloride (3.0 g).

Production Example 38

To 1-(biphenyl-4-ylmethyl)-1H-indole-7-carboxylic acid (0.20 g), methyl 4-[(1S)-1-aminoethyl]benzoate hydrochloride, and HATU was added DMF (4.0 mL), followed by adding diisopropylethylamine (0.26 mL) under ice-cooling and then stirring at room temperature for 22 hours. Again, the mixture was ice-cooled, a 10% aqueous citric acid solution (4.0 mL) was added thereto, and the precipitated solid was collected by filtration, washed with water, and dried at 60° C. under reduced pressure to obtain methyl 4-[(1S)-1-({[1-(biphenyl-4-ylmethyl)-1H-indol-7-yl]carbonyl}amino)ethyl]benzoate (0.30 g).

Production Example 39

To a mixture of cis-4-(butoxycarbonyl)cyclohexane carboxylic acid (3.3 g) and thionyl chloride (13 mL) was added DMF (2 drops), followed by stirring at 50° C. for 0.5 hours. The reaction mixture was concentrated under reduced pressure and azeotroped with toluene to obtain a residue. A mixture of copper iodide (5.2 g) and THF (13 mL) was stirred at an internal temperature of −40° C. under an argon atmosphere. To the reaction mixture was added dropwise a diethyl ether solution (1.1 M, 55 mL) of methyl lithium at an internal temperature of −30 to −40° C. over about 15 minutes, followed by stirring at the same temperature for 1 hour. The reaction mixture was cooled to an internal temperature of −60° C., and the THF solution (10 mL) of the above-described residue was added dropwise thereto at an internal temperature of −50 to −60° C. over about 5 minutes. The mixture was stirred at the same temperature for 0.5 hours, and methanol (15 mL) was added dropwise thereto, followed by warming to room temperature. To the reaction mixture were added a saturated aqueous ammonium chloride solution and ethyl acetate, and the aqueous layer was extracted with ethyl acetate. The organic layer was combined, washed with a saturated aqueous ammonium chloride solution and saturated brine, dried over anhydrous magnesium sulfate, and then filtered, and the filtrate was concentrated under reduced pressure. The residue was purified by silica gel column chromatography (hexane:ethyl acetate=9:1) to obtain butyl cis-4-acetylcyclohexane carboxylate (2.2 g).

Production Example 40

To 5-methyl-1H-indole-7-carboxylic acid (1.1 g), potassium carbonate (1.3 g) was added DMF (22 mL), and then methyl iodide (1.3 mL) was added thereto under ice-cooling. After stirring at room temperature overnight, the reaction mixture was adjusted to pH 3 by adding a 10% aqueous citric acid solution. The mixture was extracted with ethyl acetate, and the obtained organic layer was washed with water, dried over anhydrous sodium sulfate, filtered, and concentrated under reduced pressure. The residue was purified by silica gel column chromatography (hexane/ethyl acetate: 95/5-85/15) to obtain methyl 5-methyl-1H-indole-7-carboxylate (1.2 g).

Production Example 41

To a mixture of ice-cooled methyl 6-hydroxypyridine-2-carboxylate (800 mg), DME (10.5 mL), and DMF (2.6 mL) was added sodium hydride (55% oil dispersion, 240 mg), followed by stirring for 10 minutes. To this was added lithium bromide (910 mg), and then the mixture was stirred at room temperature for 15 minutes and further 4-chlorobenzylbromide (2.15 g) was added thereto. This mixture was stirred at 65° C. for 20 hours. Water was added thereto, followed by extraction with ethyl acetate-diethyl ether, and the organic layer was washed with water and saturated brine in this order, and dried over anhydrous sodium sulfate. The solvent was evaporated, and the obtained residue was purified by silica gel column chromatography (hexane-ethyl acetate) to obtain methyl 1-(4-chlorobenzyl)-6-oxo-1,6-dihydropyridine-2-carboxylate (270 mg; Example 41a) and methyl 6-[(4-chlorobenzyl)oxy]pyridine-2-carboxylate (448 mg; Example 41b), as a colorless oily substance, respectively.

Production Example 42

A mixture of methyl 5-bromo-1H-indole-7-carboxylate (300 mg), 1-methyl-2-pyrrolidinone (6 mL), sodium methanesulfinate (600 mg), and copper iodide (I) (1.10 g) was stirred at 150° C. for 17 hours under an argon atmosphere. The reaction mixture was left to be cooled to room temperature, ethyl acetate was added thereto, and then the insoluble materials were removed by filtration. To this filtrate was added water, followed by extraction with ethyl acetate. The organic layer was washed with water and saturated brine in this order, and then dried over anhydrous sodium sulfate. The solvent was evaporated under reduced pressure, and the obtained residue was purified by silica gel column chromatography (hexane-ethyl acetate) to obtain methyl 5-(methanesulfonyl)-1H-indole-7-carboxylate (91 mg).

Production Example 43

To a mixture of tert-butylcarbamate (5.60 g) and n-propanol (50 mL) were added a 0.5 M aqueous sodium hydroxide solution (94 mL) and tert-butyl hypochlorate (5.32 mL), followed by stirring at room temperature for 20 minutes. To the reaction mixture was added dropwise an n-propanol (50 mL) solution of (DHQD)2Phal (766.5 mg) under ice-cooling. In addition, at the same temperature, an n-propanol (80 mL) solution of methyl 4-vinyl benzoate (2.5 g) was added dropwise over 30 minutes, and then potassium osmate dihydrate (253.8 mg) was added thereto. The reaction mixture was stirred for 1 hour under ice-cooling, and then stirred at 4° C. overnight. The reaction mixture was concentrated under reduced pressure, and to the residue was added water (250 mL). The aqueous layer was extracted with ethyl acetate (100 mL×3). The organic layer was combined, washed with a 1 M aqueous hydrochloric acid solution (200 mL) and saturated brine, and dried over anhydrous magnesium sulfate, and then the solvent was evaporated under reduced pressure. The residue was purified by silica gel column chromatography (hexane-ethyl acetate=3:1) to obtain methyl 4-{(1R)-1-[(tert-butoxycarbonyl)amino]-2-hydroxyethyl}benzoate (850 mg) as a white solid.

Production Example 44

To methyl 1-(4-bromobenzyl)-1H-indole-7-carboxylate (0.63 g), 4,4,4',4',5,5,5',5'-octamethyl 2,2'-bi-1,3,2-dioxaborolane (0.56 g), potassium acetate (0.27 g), bis(triphenylphosphine) palladium (II) dichloride (39 mg), and triphenylphosphine (29 mg) was added toluene (6.0 mL), followed by stirring at 110° C. under an argon atmosphere. After stirring for 5 hours, the reaction mixture was purified by silica gel column chromatography (hexane-ethyl acetate=20/1-10/1) to obtain methyl 1-[4-(4,4,5,5-tetramethyl-1,3,2-dioxaborolan-2-yl)benzyl]-1H-indole-7-carboxylate (0.45 g).

Production Example 45

To a mixture of 7-bromoinden-1-ol (1.06 g), triphenylphosphine (1.86 g), 4-chlorophenol (911 mg), and toluene (30 mL) was added dropwise diethyl azodicarboxylate (2.2 M toluene solution, 3.3 mL) at room temperature. After dropwise addition, the mixture was stirred at room temperature for 2 hours. The solvent was evaporated under reduced pressure and then the obtained residue was purified by silica gel column chromatography (hexane-ethyl acetate) to obtain 7-bromo-1-(4-chlorophenoxy)indane (306 mg).

Production Example 46

To a mixture of 7-bromo-1H-pyrrolo[3,2-c]pyridine (0.16 g) and THF (6.0 mL) were added di-tert-butyl dicarbonate (0.26 g) and N,N-dimethyl-4-aminopyridine (0.010 g) at room temperature, followed by stirring at room temperature for 17 hours. The reaction mixture was concentrated under reduced pressure and the residue was purified by silica gel column chromatography (ethyl acetate/hexane=0 to 25%) to obtain tert-butyl 7-bromo-1H-pyrrolo[3,2-c]pyridine-1-carboxylate (0.22 g).

Production Example 47

To a mixture of 7-bromoindole (3.3 g) and 1,3-dimethyl-3,4,5,6-tetrahydro-2(1H)-pyrimidone (33 mL) were added 2-phenyloxirane (2.5 mL) and cesium carbonate (11 g) at room temperature, followed by stirring at 80° C. for 12 hours. To the reaction mixture were added ethyl acetate and water, followed by extraction with ethyl acetate. The organic layer was washed with water and saturated brine, dried over anhydrous sodium sulfate, and evaporated under reduced pressure. The residue was purified by silica gel column chromatography (hexane:ethyl acetate=4:1) to obtain 2-(7-bromo-1H-indol-1-yl)-1-phenylethanol (5.1 g).

Production Example 48

A mixture of tert-butyl 7-bromo-1H-pyrrolo[3,2-c]pyridine-1-carboxylate (0.20 g), 1,3-bis(diphenylphosphino)propane (0.028 g), palladium acetate (0.015 g), DMF (4.0 mL), methanol (6.0 mL), and triethylamine (0.28 mL) was stirred at 80° C. for 2 days under carbon monoxide atmosphere. The reaction mixture was left to be cooled and replaced with argon. The reaction mixture was diluted with ethyl acetate, washed with water and saturated brine, dried over anhydrous magnesium sulfate, and then filtered. The residue was purified by silica gel column chromatography (ethyl acetate/hexane=30 to 60%) to obtain methyl 1H-pyrrolo[3,2-c]pyridine-7-carboxylate (0.081 g).

Production Example 49

To a mixture of 4-[(1S)-1-({[1-(4-chlorobenzyl)-1H-indol-7-yl]carbonyl}amino)ethyl]benzoic acid (250 mg) and DMF (5 mL) was added 1,1'-carbonyldiimidazole (187 mgl)

at room temperature, followed by stirring for 5 minutes, and then 3-(aminosulfonyl)propylacetate (209 mg) and 1,8-diazabicyclo[5.4.0]undec-7-ene (173 μL) were added in this order, followed by stirring for 3 days. The reaction mixture was ice-cooled, and 10% aqueous citric acid (30 mL) was added thereto, followed by stirring for 30 minutes. The precipitated solid was collected by filtration and washed with cold ethanol (4 mL) to obtain 1-(4-chlorobenzyl)-N-[(1S)-1-(4-{[(3-acetoxypropyl)sulfonyl]carbamoyl}phenyl)ethyl]-1H-indole-7-carboxamide (210 mg) as a pale yellow solid.

Production Example 50

To methyl 1-[4-(4,4,5,5-tetramethyl-1,3,2-dioxaborolan-2-yl)benzyl]-1H-indole-7-carboxylate (0.30 g), pyridin-2-yl-trifluoromethanesulfonate (0.35 g), tripotassium phosphate (0.49 g), palladium(II) chloride (27 mg), and biphenyl-2-yl (dicyclohexyl)phosphine (0.11 g) were added dioxane (12 mL) and water (3.0 mL), followed by stirring at 100° C. for 4 hours. The reaction mixture was purified by silica gel column chromatography (hexane/ethyl acetate=5/1-4/1) to obtain methyl 1-(4-pyridin-2-yl benzyl)-1H-indole-7-carboxylate (0.15 g).

Production Example 51

To 2-(7-bromo-1H-indol-1-yl)-1-phenylethanol (0.70 g) were added DMF (7.0 mL), tert-butyl(chloro)dimethylsilane (0.47 g), and imidazole (0.23 g), followed by stirring at room temperature for 25 hours. To the reaction mixture was added a 10% aqueous citric acid solution (15 mL), followed by extraction with ethyl acetate, and the obtained organic layer was washed with brine. After drying over anhydrous sodium sulfate and concentrating under reduced pressure, the obtained residue was purified by silica gel column chromatography (hexane/ethyl acetate=99/1-90/10) to obtain 7-bromo-1-(2-{[tert-butyl(dimethyl)silyl]oxy}-2-phenylethyl)-1H-indole (0.92 g).

Production Example 52

To 7-bromo-1-(2-{[tert-butyl(dimethyl)silyl]oxy}-2-phenylethyl)-1H-indole (0.91 g) was added dehydrated THF (30 mL), and an n-butyl lithium hexane solution (1.6 M, 5.2 mL) was added thereto at −78° C. while replacing with argon. The mixture was warmed from −78° C. to −5° C., followed by stirring for 30 minutes. The reaction mixture was again cooled to −78° C., and dry ice was added thereto, followed by stirring to room temperature. To the mixture was added diethyl ether, followed by washing with a 1 M aqueous sodium hydroxide solution. The obtained aqueous layer was adjusted to pH 3 with a 10% aqueous citric acid solution, followed by extraction with ethyl acetate. The organic layer was washed with water and saturated brine, dried over anhydrous sodium sulfate, and then concentrated under reduced pressure. The residue was purified by silica gel column chromatography (hexane/ethyl acetate=3/1) to obtain 1-[(E)-2-phenyl vinyl]-1H-indole-7-carboxylic acid (0.34 g).

Production Example 53

To methyl 1H-indole-7-carboxylate (1.5 g) was added DMF (15 mL), and potassium tert-butoxide (1.5 g) was added thereto under ice-cooling, followed by stirring for 10 minutes. 4-(Bromomethyl)biphenyl (2.8 g) was added thereto, followed by stirring at room temperature for 19 hours. The reaction mixture was again ice-cooled, and a 10% aqueous citric acid solution (20 mL) was added thereto, followed by extraction with ethyl acetate. The organic layer was washed with saturated brine, dried over anhydrous sodium sulfate, and concentrated under reduced pressure. The residue was purified by silica gel column chromatography (hexane/ethyl acetate=97/3-95/5) to obtain methyl 1-(biphenyl-4-ylmethyl)-1H-indole-7-carboxylate (2.5 g).

Production Example 54

To methyl 1-(biphenyl-4-ylmethyl)-1H-indole-7-carboxylate (2.5 g) were added methanol (20 mL), THF (20 mL), and a 1 M aqueous sodium hydroxide solution (10 mL), followed by stirring at 60° C. for 16 hours. To the reaction mixture was added a 10% aqueous citric acid solution (20 mL), followed by extraction with ethyl acetate, and the organic layer was washed with brine. After dehydration over anhydrous sodium sulfate, filtering and concentrating under reduced pressure, the obtained residue was added with diisopropylether, solidified, and collected by filtration. This solid was purified by silica gel column chromatography (chloroform/methanol=99/1-97/3) to obtain 1-(biphenyl-4-ylmethyl)-1H-indole-7-carboxylic acid (0.99 g).

Production Example 55

To (6-piperidin-1-ylpyridin-3-yl)methanol (0.61 g) was added methylene chloride (6.0 mL), and thionyl chloride (1.0 mL) was added dropwise thereto under ice-cooling. In addition, a catalytic amount of DMF was added thereto, followed by stirring at room temperature for 2 hours. Methylene chloride (5.0 mL) and thionyl chloride (1.0 mL) were added thereto, followed by stirring at 60° C. overnight. The reaction mixture was concentrated under reduced pressure, and DMF (10 mL) was added thereto. Then, methyl 1H-indole-7-carboxylate (0.56 g) and potassium tert-butoxide (1.3 g) were added thereto under ice-cooling, followed by stirring at room temperature for 3 hours. The reaction mixture was extracted by adding ethyl acetate and water, and the organic layer was washed with brine, dried over anhydrous sodium sulfate, then filtered, and concentrated under reduced pressure. The residue was purified by silica gel column chromatography (hexane/ethyl acetate=95/5-70/30) to obtain methyl 1-[(6-piperidin-1-ylpyridin-3-yl)methyl]-1H-indole-7-carboxylate (0.12 g).

Production Example 56

To methyl 1-[4-(4,4,5,5-tetramethyl-1,3,2-dioxaborolan-2-yl)benzyl]-1H-indole-7-carboxylate (0.15 g), 1,1'-bis (diphenylphosphino)ferrocene palladium (14 mg), cesium fluoride (0.17 g), and 3-bromopyridine (79 mg) was added dioxane (4.5 mL), followed by stirring at 100° C. for 21 hours under an argon atmosphere. The reaction mixture was purified by silica gel column chromatography (hexane/ethyl acetate=2/1-1/1) to obtain methyl 1-(4-pyridin-3-yl benzyl)-1H-indole-7-carboxylate (0.13 g).

Production Example 57

To a mixture of (1-phenylpiperidin-4-yl)methanol (958 mg), methyl 1H-indole-7-carboxylate (590 mg), and toluene (20 mL) was added (tributylphosphoranylidene)acetonitrile (1.0 g) at room temperature. The mixture was stirred at 100° C. for 1 day. The reaction mixture was cooled to room temperature and concentrated under reduced pressure. The residue was purified by silica gel column chromatography (hexane-ethyl acetate) to obtain methyl 1-[(1-phenylpiperidin-4-yl)methyl]-1H-indole-7-carboxylate (163 mg).

Production Example 58

4-Phenyl thiophene-2-methanol (0.21 g), toluene (2.0 mL), and a catalytic amount of pyridine were added, and thionyl chloride (0.16 mL) was added dropwise thereto under ice-cooling. After stirring at room temperature for 3 hours, the reaction mixture was concentrated under reduced pressure, azeotroped with toluene, and dried at 60° C. under reduced pressure to obtain 2-(chloromethyl)-4-phenylthiophene (0.22 g).

Production Example 59

To a mixture of methyl 4-bromo-1-(4-chlorobenzyl)-1H-pyrrole-2-carboxylate (0.72 g) and DMF (21 mL) were added phenylboric acid (0.30 g), sodium carbonate (0.58 g), water (3.0 mL), and tetrakis(triphenylphosphine) palladium (0.13 g), followed by stirring at 100° C. for 24 hours. To the reaction mixture were added ethyl acetate and water, and the insoluble materials were separated by filtration through Celite. The organic layer was washed with water and saturated brine, dried over anhydrous magnesium sulfate, and then filtered. The filtrate was concentrated under reduced pressure and the residue was purified by silica gel column chromatography (ethyl acetate/hexane=0 to 10%) to obtain methyl 1-(4-chlorobenzyl)-4-phenyl-1H-pyrrole-2-carboxylate (0.26 g).

Production Example 60

To a mixture of tert-butyl 4-{[7-({(1S)-1-[4-(methoxycarbonyl)phenyl]ethyl}carbamoyl)-1H-indol-1-yl]methyl}piperidine-1-carboxylate (1.67 g), and THF (20 mL) was added a 4 M hydrogen chloride ethyl acetate solution (2.0 mL) at room temperature, followed by stirring for 1 hour. The reaction mixture was stirred at 60° C. for 6 hours. The reaction mixture was concentrated under reduced pressure. The residue was washed with ethyl acetate and diethyl ether, collected by filtration, and dried under reduced pressure to obtain methyl 4-[(1S)-1-({[1-(piperidin-4-ylmethyl)-1H-indol-7-yl]carbonyl}amino)ethyl]benzoate hydrochloride (1.46 g).

Production Example 61

To a mixture of methyl 4-[(1S)-1-({[1-(piperidin-4-ylmethyl)-1H-indol-7-yl]carbonyl}amino)ethyl]benzoate hydrochloride (150 mg) and dichloromethane (2.0 mL) were added sodium triacetoxyborohydride (210 mg) and benzaldehyde (70 mg) at room temperature, followed by stirring for 3 days. To the reaction mixture was added water. In addition, the mixture was alkalified by adding a 1 M aqueous sodium hydroxide solution and extracted with ethyl acetate. The organic layer was washed with saturated brine and dried over anhydrous sodium sulfate. After filtration, the filtrate was concentrated under reduced pressure to obtain methyl 4-{(1S)-1-[({1-[(1-benzyl piperidin-4-yl)methyl]-1H-indol-7-yl}carbonyl)amino]ethyl}benzoate (121 mg) as a white solid.

Production Example 62

To methyl 1-(1,3-benzoxazol-2-ylmethyl)-1H-indole-7-carboxylate (0.22 g), methanol (2.0 mL), and THF (2.0 mL) was added a 1 M aqueous sodium hydroxide solution (1.0 mL), followed by stirring at 70° C. for 14 hours. The reaction mixture was ice-cooled, a 10% aqueous citric acid solution (5.0 mL) was added thereto, and the precipitated solid was collected by filtration, and washed with water and diethyl ether/hexane (1/1) to obtain 1-{2-[(2-hydroxyphenyl)amino]-2-oxo ethyl}-1H-indole-7-carboxylic acid (0.18 g).

Production Example 63

To a mixture of methyl 4-{[(1H-benzimidazol-2-ylcarbonyl)amino]methyl}benzoate (230 mg), potassium carbonate (257 mg), and DMF (4.6 mL) was added p-chlorobenzylbromide (191 mg), followed by stirring at room temperature for 2.5 days. To the reaction mixture was added water (30 mL), followed by extraction with ethyl acetate (30 mL). The organic layer was sequentially washed with saturated aqueous sodium bicarbonate and saturated brine, and dried over anhydrous magnesium sulfate. After filtration and concentration, the obtained residue was washed with methanol (2 mL) to obtain methyl 4-[({[1-(4-chlorobenzyl)-1H-benzimidazol-2-yl]carbonyl}amino)methyl]benzoate (269 mg) as a white solid.

Production Example 64

To a mixture of ethyl 5-chloro-1H-indole-7-carboxylate (3.0 g) and acetic acid (30 mL) was added sodium cyanoborohydride (2.5 g), followed by stirring at room temperature for 19 hours. The reaction mixture was concentrated under reduced pressure, and the residue was adjusted to pH 8 by adding saturated aqueous sodium bicarbonate. After extraction with chloroform, the organic layer was dried over anhydrous sodium sulfate, filtered, and concentrated under reduced pressure. The residue was added with diethyl ether/hexane (1/5), solidified, and collected by filtration. To this solid was added ethyl acetate (10 mL), and 4 M hydrogen chloride ethyl acetate (10 mL) was added thereto, followed by concentration under reduced pressure. To the residue was added diethyl ether/hexane mixture (1/5), and the solid was collected by filtration and dried under reduced pressure to obtain ethyl 5-chloroindoline-7-carboxylate hydrochloride (1.6 g).

Production Example 65

A mixture of ethyl 1-[(5-bromopyridin-2-yl)methyl]-5-chloro-1H-indole-7-carboxylate (0.30 g), (9,9-dimethyl-9H-xanthene-4,5-diyl)bis(diphenylphosphine) (88 mg), sodium tert-butoxide (0.12 g), piperidine (84 mg), tris(dibenzylideneacetone)dipalladium (0) (70 mg), and dehydrated toluene (6.0 mL) was bubbled with argon for 10 minutes, followed by stirring at 110° C. for 2 hours. The reaction mixture was filtered through Celite and washed with diethyl ether. To this filtrate was added saturated aqueous sodium bicarbonate, followed by extraction with diethyl ether, and the organic layer was washed with saturated brine. After drying over anhydrous sodium sulfate, filtering and concentrating under reduced pressure, the residue was purified by silica gel column chromatography (hexane/ethyl acetate=1/1) to obtain ethyl 5-chloro-1-[(5-piperidin-1-ylpyridin-2-yl)methyl]-1H-indole-7-carboxylate (0.23 g).

Production Example 66

A mixture of 2-fluoro-5-(trifluoromethyl)benzonitrile (1000 mg), 5-chloro-1H-indole (800 mg), potassium carbonate (1.8 g), and DMSO (10 ml) was stirred at 100° C. for 14 hours. The reaction mixture was cooled to room temperature, and water was added thereto, followed by extraction with ethyl acetate. The organic layer was washed with water and saturated brine, and dried over anhydrous sodium sulfate. After filtration, the filtrate was concentrated under reduced pressure to obtain 2-(5-chloro-1H-indol-1-yl)-5-(trifluoromethyl)benzonitrile (1.66 g).

Production Example 67

To a mixture of 2-(5-chloro-1H-indol-1-yl)-5-(trifluoromethyl)benzonitrile (1.66 g) and ethylene glycol (18 mL) was added a 1 M aqueous sodium hydroxide solution (26 mL) at room temperature, followed by stirring at 180° C. for 16 hours. The reaction mixture was cooled to room temperature and neutralized by adding 1 M hydrochloric acid (26 mL), followed by extraction with ethyl acetate. The organic layer was washed with saturated brine and dried over anhydrous sodium sulfate. After filtration, the filtrate was concentrated under reduced pressure to obtain 2-(5-chloro-1H-indol-1-yl)-5-(trifluoromethyl)benzoic acid (1.67 g).

Production Example 68

To a mixture of ethyl 1-(1,2,3,4-tetrahydroisoquinolin-7-ylmethyl)-5-(trifluoromethyl)-1H-indole-7-carboxylate (0.14 g) and ethyl acetate (10 mL) was added manganese dioxide (0.30 g) at room temperature. The reaction liquid was stirred for 6.5 hours under the condition for heating with reflux. In addition, to the reaction liquid were added toluene (10 mL) and manganese dioxide (0.30 g) at room temperature, followed by stirring at 110° C. for 1 day and then at 130° C. for 1 day. The reaction liquid was left to be cooled to room temperature, and filtered using Celite, and the filtrate was concentrated under reduced pressure. The residue was purified by silica gel column chromatography (hexane:ethyl acetate=75:25-30:70) to obtain ethyl 1-(isoquinolin-7-ylmethyl)-5-(trifluoromethyl)-1H-indole-7-carboxylate (85 mg).

Production Example 505

To a mixture of 4-bromo-3-chloro-2-methyl aniline hydrochloride (1.0 g), sodium acetate (0.5 g), and acetic acid (15 mL) was added N-iodosuccinimide (1.0 g) under water-cooling. The reaction mixture was stirred at room temperature for 3.5 hours. To the reaction mixture were added ethyl acetate and water, and alkalified by adding potassium carbonate. Then, a liquid-separation operation was carried out, and the organic layer was washed with saturated brine, dried over anhydrous sodium sulfate, and then evaporated under reduced pressure. The residue was purified by silica gel column chromatography (hexane:ethyl acetate=100:0-90:10) to obtain 4-bromo-3-chloro-6-iodo-2-methylaniline (1.3 g).

Production Example 506

To a mixture of N-[2-methyl-3-(trifluoromethyl)phenyl] acetamide (6.2 g) and acetic acid (40 ml) was added an acetic acid solution (10 ml) of bromine (1.8 ml) under water-cooling. The reaction liquid was stirred at room temperature overnight and then at 50° C. for 2 hours. In addition, to the reaction liquid was added bromine (1.5 ml) under water-cooling, followed by stirring at 50° C. for 1 day. In addition, to the reaction liquid was added bromine (2.0 ml) under water-cooling, followed by stirring at 50° C. for 1 day. In addition, to the reaction liquid was added bromine (2.0 ml) under water-cooling, followed by stirring at 50° C. for 1 day. In addition, to the reaction liquid was added bromine (2.0 ml) under water-cooling, followed by stirring at 50° C. for 4 days. The reaction liquid was poured into ice water (about 200 g), ethyl acetate was added thereto, followed by neutralization with potassium carbonate. A liquid-separation operation was carried out, and the organic layer was washed with an aqueous sodium thiosulfate solution and saturated brine in this order, dried over anhydrous sodium sulfate, and then evaporated under reduced pressure to obtain N-[4-bromo-2-methyl-3-(trifluoromethyl)phenyl]acetamide (9.0 g).

Production Example 507

To a mixture of tert-butyl 5-bromo-7-(bromomethyl)-6-chloro-1H-indole-1-carboxylic acid (7.2 g) and acetonitrile (50 mL) was added 4-methyl morpholine-4-oxide (2.7 g) at room temperature. The reaction mixture was stirred at 50° C. for 7 hours and then at 70° C. overnight. The reaction mixture was concentrated under reduced pressure, ethyl acetate and water were added thereto, and a liquid-separation operation was carried out. The organic layer was washed with saturated brine, dried over anhydrous sodium sulfate, and then evaporated under reduced pressure. The residue was purified by silica gel column chromatography (hexane:ethyl acetate=100:0-90:10) to obtain tert-butyl 5-bromo-6-chloro-7-formyl 1H-indole-1-carboxylic acid (2.9 g).

Production Example 508

To a mixture of tert-butyl 5-bromo-6-chloro-7-formyl 1H-indole-1-carboxylic acid (2.9 g), sodium dihydrogen phosphate (2.0 g), 2-methyl-2-butene (2.6 g), water (10 mL), and 1,4-dioxane (30 mL) was added sodium chlorite (1.8 g) under ice-cooling. The reaction mixture was stirred under ice-cooling for 1 hour, and then at room temperature for 5 hours. The reaction mixture was concentrated under reduced pressure, and ethyl acetate and water were added thereto, and a liquid-separation operation was carried out. The organic layer was washed with saturated brine, dried over anhydrous sodium sulfate, and then evaporated under reduced pressure to obtain 5-bromo-1-(tert-butoxycarbonyl)-6-chloro-1H-indole-7-carboxylic acid (3.1 g).

Production Example 509

To a mixture of 5-bromo-1-(tert-butoxycarbonyl)-6-chloro-1H-indole-7-carboxylic acid (0.3 g), water (2.0 mL), and methanol (6.0 mL) was added potassium carbonate (0.6 g) at room temperature. The reaction mixture was stirred at 70° C. for 5.5 hours. The reaction mixture was concentrated under reduced pressure, and ethyl acetate and water were added thereto, followed by acidification with 1 M hydrochloric acid. Then, a liquid-separation operation was carried out, and the organic layer was washed with saturated brine, dried over anhydrous sodium sulfate, and then evaporated under reduced pressure to obtain 5-bromo-6-chloro-1H-indole-7-carboxylic acid (0.22 g).

Production Example 510

To a mixture of N-[4-bromo-2-methyl-3-(trifluoromethyl) phenyl]acetamide (9.0 g) and ethanol (40 mL) was added concentrated hydrochloric acid (40 mL) at room temperature. The reaction mixture was stirred at 100° C. for 4 hours. The reaction mixture was left to be cooled to room temperature, and ethyl acetate and water were added thereto, followed by alkalification with potassium carbonate. Then, a liquid-separation operation was carried out, and the organic layer was washed with saturated brine, dried over anhydrous sodium sulfate, and then evaporated under reduced pressure. The residue was purified by silica gel column chromatography (hexane:ethyl acetate 90:10-60:40) to obtain 4-bromo-2-methyl-3-(trifluoromethyl) aniline (6.9 g).

Production Example 511

To a mixture of 4-amino-3-bromo-5-iodobenzonitrile (1.0 g), copper iodide (60 mg), and triethylamine (10 mL) was added bistriphenylphosphine palladium dichloride (0.22 g) under an argon atmosphere, and degassed twice with argon. Ethynyl trimethylsilane (0.47 mL) was added thereto under ice-cooling, followed by stirring at room temperature for 24 hours. The insoluble materials in the reaction mixture were separated by filtration through Celite, and the filtrate was concentrated under reduced pressure. To the residue were added a 10% aqueous citric acid solution and ethyl acetate, and the insoluble materials were separated again by filtration. The organic layer was washed with a saturated aqueous sodium hydrogen carbonate solution, water, and saturated brine, dried over anhydrous magnesium sulfate, and then filtered. The filtrate was concentrated under reduced pressure, and the residue was purified by silica gel column chromatography (hexane:chloroform=2:1) to obtain 4-amino-3-bromo-5-[(trimethylsilyl)ethynyl]benzonitrile (0.81 g).

Production Example 512

To a mixture of 4-amino-3-bromo-5-[(trimethylsilyl)ethynyl]benzonitrile (0.80 g) and tetrahydrofuran (3.0 mL) was added a 1 M tetrabutyl ammonium fluoride-THF solution (3.0 mL) under ice-cooling, followed by stirring at room temperature for 0.5 hour. To the reaction mixture was added water under ice-cooling, followed by extraction with ethyl acetate. The organic layer was washed with saturated brine, dried over anhydrous magnesium sulfate, and then filtered. The filtrate was concentrated under reduced pressure, and the residue was purified by silica gel column chromatography (chloroform/hexane=30-50%) to obtain 4-amino-3-bromo-5-ethynylbenzonitrile (0.57 g).

Production Example 513

To a mixture of tert-butyl 5-bromo-7-methyl-6-(trifluoromethyl)-1H-indole-1-carboxylic acid (1.2 g) and carbon tetrachloride (20 mL) were added N-bromosuccinimide (0.70 g) and 2,2'-azobis(2-methylpropionitrile) (20 mg) at room temperature. The reaction mixture was stirred at 90° C. for 18 hours. The reaction mixture was left to be cooled to room temperature and filtered through Celite to remove the insoluble materials. The filtrate was evaporated under reduced pressure, and to the residue was added acetonitrile (20 mL), followed by addition of 4-methyl morpholine-4-oxide (0.50 g) under ice-cooling. The reaction mixture was stirred at room temperature for 24 hours. The reaction mixture was evaporated under reduced pressure, ethyl acetate and water were added thereto, and a liquid-separation operation was carried out. The organic layer was washed with saturated brine, dried over anhydrous sodium sulfate, and then evaporated under reduced pressure. The residue was purified by silica gel column chromatography (hexane:ethyl acetate=100:0-90:10) to obtain tert-butyl 5-bromo-7-formyl-6-(trifluoromethyl)-1H-indole-1-carboxylic acid (0.26 g).

Production Example 514

To a mixture of 4-amino-3-bromo-5-ethynylbenzonitrile (0.57 g) and 1-methyl-2-pyrrolidinone (12 mL) was added tert-butylcarbamate (0.57 g) under ice-cooling, followed by stirring at room temperature for 24 hours. To the reaction mixture was added a 10% aqueous citric acid solution under ice-cooling, followed by extraction with ethyl acetate. The organic layer was washed with water, a saturated aqueous sodium hydrogen carbonate solution, water, and saturated brine, dried over anhydrous magnesium sulfate, and then filtered. The filtrate was concentrated under reduced pressure to obtain 7-bromo-1H-indole-5-carbonitrile (0.55 g).

Production Example 515

To a mixture of methyl trans-4-[({[5-bromo-6-chloro-1-(isoquinolin-3-ylmethyl)-1H-indol-7-yl]carbonyl}amino)methyl]cyclohexane carboxylate (0.28 g), sodium formate (0.10 g), and DMSO (5.0 mL) was added tetrakis(triphenylphosphine) palladium (20 mg) at room temperature. The reaction mixture was stirred at 70° C. for 2 hours and then at 90° C. for 3 hours. In addition, to the reaction mixture were added sodium formate (0.10 g) and tetrakis(triphenylphosphine) palladium (40 mg) in this order at room temperature, followed by stirring overnight at 90° C. To the reaction liquid were added ethyl acetate and water, and the insoluble materials were removed by filtration through Celite. The filtrate was subjected to a liquid-separation operation, and the organic layer was washed with saturated brine, dried over anhydrous sodium sulfate, and then evaporated under reduced pressure. The residue was purified by silica gel column chromatography (methanol:chloroform=0:100-5:95) to obtain methyl trans-4-[({[6-chloro-1-(isoquinolin-3-ylmethyl)-1H-indol-7-yl]carbonyl}amino)methyl]cyclohexane carboxylic acid (0.14 g).

Production Example 516

To a mixture of methyl trans-4-[({[5-bromo-6-(trifluoromethyl)-1H-indol-7-yl]carbonyl}amino)methyl]cyclohexane carboxylic acid (75 mg), triethylamine (0.1 mL), and methanol (5.0 mL) was added 10% palladium-carbon (80 mg) under ice-cooling. The reaction liquid was stirred at room temperature for 1 day under 1-atom hydrogen. The insoluble materials of the reaction liquid were removed by filtration through Celite, and evaporated under reduced pressure. To the residue was added ethyl acetate and water, and a liquid-separation operation was carried out. The organic layer was washed with a 5% aqueous citric acid solution and saturated brine in this order, dried over anhydrous sodium sulfate, and then evaporated under reduced pressure. The residue was purified by silica gel column chromatography (hexane:ethyl acetate=80:20-50:50) to obtain methyl trans-4-[({[6-(trifluoromethyl)-1H-indol-7-yl]carbonyl}amino)methyl]cyclohexane carboxylic acid (41 mg).

The Production Example compounds shown in Tables below were prepared in the same manner as in Production Examples above, using the respective corresponding starting materials. The structures of the Production Example compounds are shown in Table 3 to Table 136 and the production processes, and the physical data of the Production Example compounds are shown in Tables 201 to 211.

Example 1

To a solution of methyl 4-[(1S)-1-({[1-(4-chlorobenzyl)-1,2,3,4-tetrahydroquinolin-8-yl]carbonyl}amino)ethyl]benzoate (129 mg) in THF (2.0 mL) and methanol (1.0 mL) was added a 1 M aqueous sodium hydroxide solution (1.0 mL) at room temperature, followed by stirring for 2 days. The reaction mixture was neutralized by adding 1 M hydrochloric acid (1.0 mL) at room temperature, followed by extraction with ethyl acetate. The organic layer was washed with saturated brine and dried over anhydrous sodium sulfate. After filtration, the filtrate was concentrated under reduced pressure. The residue was purified by silica gel column chromatography (hexane-ethyl acetate). The resulting product was dissolved in ethyl acetate (2.0 mL), and to the solution was added a 4 M hydrogen chloride ethyl acetate solution (2.0 mL) at room temperature, followed by stirring for 1 day. The solvent was evaporated under reduced pressure, and the residue was washed with ethyl acetate, collected by filtration, and dried under reduced pressure to obtain 4-[(1S)-1-({[1-(4-chlorobenzyl)-1,2,3,4-tetrahydroquinolin-8-yl]carbonyl}amino)ethyl]benzoic acid hydrochloride (97 mg).

Example 2

To a mixture of 1-(4-chlorobenzyl)-1H-indole-7-carboxylic acid (0.20 g), methyl 4-(aminomethyl)-3-chlorobenzoate hydrochloride (0.18 g), and HATU (0.32 g) in DMF (4.0 mL) was added diisopropylethylamine (0.29 ml) under ice-cooling, followed by stirring at room temperature for 14 hours. After ice-cooled again, a 5% aqueous citric acid solution (8.0 mL) was added thereto, and the precipitated solid was collected by filtration, sequentially washed with water and diisopropylether, and dried at 60° C. under reduced pressure. To the obtained solid were added methanol (3.0 mL), THF (3.0 mL), and a 1 M aqueous sodium hydroxide solution (2.0 mL), followed by stirring at 60° C. for 2 hours. The reaction mixture was left to be cooled, a 10% aqueous citric acid solution (5.0 mL) was added thereto, and the precipitated solid was collected by filtration, washed with water, and dried at 60° C. under reduced pressure to obtain 3-chloro-4-[({[1-(4-chlorobenzyl)-1H-indol-7-yl]carbonyl}amino)methyl]benzoic acid (0.24 g).

Example 3

To methyl 4-[(1S)-1-({[1-(biphenyl-4-ylmethyl)-1H-indol-7-yl]carbonyl}amino)ethyl]benzoate (0.30 g) were added methanol (4.0 mL), THF (4.0 mL), and a 1 M aqueous sodium hydroxide solution (3.0 mL), followed by stirring at 65° C. for 2 hours and then at room temperature for 3 days. To the reaction mixture was added a 10% aqueous citric acid solution (4.0 mL), and the precipitated solid was collected by filtration, washed with water and a mixture of diethyl ether/hexane (1/1), and dried at 60° C. under reduced pressure to obtain 4-[(1S)-1-({[1-(biphenyl-4-ylmethyl)-1H-indol-7-yl]carbonyl}amino)ethyl]benzoic acid (0.25 g).

Example 4

To a mixture of 4-{(1S)-1-[({1-[(6-chloropyridin-3-yl)methyl]-1H-indol-7-yl}carbonyl)amino]ethyl}benzoic acid (0.15 g), phenylboronic acid (84 mg), tripotassium phosphate (0.22 g), palladium (II) chloride (9.2 mg), and biphenyl-2-yl (dicyclohexyl) phosphine (36 mg) were added dioxane (6.0 mL), water (1.5 mL), followed by stirring at 100° C. for 1 hour. The reaction mixture was adjusted to pH 3 by adding a 10% aqueous citric acid solution. The mixed liquid was filtered through Celite, and the filtrate was extracted with ethyl acetate. The organic layer was washed with brine, dried over anhydrous sodium sulfate, and then filtered, and the filtrate was concentrated under reduced pressure. The residue was purified by silica gel column chromatography (hexane/THF=2/1-1/1) to obtain 4-{(1S)-1-[({1-[(6-phenylpyridin-3-yl)methyl]-1H-indol-7-yl}carbonyl)amino]ethyl}benzoic acid (66 mg).

Example 5

To 4-{(1S)-1-[({1-[(6-chloropyridin-3-yl)methyl]-1H-indol-7-yl}carbonyl)amino]ethyl}benzoic acid (95 mg) were added ethanol (2.0 mL) and piperidine (65 μL), followed by stirring at room temperature overnight. After concentration under reduced pressure, DMSO (1.0 mL), piperidine (65 μL), and potassium tert-butoxide (61 mg) were added thereto, followed by stirring at 80° C. for 2 hours. To the reaction mixture was added a 10% aqueous citric acid solution (10 mL), followed by extraction with ethyl acetate. The obtained organic layer was washed with water, dried over anhydrous sodium sulfate, filtered, and concentrated under reduced pressure. The residue was purified by silica gel column chromatography (chloroform/methanol=99/1-95/5) to obtain 4-{(1S)-1-[({1-[(6-ethoxypyridin-3-yl)methyl]-1H-indol-7-yl}carbonyl)amino]ethyl}benzoic acid (9.0 mg).

Example 6

To a mixture of 1-(4-chlorobenzyl)-N-[(1S)-1-(4-{[(3-acetoxypropyl)sulfonyl]carbamoyl}phenyl)ethyl]-1H-indole-7-carboxamide (200 mg), THF (3 mL), and methanol (3 mL) was added a 1 M aqueous sodium hydroxide solution (1.7 mL), followed by stirring at room temperature overnight. The reaction mixture was adjusted to pH 4 by adding 1 M hydrochloric acid (1.7 mL), and further, water (20 mL) was added thereto, followed by stirring at room temperature for 30 minutes. The precipitated solid was collected by filtration, washed with water (4 mL), and then washed with cold ethanol (3 mL) to obtain 1-(4-chlorobenzyl)-N-[(1S)-1-(4-{[(3-hydroxypropyl)sulfonyl]carbamoyl}phenyl)ethyl]-1H-indole-7-carboxamide (80 mg) as a pale yellow solid.

The Example compounds shown in Tables below were prepared in the same manner as in Examples above, using the respective corresponding starting materials. The structures of the Example compounds are shown in Table 137 to Table 200 and the production processes and the physical data of the Example compounds are shown in Table 212 to Table 223.

Furthermore, other embodiments of the compound of the formula (I) or a salt thereof are shown in Tables 224 to 228. These compounds can be easily prepared by the preparation methods above, the methods described in Examples, the methods apparent to a skilled person in the art, or modified methods thereof.

In addition, the following abbreviations are used in Tables below.

Pr: Production Example number (a case where in Production Example, "/Cl" is described after Production Example number means that the Production Example compound was isolated as a hydrochloride), Ex: Example number (a case where in Example, "/Cl" is described after Example number means that the Example compound was isolated as a hydrochloride), No: Compound number, Structure: Structural formula (Ac: acetyl, TMS: trimethylsilyl, TBS: tert-butyl dimethylsilyl), Syn: Production process (among Examples or Production Examples above, the Production Example number or Example number produced in the same manner is shown. For example, it represents that the compound of Production Example 69 was prepared in the same manner as for the compound of Production Example 38), Data: Physicochemical data (values measured with NMR-C: δ (ppm) in $^1$H NMR in $CDCl_3$, NMR-D: δ (ppm) in $^1$H-NMR in DMSO-$d_6$, FAB+: FAB-MS (cation), FAB−: FAB-MS (anion), ESI+: ESI-MS (cation), ESI−: ESI-MS (anion), APCI+: APCI-MS (cation), EI: ELMS (cation), CI+: CI-MS (cation), APCI/ESI+: APCI-MS (cation), or ESI-MS (cation), mp: melting point (° C., dec: decomposition)).
TABLE 3
| Pr | Structure |
|---|---|
| 1 | 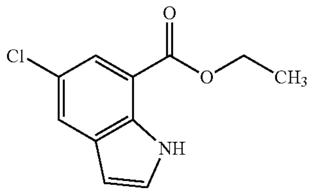 |
| 2 | 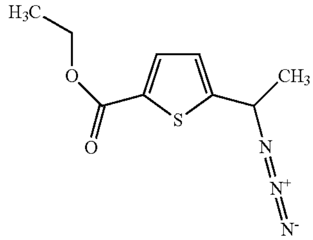 |
| 3/Cl | 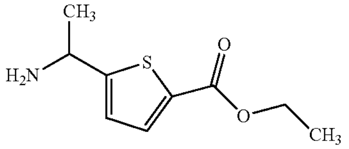 |
| 4 | 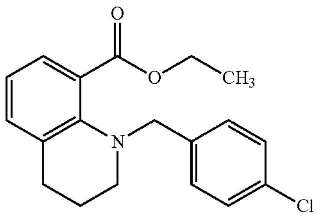 [SMILES: CCOC(=O)c1cccc2c1N(Cc1ccc(Cl)cc1)CCC2] |
| 5 | 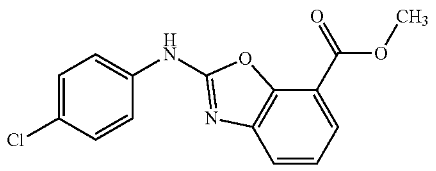 [SMILES: COC(=O)c1cccc2nc(Nc3ccc(Cl)cc3)oc12] |
| 6 | 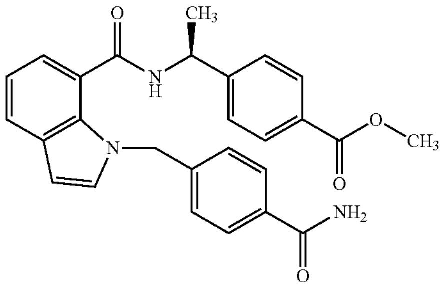 [SMILES: COC(=O)c1ccc([C@H](C)NC(=O)c2cccc3ccn(Cc4ccc(C(N)=O)cc4)c23)cc1] |
TABLE 4
| Pr | Structure |
|---|---|
| 7 | 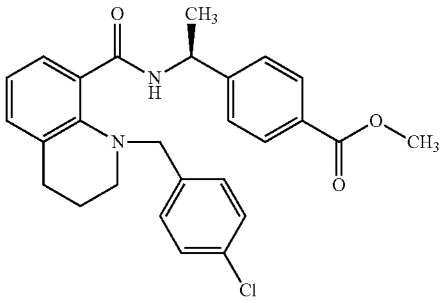 [SMILES: COC(=O)c1ccc([C@H](C)NC(=O)c2cccc3c2N(Cc2ccc(Cl)cc2)CCC3)cc1] |
| 8 | 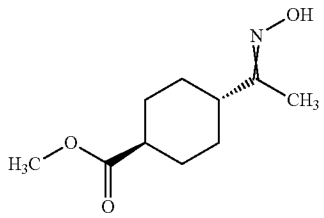 |
| 9/Cl | 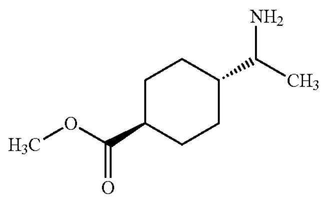 |
| 10 | 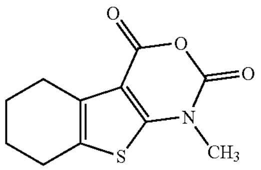 [SMILES: Cn1c(=O)oc(=O)c2c3c(sc21)CCCC3] |
| 11 | 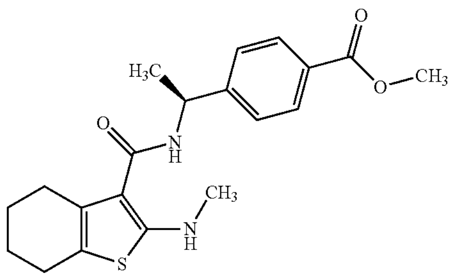 [SMILES: CNc1sc2c(c1C(=O)N[C@@H](C)c1ccc(C(=O)OC)cc1)CCCC2] |

TABLE 5
| Pr | Structure |
| --- | --- |
| 12 | 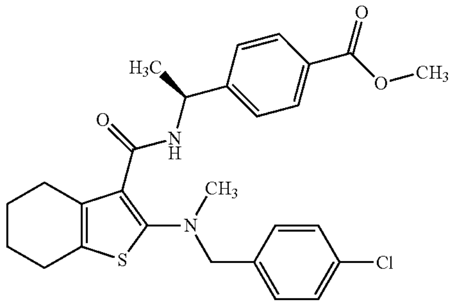 [SMILES: COC(=O)c1ccc([C@H](C)NC(=O)c2c(N(C)Cc3ccc(Cl)cc3)sc3c2CCCC3)cc1] |
| 13 | 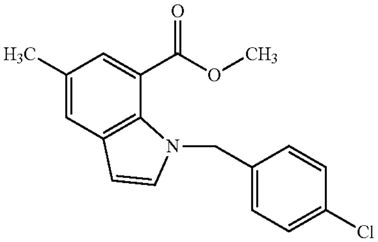 [SMILES: COC(=O)c1cc(C)cc2ccn(Cc3ccc(Cl)cc3)c12] |
| 14 | 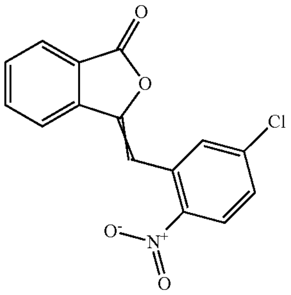 [SMILES: O=C1OC(=Cc2cc(Cl)ccc2[N+](=O)[O-])c2ccccc21] |
| 15 | 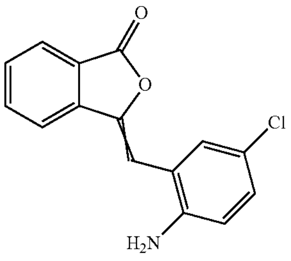 [SMILES: Nc1ccc(Cl)cc1C=C1OC(=O)c2ccccc21] |
| 16 | 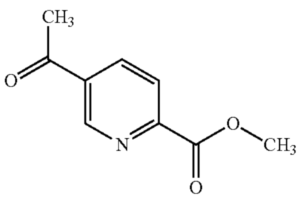 |
TABLE 6
| Pr | Structure |
| --- | --- |
| 17 | 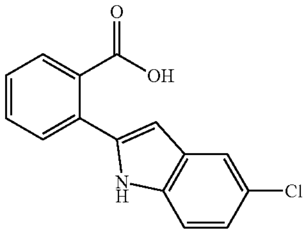 [SMILES: O=C(O)c1ccccc1-c1cc2cc(Cl)ccc2[nH]1] |
| 18 | 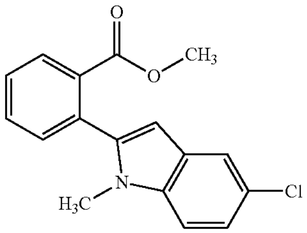 [SMILES: COC(=O)c1ccccc1-c1cc2cc(Cl)ccc2n1C] |
| 19/Cl | 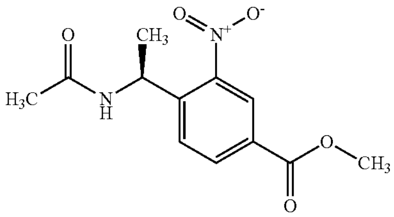 [SMILES: COC(=O)c1ccc([C@H](C)NC(C)=O)c([N+](=O)[O-])c1] |
| 20 | 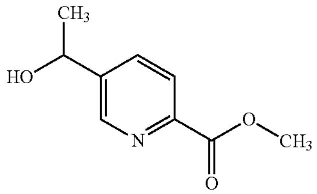 |
| 21 | 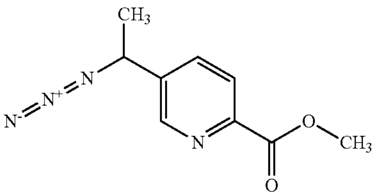 |
| 22 | 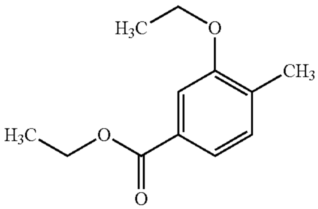 |

TABLE 7
| Pr | Structure |
|---|---|
| 23 | 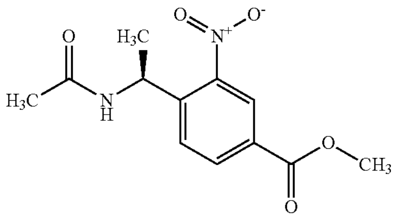 [SMILES: COC(=O)c1ccc([C@H](C)NC(C)=O)c([N+](=O)[O-])c1] |
| 24 | 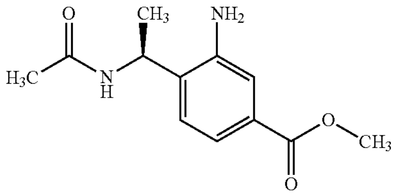 [SMILES: COC(=O)c1ccc([C@H](C)NC(C)=O)c(N)c1] |
| 25 | 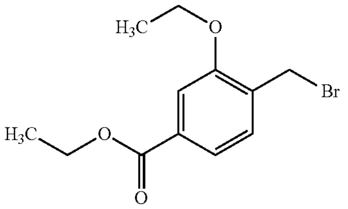 [SMILES: CCOC(=O)c1ccc(CBr)c(OCC)c1] |
| 26 | 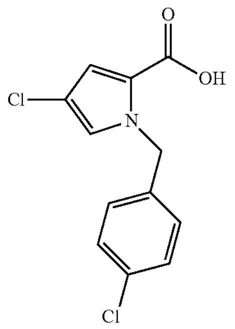 [SMILES: O=C(O)c1cc(Cl)cn1Cc1ccc(Cl)cc1] |
| 27 | 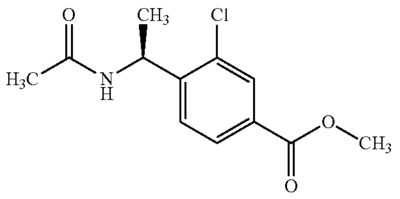 |
| 28 | 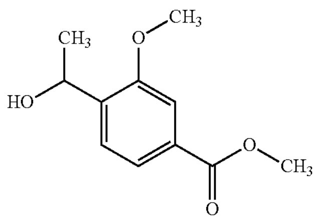 |
TABLE 8
| Pr | Structure |
|---|---|
| 29 | 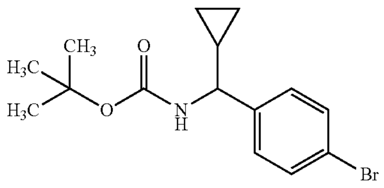 [SMILES: CC(C)(C)OC(=O)NC(c1ccc(Br)cc1)C1CC1] |
| 30/Cl | 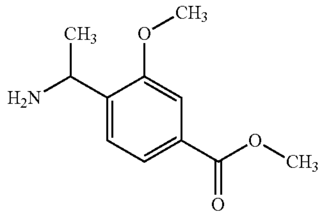 |
| 31/Cl | 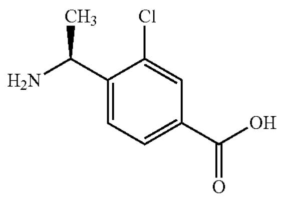 |
| 32 | 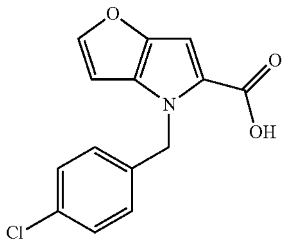 [SMILES: O=C(O)c1cc2occc2n1Cc1ccc(Cl)cc1] |
| 33/Cl | 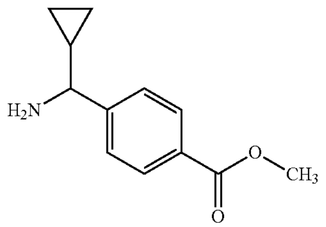 |
| 34 | 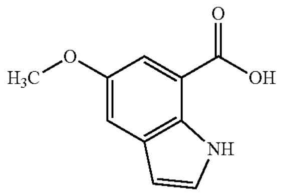 |

TABLE 9
| Pr | Structure |
|---|---|
| 35/Cl | 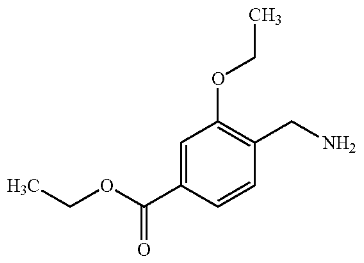 [SMILES: CCOC(=O)c1ccc(CN)c(OCC)c1] |
| 36 | 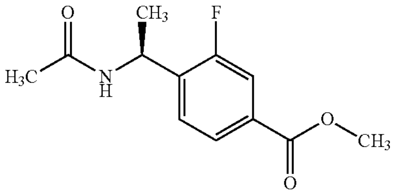 [SMILES: COC(=O)c1ccc([C@H](C)NC(C)=O)c(F)c1] |
| 37/Cl | 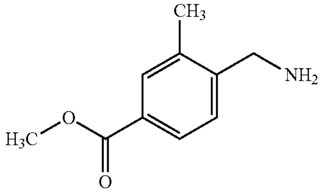 |
| 38 | 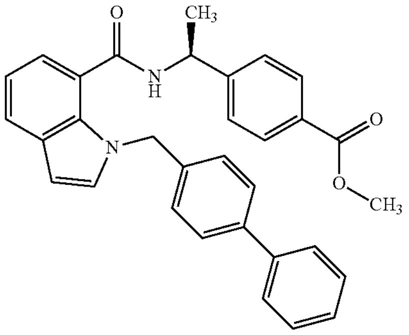 [SMILES: COC(=O)c1ccc([C@H](C)NC(=O)c2cccc3ccn(Cc4ccc(-c5ccccc5)cc4)c23)cc1] |
| 39 | 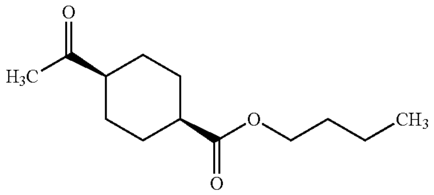 [SMILES: CCCCOC(=O)[C@H]1CC[C@@H](C(C)=O)CC1] |
| 40 | 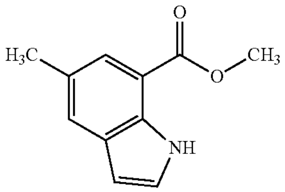 |
TABLE 10
| Pr | Structure |
|---|---|
| 41a | 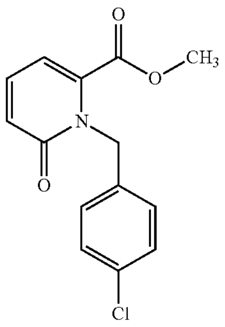 [SMILES: COC(=O)c1cccc(=O)n1Cc1ccc(Cl)cc1] |
| 41b | 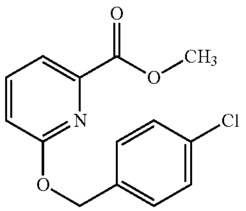 [SMILES: COC(=O)c1cccc(OCc2ccc(Cl)cc2)n1] |
| 42 | 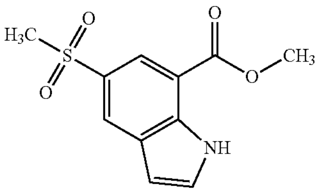 |
| 43 | 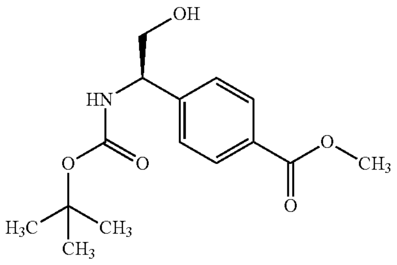 [SMILES: COC(=O)c1ccc([C@H](CO)NC(=O)OC(C)(C)C)cc1] |
TABLE 11
| Pr | Structure |
|---|---|
| 44 | 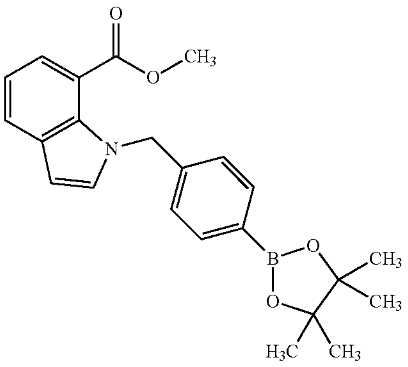 [SMILES: COC(=O)c1cccc2ccn(Cc3ccc(B4OC(C)(C)C(C)(C)O4)cc3)c12] |

TABLE 11-continued
| Pr | Structure |
|---|---|
| 45 | 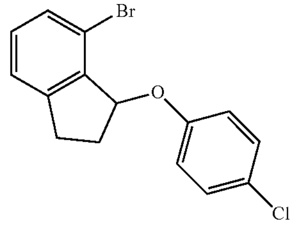 [SMILES: Clc1ccc(OC2CCc3cccc(Br)c32)cc1] |
| 46 | 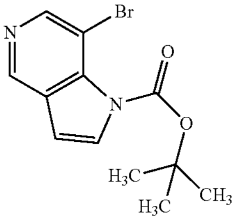 [SMILES: CC(C)(C)OC(=O)n1ccc2cncc(Br)c21] |
| 47 | 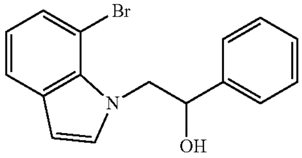 [SMILES: OC(Cn1ccc2cccc(Br)c21)c1ccccc1] |
| 48 | 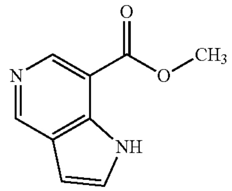 |
TABLE 12
| Pr | Structure |
|---|---|
| 49 | 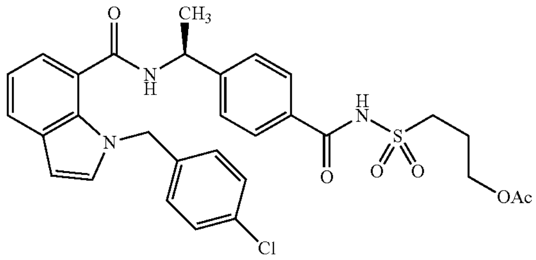 [SMILES: CC(=O)OCCCS(=O)(=O)NC(=O)c1ccc([C@H](C)NC(=O)c2cccc3ccn(Cc4ccc(Cl)cc4)c23)cc1] |
| 50 | 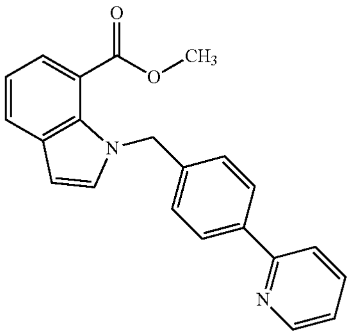 [SMILES: COC(=O)c1cccc2ccn(Cc3ccc(-c4ccccn4)cc3)c12] |
TABLE 12-continued
| Pr | Structure |
|---|---|
| 51 | 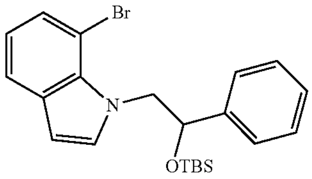 [SMILES: CC(C)(C)[Si](C)(C)OC(Cn1ccc2cccc(Br)c21)c1ccccc1] |
| 52 | 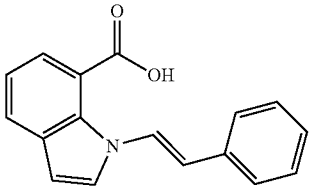 [SMILES: O=C(O)c1cccc2ccn(/C=C/c3ccccc3)c12] |
| 53 | 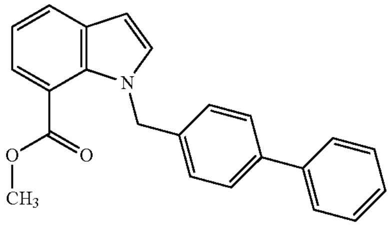 [SMILES: COC(=O)c1cccc2ccn(Cc3ccc(-c4ccccc4)cc3)c12] |
TABLE 13
| Pr | Structure |
|---|---|
| 54 | 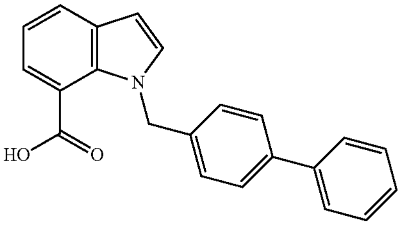 [SMILES: O=C(O)c1cccc2ccn(Cc3ccc(-c4ccccc4)cc3)c12] |
| 55 | 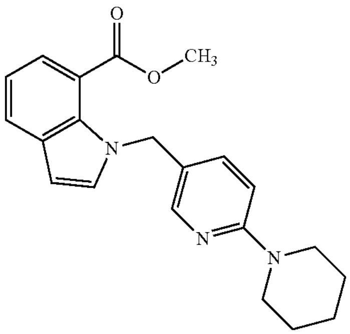 [SMILES: COC(=O)c1cccc2ccn(Cc3ccc(N4CCCCC4)nc3)c12] |

TABLE 13-continued
| Pr | Structure |
|---|---|
| 56 | 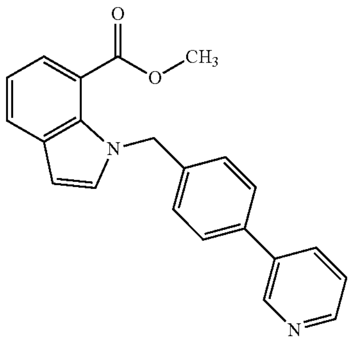 [SMILES: COC(=O)c1cccc2ccn(Cc3ccc(-c4cccnc4)cc3)c12] |
| 57 | 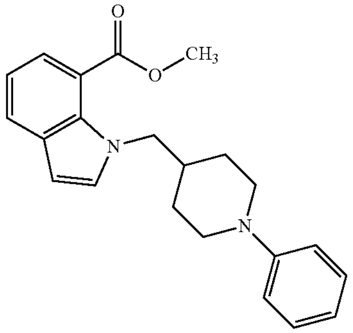 [SMILES: COC(=O)c1cccc2ccn(CC3CCN(c4ccccc4)CC3)c12] |
TABLE 14
| Pr | Structure |
|---|---|
| 58 | 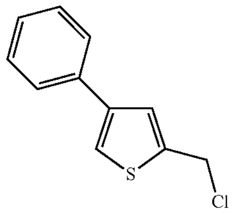 [SMILES: ClCc1cc(-c2ccccc2)cs1] |
| 59 | 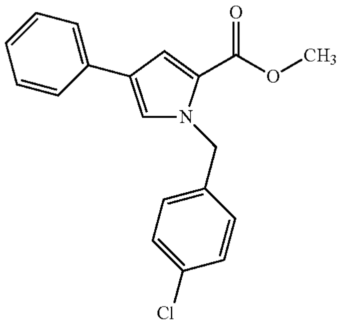 [SMILES: COC(=O)c1cc(-c2ccccc2)cn1Cc1ccc(Cl)cc1] |
| 60/Cl | 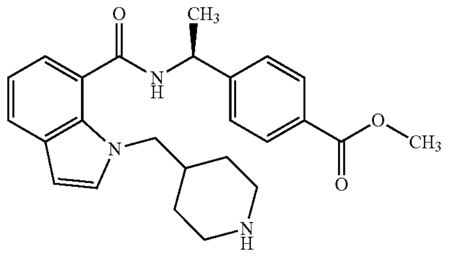 [SMILES: COC(=O)c1ccc([C@H](C)NC(=O)c2cccc3ccn(CC4CCNCC4)c23)cc1] |
TABLE 14-continued
| Pr | Structure |
|---|---|
| 61 | 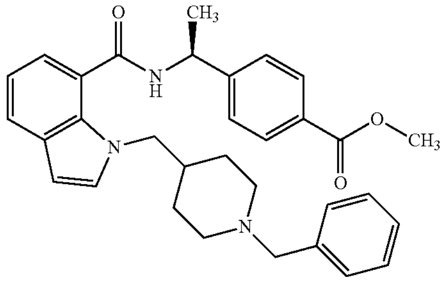 [SMILES: COC(=O)c1ccc([C@H](C)NC(=O)c2cccc3ccn(CC4CCN(Cc5ccccc5)CC4)c23)cc1] |
TABLE 15
| Pr | Structure |
|---|---|
| 62 | 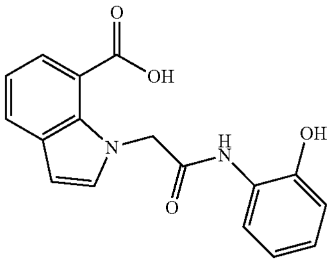 [SMILES: O=C(Cn1ccc2cccc(C(=O)O)c21)Nc1ccccc1O] |
| 63 | 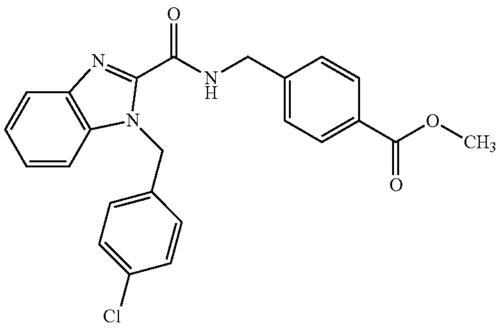 [SMILES: COC(=O)c1ccc(CNC(=O)c2nc3ccccc3n2Cc2ccc(Cl)cc2)cc1] |
| 64/Cl | 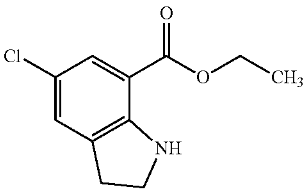 |
| 65 | 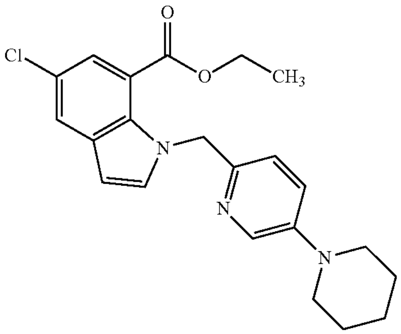 [SMILES: CCOC(=O)c1cc(Cl)cc2ccn(Cc3ccc(N4CCCCC4)cn3)c12] |

TABLE 16
| Pr | Structure |
|---|---|
| 66 | 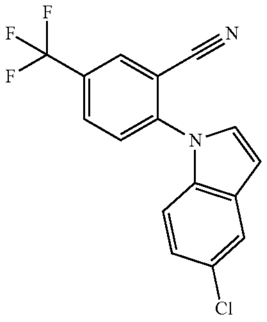 [SMILES: N#Cc1cc(C(F)(F)F)ccc1-n1ccc2cc(Cl)ccc21] |
| 67 | 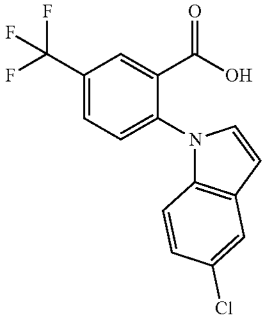 [SMILES: O=C(O)c1cc(C(F)(F)F)ccc1-n1ccc2cc(Cl)ccc21] |
| 68 | 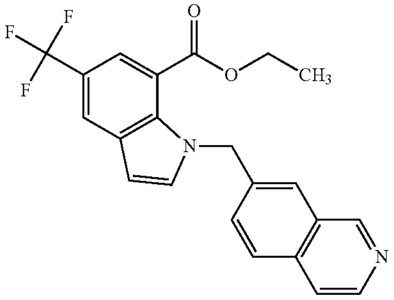 [SMILES: CCOC(=O)c1cc(C(F)(F)F)cc2ccn(Cc3ccc4ccncc4c3)c12] |
| 69 | 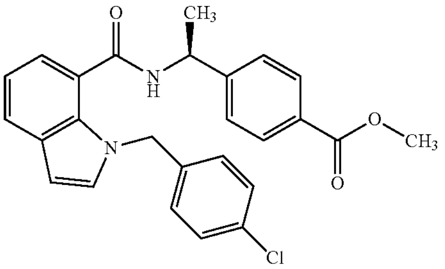 [SMILES: COC(=O)c1ccc([C@H](C)NC(=O)c2cccc3ccn(Cc4ccc(Cl)cc4)c23)cc1] |
TABLE 17
| Pr | Structure |
|---|---|
| 70 | 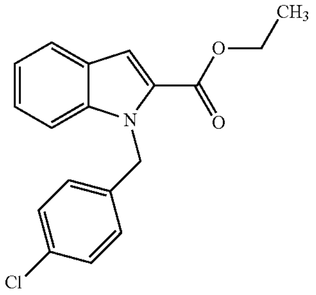 [SMILES: CCOC(=O)c1cc2ccccc2n1Cc1ccc(Cl)cc1] |
| 71 | 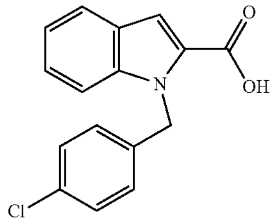 [SMILES: O=C(O)c1cc2ccccc2n1Cc1ccc(Cl)cc1] |
| 72 | 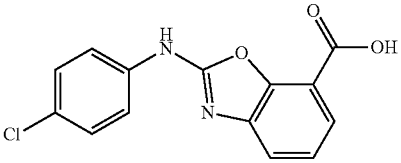 [SMILES: O=C(O)c1cccc2nc(Nc3ccc(Cl)cc3)oc12] |
| 73 | 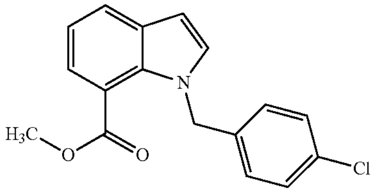 [SMILES: COC(=O)c1cccc2ccn(Cc3ccc(Cl)cc3)c12] |
| 74 | 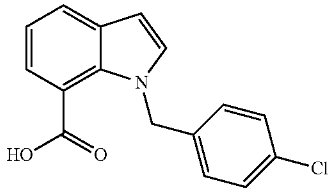 [SMILES: O=C(O)c1cccc2ccn(Cc3ccc(Cl)cc3)c12] |
TABLE 18
| Pr | Structure |
|---|---|
| 75 | 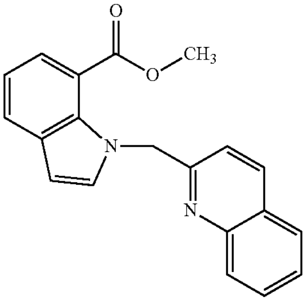 [SMILES: COC(=O)c1cccc2ccn(Cc3ccc4ccccc4n3)c12] |

TABLE 18-continued
| Pr | Structure |
|---|---|
| 76 | 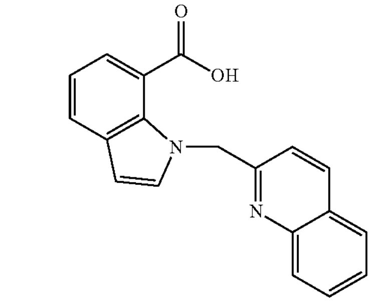 [SMILES: O=C(O)c1cccc2ccn(Cc3ccc4ccccc4n3)c12] |
| 77 | 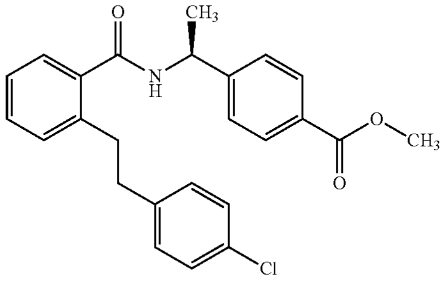 [SMILES: COC(=O)c1ccc([C@H](C)NC(=O)c2ccccc2CCc2ccc(Cl)cc2)cc1] |
| 78 | 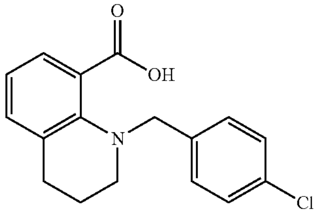 [SMILES: O=C(O)c1cccc2c1N(Cc1ccc(Cl)cc1)CCC2] |
TABLE 19
| Pr | Structure |
|---|---|
| 79 | 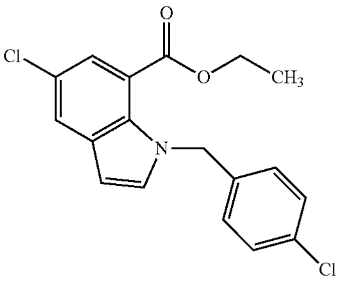 [SMILES: CCOC(=O)c1cc(Cl)cc2ccn(Cc3ccc(Cl)cc3)c12] |
| 80 | 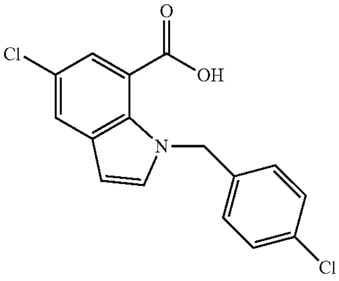 [SMILES: O=C(O)c1cc(Cl)cc2ccn(Cc3ccc(Cl)cc3)c12] |
TABLE 19-continued
| Pr | Structure |
|---|---|
| 81 | 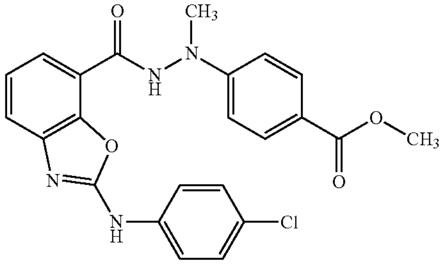 [SMILES: COC(=O)c1ccc(N(C)NC(=O)c2cccc3nc(Nc4ccc(Cl)cc4)oc23)cc1] |
| 82 | 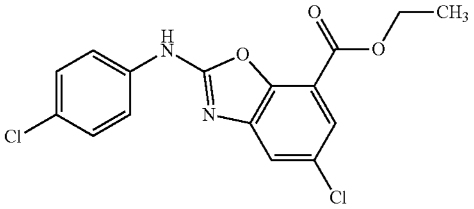 [SMILES: CCOC(=O)c1cc(Cl)cc2nc(Nc3ccc(Cl)cc3)oc12] |
| 83 | 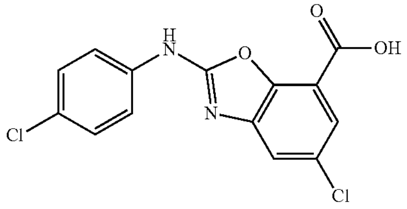 [SMILES: O=C(O)c1cc(Cl)cc2nc(Nc3ccc(Cl)cc3)oc12] |
TABLE 20
| Pr | Structure |
|---|---|
| 84 | 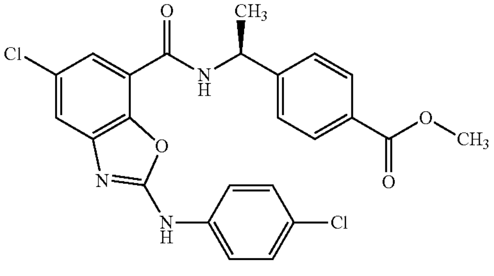 |
| 85 | 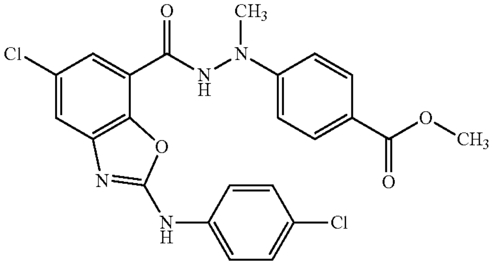 [SMILES: COC(=O)c1ccc(N(C)NC(=O)c2cc(Cl)cc3nc(Nc4ccc(Cl)cc4)oc23)cc1] |
| 86 | 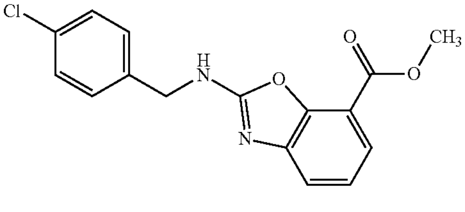 [SMILES: COC(=O)c1cccc2nc(NCc3ccc(Cl)cc3)oc12] |

TABLE 20-continued
| Pr | Structure |
| --- | --- |
| 87 | 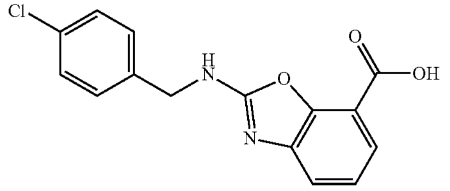 [SMILES: O=C(O)c1cccc2nc(NCc3ccc(Cl)cc3)oc12] |
| 88 | 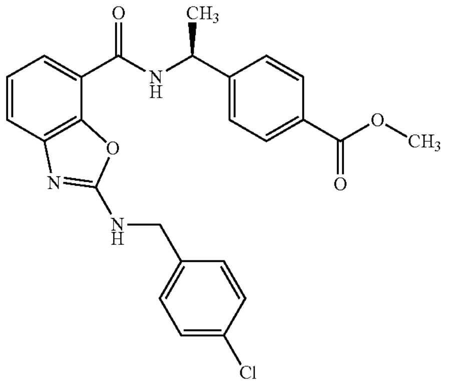 [SMILES: COC(=O)c1ccc([C@H](C)NC(=O)c2cccc3nc(NCc4ccc(Cl)cc4)oc23)cc1] |
TABLE 21
| Pr | Structure |
| --- | --- |
| 89 | 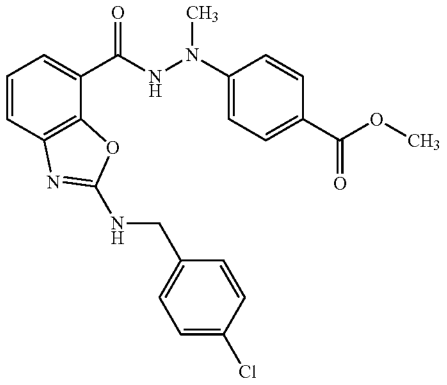 [SMILES: COC(=O)c1ccc(N(C)NC(=O)c2cccc3nc(NCc4ccc(Cl)cc4)oc23)cc1] |
| 90 | 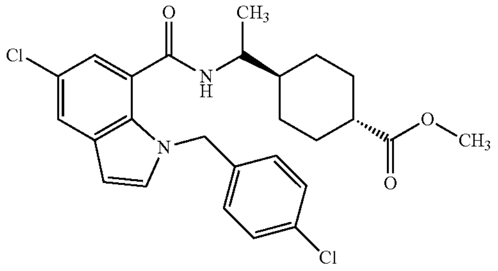 [SMILES: COC(=O)[C@H]1CC[C@H](C(C)NC(=O)c2cc(Cl)cc3ccn(Cc4ccc(Cl)cc4)c23)CC1] |
TABLE 21-continued
| Pr | Structure |
| --- | --- |
| 91 | 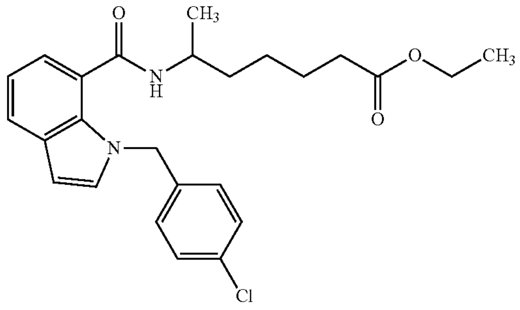 [SMILES: CCOC(=O)CCCCC(C)NC(=O)c1cccc2ccn(Cc3ccc(Cl)cc3)c12] |
| 92 | 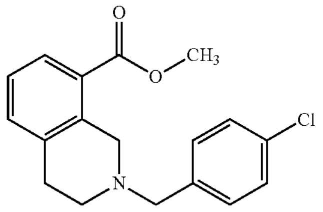 [SMILES: COC(=O)c1cccc2c1CN(Cc1ccc(Cl)cc1)CC2] |
TABLE 22
| Pr | Structure |
| --- | --- |
| 93 | 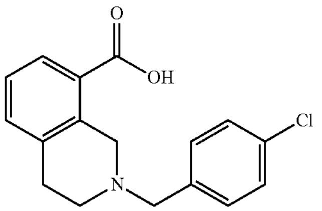 [SMILES: O=C(O)c1cccc2c1CN(Cc1ccc(Cl)cc1)CC2] |
| 94 | 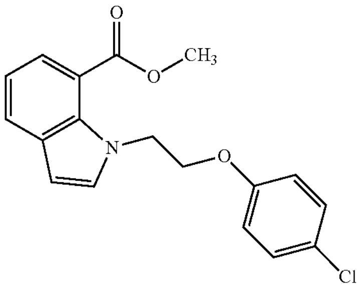 [SMILES: COC(=O)c1cccc2ccn(CCOc3ccc(Cl)cc3)c12] |
| 95 | 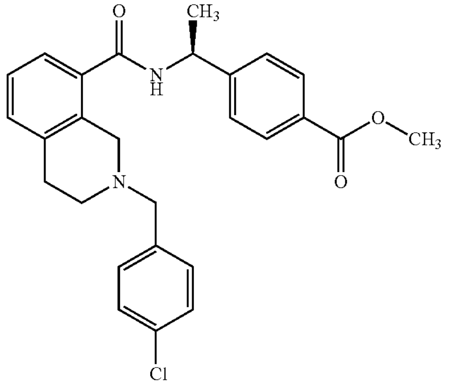 [SMILES: COC(=O)c1ccc([C@H](C)NC(=O)c2cccc3c2CN(Cc2ccc(Cl)cc2)CC3)cc1] |

TABLE 22-continued
| Pr | Structure |
|---|---|
| 96 | 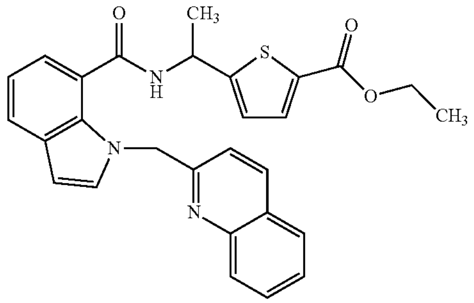 [SMILES: CCOC(=O)c1ccc(C(C)NC(=O)c2cccc3ccn(Cc4ccc5ccccc5n4)c23)s1] |
TABLE 23
| Pr | Structure |
|---|---|
| 97 | 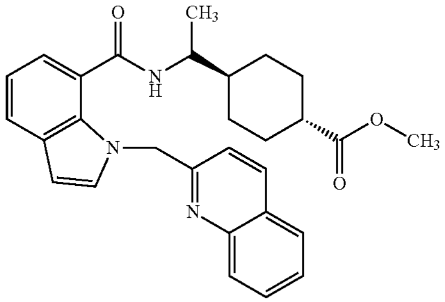 [SMILES: COC(=O)[C@H]1CC[C@H](C(C)NC(=O)c2cccc3ccn(Cc4ccc5ccccc5n4)c23)CC1] |
| 98 | 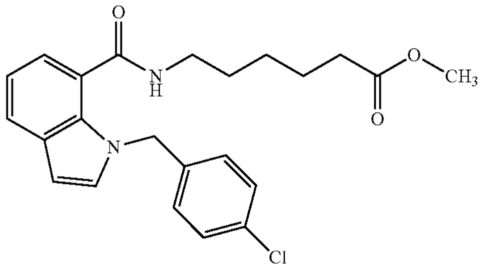 [SMILES: COC(=O)CCCCCNC(=O)c1cccc2ccn(Cc3ccc(Cl)cc3)c12] |
| 99 | 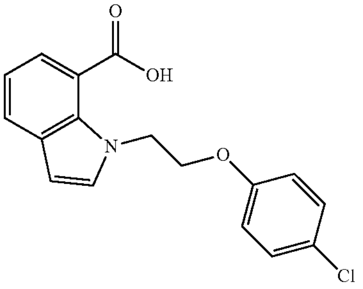 [SMILES: O=C(O)c1cccc2ccn(CCOc3ccc(Cl)cc3)c12] |
| 100 | 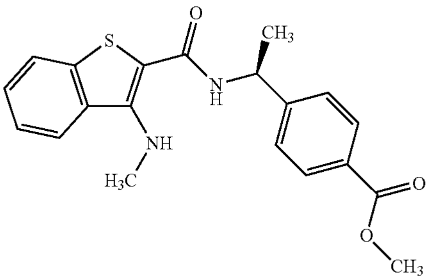 [SMILES: CNc1c(C(=O)N[C@@H](C)c2ccc(C(=O)OC)cc2)sc2ccccc12] |
TABLE 24
| Pr | Structure |
|---|---|
| 101 | 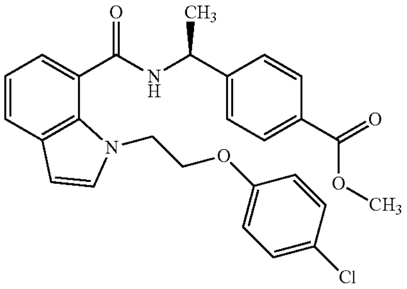 [SMILES: COC(=O)c1ccc([C@H](C)NC(=O)c2cccc3ccn(CCOc4ccc(Cl)cc4)c23)cc1] |
| 102 | 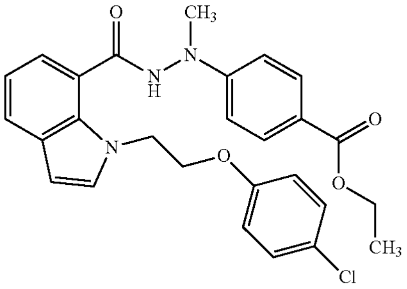 [SMILES: CCOC(=O)c1ccc(N(C)NC(=O)c2cccc3ccn(CCOc4ccc(Cl)cc4)c23)cc1] |
| 103 | 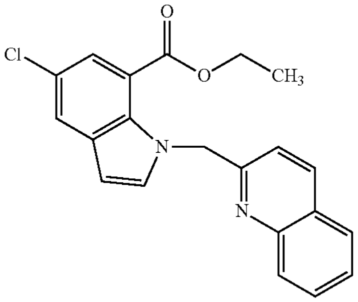 [SMILES: CCOC(=O)c1cc(Cl)cc2ccn(Cc3ccc4ccccc4n3)c12] |
| 104 | 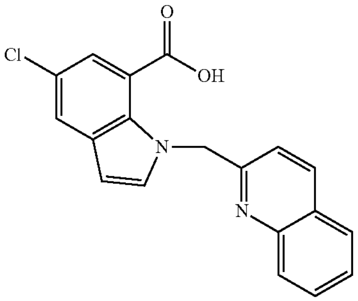 [SMILES: O=C(O)c1cc(Cl)cc2ccn(Cc3ccc4ccccc4n3)c12] |

TABLE 25
| Pr | Structure |
|---|---|
| 105 | 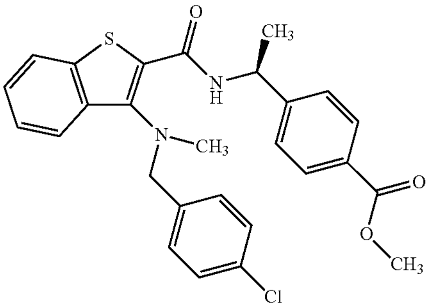 [SMILES: COC(=O)c1ccc([C@H](C)NC(=O)c2sc3ccccc3c2N(C)Cc2ccc(Cl)cc2)cc1] |
| 106 | 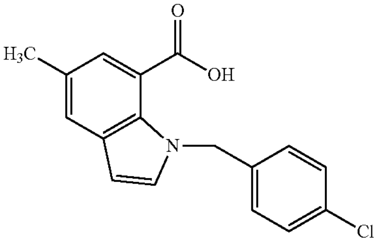 [SMILES: Cc1cc(C(=O)O)c2c(ccn2Cc2ccc(Cl)cc2)c1] |
| 107 | 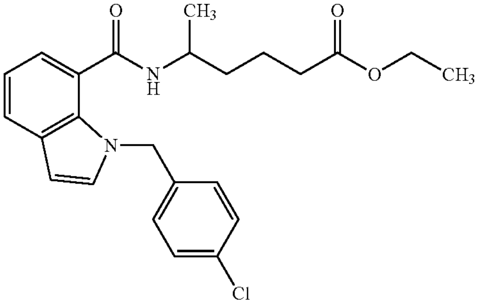 [SMILES: CCOC(=O)CCCC(C)NC(=O)c1cccc2ccn(Cc3ccc(Cl)cc3)c12] |
| 108 | 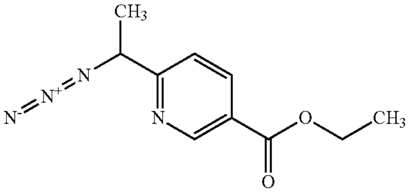 [SMILES: CCOC(=O)c1ccc(C(C)N=[N+]=[N-])nc1] |
TABLE 26
| Pr | Structure |
|---|---|
| 109 | 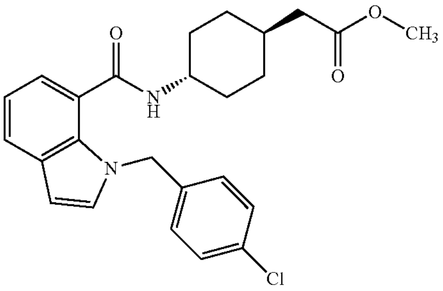 [SMILES: COC(=O)C[C@H]1CC[C@H](NC(=O)c2cccc3ccn(Cc4ccc(Cl)cc4)c23)CC1] |
TABLE 26-continued
| Pr | Structure |
|---|---|
| 110 | 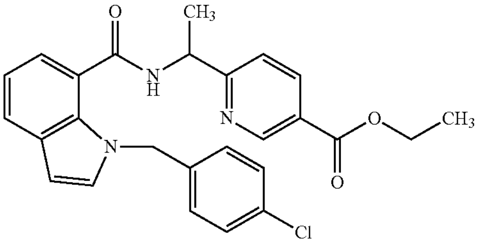 [SMILES: CCOC(=O)c1ccc(C(C)NC(=O)c2cccc3ccn(Cc4ccc(Cl)cc4)c23)nc1] |
| 111 | 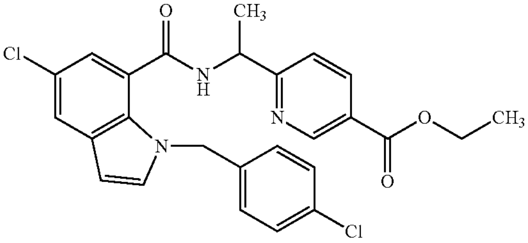 [SMILES: CCOC(=O)c1ccc(C(C)NC(=O)c2cc(Cl)cc3ccn(Cc4ccc(Cl)cc4)c23)nc1] |
| 112 | 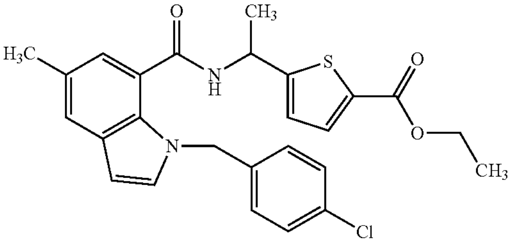 [SMILES: CCOC(=O)c1ccc(C(C)NC(=O)c2cc(C)cc3ccn(Cc4ccc(Cl)cc4)c23)s1] |
| 113 | 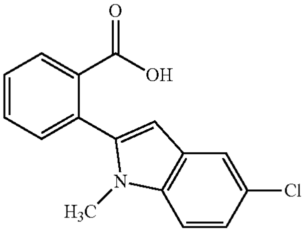 [SMILES: Cn1c(-c2ccccc2C(=O)O)cc2cc(Cl)ccc21] |
TABLE 27
| Pr | Structure |
|---|---|
| 114 | 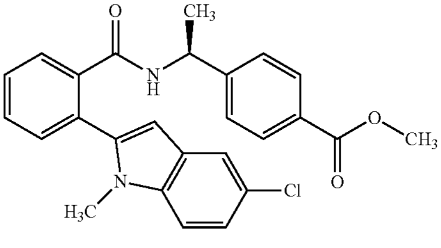 [SMILES: COC(=O)c1ccc([C@H](C)NC(=O)c2ccccc2-c2cc3cc(Cl)ccc3n2C)cc1] |

TABLE 27-continued
| Pr | Structure |
| --- | --- |
| 115 | 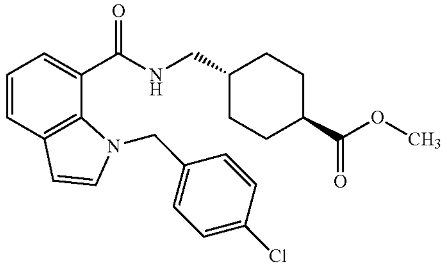 [SMILES: COC(=O)[C@H]1CC[C@H](CNC(=O)c2cccc3ccn(Cc4ccc(Cl)cc4)c23)CC1] |
| 116 | 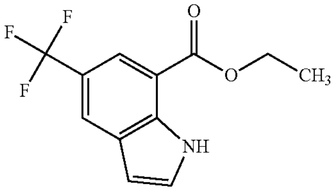 [SMILES: CCOC(=O)c1cc(C(F)(F)F)cc2cc[nH]c12] |
| 117 | 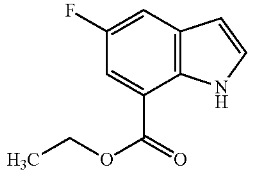 |
| 118 | 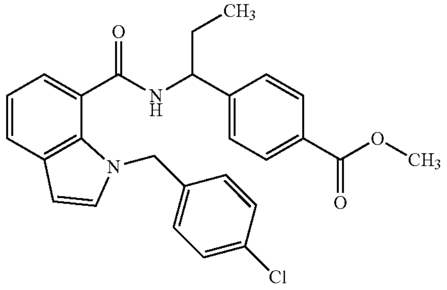 [SMILES: CCC(NC(=O)c1cccc2ccn(Cc3ccc(Cl)cc3)c12)c1ccc(C(=O)OC)cc1] |
TABLE 28
| Pr | Structure |
| --- | --- |
| 119 | 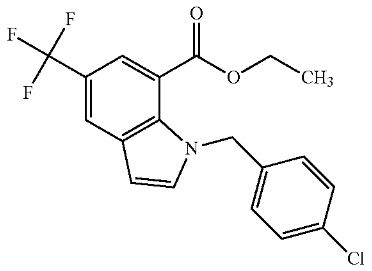 [SMILES: CCOC(=O)c1cc(C(F)(F)F)cc2ccn(Cc3ccc(Cl)cc3)c12] |
| 120 | 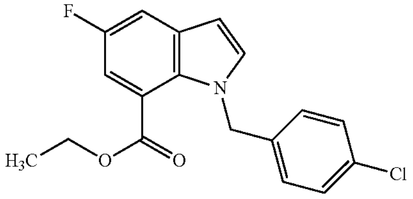 [SMILES: CCOC(=O)c1cc(F)cc2ccn(Cc3ccc(Cl)cc3)c12] |
TABLE 28-continued
| Pr | Structure |
| --- | --- |
| 121/Cl | 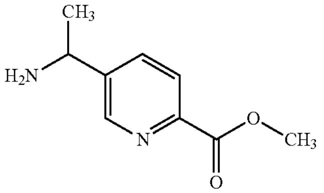 |
| 122 | 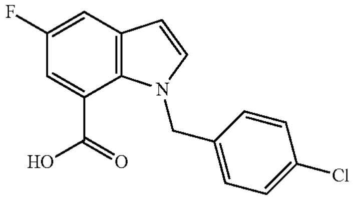 [SMILES: O=C(O)c1cc(F)cc2ccn(Cc3ccc(Cl)cc3)c12] |
| 123 | 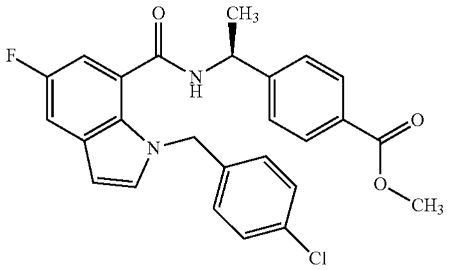 [SMILES: COC(=O)c1ccc([C@H](C)NC(=O)c2cc(F)cc3ccn(Cc4ccc(Cl)cc4)c23)cc1] |
TABLE 29
| Pr | Structure |
| --- | --- |
| 124 | 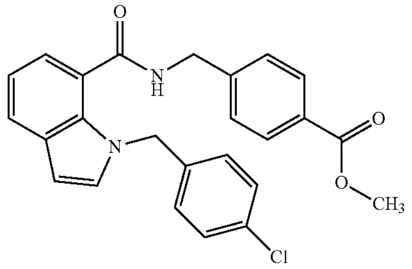 [SMILES: COC(=O)c1ccc(CNC(=O)c2cccc3ccn(Cc4ccc(Cl)cc4)c23)cc1] |
| 125 | 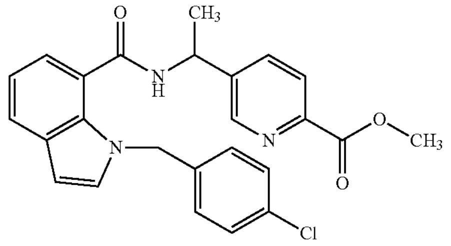 [SMILES: COC(=O)c1ccc(C(C)NC(=O)c2cccc3ccn(Cc4ccc(Cl)cc4)c23)cn1] |
| 126 | 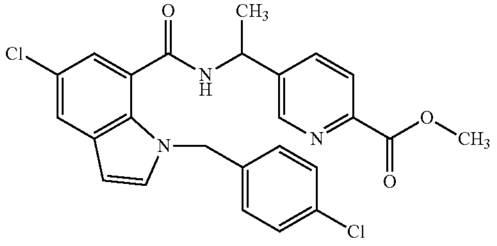 [SMILES: COC(=O)c1ccc(C(C)NC(=O)c2cc(Cl)cc3ccn(Cc4ccc(Cl)cc4)c23)cn1] |

TABLE 29-continued
| Pr | Structure |
| --- | --- |
| 127 | 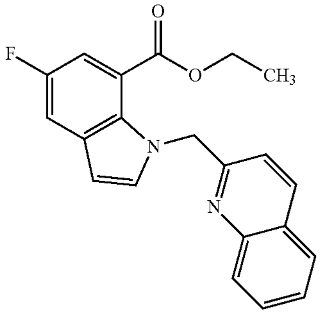 [SMILES: CCOC(=O)c1cc(F)cc2ccn(Cc3ccc4ccccc4n3)c12] |
TABLE 30
| Pr | Structure |
| --- | --- |
| 128 | 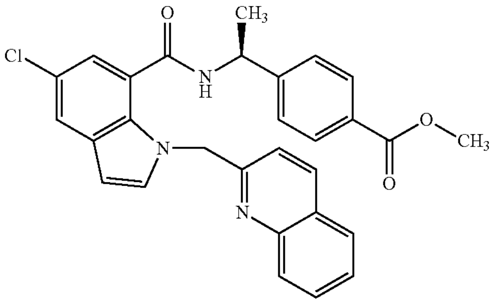 [SMILES: COC(=O)c1ccc([C@H](C)NC(=O)c2cc(Cl)cc3ccn(Cc4ccc5ccccc5n4)c23)cc1] |
| 129 | 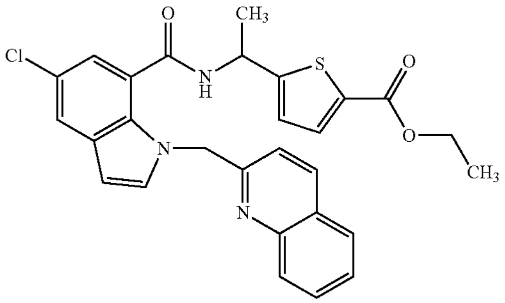 [SMILES: CCOC(=O)c1ccc(C(C)NC(=O)c2cc(Cl)cc3ccn(Cc4ccc5ccccc5n4)c23)s1] |
| 130 | 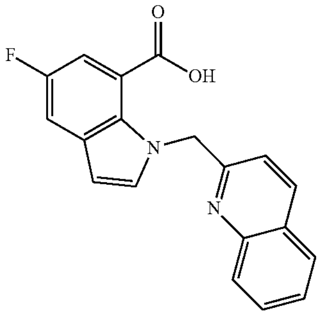 [SMILES: O=C(O)c1cc(F)cc2ccn(Cc3ccc4ccccc4n3)c12] |
TABLE 30-continued
| Pr | Structure |
| --- | --- |
| 131 | 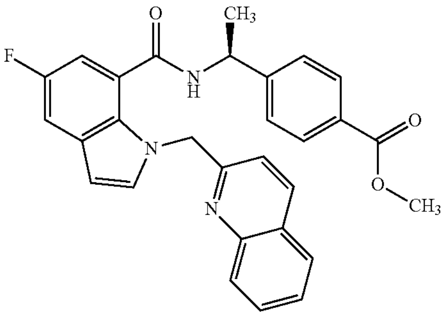 [SMILES: COC(=O)c1ccc([C@H](C)NC(=O)c2cc(F)cc3ccn(Cc4ccc5ccccc5n4)c23)cc1] |
TABLE 31
| Pr | Structure |
| --- | --- |
| 132 | 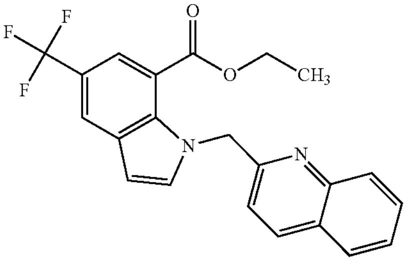 [SMILES: CCOC(=O)c1cc(C(F)(F)F)cc2ccn(Cc3ccc4ccccc4n3)c12] |
| 133 | 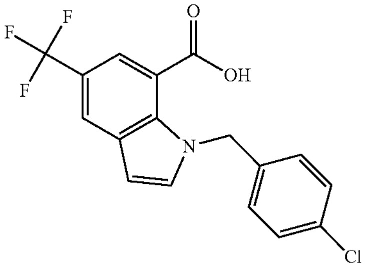 [SMILES: O=C(O)c1cc(C(F)(F)F)cc2ccn(Cc3ccc(Cl)cc3)c12] |
| 134 | 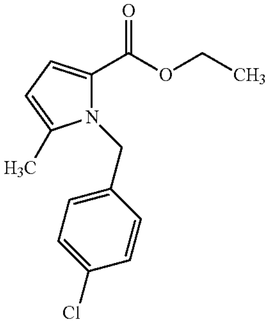 [SMILES: CCOC(=O)c1ccc(C)n1Cc1ccc(Cl)cc1] |

TABLE 31-continued
| Pr | Structure |
|---|---|
| 135 | 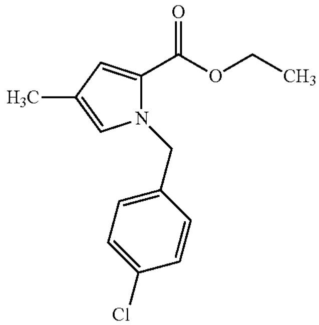 [SMILES: CCOC(=O)c1cc(C)cn1Cc1ccc(Cl)cc1] |
TABLE 32
| Pr | Structure |
|---|---|
| 136 | 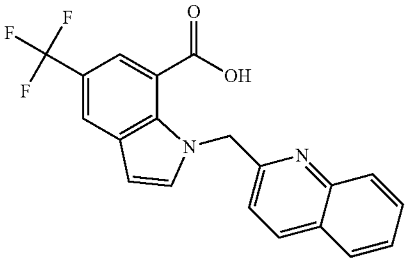 [SMILES: O=C(O)c1cc(C(F)(F)F)cc2ccn(Cc3ccc4ccccc4n3)c12] |
| 137 | 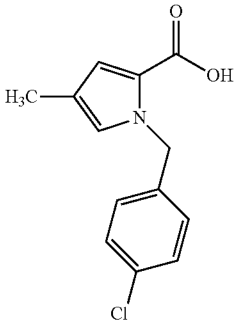 [SMILES: Cc1cc(C(=O)O)n(Cc2ccc(Cl)cc2)c1] |
| 138 | 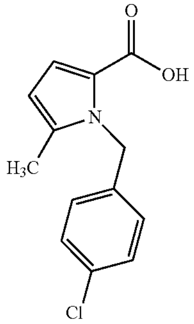 [SMILES: Cc1ccc(C(=O)O)n1Cc1ccc(Cl)cc1] |
TABLE 32-continued
| Pr | Structure |
|---|---|
| 139 | 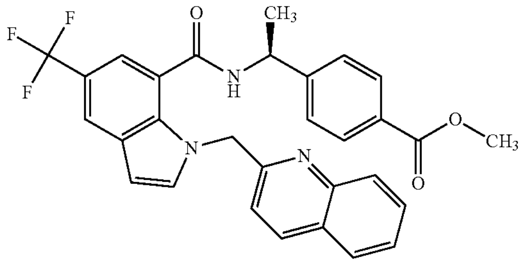 [SMILES: COC(=O)c1ccc([C@H](C)NC(=O)c2cc(C(F)(F)F)cc3ccn(Cc4ccc5ccccc5n4)c23)cc1] |
TABLE 33
| Pr | Structure |
|---|---|
| 140 | 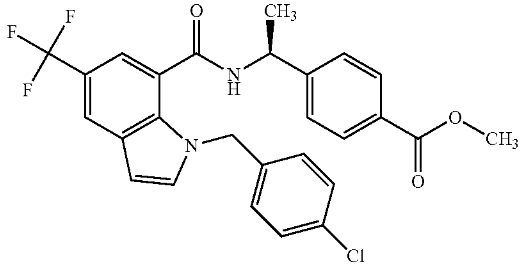 [SMILES: COC(=O)c1ccc([C@H](C)NC(=O)c2cc(C(F)(F)F)cc3ccn(Cc4ccc(Cl)cc4)c23)cc1] |
| 141 | 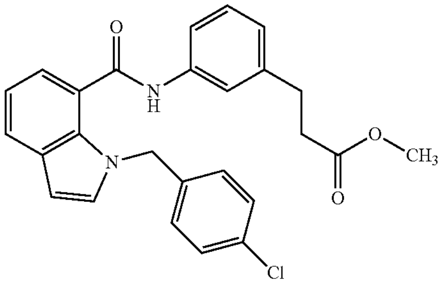 [SMILES: COC(=O)CCc1cccc(NC(=O)c2cccc3ccn(Cc4ccc(Cl)cc4)c23)c1] |
| 142 | 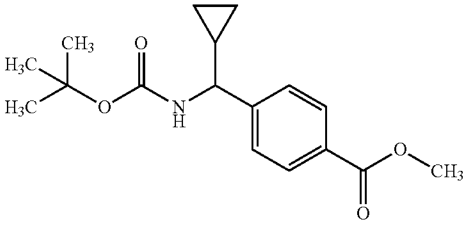 [SMILES: COC(=O)c1ccc(C(NC(=O)OC(C)(C)C)C2CC2)cc1] |
| 143 | 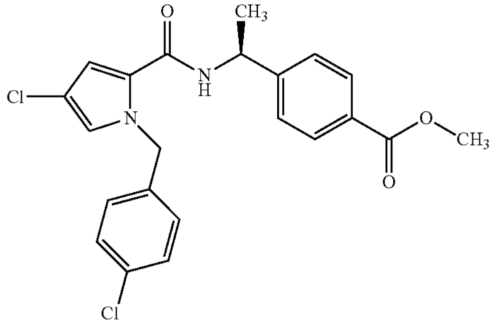 [SMILES: COC(=O)c1ccc([C@H](C)NC(=O)c2cc(Cl)cn2Cc2ccc(Cl)cc2)cc1] |

TABLE 34
| Pr | Structure |
|---|---|
| 144 | 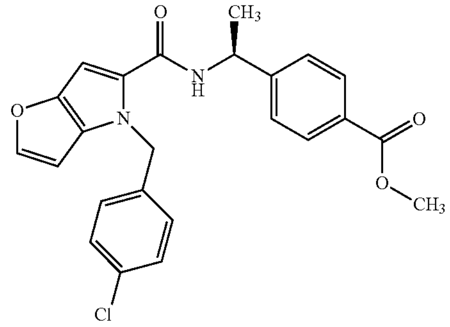 [SMILES: COC(=O)c1ccc([C@H](C)NC(=O)c2cc3occc3n2Cc2ccc(Cl)cc2)cc1] |
| 145 | 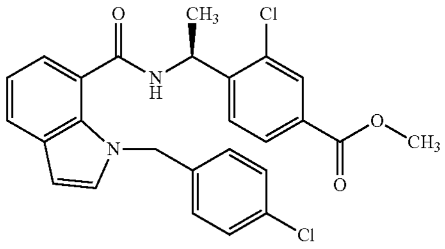 [SMILES: COC(=O)c1ccc([C@H](C)NC(=O)c2cccc3ccn(Cc4ccc(Cl)cc4)c23)c(Cl)c1] |
| 146 | 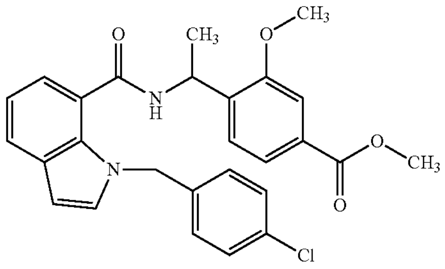 [SMILES: COC(=O)c1ccc(C(C)NC(=O)c2cccc3ccn(Cc4ccc(Cl)cc4)c23)c(OC)c1] |
| 147 | 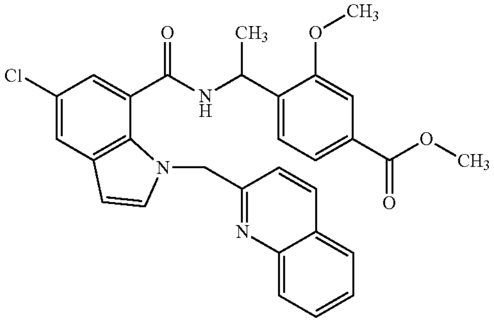 [SMILES: COC(=O)c1ccc(C(C)NC(=O)c2cc(Cl)cc3ccn(Cc4ccc5ccccc5n4)c23)c(OC)c1] |
TABLE 35
| Pr | Structure |
|---|---|
| 148 | 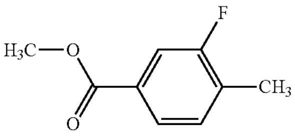 |
TABLE 35-continued
| Pr | Structure |
|---|---|
| 149 | 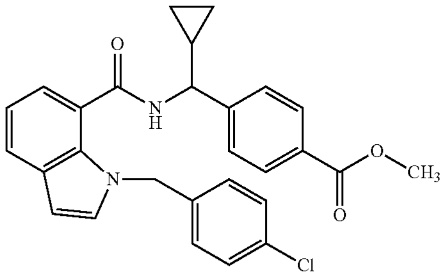 [SMILES: COC(=O)c1ccc(C(NC(=O)c2cccc3ccn(Cc4ccc(Cl)cc4)c23)C2CC2)cc1] |
| 150 | 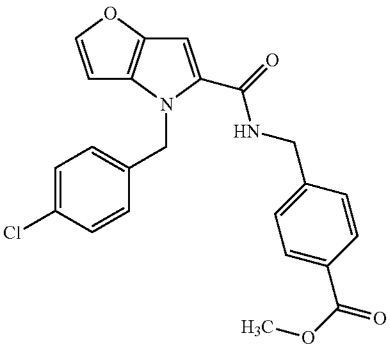 [SMILES: COC(=O)c1ccc(CNC(=O)c2cc3occc3n2Cc2ccc(Cl)cc2)cc1] |
| 151 | 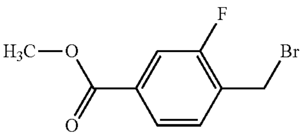 |
| 152 | 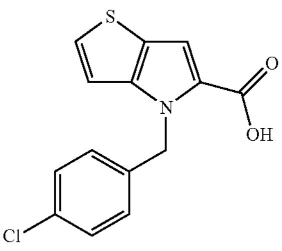 |
TABLE 36
| Pr | Structure |
|---|---|
| 153 | 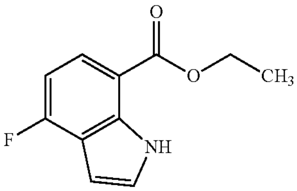 |

TABLE 36-continued
| Pr | Structure |
|---|---|
| 154 | 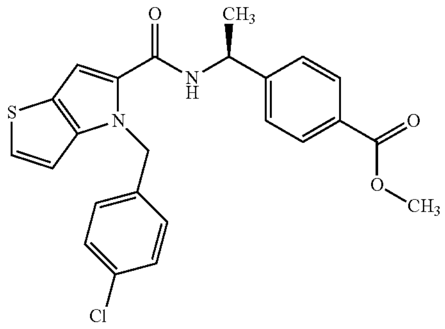 [SMILES: COC(=O)c1ccc([C@H](C)NC(=O)c2cc3sccc3n2Cc2ccc(Cl)cc2)cc1] |
| 155 | 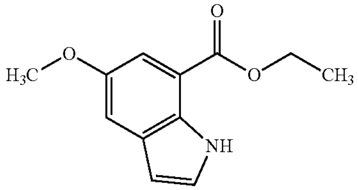 [SMILES: CCOC(=O)c1cc(OC)cc2cc[nH]c12] |
| 156 | 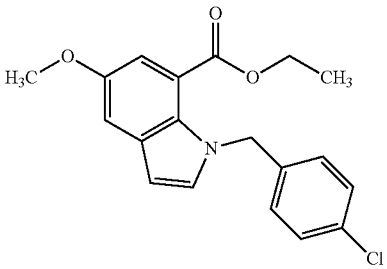 [SMILES: CCOC(=O)c1cc(OC)cc2ccn(Cc3ccc(Cl)cc3)c12] |
TABLE 37
| Pr | Structure |
|---|---|
| 157 | 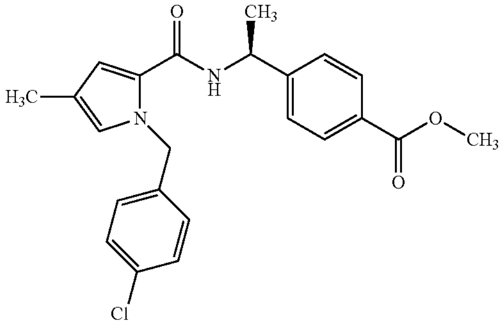 |
| 158 | 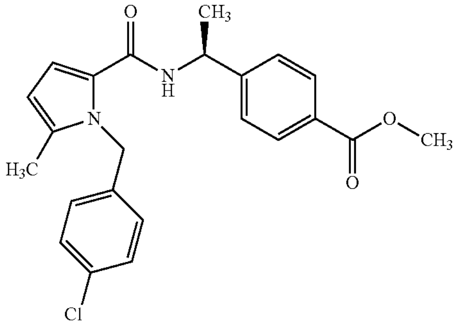 [SMILES: COC(=O)c1ccc([C@H](C)NC(=O)c2ccc(C)n2Cc2ccc(Cl)cc2)cc1] |
TABLE 37-continued
| Pr | Structure |
|---|---|
| 159 | 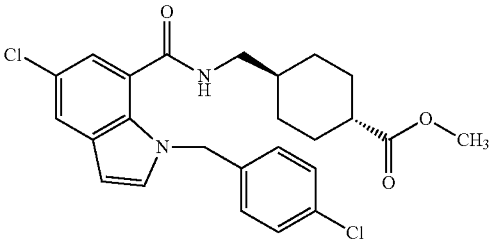 [SMILES: COC(=O)[C@H]1CC[C@H](CNC(=O)c2cc(Cl)cc3ccn(Cc4ccc(Cl)cc4)c23)CC1] |
| 160 | 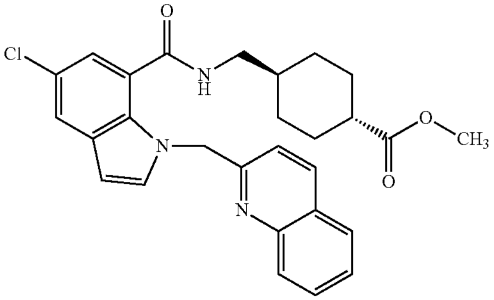 [SMILES: COC(=O)[C@H]1CC[C@H](CNC(=O)c2cc(Cl)cc3ccn(Cc4ccc5ccccc5n4)c23)CC1] |
TABLE 38
| Pr | Structure |
|---|---|
| 161/Cl | 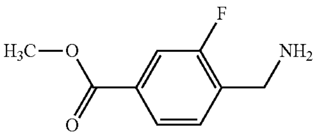 |
| 162 | 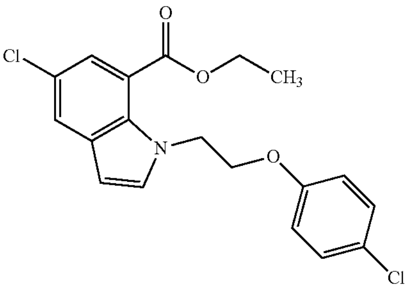 [SMILES: CCOC(=O)c1cc(Cl)cc2ccn(CCOc3ccc(Cl)cc3)c12] |
| 163 | 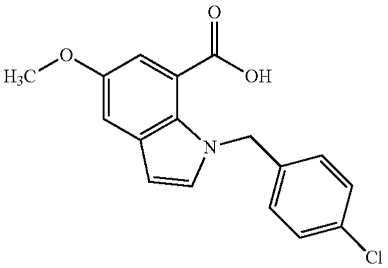 [SMILES: COc1cc(C(=O)O)c2c(ccn2Cc2ccc(Cl)cc2)c1] |

TABLE 38-continued
| Pr | Structure |
| --- | --- |
| 164 | 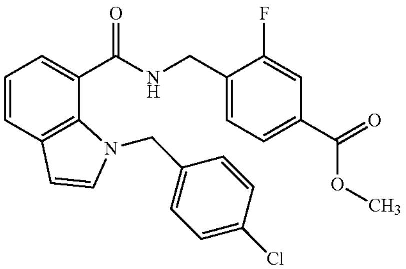 [SMILES: COC(=O)c1ccc(CNC(=O)c2cccc3ccn(Cc4ccc(Cl)cc4)c23)c(F)c1] |
TABLE 39
| Pr | Structure |
| --- | --- |
| 165 | 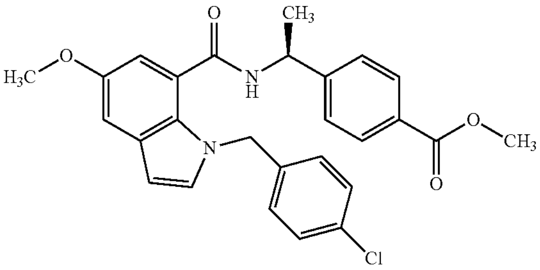 |
| 166 | 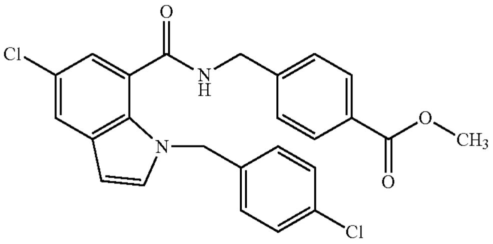 [SMILES: COC(=O)c1ccc(CNC(=O)c2cc(Cl)cc3ccn(Cc4ccc(Cl)cc4)c23)cc1] |
| 167 | 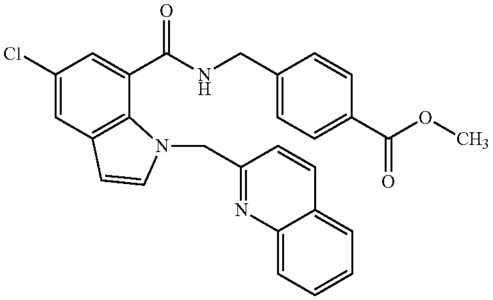 [SMILES: COC(=O)c1ccc(CNC(=O)c2cc(Cl)cc3ccn(Cc4ccc5ccccc5n4)c23)cc1] |
| 168 | 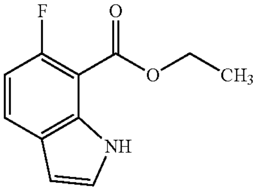 |
TABLE 40
| Pr | Structure |
| --- | --- |
| 169 | 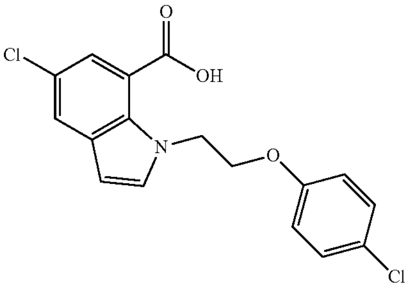 [SMILES: O=C(O)c1cc(Cl)cc2ccn(CCOc3ccc(Cl)cc3)c12] |
| 170 | 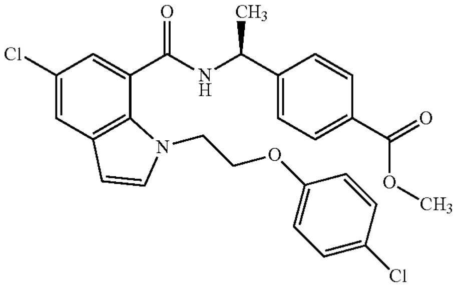 [SMILES: COC(=O)c1ccc([C@H](C)NC(=O)c2cc(Cl)cc3ccn(CCOc4ccc(Cl)cc4)c23)cc1] |
| 171 | 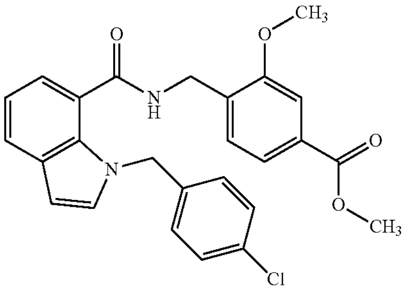 [SMILES: COC(=O)c1ccc(CNC(=O)c2cccc3ccn(Cc4ccc(Cl)cc4)c23)c(OC)c1] |
| 172 | 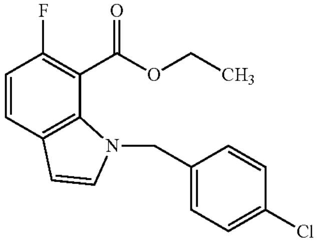 [SMILES: CCOC(=O)c1c(F)ccc2ccn(Cc3ccc(Cl)cc3)c12] |
TABLE 41
| Pr | Structure |
| --- | --- |
| 173 | 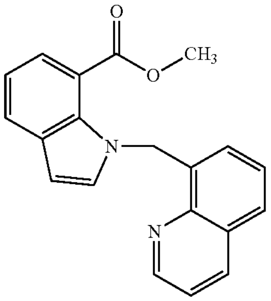 [SMILES: COC(=O)c1cccc2ccn(Cc3cccc4cccnc34)c12] |

TABLE 41-continued
| Pr | Structure |
|---|---|
| 174 | 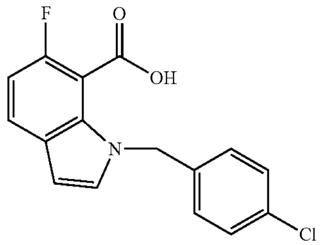 [SMILES: O=C(O)c1c(F)ccc2ccn(Cc3ccc(Cl)cc3)c12] |
| 175 | 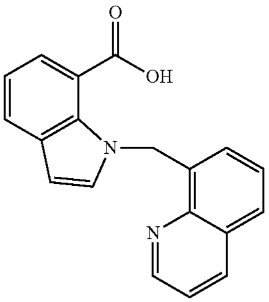 [SMILES: O=C(O)c1cccc2ccn(Cc3cccc4cccnc34)c12] |
| 176 | 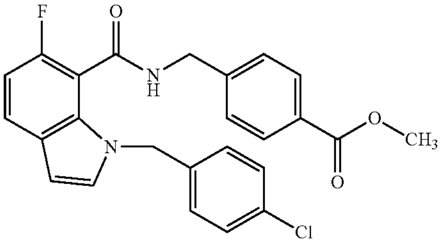 [SMILES: COC(=O)c1ccc(CNC(=O)c2c(F)ccc3ccn(Cc4ccc(Cl)cc4)c23)cc1] |
TABLE 42
| Pr | Structure |
|---|---|
| 177 | 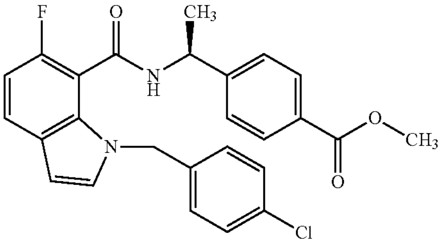 [SMILES: COC(=O)c1ccc([C@H](C)NC(=O)c2c(F)ccc3ccn(Cc4ccc(Cl)cc4)c23)cc1] |
| 178 | 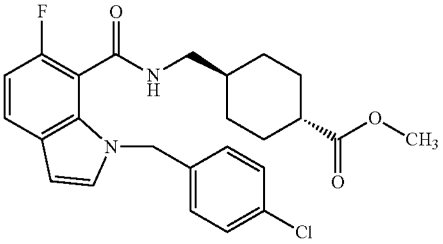 [SMILES: COC(=O)[C@H]1CC[C@H](CNC(=O)c2c(F)ccc3ccn(Cc4ccc(Cl)cc4)c23)CC1] |
TABLE 42-continued
| Pr | Structure |
|---|---|
| 179 | 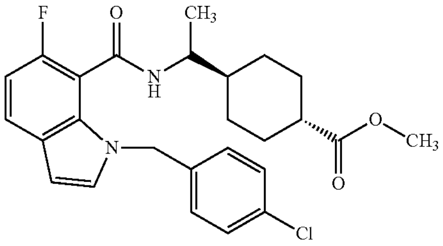 [SMILES: COC(=O)[C@H]1CC[C@H](C(C)NC(=O)c2c(F)ccc3ccn(Cc4ccc(Cl)cc4)c23)CC1] |
| 180 | 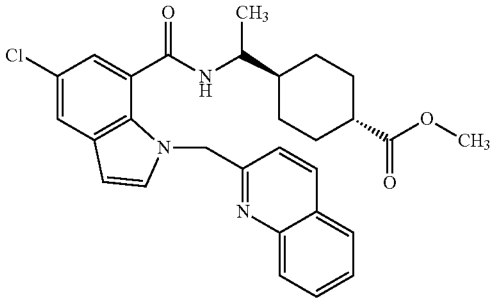 |
TABLE 43
| Pr | Structure |
|---|---|
| 181 | 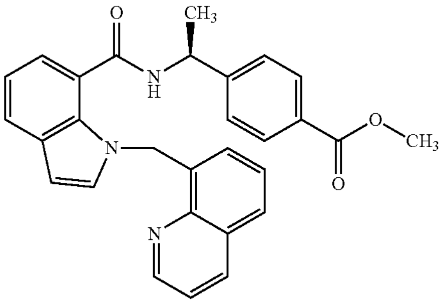 [SMILES: COC(=O)c1ccc([C@H](C)NC(=O)c2cccc3ccn(Cc4cccc5cccnc45)c23)cc1] |
| 182 | 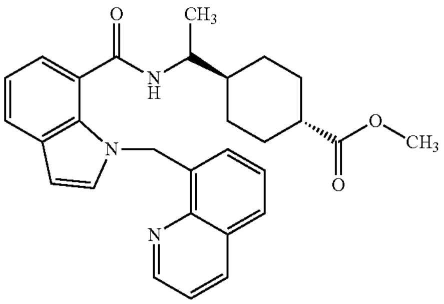 [SMILES: COC(=O)[C@H]1CC[C@H](C(C)NC(=O)c2cccc3ccn(Cc4cccc5cccnc45)c23)CC1] |
| 183 | 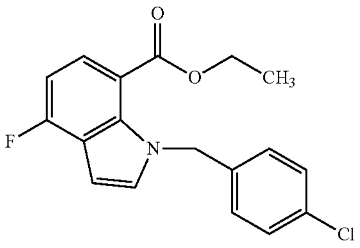 [SMILES: CCOC(=O)c1ccc(F)c2ccn(Cc3ccc(Cl)cc3)c12] |

TABLE 43-continued
| Pr | Structure |
|---|---|
| 184 | 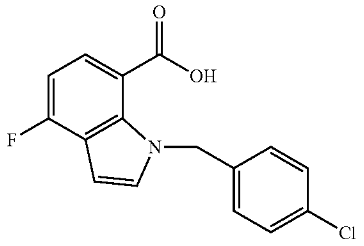 [SMILES: O=C(O)c1ccc(F)c2ccn(Cc3ccc(Cl)cc3)c12] |
TABLE 44
| Pr | Structure |
|---|---|
| 185 | 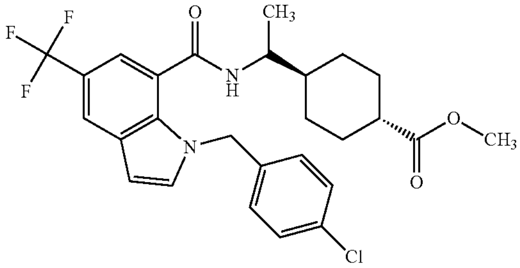 [SMILES: COC(=O)[C@H]1CC[C@H](C(C)NC(=O)c2cc(C(F)(F)F)cc3ccn(Cc4ccc(Cl)cc4)c23)CC1] |
| 186 | 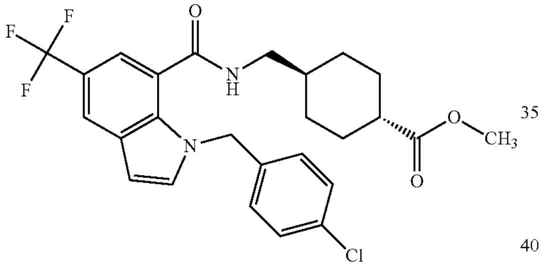 |
| 187/Cl | 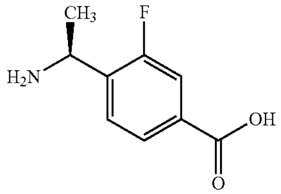 |
| 188/Cl | 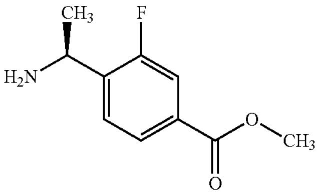 |
| 189 | 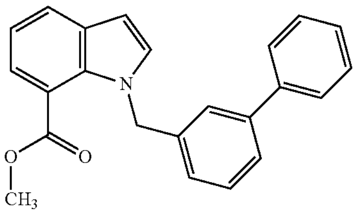 [SMILES: COC(=O)c1cccc2ccn(Cc3cccc(-c4ccccc4)c3)c12] |
TABLE 45
| Pr | Structure |
|---|---|
| 190 | 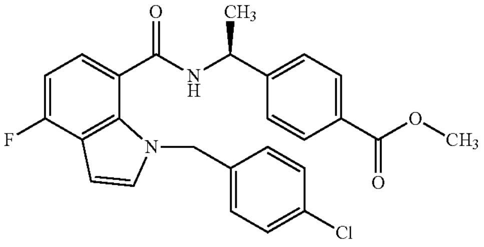 [SMILES: COC(=O)c1ccc([C@H](C)NC(=O)c2ccc(F)c3ccn(Cc4ccc(Cl)cc4)c23)cc1] |
| 191 | 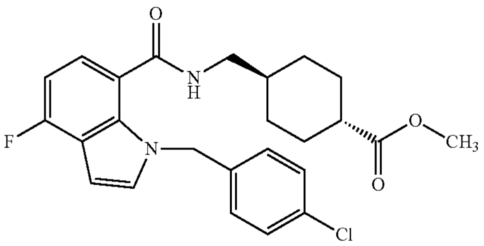 [SMILES: COC(=O)[C@H]1CC[C@H](CNC(=O)c2ccc(F)c3ccn(Cc4ccc(Cl)cc4)c23)CC1] |
| 192 | 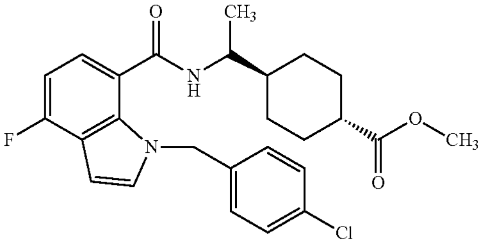 [SMILES: COC(=O)[C@H]1CC[C@H](C(C)NC(=O)c2ccc(F)c3ccn(Cc4ccc(Cl)cc4)c23)CC1] |
| 193 | 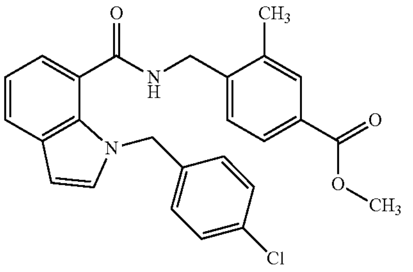 [SMILES: COC(=O)c1ccc(CNC(=O)c2cccc3ccn(Cc4ccc(Cl)cc4)c23)c(C)c1] |
| 194 | 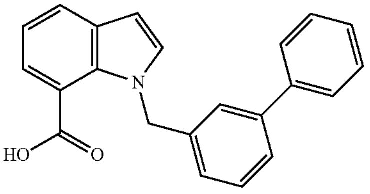 [SMILES: O=C(O)c1cccc2ccn(Cc3cccc(-c4ccccc4)c3)c12] |

TABLE 46
| Pr | Structure |
|---|---|
| 195 | 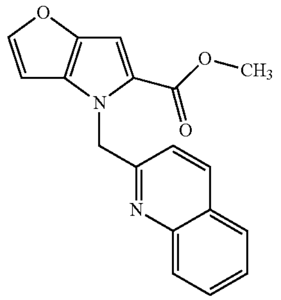 [SMILES: COC(=O)c1cc2occc2n1Cc1ccc2ccccc2n1] |
| 196 | 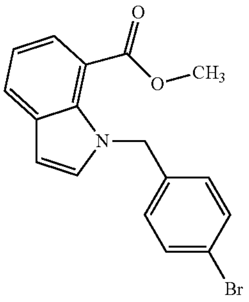 [SMILES: COC(=O)c1cccc2ccn(Cc3ccc(Br)cc3)c12] |
| 197 | 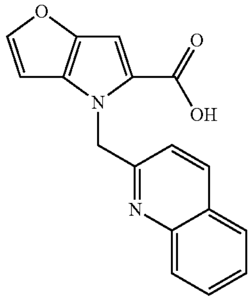 [SMILES: O=C(O)c1cc2occc2n1Cc1ccc2ccccc2n1] |
| 198 | 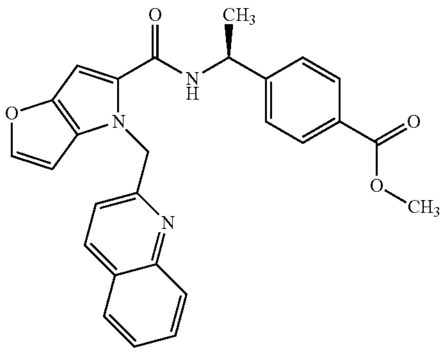 [SMILES: COC(=O)c1ccc([C@H](C)NC(=O)c2cc3occc3n2Cc2ccc3ccccc3n2)cc1] |
TABLE 47
| Pr | Structure |
|---|---|
| 199 | 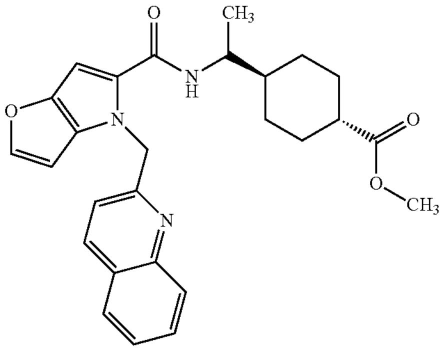 [SMILES: COC(=O)[C@H]1CC[C@H](C(C)NC(=O)c2cc3occc3n2Cc2ccc3ccccc3n2)CC1] |
| 200 | 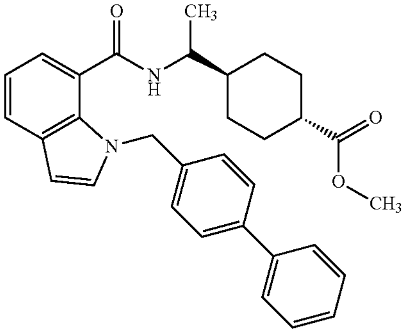 [SMILES: COC(=O)[C@H]1CC[C@H](C(C)NC(=O)c2cccc3ccn(Cc4ccc(-c5ccccc5)cc4)c23)CC1] |
| 201 | 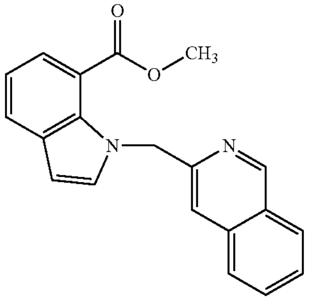 [SMILES: COC(=O)c1cccc2ccn(Cc3cc4ccccc4cn3)c12] |
| 202 | 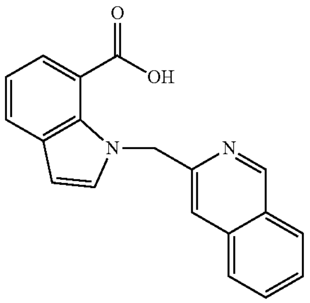 [SMILES: O=C(O)c1cccc2ccn(Cc3cc4ccccc4cn3)c12] |

TABLE 48
| Pr | Structure |
|---|---|
| 203 | 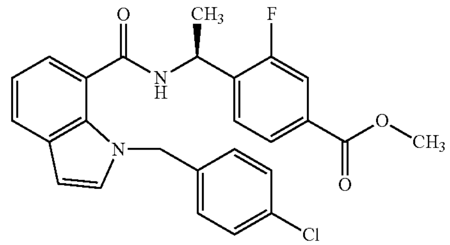 [SMILES: COC(=O)c1ccc([C@H](C)NC(=O)c2cccc3ccn(Cc4ccc(Cl)cc4)c23)c(F)c1] |
| 204 | 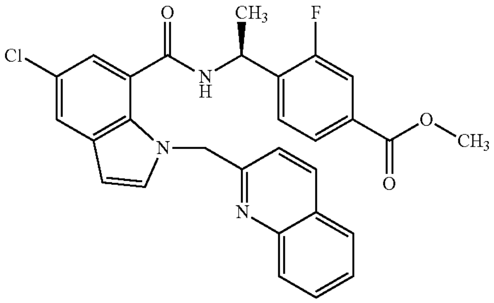 [SMILES: COC(=O)c1ccc([C@H](C)NC(=O)c2cc(Cl)cc3ccn(Cc4ccc5ccccc5n4)c23)c(F)c1] |
| 205 | 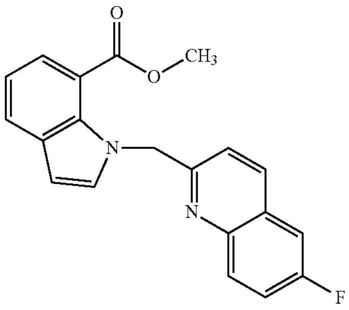 [SMILES: COC(=O)c1cccc2ccn(Cc3ccc4cc(F)ccc4n3)c12] |
| 206 | 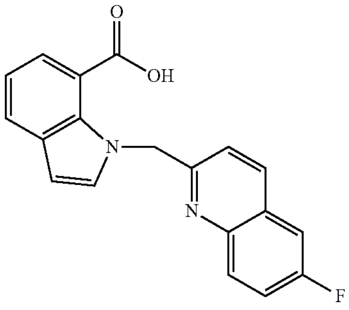 [SMILES: O=C(O)c1cccc2ccn(Cc3ccc4cc(F)ccc4n3)c12] |
TABLE 49
| Pr | Structure |
|---|---|
| 207 | 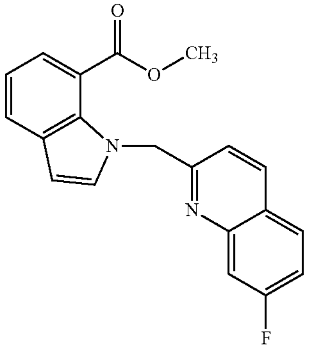 [SMILES: COC(=O)c1cccc2ccn(Cc3ccc4ccc(F)cc4n3)c12] |
| 208 | 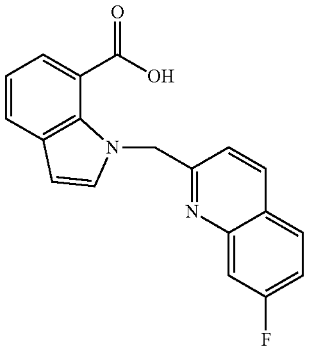 [SMILES: O=C(O)c1cccc2ccn(Cc3ccc4ccc(F)cc4n3)c12] |
| 209 | 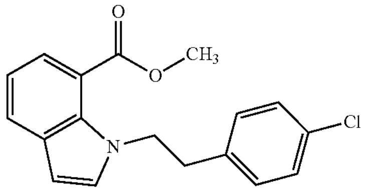 [SMILES: COC(=O)c1cccc2ccn(CCc3ccc(Cl)cc3)c12] |
| 210 | 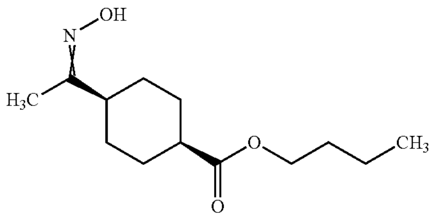 [SMILES: CCCCOC(=O)[C@H]1CC[C@@H](C(C)=NO)CC1] |
TABLE 50
| Pr | Structure |
|---|---|
| 211/Cl | 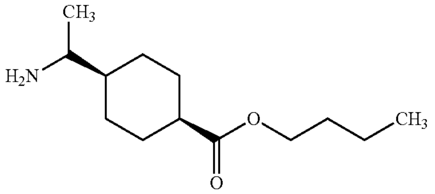 [SMILES: CCCCOC(=O)[C@H]1CC[C@@H](C(C)N)CC1] |

TABLE 50-continued
| Pr | Structure |
|---|---|
| 212 | 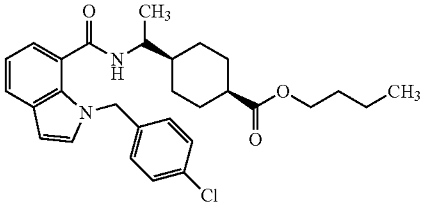 [SMILES: CCCCOC(=O)[C@H]1CC[C@@H](C(C)NC(=O)c2cccc3ccn(Cc4ccc(Cl)cc4)c23)CC1] |
| 213 | 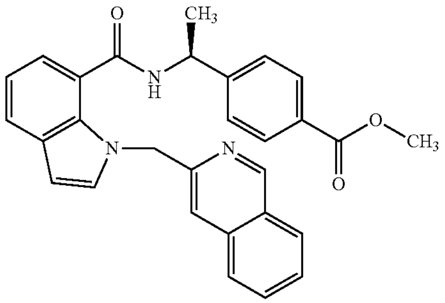 [SMILES: COC(=O)c1ccc([C@H](C)NC(=O)c2cccc3ccn(Cc4cc5ccccc5cn4)c23)cc1] |
| 214 | 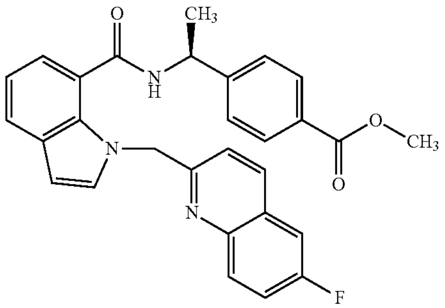 [SMILES: COC(=O)c1ccc([C@H](C)NC(=O)c2cccc3ccn(Cc4ccc5cc(F)ccc5n4)c23)cc1] |
TABLE 51
| Pr | Structure |
|---|---|
| 215 | 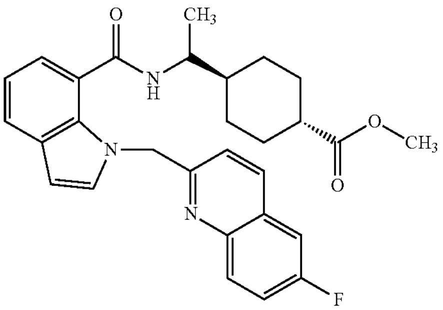 [SMILES: COC(=O)[C@H]1CC[C@H](C(C)NC(=O)c2cccc3ccn(Cc4ccc5cc(F)ccc5n4)c23)CC1] |
TABLE 51-continued
| Pr | Structure |
|---|---|
| 216 | 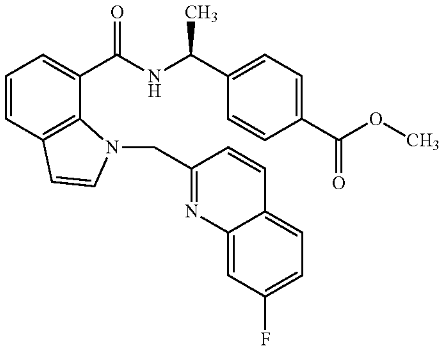 [SMILES: COC(=O)c1ccc([C@H](C)NC(=O)c2cccc3ccn(Cc4ccc5ccc(F)cc5n4)c23)cc1] |
| 217 | 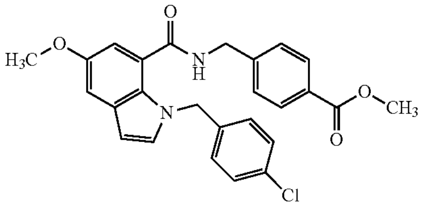 |
| 218 | 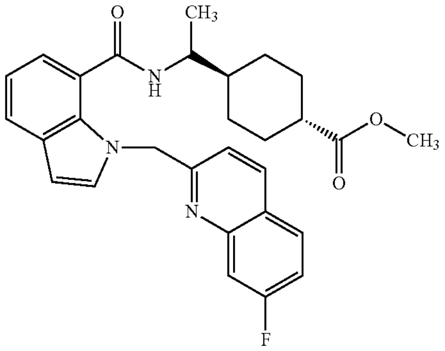 [SMILES: COC(=O)[C@H]1CC[C@H](C(C)NC(=O)c2cccc3ccn(Cc4ccc5ccc(F)cc5n4)c23)CC1] |
TABLE 52
| Pr | Structure |
|---|---|
| 219 | 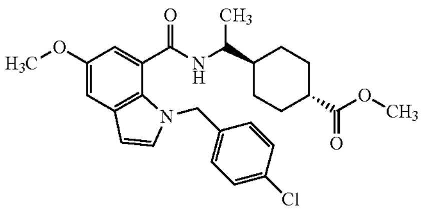 |
| 220 | 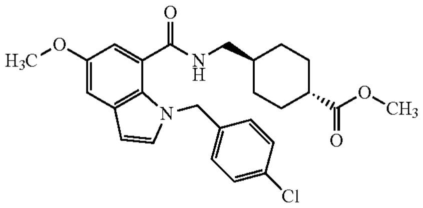 |

TABLE 52-continued
| Pr | Structure |
|---|---|
| 222 | 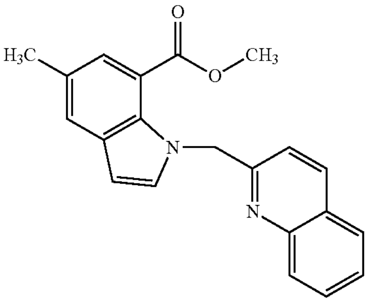 [SMILES: COC(=O)c1cc(C)cc2ccn(Cc3ccc4ccccc4n3)c12] |
| 223 | 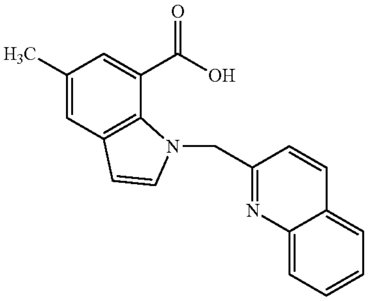 [SMILES: Cc1cc(C(=O)O)c2c(ccn2Cc2ccc3ccccc3n2)c1] |
TABLE 53
| Pr | Structure |
|---|---|
| 225 | 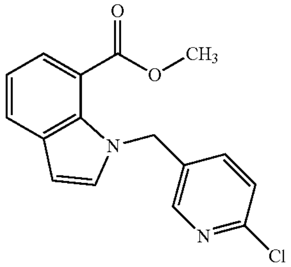 [SMILES: COC(=O)c1cccc2ccn(Cc3ccc(Cl)nc3)c12] |
| 226 | 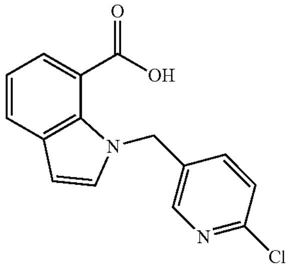 [SMILES: O=C(O)c1cccc2ccn(Cc3ccc(Cl)nc3)c12] |
| 227 | 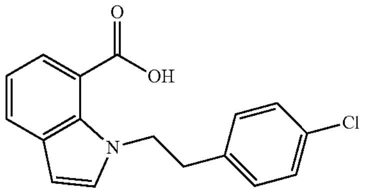 [SMILES: O=C(O)c1cccc2ccn(CCc3ccc(Cl)cc3)c12] |
TABLE 53-continued
| Pr | Structure |
|---|---|
| 228 | 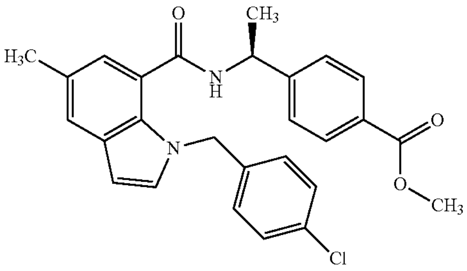 |
TABLE 54
| Pr | Structure |
|---|---|
| 229 | 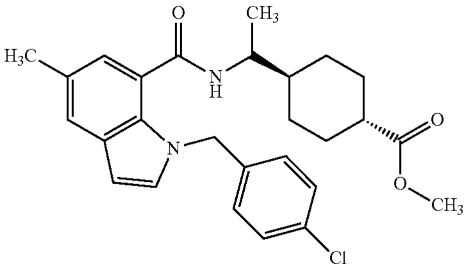 |
| 230 | 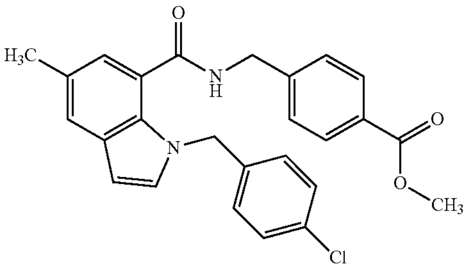 |
| 231 | 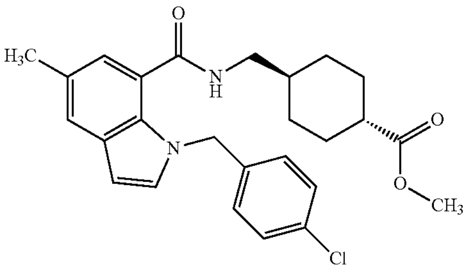 |
| 232 | 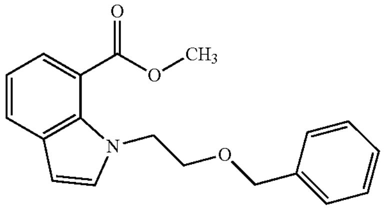 [SMILES: COC(=O)c1cccc2ccn(CCOCc3ccccc3)c12] |

TABLE 55
| Pr | Structure |
|---|---|
| 233 | 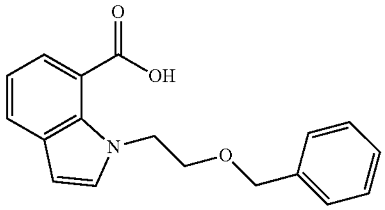 [SMILES: O=C(O)c1cccc2ccn(CCOCc3ccccc3)c12] |
| 234 | 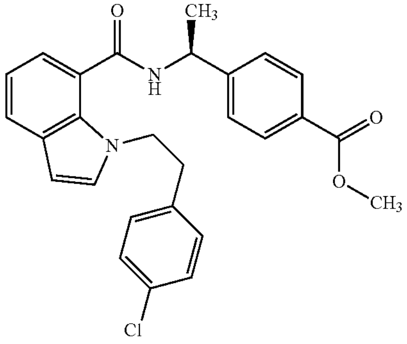 [SMILES: COC(=O)c1ccc([C@H](C)NC(=O)c2cccc3ccn(CCc4ccc(Cl)cc4)c23)cc1] |
| 235 | 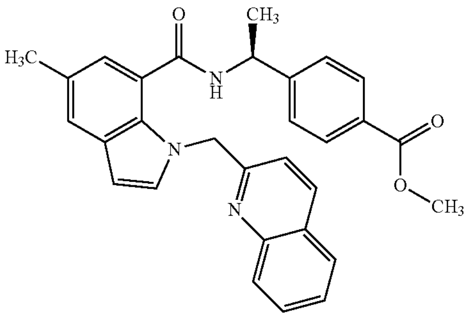 |
| 236 | 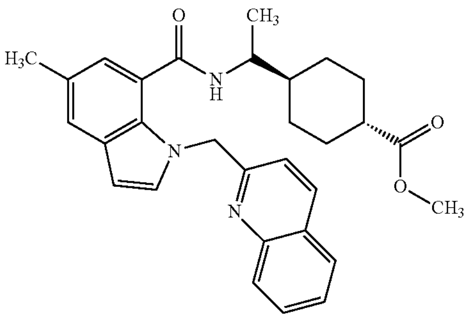 |
TABLE 56
| Pr | Structure |
|---|---|
| 237 | 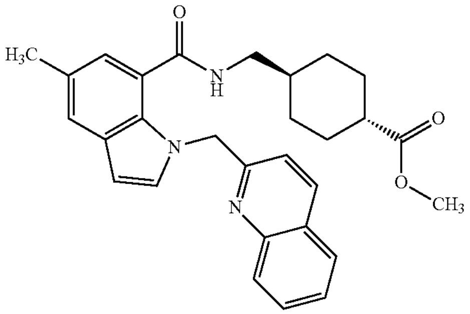 |
| 238 | 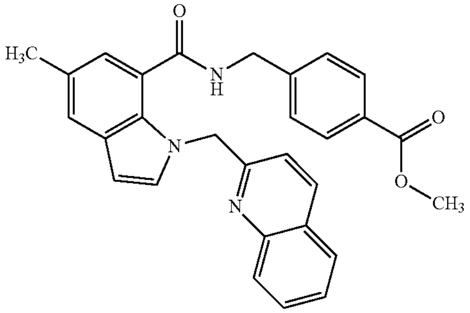 |
| 239 | 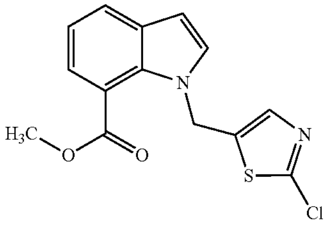 [SMILES: COC(=O)c1cccc2ccn(Cc3cnc(Cl)s3)c12] |
| 240 | 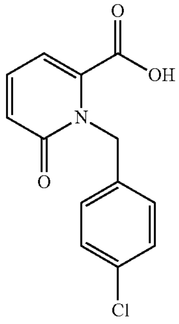 [SMILES: O=C(O)c1cccc(=O)n1Cc1ccc(Cl)cc1] |
TABLE 57
| Pr | Structure |
|---|---|
| 241 | 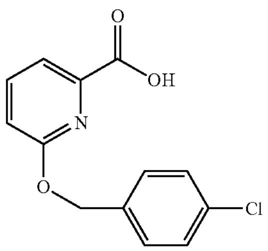 [SMILES: O=C(O)c1cccc(OCc2ccc(Cl)cc2)n1] |

TABLE 57-continued
| Pr | Structure |
|---|---|
| 242 | 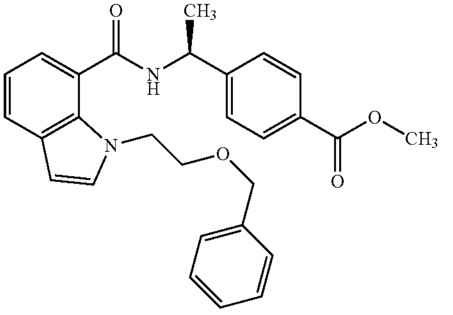 [SMILES: COC(=O)c1ccc([C@H](C)NC(=O)c2cccc3ccn(CCOCc4ccccc4)c23)cc1] |
| 243 | 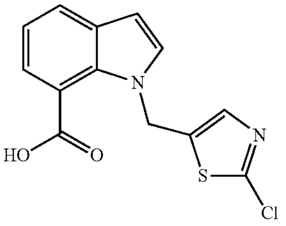 [SMILES: O=C(O)c1cccc2ccn(Cc3cnc(Cl)s3)c12] |
| 244 | 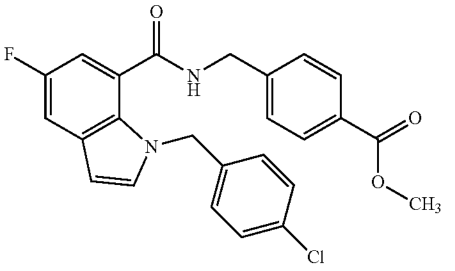 [SMILES: COC(=O)c1ccc(CNC(=O)c2cc(F)cc3ccn(Cc4ccc(Cl)cc4)c23)cc1] |
TABLE 58
| Pr | Structure |
|---|---|
| 245 | 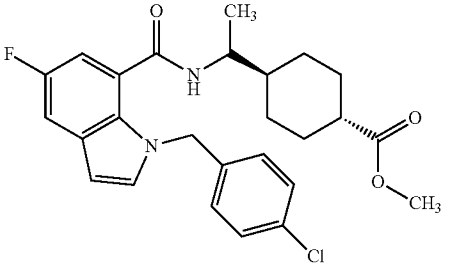 [SMILES: COC(=O)[C@H]1CC[C@H](C(C)NC(=O)c2cc(F)cc3ccn(Cc4ccc(Cl)cc4)c23)CC1] |
| 246 | 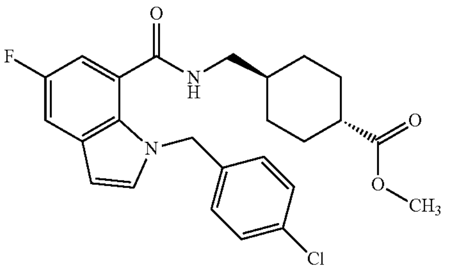 [SMILES: COC(=O)[C@H]1CC[C@H](CNC(=O)c2cc(F)cc3ccn(Cc4ccc(Cl)cc4)c23)CC1] |
TABLE 58-continued
| Pr | Structure |
|---|---|
| 247 | 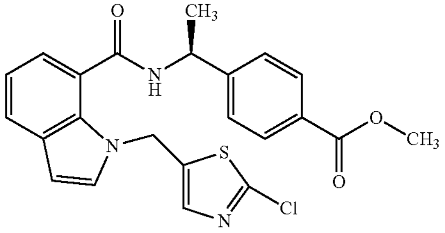 [SMILES: COC(=O)c1ccc([C@H](C)NC(=O)c2cccc3ccn(Cc4cnc(Cl)s4)c23)cc1] |
| 248 | 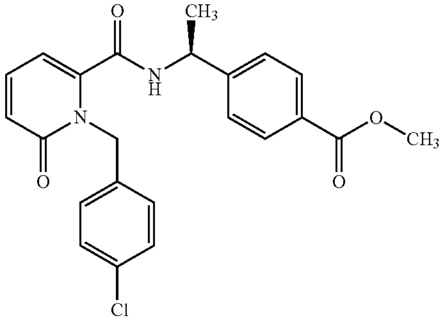 [SMILES: COC(=O)c1ccc([C@H](C)NC(=O)c2cccc(=O)n2Cc2ccc(Cl)cc2)cc1] |
TABLE 59
| Pr | Structure |
|---|---|
| 249 | 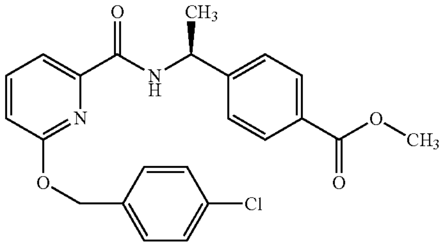 [SMILES: COC(=O)c1ccc([C@H](C)NC(=O)c2cccc(OCc3ccc(Cl)cc3)n2)cc1] |
| 250 | 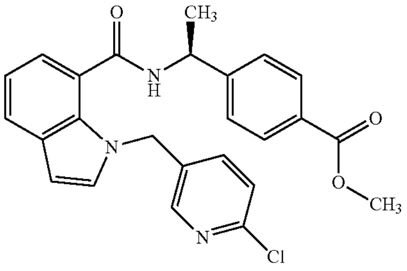 [SMILES: COC(=O)c1ccc([C@H](C)NC(=O)c2cccc3ccn(Cc4ccc(Cl)nc4)c23)cc1] |
| 251 | 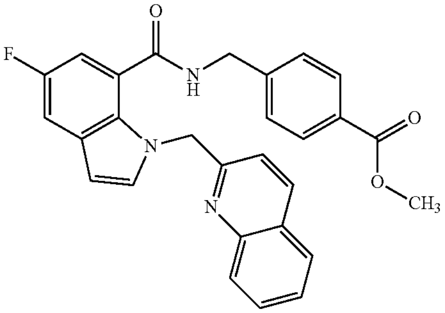 [SMILES: COC(=O)c1ccc(CNC(=O)c2cc(F)cc3ccn(Cc4ccc5ccccc5n4)c23)cc1] |

TABLE 59-continued
| Pr | Structure |
|---|---|
| 252 | 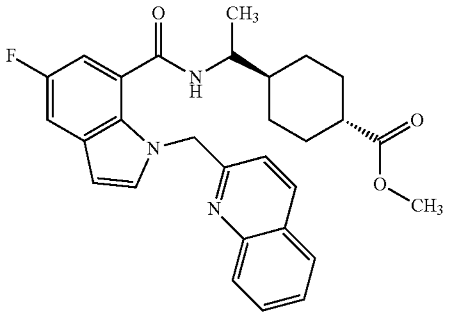 [SMILES: COC(=O)[C@H]1CC[C@H](C(C)NC(=O)c2cc(F)cc3ccn(Cc4ccc5ccccc5n4)c23)CC1] |
TABLE 60
| Pr | Structure |
|---|---|
| 253 | 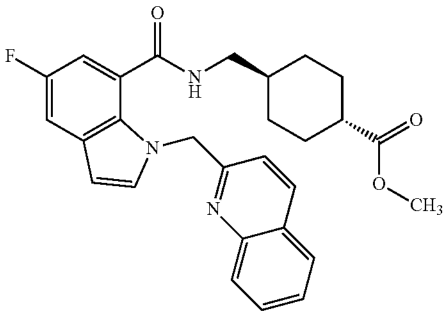 [SMILES: COC(=O)[C@H]1CC[C@H](CNC(=O)c2cc(F)cc3ccn(Cc4ccc5ccccc5n4)c23)CC1] |
| 254/Cl | 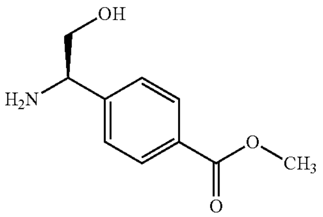 |
| 255 | 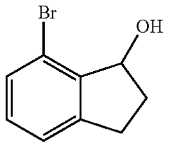 [SMILES: OC1CCc2cccc(Br)c21] |
| 256 | 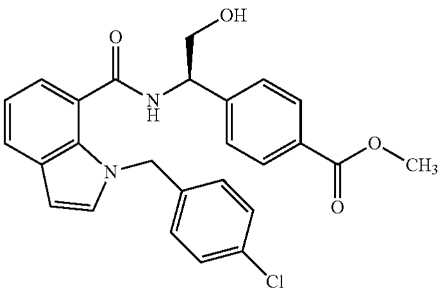 [SMILES: COC(=O)c1ccc([C@H](CO)NC(=O)c2cccc3ccn(Cc4ccc(Cl)cc4)c23)cc1] |
TABLE 61
| Pr | Structure |
|---|---|
| 257 | 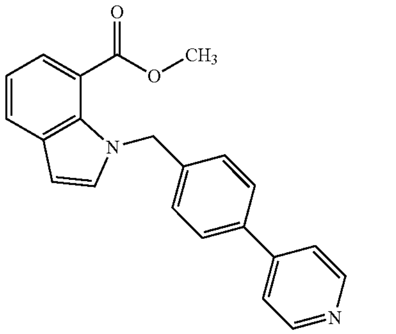 [SMILES: COC(=O)c1cccc2ccn(Cc3ccc(-c4ccncc4)cc3)c12] |
| 258 | 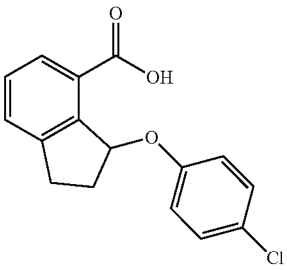 [SMILES: O=C(O)c1cccc2c1C(Oc1ccc(Cl)cc1)CC2] |
| 259 | 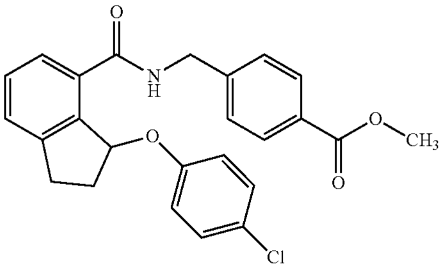 [SMILES: COC(=O)c1ccc(CNC(=O)c2cccc3c2C(Oc2ccc(Cl)cc2)CC3)cc1] |
| 260 | 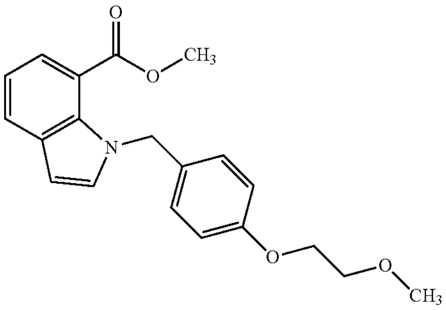 [SMILES: COCCOc1ccc(Cn2ccc3cccc(C(=O)OC)c32)cc1] |

TABLE 62
| Pr | Structure |
| --- | --- |
| 261 | 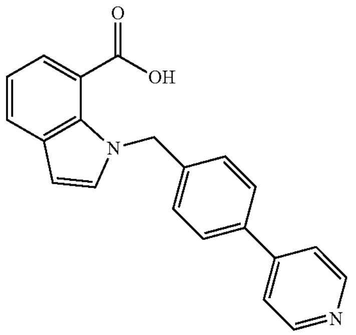 |
| 262 | 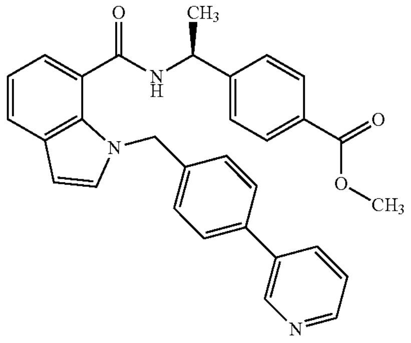 [SMILES: COC(=O)c1ccc([C@H](C)NC(=O)c2cccc3ccn(Cc4ccc(-c5cccnc5)cc4)c23)cc1] |
| 263 | 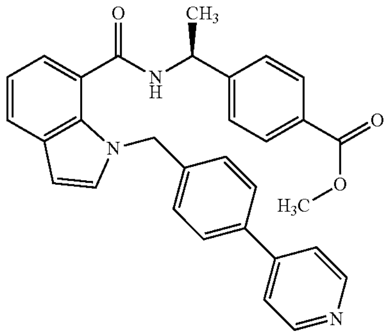 [SMILES: COC(=O)c1ccc([C@H](C)NC(=O)c2cccc3ccn(Cc4ccc(-c5ccncc5)cc4)c23)cc1] |
TABLE 63
| Pr | Structure |
| --- | --- |
| 264 | 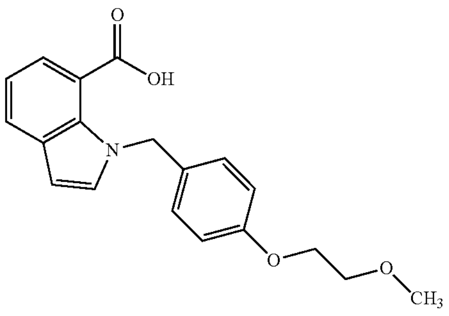 [SMILES: COCCOc1ccc(Cn2ccc3cccc(C(=O)O)c32)cc1] |
TABLE 63-continued
| Pr | Structure |
| --- | --- |
| 266 | 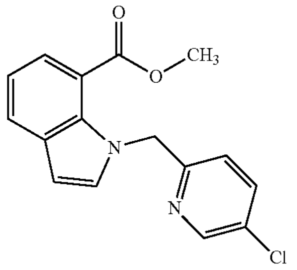 [SMILES: COC(=O)c1cccc2ccn(Cc3ccc(Cl)cn3)c12] |
| 267 | 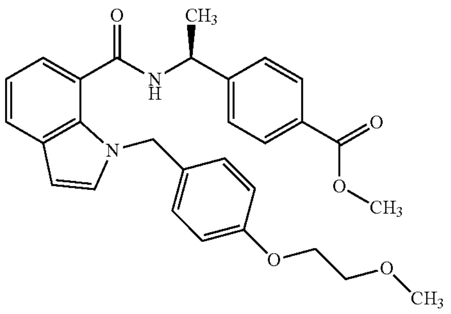 [SMILES: COCCOc1ccc(Cn2ccc3cccc(C(=O)N[C@@H](C)c4ccc(C(=O)OC)cc4)c32)cc1] |
| 268 | 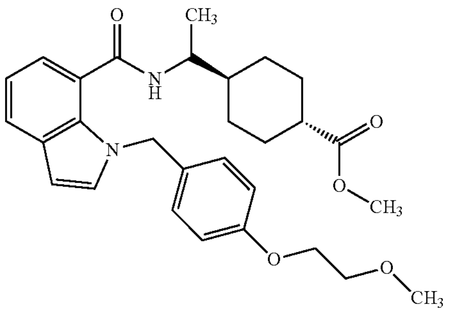 [SMILES: COCCOc1ccc(Cn2ccc3cccc(C(=O)NC(C)[C@H]4CC[C@H](C(=O)OC)CC4)c32)cc1] |
TABLE 64
| Pr | Structure |
| --- | --- |
| 269 | 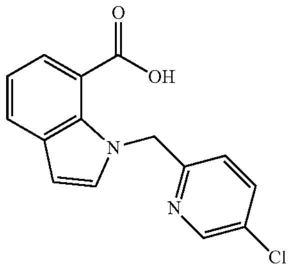 [SMILES: O=C(O)c1cccc2ccn(Cc3ccc(Cl)cn3)c12] |
| 270 | 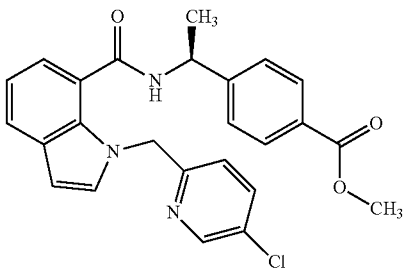 [SMILES: COC(=O)c1ccc([C@H](C)NC(=O)c2cccc3ccn(Cc4ccc(Cl)cn4)c23)cc1] |

TABLE 64-continued
| Pr | Structure |
|---|---|
| 271 | 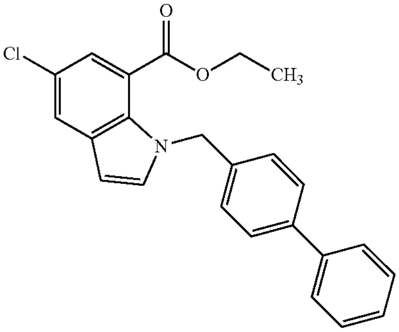 [SMILES: CCOC(=O)c1cc(Cl)cc2ccn(Cc3ccc(-c4ccccc4)cc3)c12] |
| 272 | 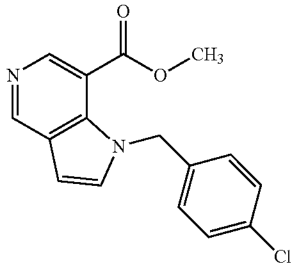 [SMILES: COC(=O)c1cncc2ccn(Cc3ccc(Cl)cc3)c12] |
TABLE 65
| Pr | Structure |
|---|---|
| 273 | 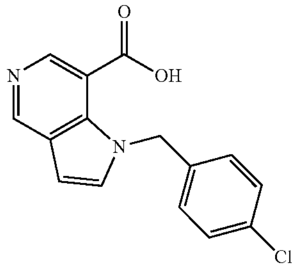 [SMILES: O=C(O)c1cncc2ccn(Cc3ccc(Cl)cc3)c12] |
| 274 | 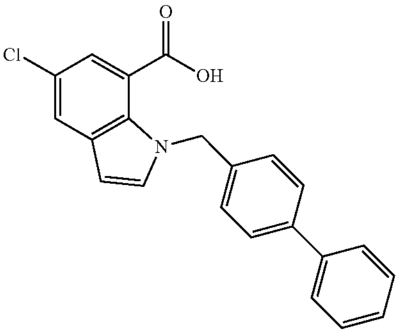 [SMILES: O=C(O)c1cc(Cl)cc2ccn(Cc3ccc(-c4ccccc4)cc3)c12] |
TABLE 65-continued
| Pr | Structure |
|---|---|
| 275 | 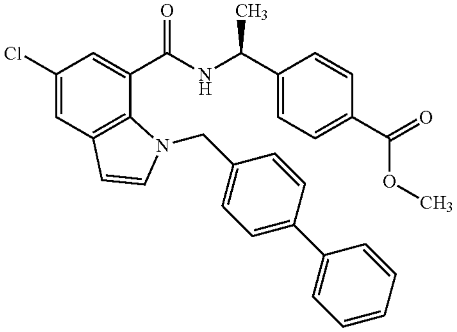 [SMILES: COC(=O)c1ccc([C@H](C)NC(=O)c2cc(Cl)cc3ccn(Cc4ccc(-c5ccccc5)cc4)c23)cc1] |
| 276 | 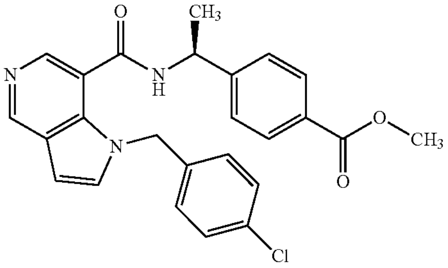 [SMILES: COC(=O)c1ccc([C@H](C)NC(=O)c2cncc3ccn(Cc4ccc(Cl)cc4)c23)cc1] |
TABLE 66
| Pr | Structure |
|---|---|
| 277 | 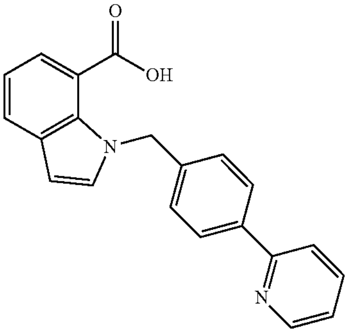 |
| 278 | 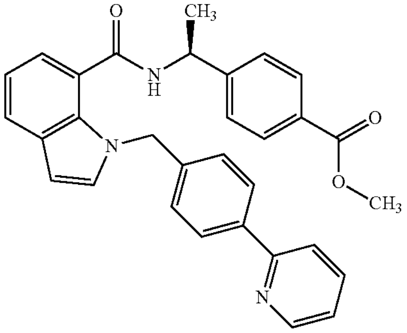 |

TABLE 66-continued
| Pr | Structure |
|---|---|
| 279 | 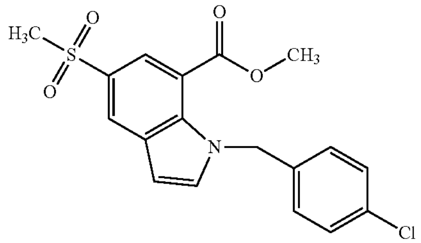 [SMILES: COC(=O)c1cc(S(C)(=O)=O)cc2ccn(Cc3ccc(Cl)cc3)c12] |
| 280 | 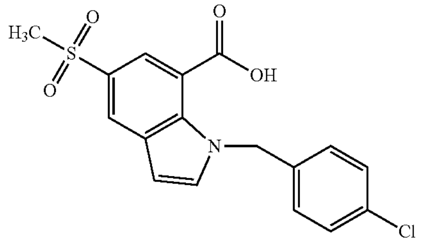 [SMILES: CS(=O)(=O)c1cc(C(=O)O)c2c(ccn2Cc2ccc(Cl)cc2)c1] |
TABLE 67
| Pr | Structure |
|---|---|
| 281 | 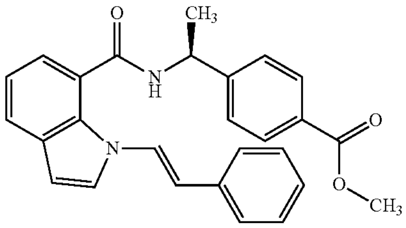 [SMILES: COC(=O)c1ccc([C@H](C)NC(=O)c2cccc3ccn(/C=C/c4ccccc4)c23)cc1] |
| 282 | 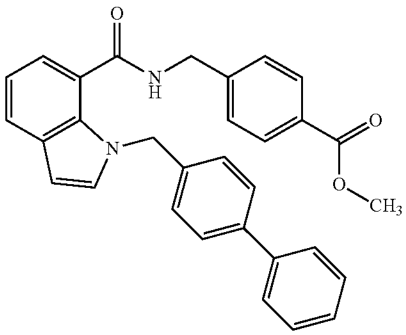 [SMILES: COC(=O)c1ccc(CNC(=O)c2cccc3ccn(Cc4ccc(-c5ccccc5)cc4)c23)cc1] |
| 283 | 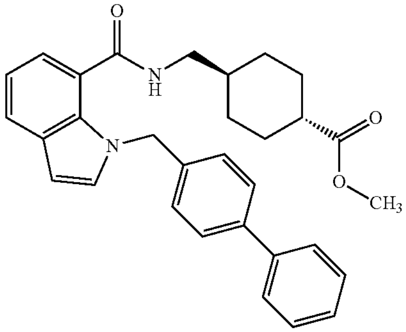 [SMILES: COC(=O)[C@H]1CC[C@H](CNC(=O)c2cccc3ccn(Cc4ccc(-c5ccccc5)cc4)c23)CC1] |
TABLE 67-continued
| Pr | Structure |
|---|---|
| 284 | 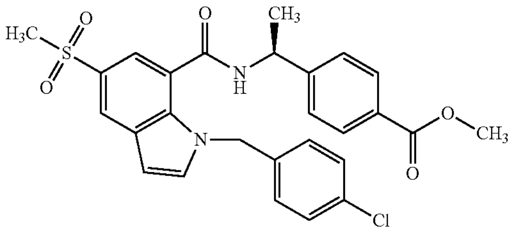 |
TABLE 68
| Pr | Structure |
|---|---|
| 285 | 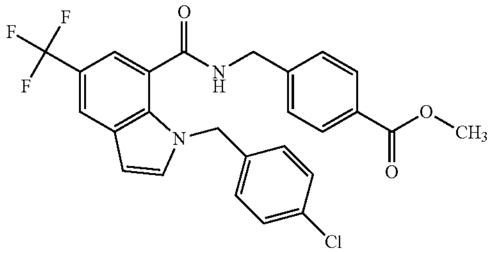 [SMILES: COC(=O)c1ccc(CNC(=O)c2cc(C(F)(F)F)cc3ccn(Cc4ccc(Cl)cc4)c23)cc1] |
| 286 | 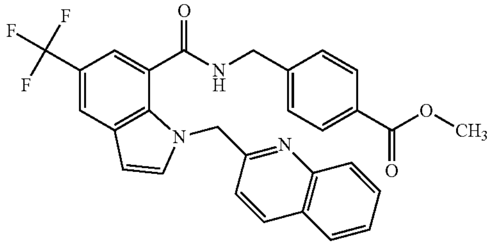 [SMILES: COC(=O)c1ccc(CNC(=O)c2cc(C(F)(F)F)cc3ccn(Cc4ccc5ccccc5n4)c23)cc1] |
| 287 | 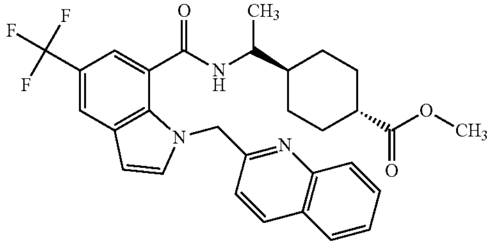 [SMILES: COC(=O)[C@H]1CC[C@H](C(C)NC(=O)c2cc(C(F)(F)F)cc3ccn(Cc4ccc5ccccc5n4)c23)CC1] |
| 288 | 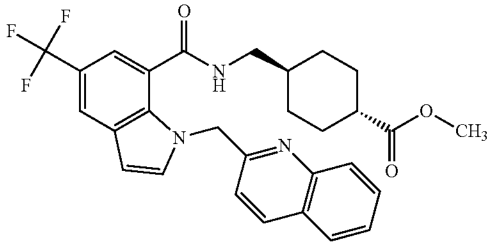 [SMILES: COC(=O)[C@H]1CC[C@H](CNC(=O)c2cc(C(F)(F)F)cc3ccn(Cc4ccc5ccccc5n4)c23)CC1] |

TABLE 69
| Pr | Structure |
|---|---|
| 289 | 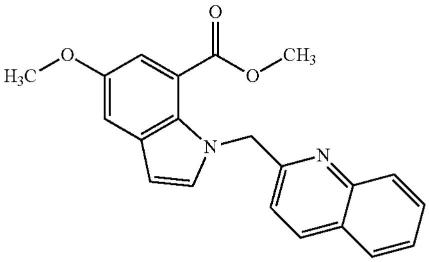 [SMILES: COC(=O)c1cc(OC)cc2ccn(Cc3ccc4ccccc4n3)c12] |
| 290 | 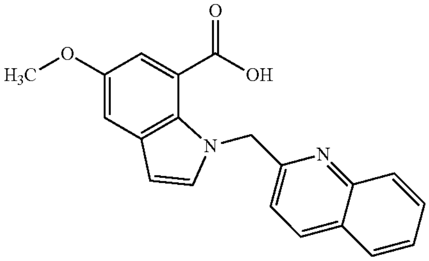 [SMILES: COc1cc(C(=O)O)c2c(ccn2Cc2ccc3ccccc3n2)c1] |
| 291 | 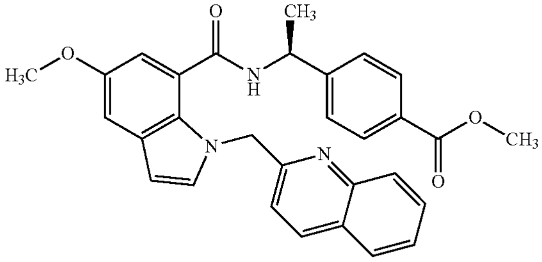 |
| 292 | 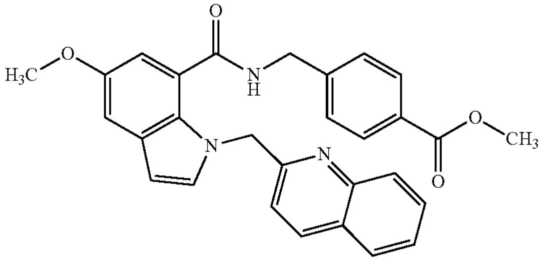 |
TABLE 70
| Pr | Structure |
|---|---|
| 293 | 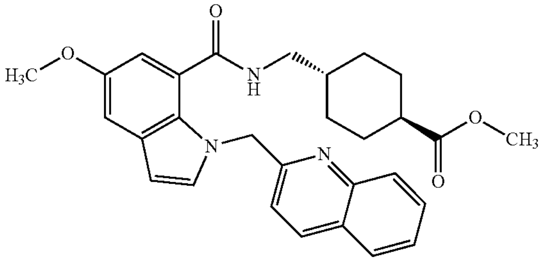 |
TABLE 70-continued
| Pr | Structure |
|---|---|
| 294 | 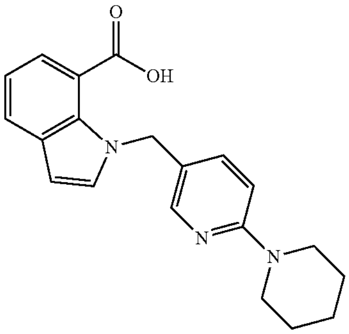 [SMILES: O=C(O)c1cccc2ccn(Cc3ccc(N4CCCCC4)nc3)c12] |
| 295 | 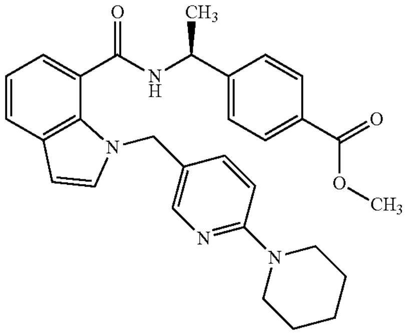 [SMILES: COC(=O)c1ccc([C@H](C)NC(=O)c2cccc3ccn(Cc4ccc(N5CCCCC5)nc4)c23)cc1] |
TABLE 71
| Pr | Structure |
|---|---|
| 296 | 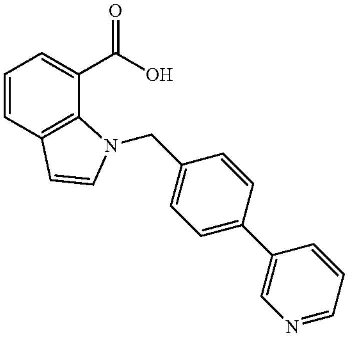 [SMILES: O=C(O)c1cccc2ccn(Cc3ccc(-c4cccnc4)cc3)c12] |
| 297 | 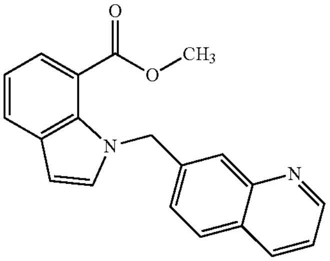 [SMILES: COC(=O)c1cccc2ccn(Cc3ccc4cccnc4c3)c12] |

TABLE 71-continued
| Pr | Structure |
|---|---|
| 298 | 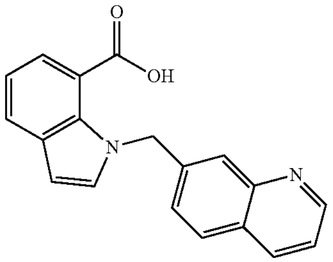 [SMILES: O=C(O)c1cccc2ccn(Cc3ccc4cccnc4c3)c12] |
| 299 | 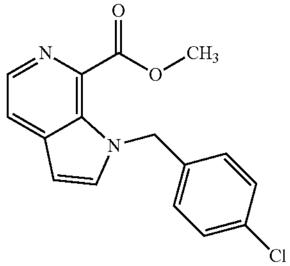 [SMILES: COC(=O)c1nccc2ccn(Cc3ccc(Cl)cc3)c12] |
TABLE 72
| Pr | Structure |
|---|---|
| 300 | 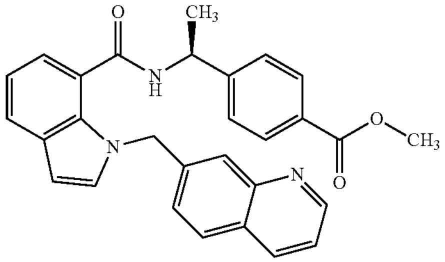 [SMILES: COC(=O)c1ccc([C@H](C)NC(=O)c2cccc3ccn(Cc4ccc5cccnc5c4)c23)cc1] |
| 301 | 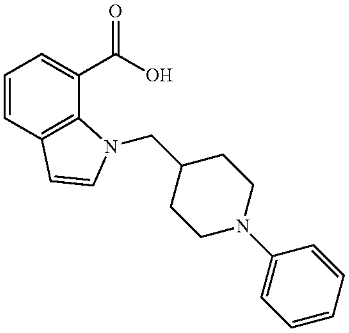 [SMILES: O=C(O)c1cccc2ccn(CC3CCN(c4ccccc4)CC3)c12] |
| 302 | 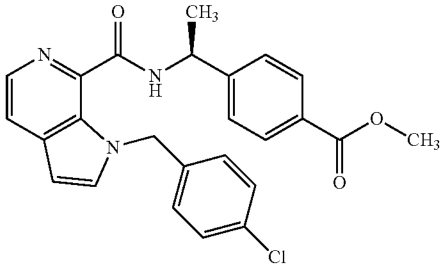 [SMILES: COC(=O)c1ccc([C@H](C)NC(=O)c2nccc3ccn(Cc4ccc(Cl)cc4)c23)cc1] |
TABLE 72-continued
| Pr | Structure |
|---|---|
| 303 | 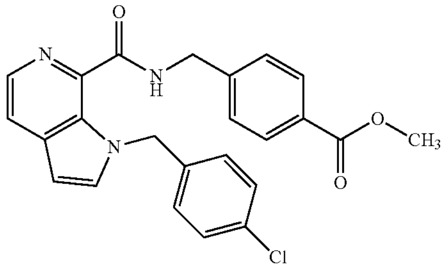 [SMILES: COC(=O)c1ccc(CNC(=O)c2nccc3ccn(Cc4ccc(Cl)cc4)c23)cc1] |
TABLE 73
| Pr | Structure |
|---|---|
| 304 | 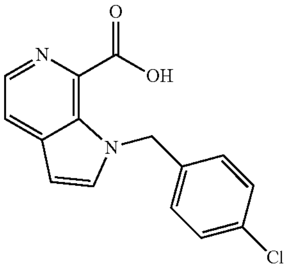 [SMILES: O=C(O)c1nccc2ccn(Cc3ccc(Cl)cc3)c12] |
| 305 | 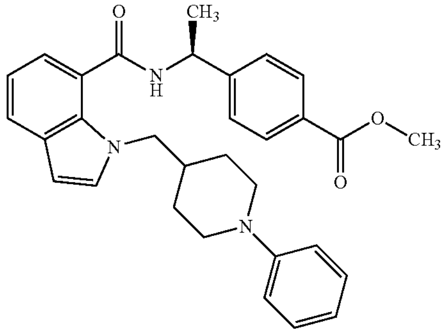 [SMILES: COC(=O)c1ccc([C@H](C)NC(=O)c2cccc3ccn(CC4CCN(c5ccccc5)CC4)c23)cc1] |
| 306 | 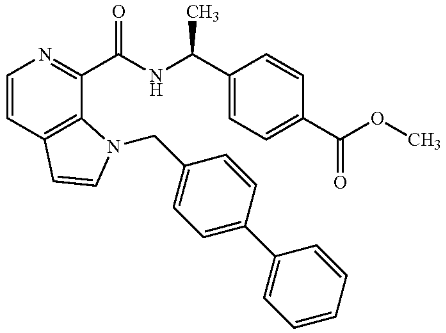 [SMILES: COC(=O)c1ccc([C@H](C)NC(=O)c2nccc3ccn(Cc4ccc(-c5ccccc5)cc4)c23)cc1] |
| 307 | 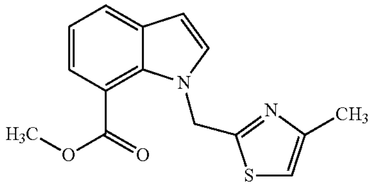 |

TABLE 74
| Pr | Structure |
|---|---|
| 309 | 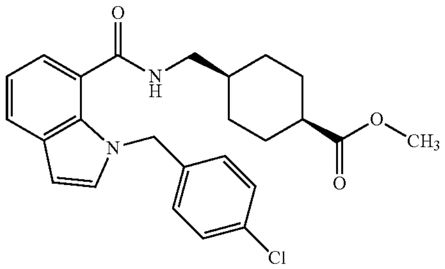 [SMILES: COC(=O)[C@H]1CC[C@@H](CNC(=O)c2cccc3ccn(Cc4ccc(Cl)cc4)c23)CC1] |
| 309 | 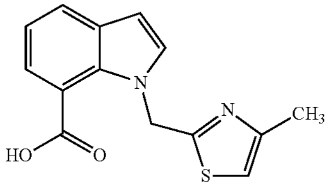 [SMILES: Cc1csc(Cn2ccc3cccc(C(=O)O)c32)n1] |
| 310 | 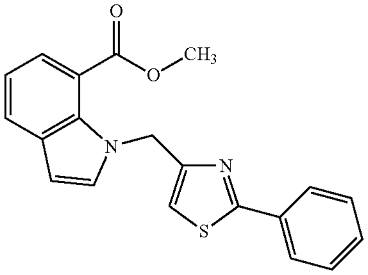 [SMILES: COC(=O)c1cccc2ccn(Cc3csc(-c4ccccc4)n3)c12] |
| 311 | 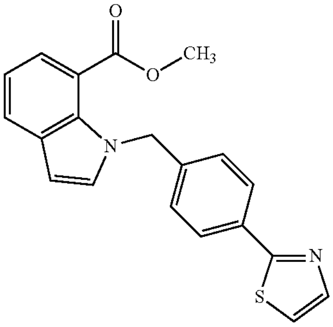 [SMILES: COC(=O)c1cccc2ccn(Cc3ccc(-c4nccs4)cc3)c12] |
| 312 | 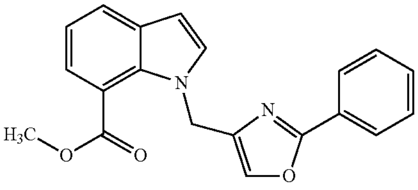 [SMILES: COC(=O)c1cccc2ccn(Cc3coc(-c4ccccc4)n3)c12] |
TABLE 75
| Pr | Structure |
|---|---|
| 313 | 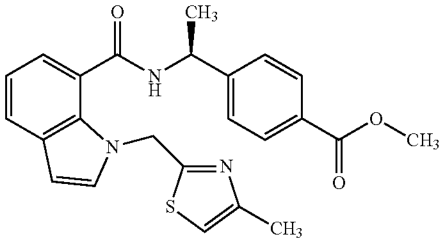 [SMILES: COC(=O)c1ccc([C@H](C)NC(=O)c2cccc3ccn(Cc4nc(C)cs4)c23)cc1] |
| 314 | 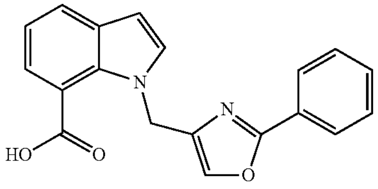 [SMILES: O=C(O)c1cccc2ccn(Cc3coc(-c4ccccc4)n3)c12] |
| 315 | 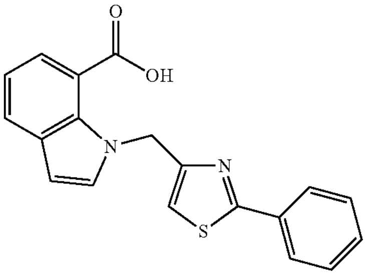 [SMILES: O=C(O)c1cccc2ccn(Cc3csc(-c4ccccc4)n3)c12] |
| 316 | 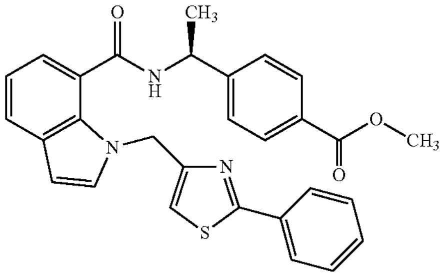 [SMILES: COC(=O)c1ccc([C@H](C)NC(=O)c2cccc3ccn(Cc4csc(-c5ccccc5)n4)c23)cc1] |
| 317 | 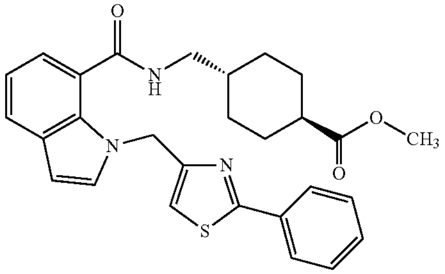 [SMILES: COC(=O)[C@H]1CC[C@H](CNC(=O)c2cccc3ccn(Cc4csc(-c5ccccc5)n4)c23)CC1] |

TABLE 76
| Pr | Structure |
|---|---|
| 318 | 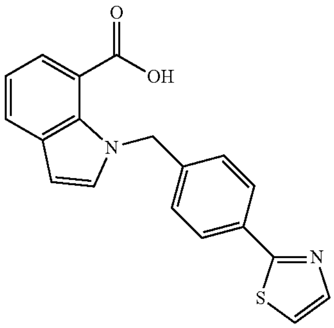 [SMILES: O=C(O)c1cccc2ccn(Cc3ccc(-c4nccs4)cc3)c12] |
| 319 | 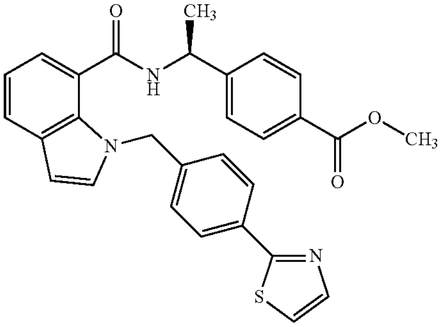 [SMILES: COC(=O)c1ccc([C@H](C)NC(=O)c2cccc3ccn(Cc4ccc(-c5nccs5)cc4)c23)cc1] |
| 320 | 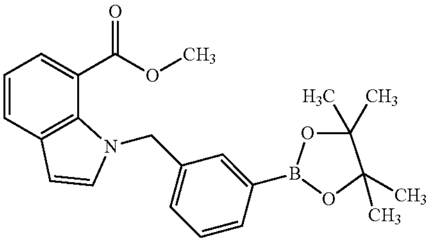 [SMILES: COC(=O)c1cccc2ccn(Cc3cccc(B4OC(C)(C)C(C)(C)O4)c3)c12] |
| 321 | 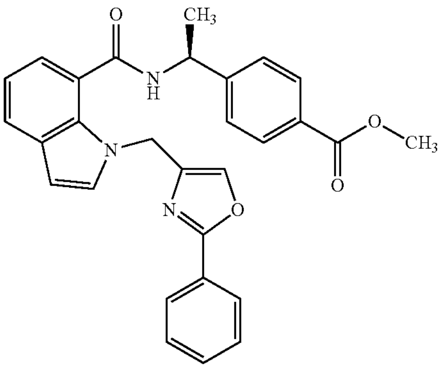 [SMILES: COC(=O)c1ccc([C@H](C)NC(=O)c2cccc3ccn(Cc4coc(-c5ccccc5)n4)c23)cc1] |
TABLE 77
| Pr | Structure |
|---|---|
| 322 | 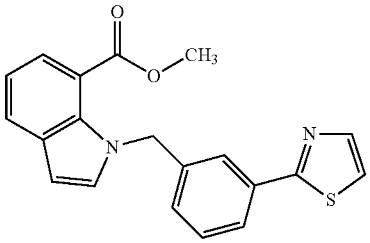 [SMILES: COC(=O)c1cccc2ccn(Cc3cccc(-c4nccs4)c3)c12] |
| 323 | 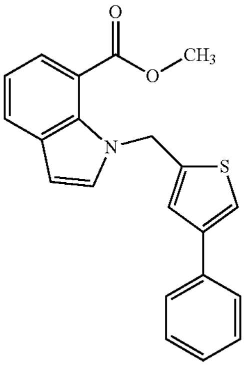 [SMILES: COC(=O)c1cccc2ccn(Cc3cc(-c4ccccc4)cs3)c12] |
| 324 | 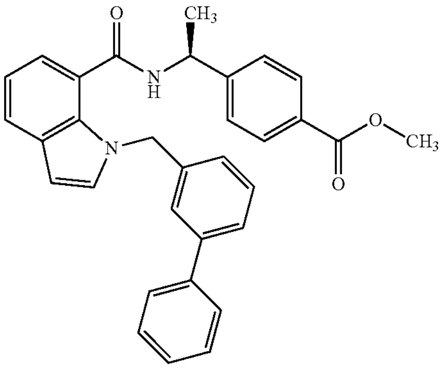 [SMILES: COC(=O)c1ccc([C@H](C)NC(=O)c2cccc3ccn(Cc4cccc(-c5ccccc5)c4)c23)cc1] |
TABLE 78
| Pr | Structure |
|---|---|
| 325 | 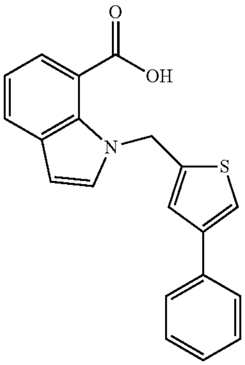 [SMILES: O=C(O)c1cccc2ccn(Cc3cc(-c4ccccc4)cs3)c12] |

TABLE 78-continued
| Pr | Structure |
|---|---|
| 326 | 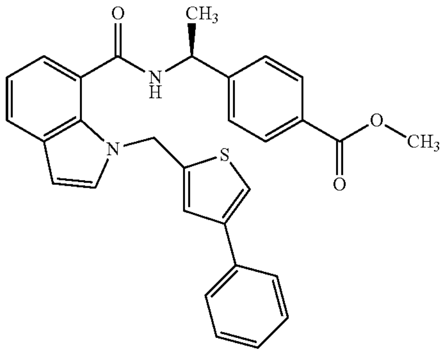 [SMILES: COC(=O)c1ccc([C@H](C)NC(=O)c2cccc3ccn(Cc4cc(-c5ccccc5)cs4)c23)cc1] |
| 327 | 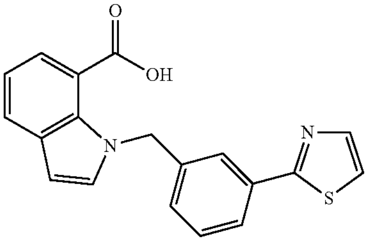 [SMILES: O=C(O)c1cccc2ccn(Cc3cccc(-c4nccs4)c3)c12] |
TABLE 79
| Pr | Structure |
|---|---|
| 328 | 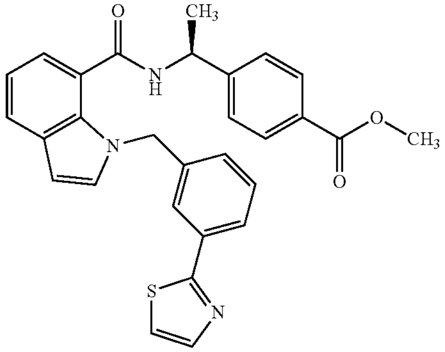 [SMILES: COC(=O)c1ccc([C@H](C)NC(=O)c2cccc3ccn(Cc4cccc(-c5nccs5)c4)c23)cc1] |
| 329 | 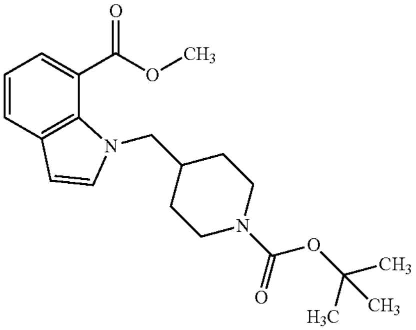 [SMILES: COC(=O)c1cccc2ccn(CC3CCN(C(=O)OC(C)(C)C)CC3)c12] |
TABLE 79-continued
| Pr | Structure |
|---|---|
| 330 | 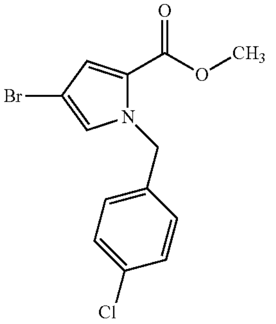 [SMILES: COC(=O)c1cc(Br)cn1Cc1ccc(Cl)cc1] |
TABLE 80
| Pr | Structure |
|---|---|
| 331 | 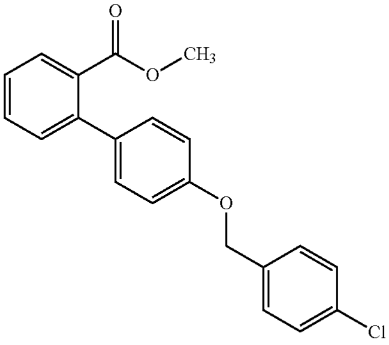 [SMILES: COC(=O)c1ccccc1-c1ccc(OCc2ccc(Cl)cc2)cc1] |
| 332 | 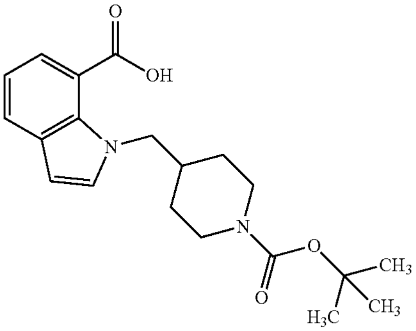 [SMILES: CC(C)(C)OC(=O)N1CCC(Cn2ccc3cccc(C(=O)O)c32)CC1] |
| 333 | 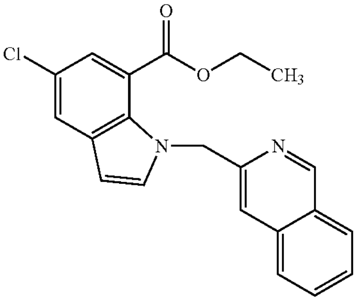 [SMILES: CCOC(=O)c1cc(Cl)cc2ccn(Cc3cc4ccccc4cn3)c12] |

TABLE 81
| Pr | Structure |
|---|---|
| 334 | 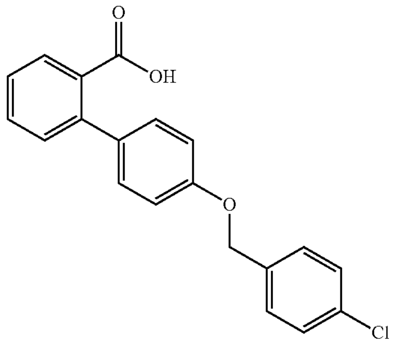 [SMILES: O=C(O)c1ccccc1-c1ccc(OCc2ccc(Cl)cc2)cc1] |
| 335 | 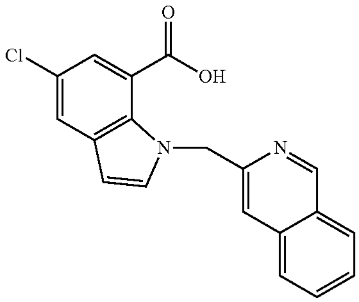 [SMILES: O=C(O)c1cc(Cl)cc2ccn(Cc3cc4ccccc4cn3)c12] |
| 336 | 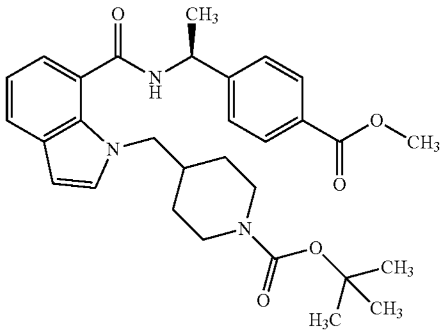 [SMILES: COC(=O)c1ccc([C@H](C)NC(=O)c2cccc3ccn(CC4CCN(C(=O)OC(C)(C)C)CC4)c23)cc1] |
TABLE 82
| Pr | Structure |
|---|---|
| 337 | 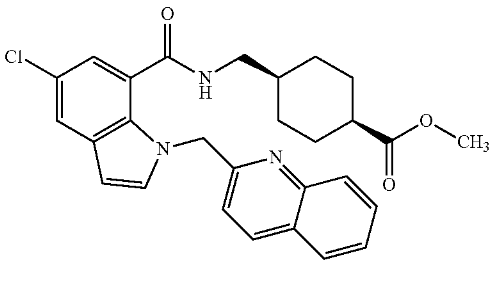 [SMILES: COC(=O)[C@H]1CC[C@@H](CNC(=O)c2cc(Cl)cc3ccn(Cc4ccc5ccccc5n4)c23)CC1] |
TABLE 82-continued
| Pr | Structure |
|---|---|
| 338 | 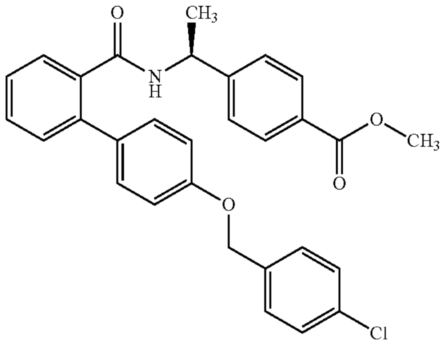 [SMILES: COC(=O)c1ccc([C@H](C)NC(=O)c2ccccc2-c2ccc(OCc3ccc(Cl)cc3)cc2)cc1] |
| 339 | 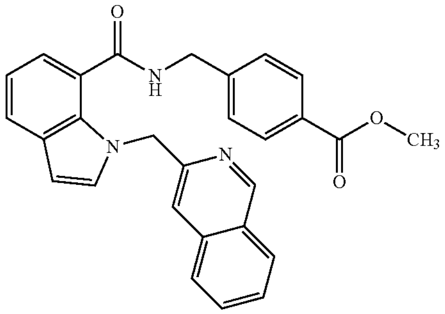 [SMILES: COC(=O)c1ccc(CNC(=O)c2cccc3ccn(Cc4cc5ccccc5cn4)c23)cc1] |
| 340 | 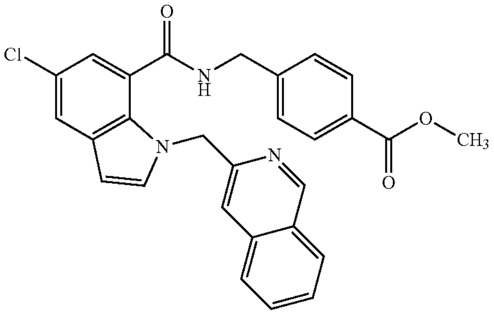 [SMILES: COC(=O)c1ccc(CNC(=O)c2cc(Cl)cc3ccn(Cc4cc5ccccc5cn4)c23)cc1] |
TABLE 83
| Pr | Structure |
|---|---|
| 341 | 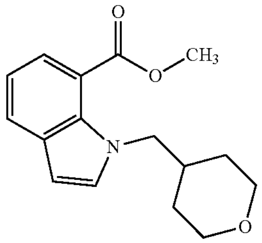 [SMILES: COC(=O)c1cccc2ccn(CC3CCOCC3)c12] |

TABLE 83-continued
| Pr | Structure |
|---|---|
| 342 | 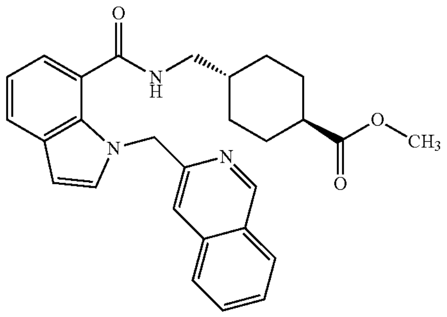 [SMILES: COC(=O)[C@H]1CC[C@H](CNC(=O)c2cccc3ccn(Cc4cc5ccccc5cn4)c23)CC1] |
| 343 | 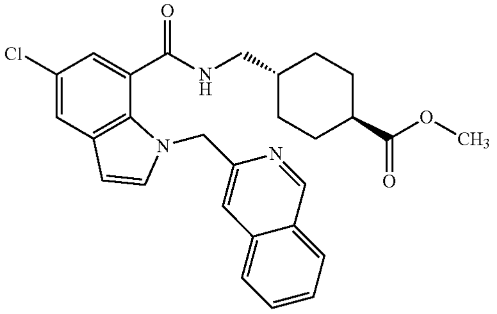 [SMILES: COC(=O)[C@H]1CC[C@H](CNC(=O)c2cc(Cl)cc3ccn(Cc4cc5ccccc5cn4)c23)CC1] |
| 344 | 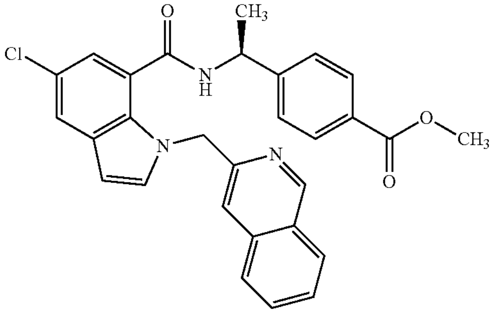 [SMILES: COC(=O)c1ccc([C@H](C)NC(=O)c2cc(Cl)cc3ccn(Cc4cc5ccccc5cn4)c23)cc1] |
TABLE 84
| Pr | Structure |
|---|---|
| 345 | 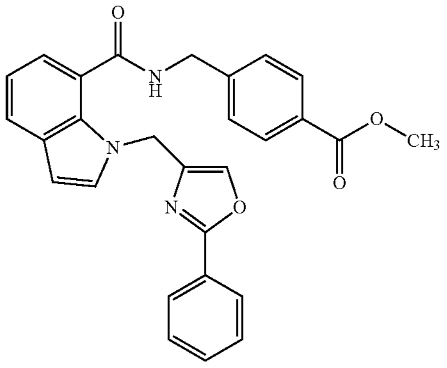 [SMILES: COC(=O)c1ccc(CNC(=O)c2cccc3ccn(Cc4coc(-c5ccccc5)n4)c23)cc1] |
TABLE 84-continued
| Pr | Structure |
|---|---|
| 346 | 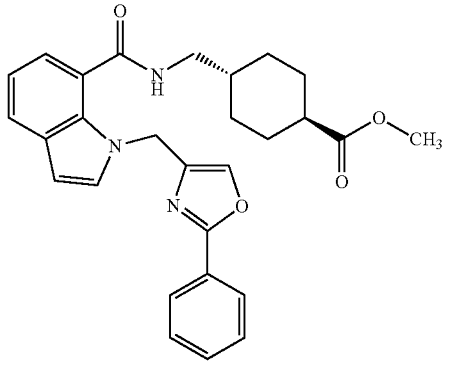 [SMILES: COC(=O)[C@H]1CC[C@H](CNC(=O)c2cccc3ccn(Cc4coc(-c5ccccc5)n4)c23)CC1] |
| 347 | 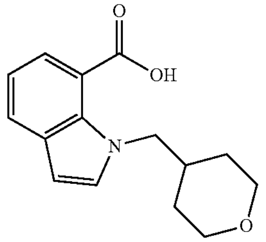 [SMILES: O=C(O)c1cccc2ccn(CC3CCOCC3)c12] |
| 348 | 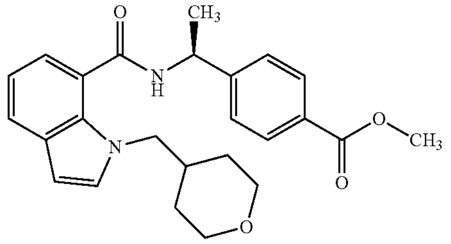 [SMILES: COC(=O)c1ccc([C@H](C)NC(=O)c2cccc3ccn(CC4CCOCC4)c23)cc1] |
TABLE 85
| Pr | Structure |
|---|---|
| 349 | 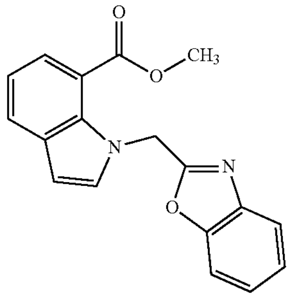 [SMILES: COC(=O)c1cccc2ccn(Cc3nc4ccccc4o3)c12] |
| 350 | 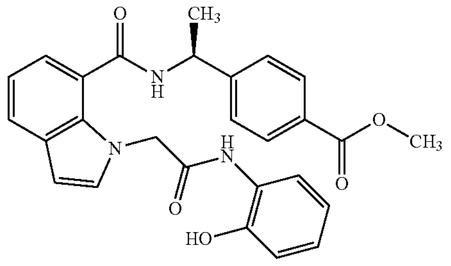 [SMILES: COC(=O)c1ccc([C@H](C)NC(=O)c2cccc3ccn(CC(=O)Nc4ccccc4O)c23)cc1] |

TABLE 85-continued
| Pr | Structure |
|---|---|
| 351 | 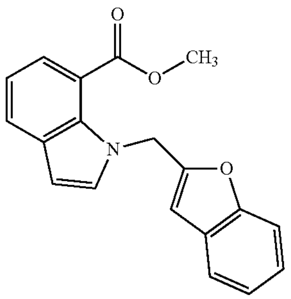 [SMILES: COC(=O)c1cccc2ccn(Cc3cc4ccccc4o3)c12] |
| 352 | 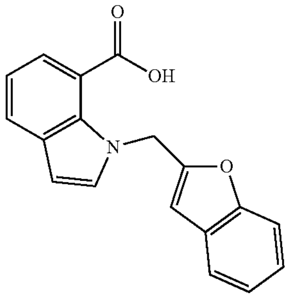 [SMILES: O=C(O)c1cccc2ccn(Cc3cc4ccccc4o3)c12] |
TABLE 86
| Pr | Structure |
|---|---|
| 353 | 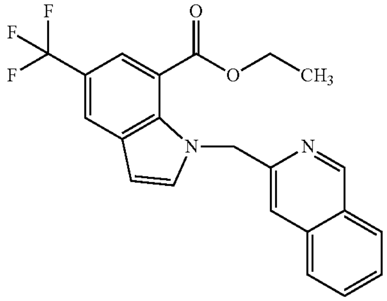 [SMILES: CCOC(=O)c1cc(C(F)(F)F)cc2ccn(Cc3cc4ccccc4cn3)c12] |
| 354 | 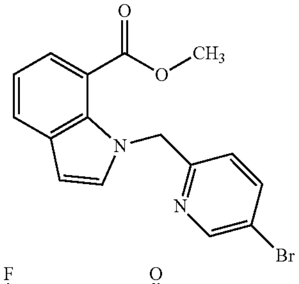 |
| 355 | 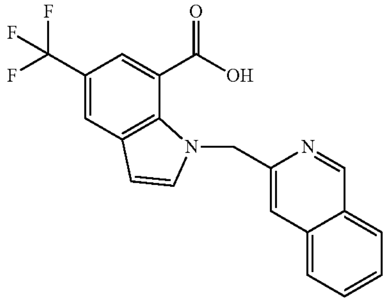 [SMILES: O=C(O)c1cc(C(F)(F)F)cc2ccn(Cc3cc4ccccc4cn3)c12] |
TABLE 86-continued
| Pr | Structure |
|---|---|
| 356 | 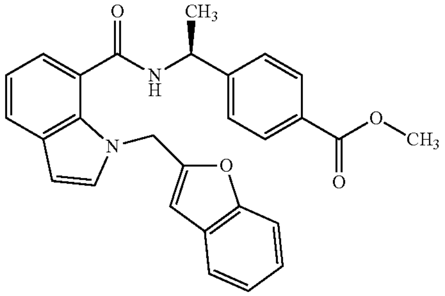 [SMILES: COC(=O)c1ccc([C@H](C)NC(=O)c2cccc3ccn(Cc4cc5ccccc5o4)c23)cc1] |
TABLE 87
| Pr | Structure |
|---|---|
| 357 | 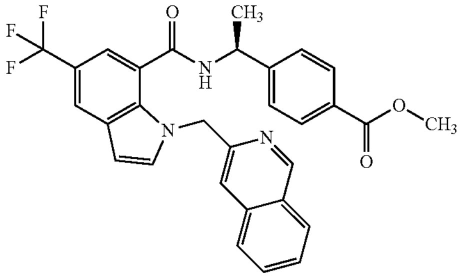 [SMILES: COC(=O)c1ccc([C@H](C)NC(=O)c2cc(C(F)(F)F)cc3ccn(Cc4cc5ccccc5cn4)c23)cc1] |
| 358 | 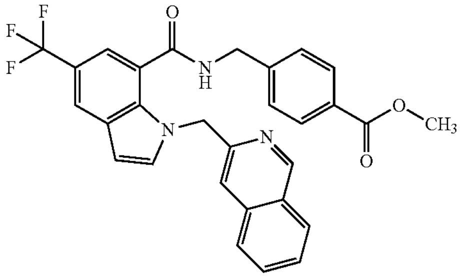 [SMILES: COC(=O)c1ccc(CNC(=O)c2cc(C(F)(F)F)cc3ccn(Cc4cc5ccccc5cn4)c23)cc1] |
| 359 | 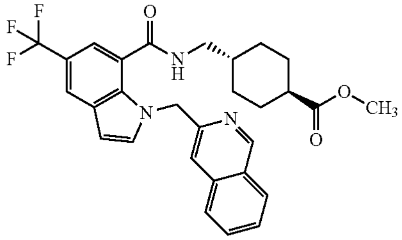 [SMILES: COC(=O)[C@H]1CC[C@H](CNC(=O)c2cc(C(F)(F)F)cc3ccn(Cc4cc5ccccc5cn4)c23)CC1] |
| 360 | 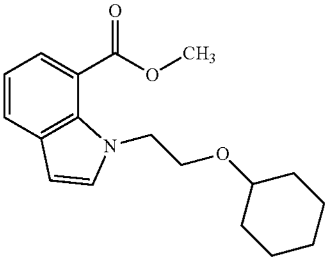 [SMILES: COC(=O)c1cccc2ccn(CCOC3CCCCC3)c12] |

TABLE 88
| Pr | Structure |
|---|---|
| 361 | 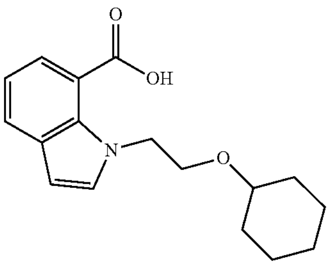 [SMILES: O=C(O)c1cccc2ccn(CCOC3CCCCC3)c12] |
| 362 | 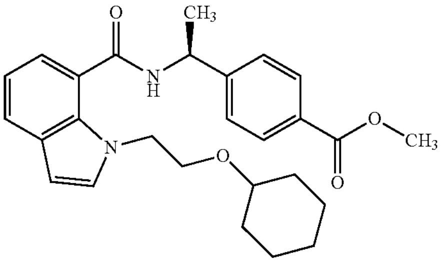 [SMILES: COC(=O)c1ccc([C@H](C)NC(=O)c2cccc3ccn(CCOC4CCCCC4)c23)cc1] |
| 363 | 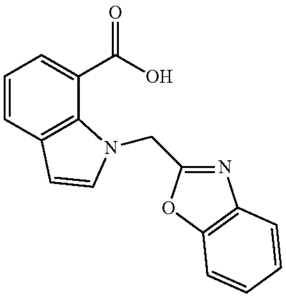 [SMILES: O=C(O)c1cccc2ccn(Cc3nc4ccccc4o3)c12] |
| 364 | 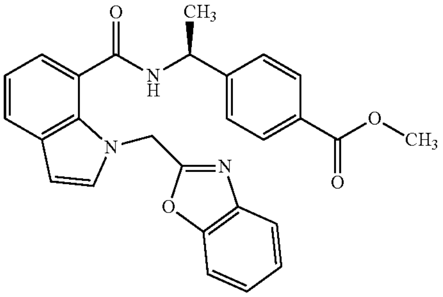 [SMILES: COC(=O)c1ccc([C@H](C)NC(=O)c2cccc3ccn(Cc4nc5ccccc5o4)c23)cc1] |
TABLE 89
| Pr | Structure |
|---|---|
| 366 | 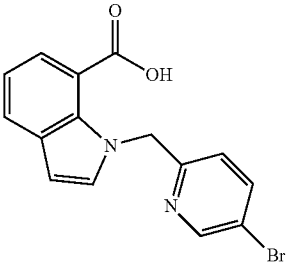 [SMILES: O=C(O)c1cccc2ccn(Cc3ccc(Br)cn3)c12] |
TABLE 89-continued
| Pr | Structure |
|---|---|
| 367 | 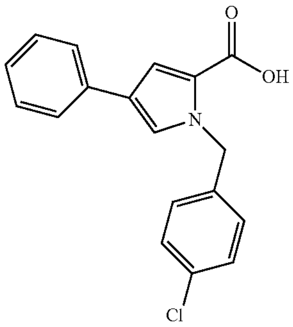 [SMILES: O=C(O)c1cc(-c2ccccc2)cn1Cc1ccc(Cl)cc1] |
| 368 | 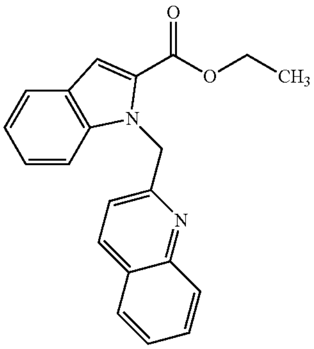 [SMILES: CCOC(=O)c1cc2ccccc2n1Cc1ccc2ccccc2n1] |
TABLE 90
| Pr | Structure |
|---|---|
| 369 | 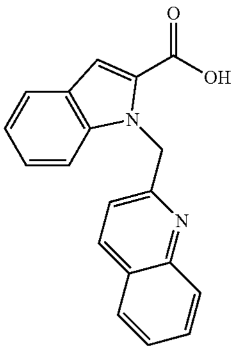 [SMILES: O=C(O)c1cc2ccccc2n1Cc1ccc2ccccc2n1] |
| 370 | 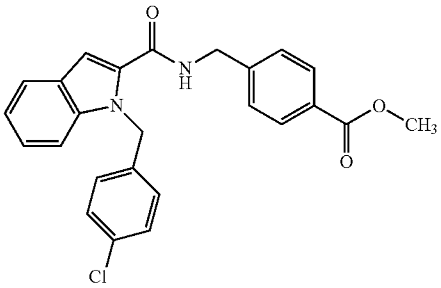 [SMILES: COC(=O)c1ccc(CNC(=O)c2cc3ccccc3n2Cc2ccc(Cl)cc2)cc1] |

TABLE 90-continued
| Pr | Structure |
|---|---|
| 371 | 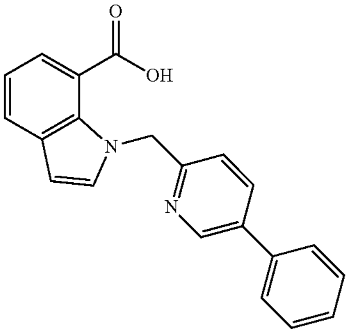 [SMILES: O=C(O)c1cccc2ccn(Cc3ccc(-c4ccccc4)cn3)c12] |
TABLE 91
| Pr | Structure |
|---|---|
| 372 | 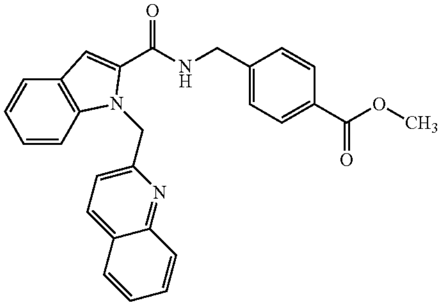 [SMILES: COC(=O)c1ccc(CNC(=O)c2cc3ccccc3n2Cc2ccc3ccccc3n2)cc1] |
| 373 | 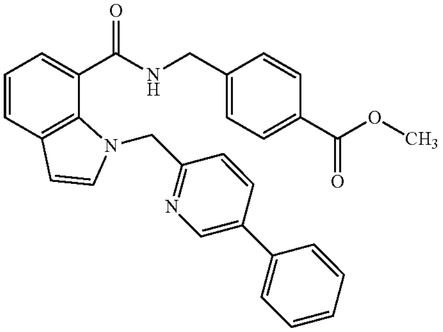 [SMILES: COC(=O)c1ccc(CNC(=O)c2cccc3ccn(Cc4ccc(-c5ccccc5)cn4)c23)cc1] |
| 374 | 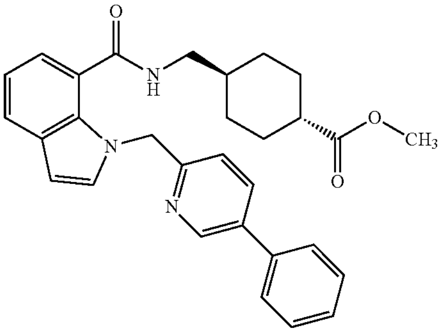 [SMILES: COC(=O)[C@H]1CC[C@H](CNC(=O)c2cccc3ccn(Cc4ccc(-c5ccccc5)cn4)c23)CC1] |
TABLE 92
| Pr | Structure |
|---|---|
| 375 | 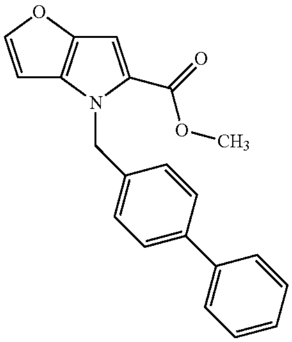 [SMILES: COC(=O)c1cc2occc2n1Cc1ccc(-c2ccccc2)cc1] |
| 376 | 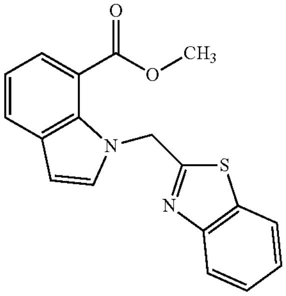 [SMILES: COC(=O)c1cccc2ccn(Cc3nc4ccccc4s3)c12] |
| 377 | 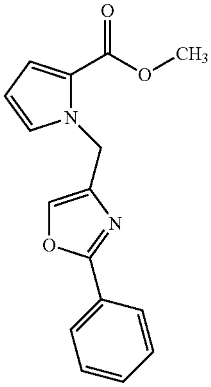 [SMILES: COC(=O)c1cccn1Cc1coc(-c2ccccc2)n1] |
TABLE 93
| Pr | Structure |
|---|---|
| 378 | 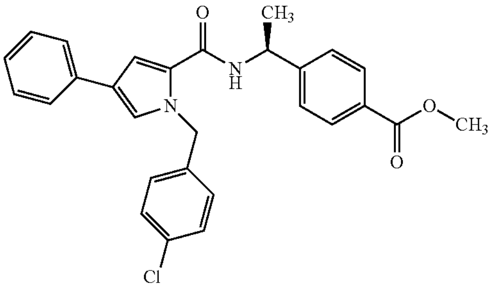 [SMILES: COC(=O)c1ccc([C@H](C)NC(=O)c2cc(-c3ccccc3)cn2Cc2ccc(Cl)cc2)cc1] |

TABLE 93-continued
| Pr | Structure |
|---|---|
| 379 | 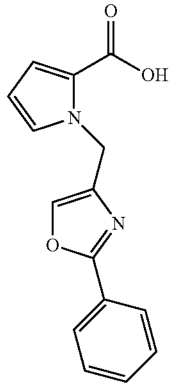 [SMILES: O=C(O)c1cccn1Cc1coc(-c2ccccc2)n1] |
| 380 | 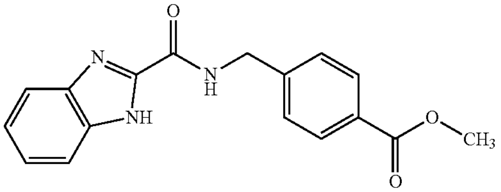 [SMILES: COC(=O)c1ccc(CNC(=O)c2nc3ccccc3[nH]2)cc1] |
| 381 | 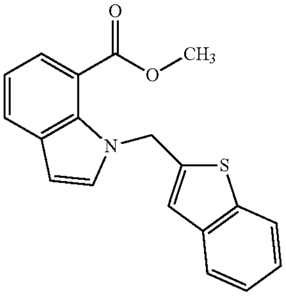 [SMILES: COC(=O)c1cccc2ccn(Cc3cc4ccccc4s3)c12] |
TABLE 94
| Pr | Structure |
|---|---|
| 382 | 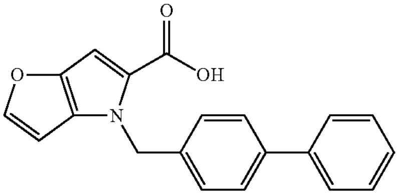 [SMILES: O=C(O)c1cc2occc2n1Cc1ccc(-c2ccccc2)cc1] |
| 383 | 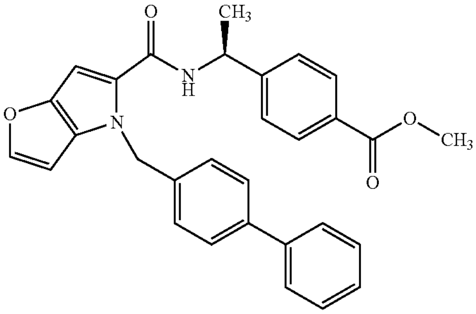 [SMILES: COC(=O)c1ccc([C@H](C)NC(=O)c2cc3occc3n2Cc2ccc(-c3ccccc3)cc2)cc1] |
TABLE 94-continued
| Pr | Structure |
|---|---|
| 384 | 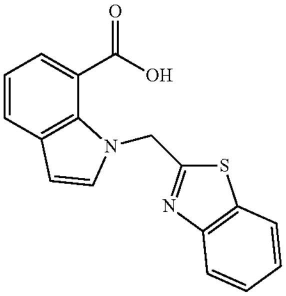 [SMILES: O=C(O)c1cccc2ccn(Cc3nc4ccccc4s3)c12] |
| 385 | 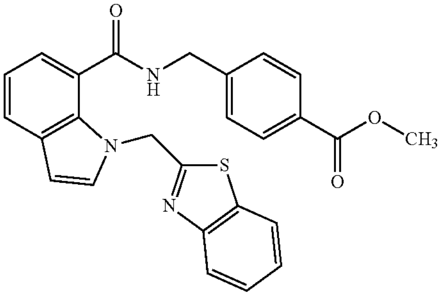 [SMILES: COC(=O)c1ccc(CNC(=O)c2cccc3ccn(Cc4nc5ccccc5s4)c23)cc1] |
TABLE 95
| Pr | Structure |
|---|---|
| 386 | 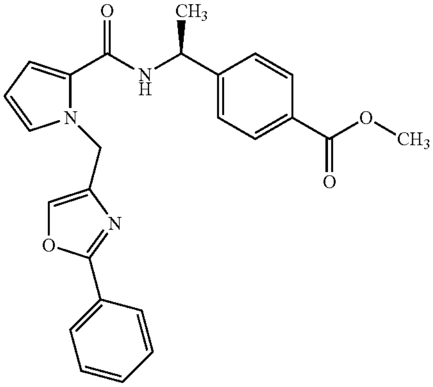 [SMILES: COC(=O)c1ccc([C@H](C)NC(=O)c2cccn2Cc2coc(-c3ccccc3)n2)cc1] |
| 387 | 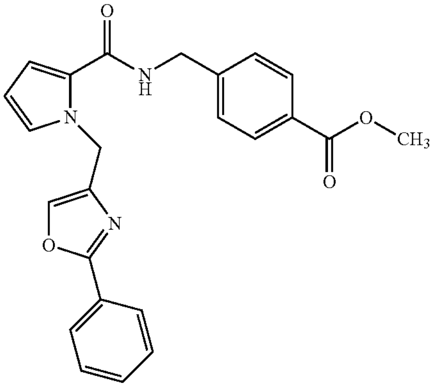 [SMILES: COC(=O)c1ccc(CNC(=O)c2cccn2Cc2coc(-c3ccccc3)n2)cc1] |

TABLE 95-continued
| Pr | Structure |
| --- | --- |
| 388 | 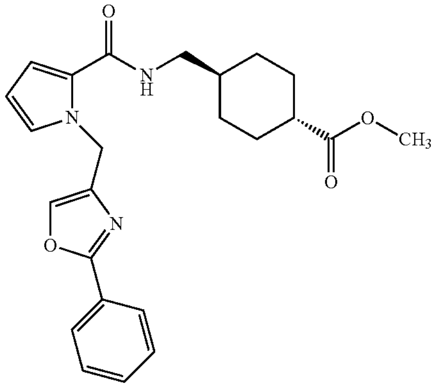 [SMILES: COC(=O)[C@H]1CC[C@H](CNC(=O)c2cccn2Cc2coc(-c3ccccc3)n2)CC1] |
TABLE 96
| Pr | Structure |
| --- | --- |
| 389 | 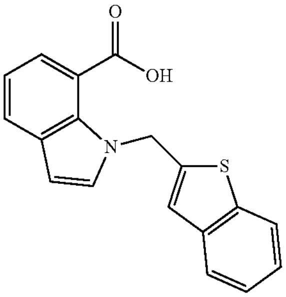 [SMILES: O=C(O)c1cccc2ccn(Cc3cc4ccccc4s3)c12] |
| 390 | 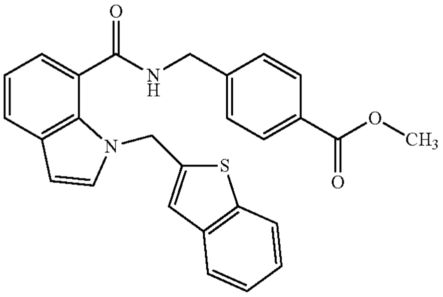 |
| 391 | 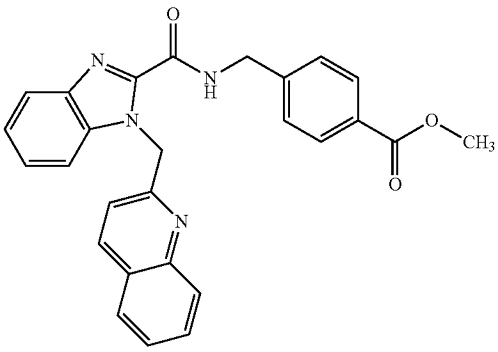 [SMILES: COC(=O)c1ccc(CNC(=O)c2nc3ccccc3n2Cc2ccc3ccccc3n2)cc1] |
TABLE 96-continued
| Pr | Structure |
| --- | --- |
| 392 | 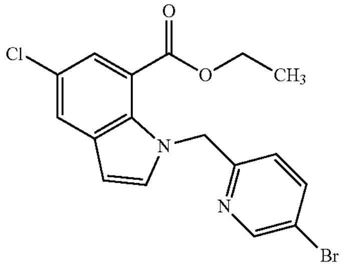 [SMILES: CCOC(=O)c1cc(Cl)cc2ccn(Cc3ccc(Br)cn3)c12] |
TABLE 97
| Pr | Structure |
| --- | --- |
| 393 | 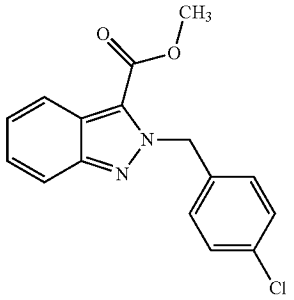 [SMILES: COC(=O)c1c2ccccc2nn1Cc1ccc(Cl)cc1] |
| 394 | 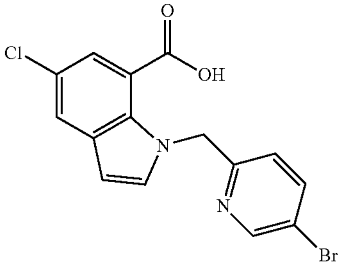 [SMILES: O=C(O)c1cc(Cl)cc2ccn(Cc3ccc(Br)cn3)c12] |
| 395 | 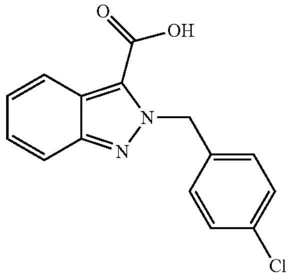 [SMILES: O=C(O)c1c2ccccc2nn1Cc1ccc(Cl)cc1] |
| 396 | 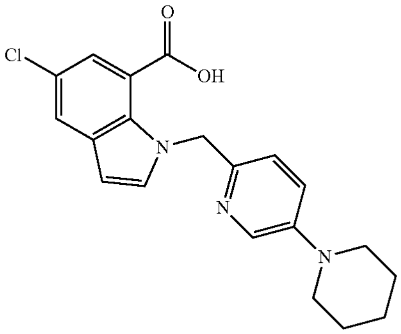 [SMILES: O=C(O)c1cc(Cl)cc2ccn(Cc3ccc(N4CCCCC4)cn3)c12] |

TABLE 97-continued
| Pr | Structure |
|---|---|
TABLE 98
| Pr | Structure |
|---|---|
| 397 | 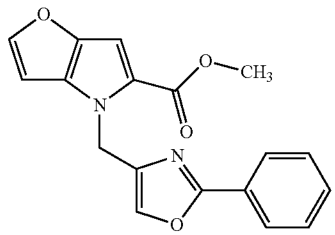 [SMILES: COC(=O)c1cc2occc2n1Cc1coc(-c2ccccc2)n1] |
| 398 | 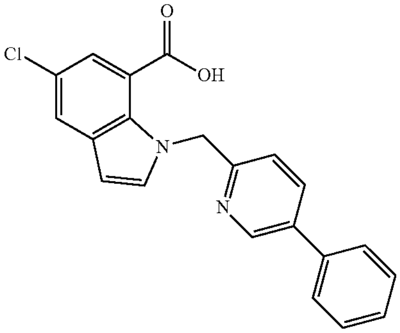 |
| 399 | 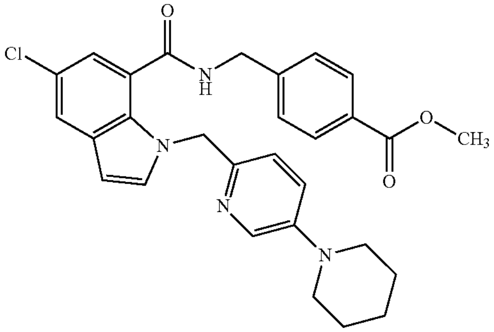 [SMILES: COC(=O)c1ccc(CNC(=O)c2cc(Cl)cc3ccn(Cc4ccc(N5CCCCC5)cn4)c23)cc1] |
| 400 | 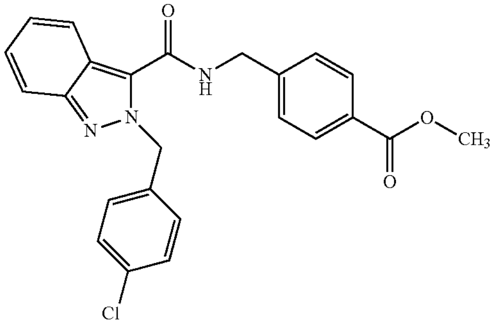 [SMILES: COC(=O)c1ccc(CNC(=O)c2c3ccccc3nn2Cc2ccc(Cl)cc2)cc1] |
TABLE 99
| Pr | Structure |
|---|---|
| 401 | 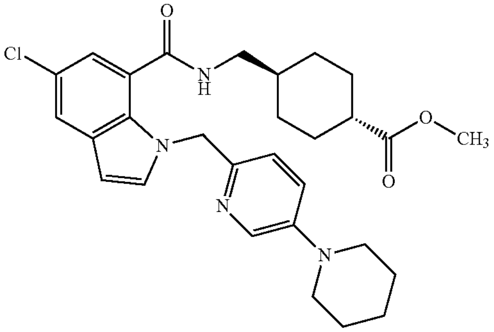 [SMILES: COC(=O)[C@H]1CC[C@H](CNC(=O)c2cc(Cl)cc3ccn(Cc4ccc(N5CCCCC5)cn4)c23)CC1] |
| 402 | 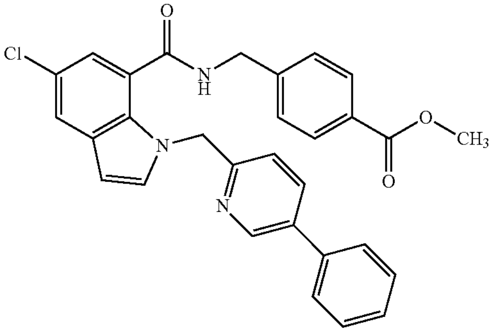 |
| 403 | 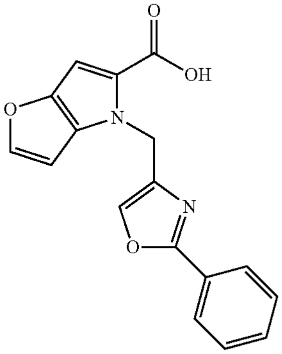 [SMILES: O=C(O)c1cc2occc2n1Cc1coc(-c2ccccc2)n1] |
TABLE 100
| Pr | Structure |
|---|---|
| 404 | 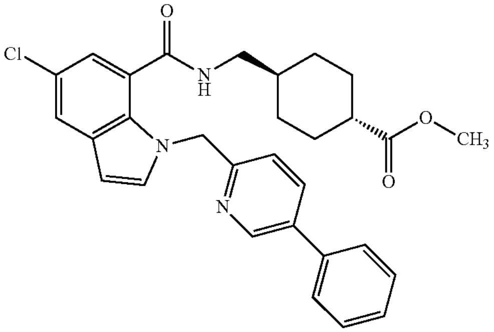 |

TABLE 100-continued
| Pr | Structure |
|---|---|
| 405 | 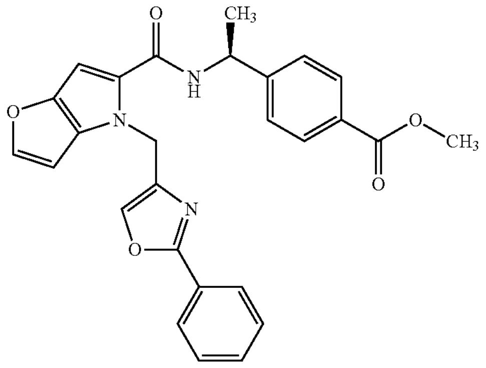 [SMILES: COC(=O)c1ccc([C@H](C)NC(=O)c2cc3occc3n2Cc2coc(-c3ccccc3)n2)cc1] |
| 406 | 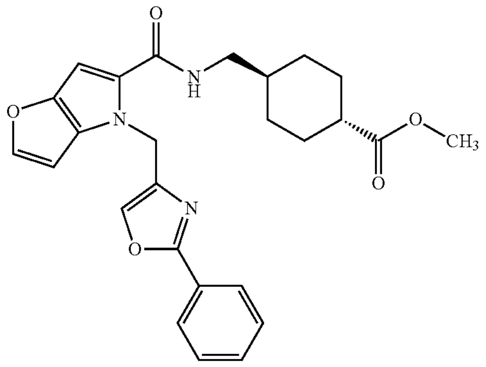 [SMILES: COC(=O)[C@H]1CC[C@H](CNC(=O)c2cc3occc3n2Cc2coc(-c3ccccc3)n2)CC1] |
TABLE 101
| Pr | Structure |
|---|---|
| 407 | 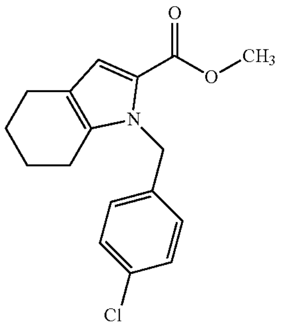 [SMILES: COC(=O)c1cc2c(n1Cc1ccc(Cl)cc1)CCCC2] |
| 408 | 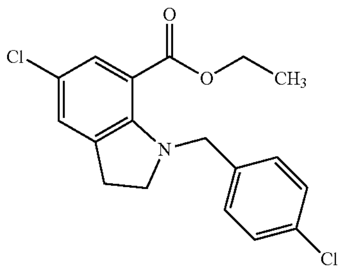 [SMILES: CCOC(=O)c1cc(Cl)cc2c1N(Cc1ccc(Cl)cc1)CC2] |
TABLE 101-continued
| Pr | Structure |
|---|---|
| 409 | 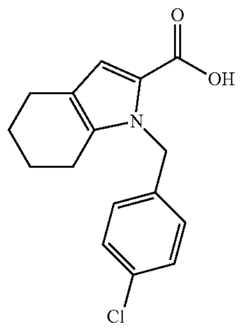 [SMILES: O=C(O)c1cc2c(n1Cc1ccc(Cl)cc1)CCCC2] |
| 410 | 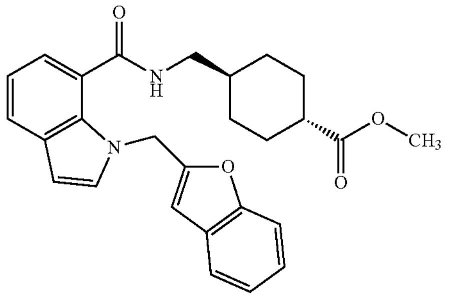 [SMILES: COC(=O)[C@H]1CC[C@H](CNC(=O)c2cccc3ccn(Cc4cc5ccccc5o4)c23)CC1] |
TABLE 102
| Pr | Structure |
|---|---|
| 411 | 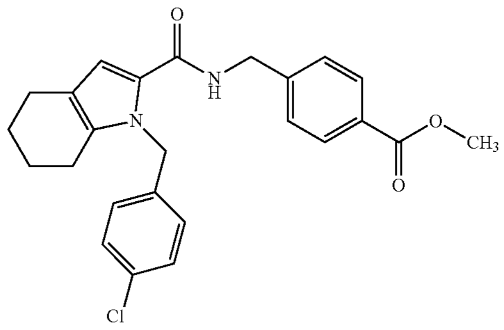 [SMILES: COC(=O)c1ccc(CNC(=O)c2cc3c(n2Cc2ccc(Cl)cc2)CCCC3)cc1] |
| 412 | 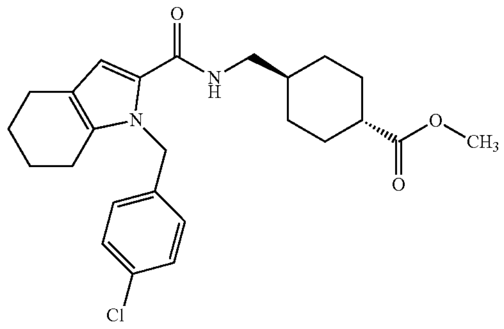 [SMILES: COC(=O)[C@H]1CC[C@H](CNC(=O)c2cc3c(n2Cc2ccc(Cl)cc2)CCCC3)CC1] |

TABLE 102-continued
| Pr | Structure |
|---|---|
| 413 | 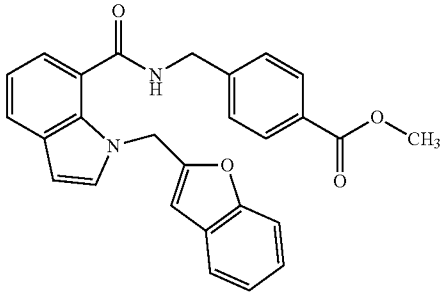 |
| 414 | 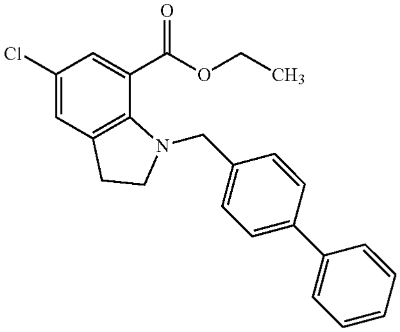 [SMILES: CCOC(=O)c1cc(Cl)cc2c1N(Cc1ccc(-c3ccccc3)cc1)CC2] |
TABLE 103
| Pr | Structure |
|---|---|
| 415 | 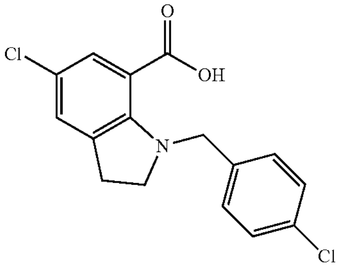 [SMILES: O=C(O)c1cc(Cl)cc2c1N(Cc1ccc(Cl)cc1)CC2] |
| 416 | 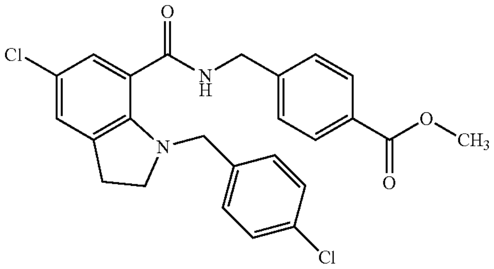 [SMILES: COC(=O)c1ccc(CNC(=O)c2cc(Cl)cc3c2N(Cc2ccc(Cl)cc2)CC3)cc1] |
| 417 | 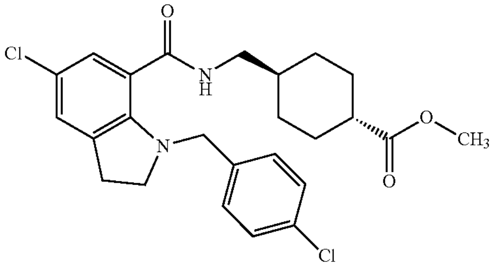 [SMILES: COC(=O)[C@H]1CC[C@H](CNC(=O)c2cc(Cl)cc3c2N(Cc2ccc(Cl)cc2)CC3)CC1] |
TABLE 103-continued
| Pr | Structure |
|---|---|
| 418 | 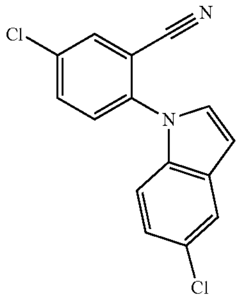 [SMILES: N#Cc1cc(Cl)ccc1-n1ccc2cc(Cl)ccc21] |
TABLE 104
| Pr | Structure |
|---|---|
| 419 | 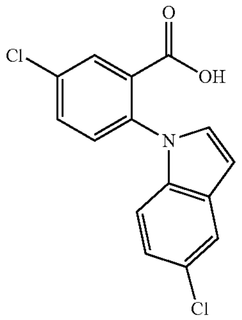 [SMILES: O=C(O)c1cc(Cl)ccc1-n1ccc2cc(Cl)ccc21] |
| 420 | 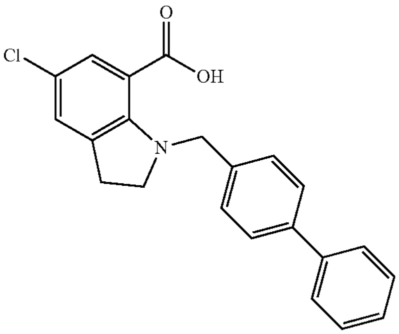 [SMILES: O=C(O)c1cc(Cl)cc2c1N(Cc1ccc(-c3ccccc3)cc1)CC2] |
| 421 | 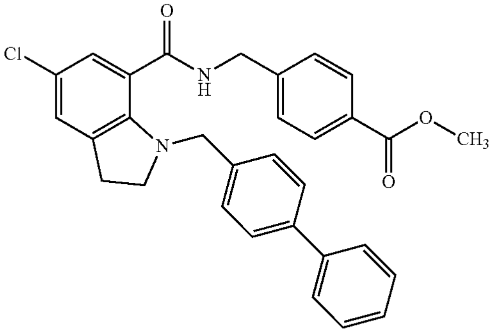 [SMILES: COC(=O)c1ccc(CNC(=O)c2cc(Cl)cc3c2N(Cc2ccc(-c4ccccc4)cc2)CC3)cc1] |

TABLE 105
| Pr | Structure |
|---|---|
| 422 | 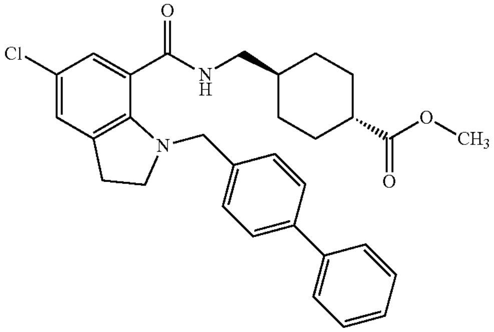 [SMILES: COC(=O)[C@H]1CC[C@H](CNC(=O)c2cc(Cl)cc3c2N(Cc2ccc(-c4ccccc4)cc2)CC3)CC1] |
| 423 | 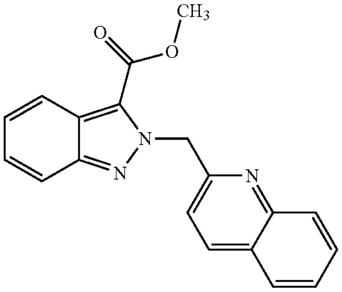 [SMILES: COC(=O)c1c2ccccc2nn1Cc1ccc2ccccc2n1] |
| 424 | 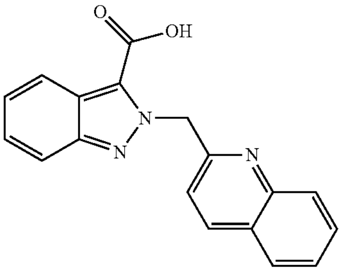 [SMILES: O=C(O)c1c2ccccc2nn1Cc1ccc2ccccc2n1] |
| 425 | 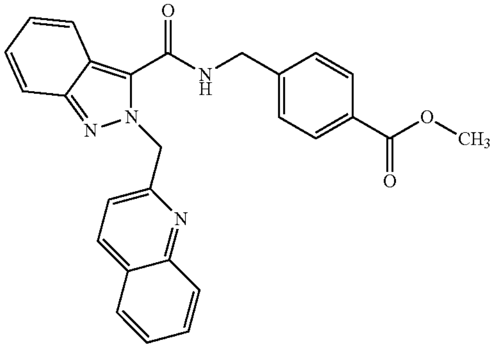 [SMILES: COC(=O)c1ccc(CNC(=O)c2c3ccccc3nn2Cc2ccc3ccccc3n2)cc1] |
TABLE 106
| Pr | Structure |
|---|---|
| 426 | 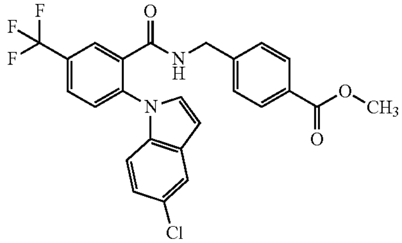 [SMILES: COC(=O)c1ccc(CNC(=O)c2cc(C(F)(F)F)ccc2-n2ccc3cc(Cl)ccc32)cc1] |
| 427 | 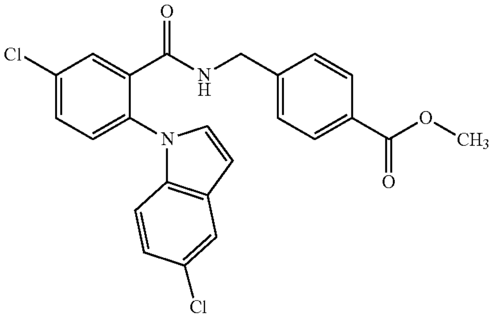 [SMILES: COC(=O)c1ccc(CNC(=O)c2cc(Cl)ccc2-n2ccc3cc(Cl)ccc32)cc1] |
| 428 | 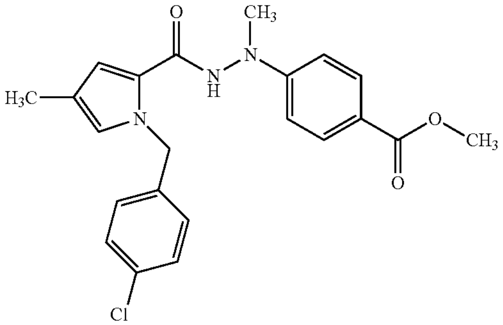 |
| 429 | 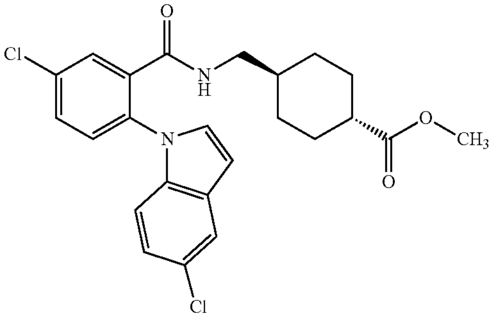 [SMILES: COC(=O)[C@H]1CC[C@H](CNC(=O)c2cc(Cl)ccc2-n2ccc3cc(Cl)ccc32)CC1] |

TABLE 107
| Pr | Structure |
| --- | --- |
| 430 | 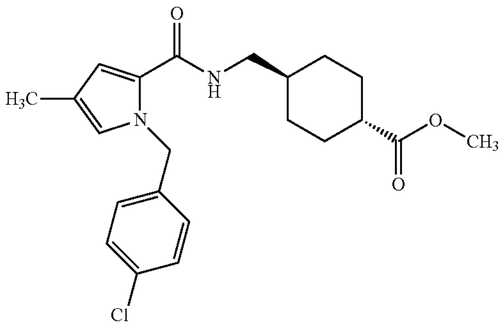 |
| 431 | 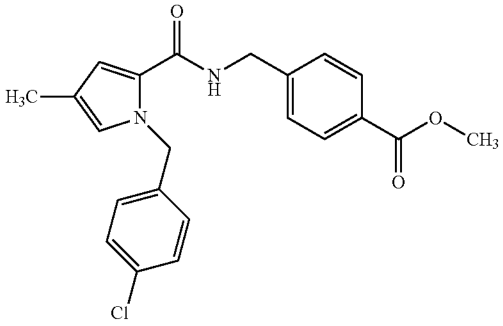 |
| 432 | 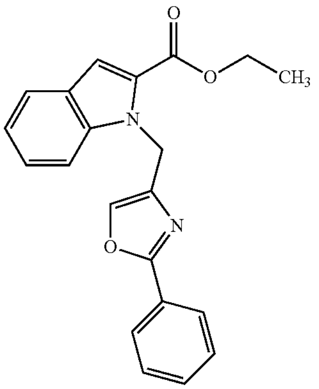 [SMILES: CCOC(=O)c1cc2ccccc2n1Cc1coc(-c2ccccc2)n1] |
TABLE 108
| Pr | Structure |
| --- | --- |
| 433 | 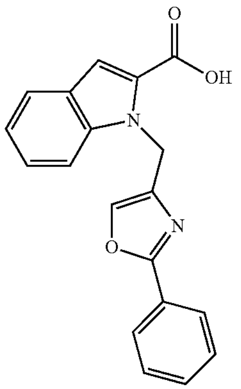 [SMILES: O=C(O)c1cc2ccccc2n1Cc1coc(-c2ccccc2)n1] |
TABLE 108-continued
| Pr | Structure |
| --- | --- |
| 434 | 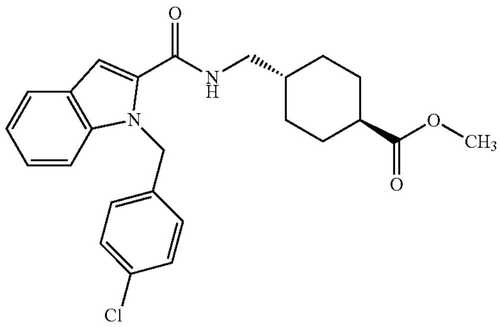 [SMILES: COC(=O)[C@H]1CC[C@H](CNC(=O)c2cc3ccccc3n2Cc2ccc(Cl)cc2)CC1] |
| 435 | 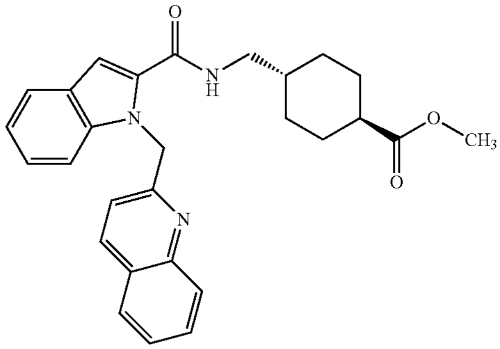 [SMILES: COC(=O)[C@H]1CC[C@H](CNC(=O)c2cc3ccccc3n2Cc2ccc3ccccc3n2)CC1] |
TABLE 109
| Pr | Structure |
| --- | --- |
| 436 | 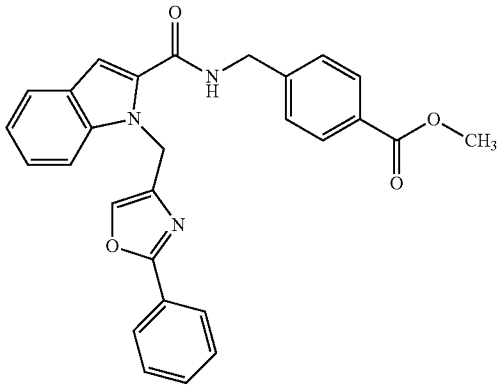 [SMILES: COC(=O)c1ccc(CNC(=O)c2cc3ccccc3n2Cc2coc(-c3ccccc3)n2)cc1] |
| 437 | 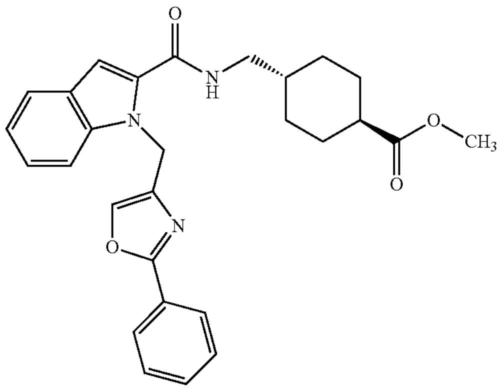 [SMILES: COC(=O)[C@H]1CC[C@H](CNC(=O)c2cc3ccccc3n2Cc2coc(-c3ccccc3)n2)CC1] |

TABLE 109-continued
| Pr | Structure |
|---|---|
| 438 | 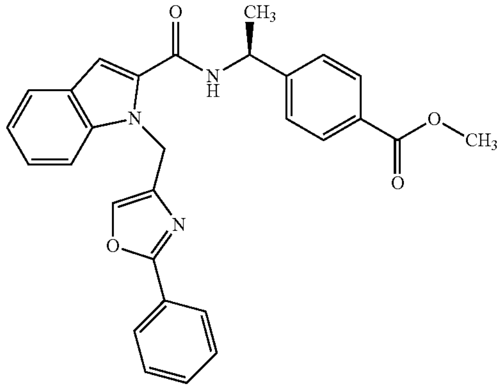 [SMILES: COC(=O)c1ccc([C@H](C)NC(=O)c2cc3ccccc3n2Cc2coc(-c3ccccc3)n2)cc1] |
TABLE 110
| Pr | Structure |
|---|---|
| 439 | 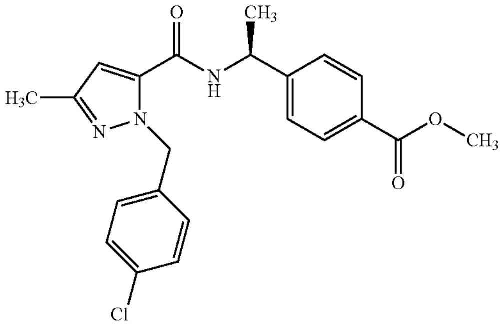 |
| 440 | 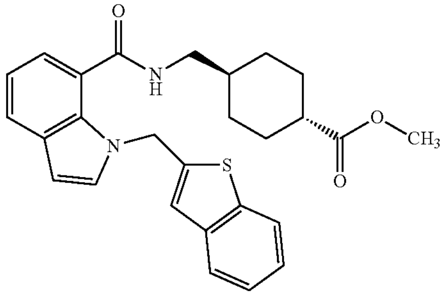 [SMILES: COC(=O)[C@H]1CC[C@H](CNC(=O)c2cccc3ccn(Cc4cc5ccccc5s4)c23)CC1] |
| 441 | 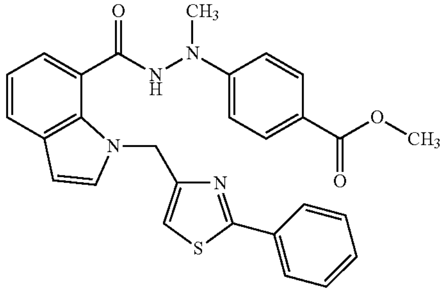 [SMILES: COC(=O)c1ccc(N(C)NC(=O)c2cccc3ccn(Cc4csc(-c5ccccc5)n4)c23)cc1] |
TABLE 110-continued
| Pr | Structure |
|---|---|
| 442 | 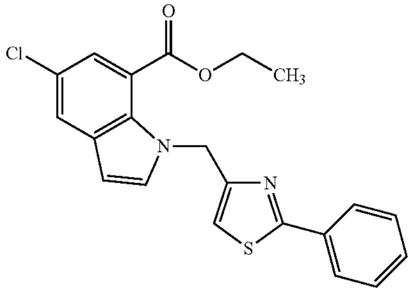 [SMILES: CCOC(=O)c1cc(Cl)cc2ccn(Cc3csc(-c4ccccc4)n3)c12] |
TABLE 111
| Pr | Structure |
|---|---|
| 443 | 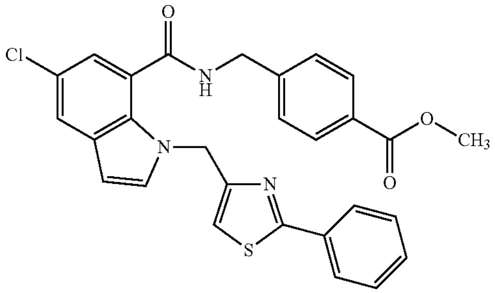 [SMILES: COC(=O)c1ccc(CNC(=O)c2cc(Cl)cc3ccn(Cc4csc(-c5ccccc5)n4)c23)cc1] |
| 444 | 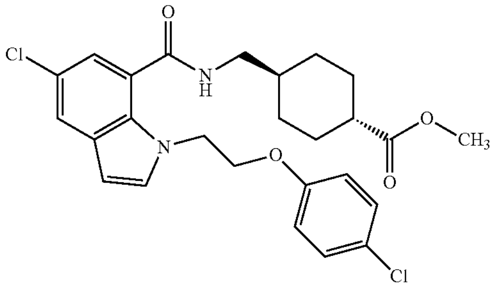 [SMILES: COC(=O)[C@H]1CC[C@H](CNC(=O)c2cc(Cl)cc3ccn(CCOc4ccc(Cl)cc4)c23)CC1] |
| 445 | 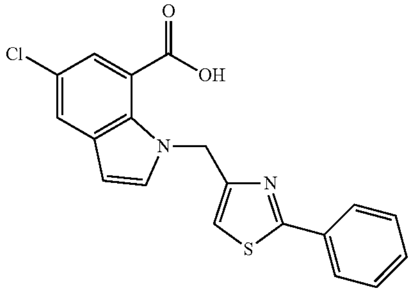 [SMILES: O=C(O)c1cc(Cl)cc2ccn(Cc3csc(-c4ccccc4)n3)c12] |
| 446 | 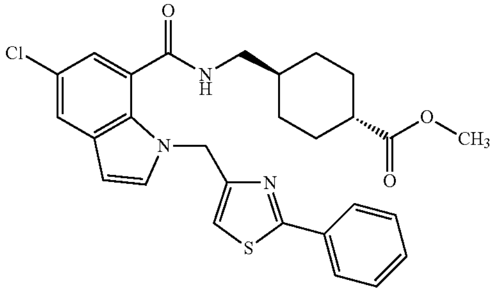 [SMILES: COC(=O)[C@H]1CC[C@H](CNC(=O)c2cc(Cl)cc3ccn(Cc4csc(-c5ccccc5)n4)c23)CC1] |

TABLE 112
| Pr | Structure |
| --- | --- |
| 447 | 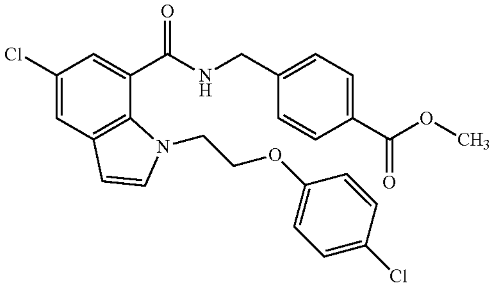 [SMILES: COC(=O)c1ccc(CNC(=O)c2cc(Cl)cc3ccn(CCOc4ccc(Cl)cc4)c23)cc1] |
| 448 | 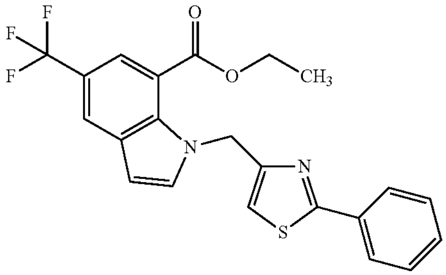 [SMILES: CCOC(=O)c1cc(C(F)(F)F)cc2ccn(Cc3csc(-c4ccccc4)n3)c12] |
| 449 | 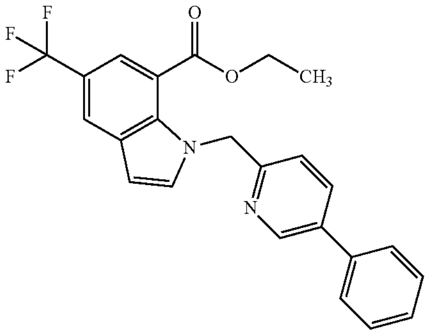 [SMILES: CCOC(=O)c1cc(C(F)(F)F)cc2ccn(Cc3ccc(-c4ccccc4)cn3)c12] |
| 450 | 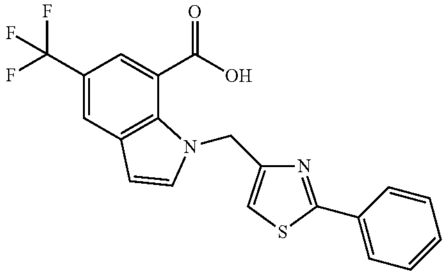 [SMILES: O=C(O)c1cc(C(F)(F)F)cc2ccn(Cc3csc(-c4ccccc4)n3)c12] |
TABLE 113
| Pr | Structure |
| --- | --- |
| 451 | 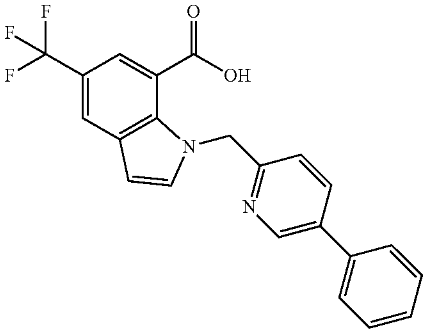 [SMILES: O=C(O)c1cc(C(F)(F)F)cc2ccn(Cc3ccc(-c4ccccc4)cn3)c12] |
| 452 | 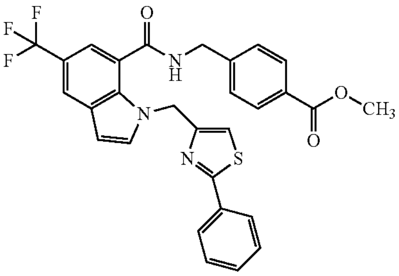 [SMILES: COC(=O)c1ccc(CNC(=O)c2cc(C(F)(F)F)cc3ccn(Cc4csc(-c5ccccc5)n4)c23)cc1] |
| 453 | 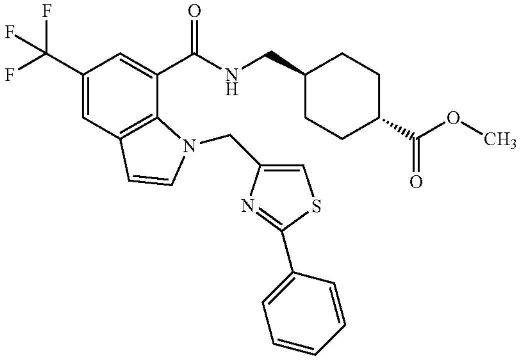 [SMILES: COC(=O)[C@H]1CC[C@H](CNC(=O)c2cc(C(F)(F)F)cc3ccn(Cc4csc(-c5ccccc5)n4)c23)CC1] |
TABLE 114
| Pr | Structure |
| --- | --- |
| 454 | 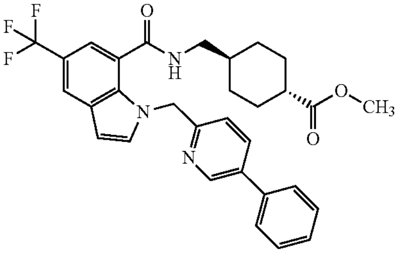 [SMILES: COC(=O)[C@H]1CC[C@H](CNC(=O)c2cc(C(F)(F)F)cc3ccn(Cc4ccc(-c5ccccc5)cn4)c23)CC1] |

TABLE 114-continued
| Pr | Structure |
| --- | --- |
| 455 | 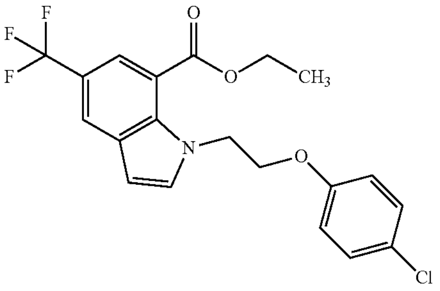 [SMILES: CCOC(=O)c1cc(C(F)(F)F)cc2ccn(CCOc3ccc(Cl)cc3)c12] |
| 456 | 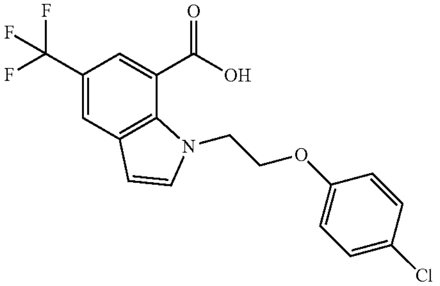 [SMILES: O=C(O)c1cc(C(F)(F)F)cc2ccn(CCOc3ccc(Cl)cc3)c12] |
| 457 | 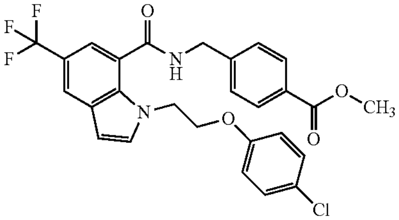 [SMILES: COC(=O)c1ccc(CNC(=O)c2cc(C(F)(F)F)cc3ccn(CCOc4ccc(Cl)cc4)c23)cc1] |
TABLE 115
| Pr | Structure |
| --- | --- |
| 458 | 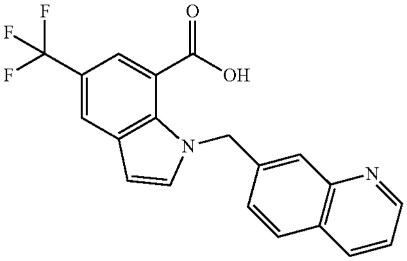 [SMILES: O=C(O)c1cc(C(F)(F)F)cc2ccn(Cc3ccc4cccnc4c3)c12] |
| 459 | 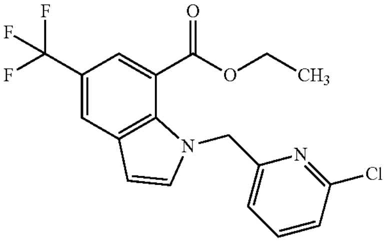 [SMILES: CCOC(=O)c1cc(C(F)(F)F)cc2ccn(Cc3cccc(Cl)n3)c12] |
TABLE 115-continued
| Pr | Structure |
| --- | --- |
| 460 | 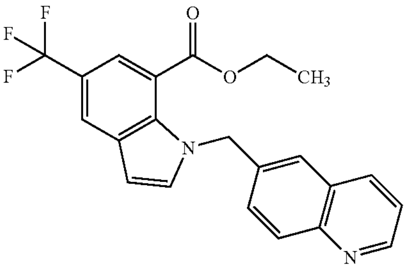 [SMILES: CCOC(=O)c1cc(C(F)(F)F)cc2ccn(Cc3ccc4ncccc4c3)c12] |
| 461 | 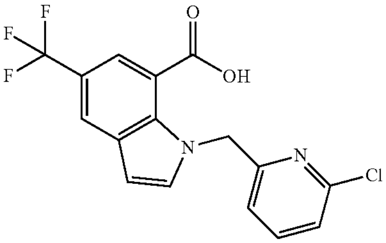 [SMILES: O=C(O)c1cc(C(F)(F)F)cc2ccn(Cc3cccc(Cl)n3)c12] |
| 462 | 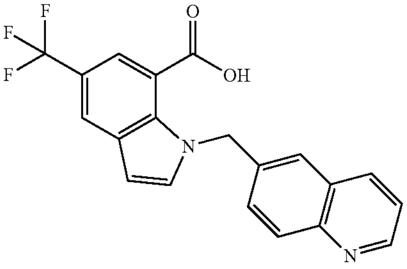 [SMILES: O=C(O)c1cc(C(F)(F)F)cc2ccn(Cc3ccc4ncccc4c3)c12] |
TABLE 116
| Pr | Structure |
| --- | --- |
| 463 | 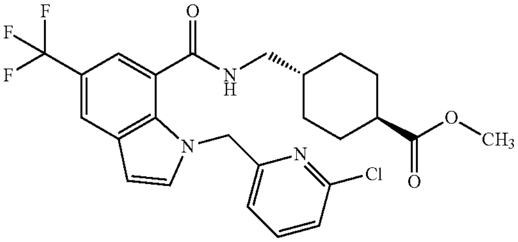 [SMILES: COC(=O)[C@H]1CC[C@H](CNC(=O)c2cc(C(F)(F)F)cc3ccn(Cc4cccc(Cl)n4)c23)CC1] |
| 464 | 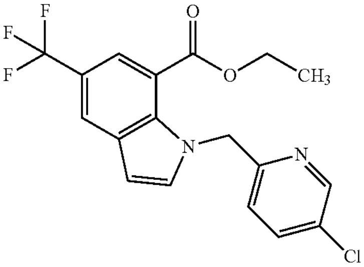 [SMILES: CCOC(=O)c1cc(C(F)(F)F)cc2ccn(Cc3ccc(Cl)cn3)c12] |

TABLE 116-continued
| Pr | Structure |
| --- | --- |
| 465 | 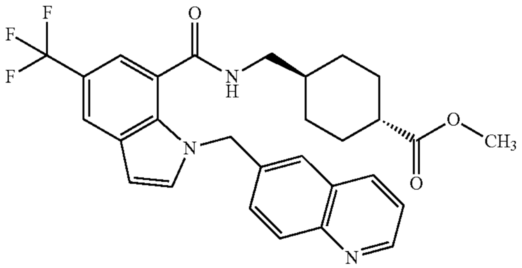 [SMILES: COC(=O)[C@H]1CC[C@H](CNC(=O)c2cc(C(F)(F)F)cc3ccn(Cc4ccc5ncccc5c4)c23)CC1] |
| 466 | 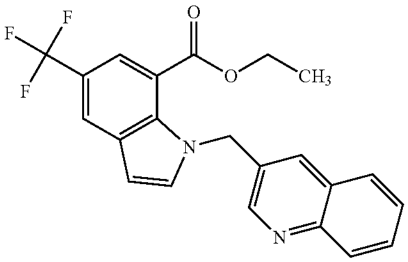 [SMILES: CCOC(=O)c1cc(C(F)(F)F)cc2ccn(Cc3cnc4ccccc4c3)c12] |
TABLE 117
| Pr | Structure |
| --- | --- |
| 467 | 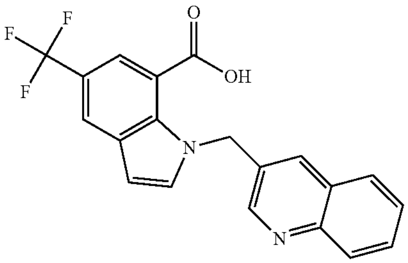 [SMILES: O=C(O)c1cc(C(F)(F)F)cc2ccn(Cc3cnc4ccccc4c3)c12] |
| 468 | 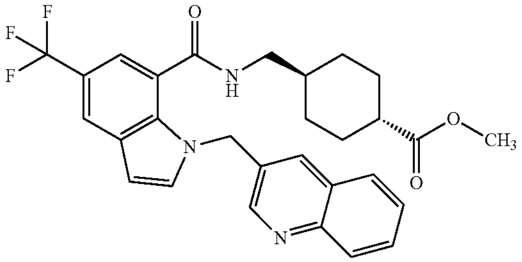 [SMILES: COC(=O)[C@H]1CC[C@H](CNC(=O)c2cc(C(F)(F)F)cc3ccn(Cc4cnc5ccccc5c4)c23)CC1] |
| 469 | 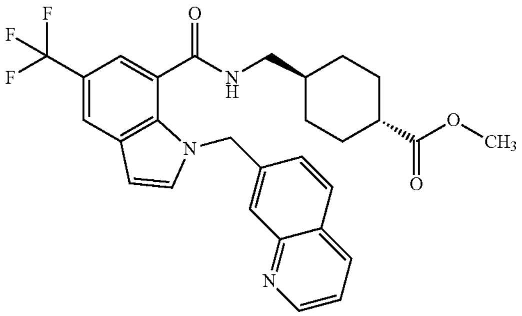 [SMILES: COC(=O)[C@H]1CC[C@H](CNC(=O)c2cc(C(F)(F)F)cc3ccn(Cc4ccc5cccnc5c4)c23)CC1] |
TABLE 117-continued
| Pr | Structure |
| --- | --- |
| 470 | 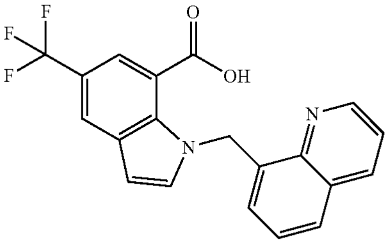 [SMILES: O=C(O)c1cc(C(F)(F)F)cc2ccn(Cc3cccc4cccnc34)c12] |
TABLE 118
| Pr | Structure |
| --- | --- |
| 471 | 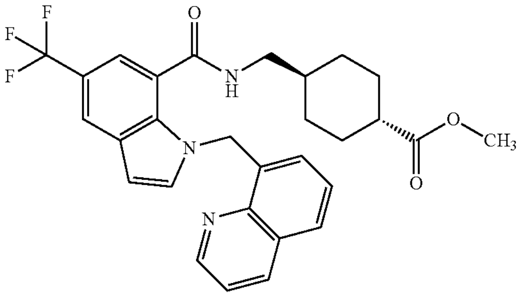 [SMILES: COC(=O)[C@H]1CC[C@H](CNC(=O)c2cc(C(F)(F)F)cc3ccn(Cc4cccc5cccnc45)c23)CC1] |
| 472 | 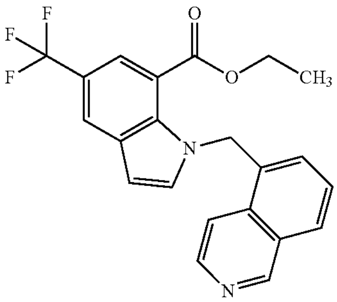 [SMILES: CCOC(=O)c1cc(C(F)(F)F)cc2ccn(Cc3cccc4cnccc34)c12] |
| 473 | 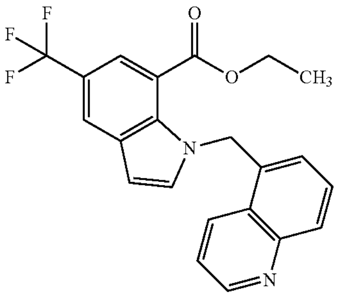 [SMILES: CCOC(=O)c1cc(C(F)(F)F)cc2ccn(Cc3cccc4ncccc34)c12] |
| 474 | 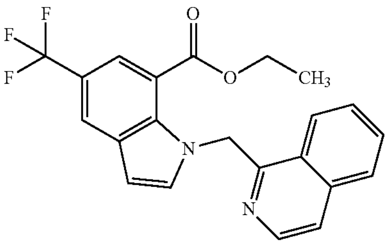 [SMILES: CCOC(=O)c1cc(C(F)(F)F)cc2ccn(Cc3nccc4ccccc34)c12] |

TABLE 119
| Pr | Structure |
|---|---|
| 475 | 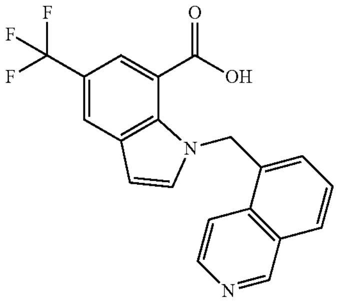 [SMILES: O=C(O)c1cc(C(F)(F)F)cc2ccn(Cc3cccc4cnccc34)c12] |
| 476 | 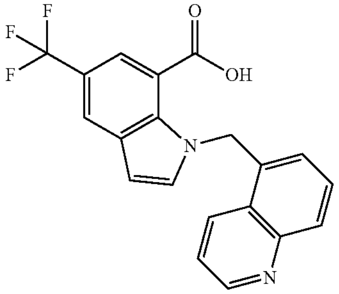 [SMILES: O=C(O)c1cc(C(F)(F)F)cc2ccn(Cc3cccc4ncccc34)c12] |
| 477 | 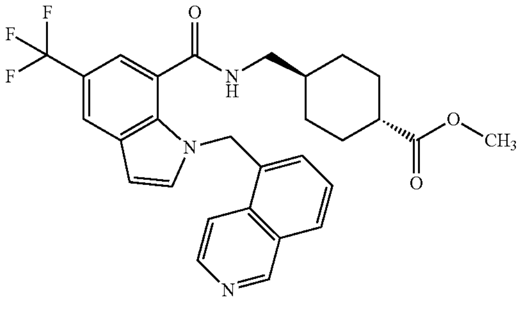 [SMILES: COC(=O)[C@H]1CC[C@H](CNC(=O)c2cc(C(F)(F)F)cc3ccn(Cc4cccc5cnccc45)c23)CC1] |
| 478 | 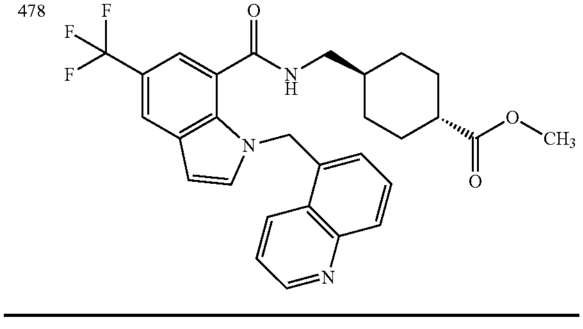 |
TABLE 120
| Pr | Structure |
|---|---|
| 479 | 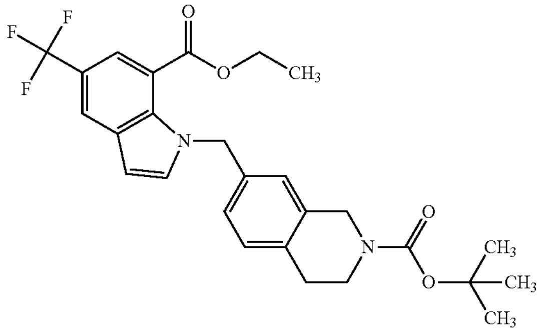 [SMILES: CCOC(=O)c1cc(C(F)(F)F)cc2ccn(Cc3ccc4c(c3)CN(C(=O)OC(C)(C)C)CC4)c12] |
| 480 | 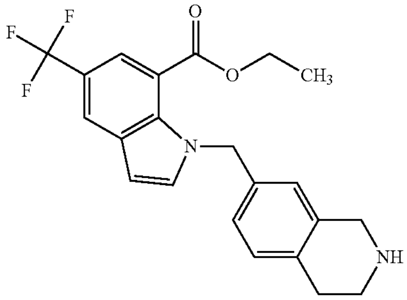 [SMILES: CCOC(=O)c1cc(C(F)(F)F)cc2ccn(Cc3ccc4c(c3)CNCC4)c12] |
| 481 | 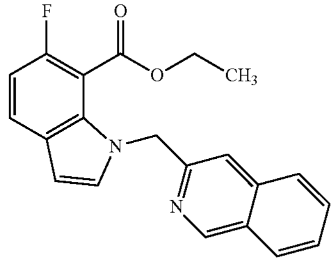 [SMILES: CCOC(=O)c1c(F)ccc2ccn(Cc3cc4ccccc4cn3)c12] |
| 482 | 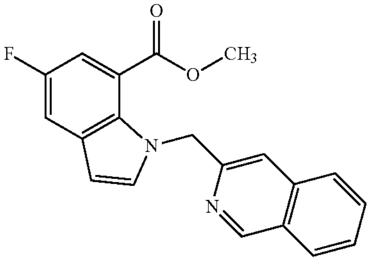 [SMILES: COC(=O)c1cc(F)cc2ccn(Cc3cc4ccccc4cn3)c12] |
TABLE 121
| Pr | Structure |
|---|---|
| 483 | 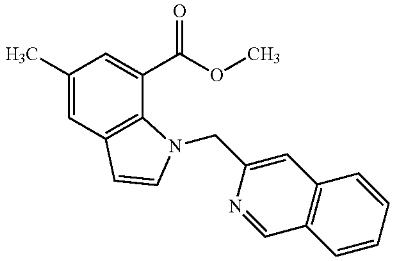 [SMILES: COC(=O)c1cc(C)cc2ccn(Cc3cc4ccccc4cn3)c12] |

TABLE 121-continued
| Pr | Structure |
|---|---|
| 484 | 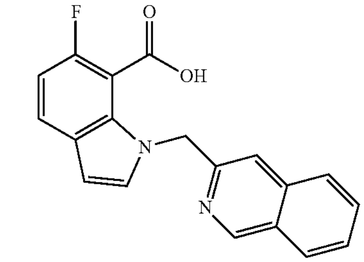 [SMILES: O=C(O)c1c(F)ccc2ccn(Cc3cc4ccccc4cn3)c12] |
| 485 | 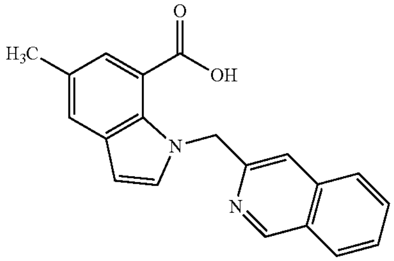 [SMILES: Cc1cc(C(=O)O)c2c(ccn2Cc2cc3ccccc3cn2)c1] |
| 486 | 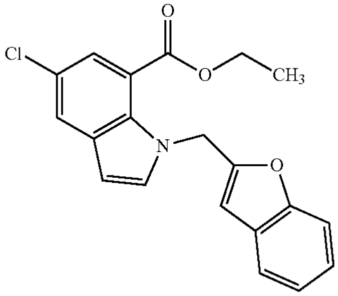 [SMILES: CCOC(=O)c1cc(Cl)cc2ccn(Cc3cc4ccccc4o3)c12] |
TABLE 122
| Pr | Structure |
|---|---|
| 487 | 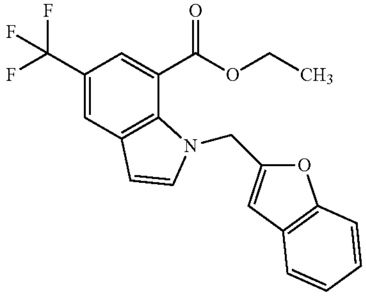 [SMILES: CCOC(=O)c1cc(C(F)(F)F)cc2ccn(Cc3cc4ccccc4o3)c12] |
| 488 | 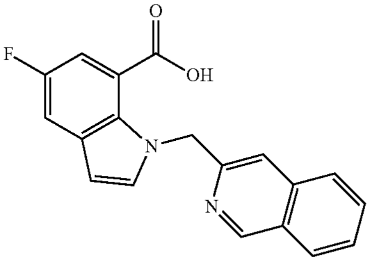 [SMILES: O=C(O)c1cc(F)cc2ccn(Cc3cc4ccccc4cn3)c12] |
TABLE 122-continued
| Pr | Structure |
|---|---|
| 489 | 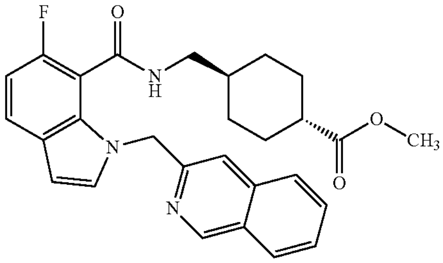 [SMILES: COC(=O)[C@H]1CC[C@H](CNC(=O)c2c(F)ccc3ccn(Cc4cc5ccccc5cn4)c23)CC1] |
| 490 | 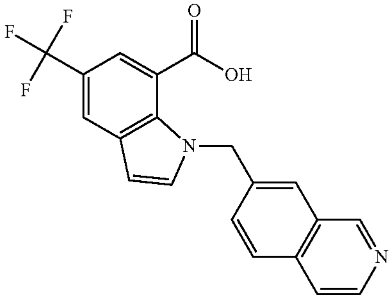 [SMILES: O=C(O)c1cc(C(F)(F)F)cc2ccn(Cc3ccc4ccncc4c3)c12] |
TABLE 123
| Pr | Structure |
|---|---|
| 491 | 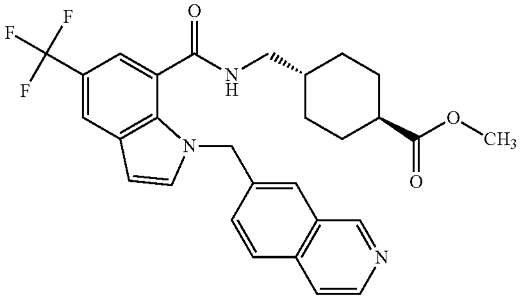 [SMILES: COC(=O)[C@H]1CC[C@H](CNC(=O)c2cc(C(F)(F)F)cc3ccn(Cc4ccc5ccncc5c4)c23)CC1] |
| 492 | 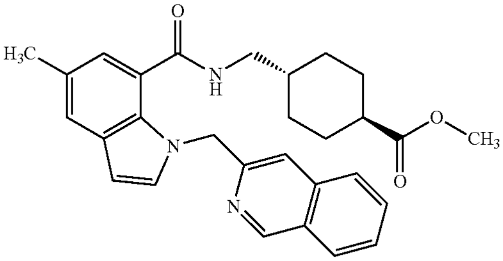 |
| 493 | 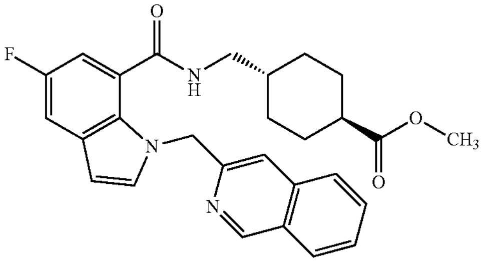 [SMILES: COC(=O)[C@H]1CC[C@H](CNC(=O)c2cc(F)cc3ccn(Cc4cc5ccccc5cn4)c23)CC1] |

TABLE 123-continued
| Pr | Structure |
|---|---|
| 494 | 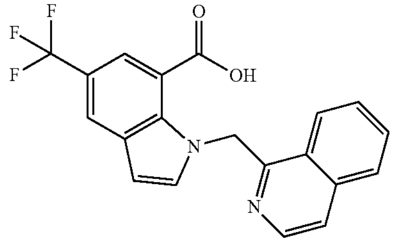 [SMILES: O=C(O)c1cc(C(F)(F)F)cc2ccn(Cc3nccc4ccccc34)c12] |
TABLE 124
| Pr | Structure |
|---|---|
| 495 | 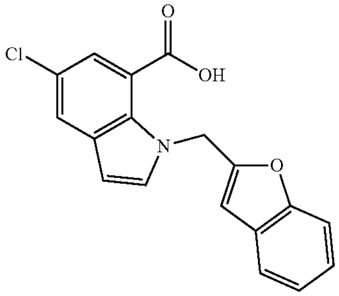 [SMILES: O=C(O)c1cc(Cl)cc2ccn(Cc3cc4ccccc4o3)c12] |
| 496 | 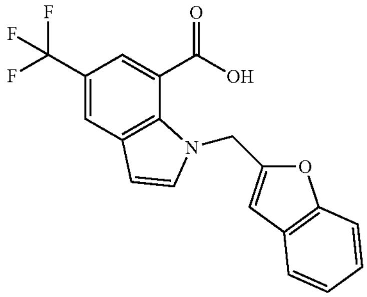 [SMILES: O=C(O)c1cc(C(F)(F)F)cc2ccn(Cc3cc4ccccc4o3)c12] |
| 497 | 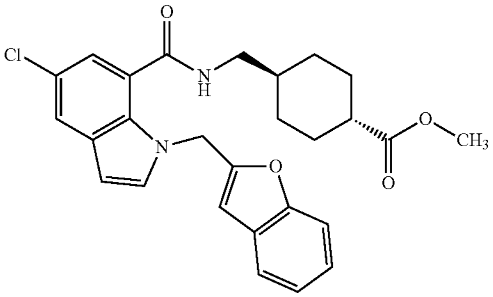 [SMILES: COC(=O)[C@H]1CC[C@H](CNC(=O)c2cc(Cl)cc3ccn(Cc4cc5ccccc5o4)c23)CC1] |
| 498 | 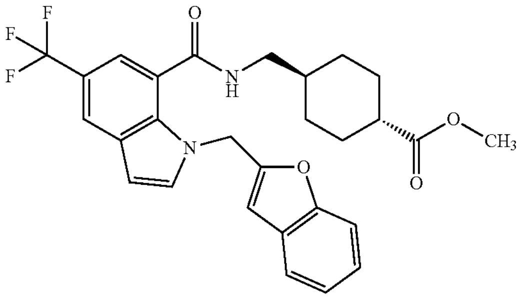 [SMILES: COC(=O)[C@H]1CC[C@H](CNC(=O)c2cc(C(F)(F)F)cc3ccn(Cc4cc5ccccc5o4)c23)CC1] |
TABLE 125
| Pr | Structure |
|---|---|
| 499 | 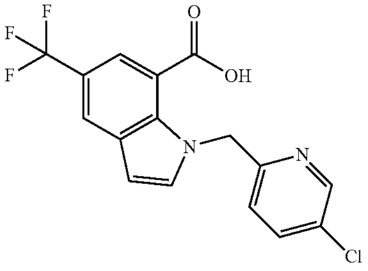 [SMILES: O=C(O)c1cc(C(F)(F)F)cc2ccn(Cc3ccc(Cl)cn3)c12] |
| 500 | 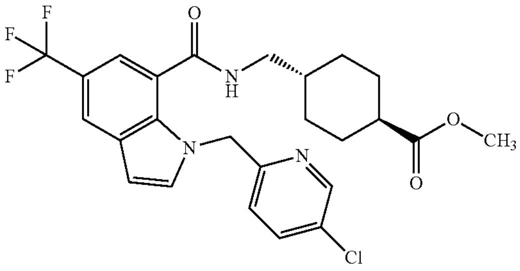 [SMILES: COC(=O)[C@H]1CC[C@H](CNC(=O)c2cc(C(F)(F)F)cc3ccn(Cc4ccc(Cl)cn4)c23)CC1] |
| 501 | 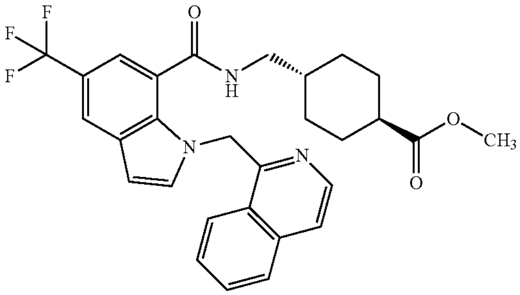 [SMILES: COC(=O)[C@H]1CC[C@H](CNC(=O)c2cc(C(F)(F)F)cc3ccn(Cc4nccc5ccccc45)c23)CC1] |
| 502 | 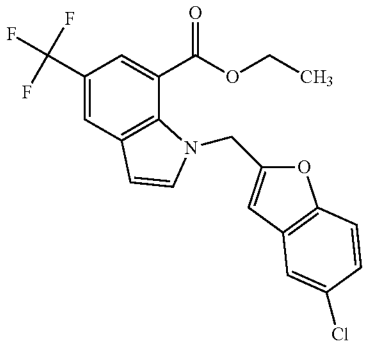 [SMILES: CCOC(=O)c1cc(C(F)(F)F)cc2ccn(Cc3cc4cc(Cl)ccc4o3)c12] |

TABLE 126
| Pr | Structure |
| --- | --- |
| 503 | 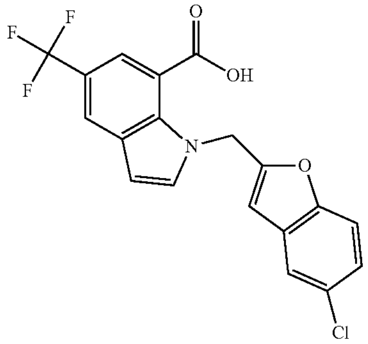 [SMILES: O=C(O)c1cc(C(F)(F)F)cc2ccn(Cc3cc4cc(Cl)ccc4o3)c12] |
| 504 | 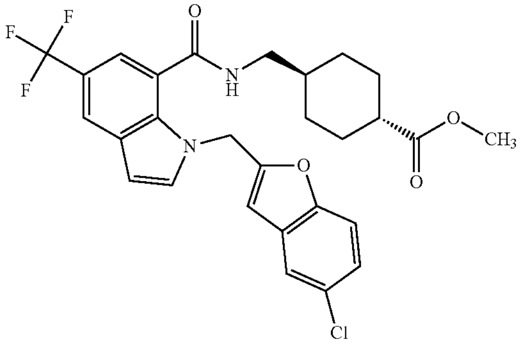 [SMILES: COC(=O)[C@H]1CC[C@H](CNC(=O)c2cc(C(F)(F)F)cc3ccn(Cc4cc5cc(Cl)ccc5o4)c23)CC1] |
| 505 | 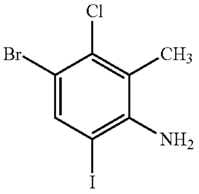 |
| 506 | 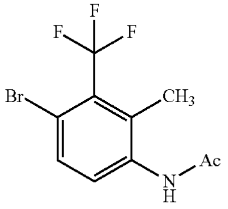 [SMILES: CC(=O)Nc1ccc(Br)c(C(F)(F)F)c1C] |
TABLE 127
| Pr | Structure |
| --- | --- |
| 507 | 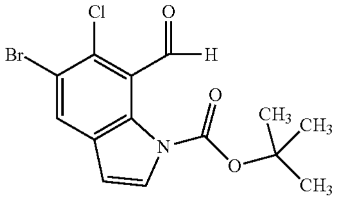 [SMILES: CC(C)(C)OC(=O)n1ccc2cc(Br)c(Cl)c(C=O)c21] |
TABLE 127-continued
| Pr | Structure |
| --- | --- |
| 508 | 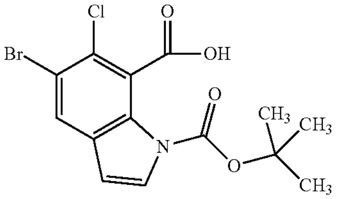 [SMILES: CC(C)(C)OC(=O)n1ccc2cc(Br)c(Cl)c(C(=O)O)c21] |
| 509 | 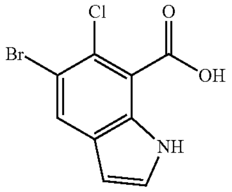 [SMILES: O=C(O)c1c(Cl)c(Br)cc2cc[nH]c12] |
| 510 | 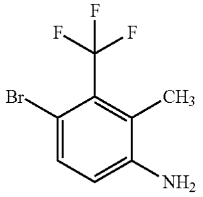 |
| 511 | 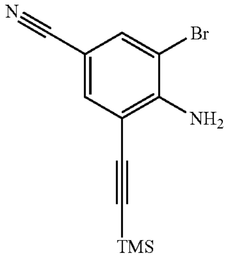 [SMILES: C[Si](C)(C)C#Cc1cc(C#N)cc(Br)c1N] |
TABLE 128
| Pr | Structure |
| --- | --- |
| 512 | 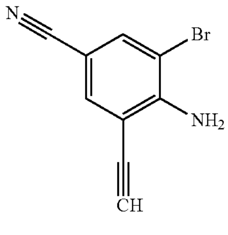 |
| 513 | 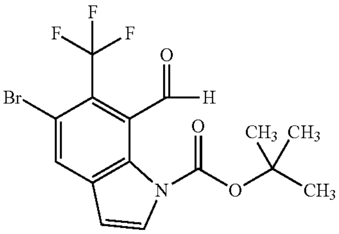 [SMILES: CC(C)(C)OC(=O)n1ccc2cc(Br)c(C(F)(F)F)c(C=O)c21] |

TABLE 128-continued
| Pr | Structure |
| --- | --- |
| 514 | 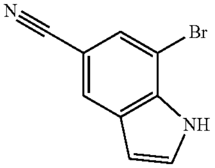 [SMILES: N#Cc1cc(Br)c2[nH]ccc2c1] |
| 515 | 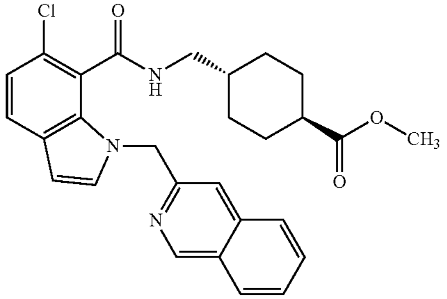 [SMILES: COC(=O)[C@H]1CC[C@H](CNC(=O)c2c(Cl)ccc3ccn(Cc4cc5ccccc5cn4)c23)CC1] |
| 516 | 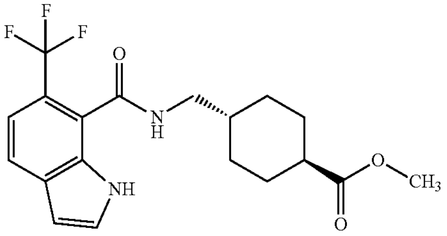 [SMILES: COC(=O)[C@H]1CC[C@H](CNC(=O)c2c(C(F)(F)F)ccc3cc[nH]c23)CC1] |
TABLE 129
| Pr | Structure |
| --- | --- |
| 517 | 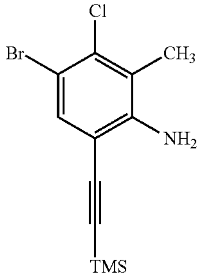 [SMILES: Cc1c(N)c(C#C[Si](C)(C)C)cc(Br)c1Cl] |
| 518 | 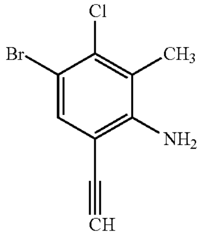 |
| 519 | 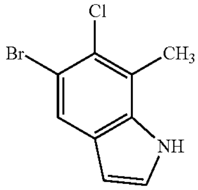 |
TABLE 129-continued
| Pr | Structure |
| --- | --- |
| 520 | 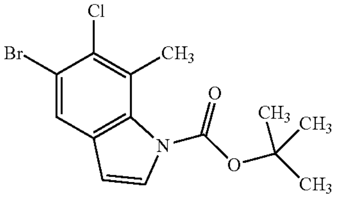 [SMILES: Cc1c(Cl)c(Br)cc2ccn(C(=O)OC(C)(C)C)c12] |
| 521 | 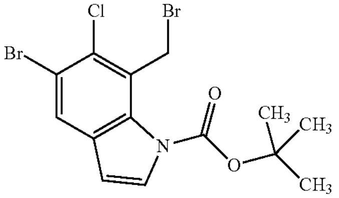 [SMILES: CC(C)(C)OC(=O)n1ccc2cc(Br)c(Cl)c(CBr)c21] |
TABLE 130
| Pr | Structure |
| --- | --- |
| 522 | 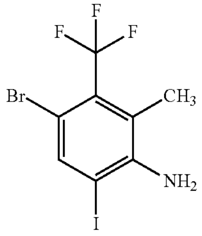 |
| 523 | 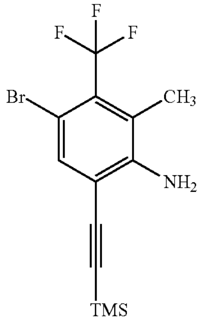 [SMILES: Cc1c(N)c(C#C[Si](C)(C)C)cc(Br)c1C(F)(F)F] |
| 524 | 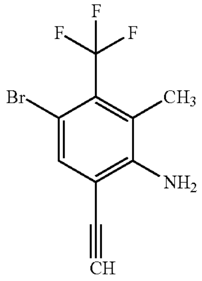 |

TABLE 130-continued
| Pr | Structure |
|---|---|
| 525 | 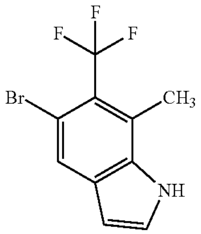 |
TABLE 131
| Pr | Structure |
|---|---|
| 526 | 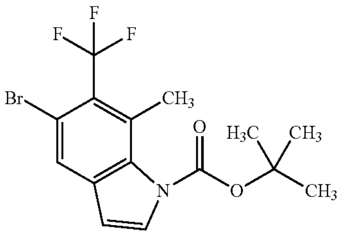 [SMILES: Cc1c(C(F)(F)F)c(Br)cc2ccn(C(=O)OC(C)(C)C)c12] |
| 527 | 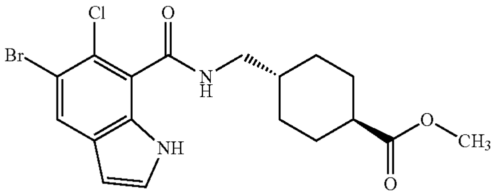 [SMILES: COC(=O)[C@H]1CC[C@H](CNC(=O)c2c(Cl)c(Br)cc3cc[nH]c23)CC1] |
| 528 | 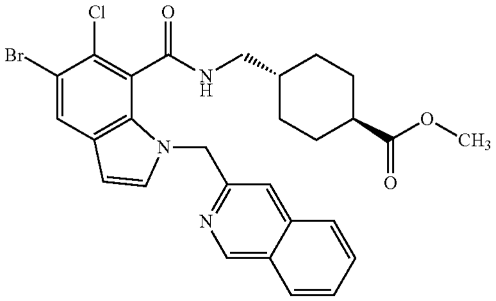 [SMILES: COC(=O)[C@H]1CC[C@H](CNC(=O)c2c(Cl)c(Br)cc3ccn(Cc4cc5ccccc5cn4)c23)CC1] |
| 529 | 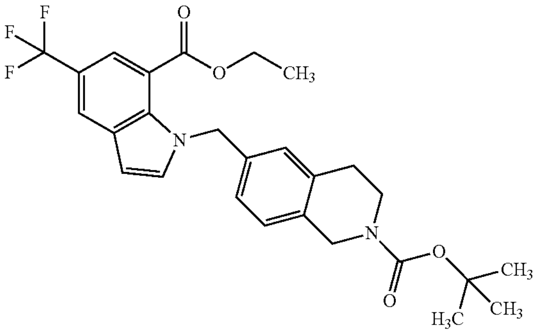 [SMILES: CCOC(=O)c1cc(C(F)(F)F)cc2ccn(Cc3ccc4c(c3)CCN(C(=O)OC(C)(C)C)C4)c12] |
TABLE 132
| Pr | Structure |
|---|---|
| 530 | 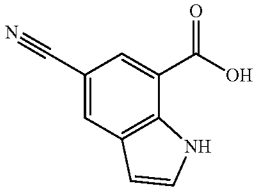 [SMILES: N#Cc1cc(C(=O)O)c2[nH]ccc2c1] |
| 531 | 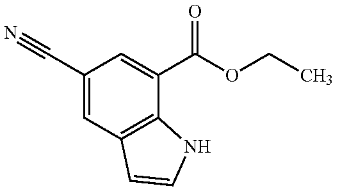 [SMILES: CCOC(=O)c1cc(C#N)cc2cc[nH]c12] |
| 532 | 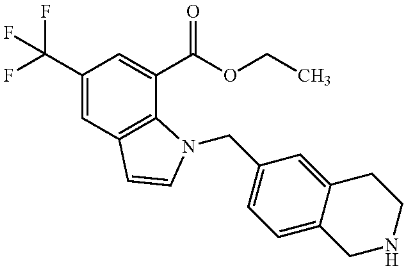 [SMILES: CCOC(=O)c1cc(C(F)(F)F)cc2ccn(Cc3ccc4c(c3)CCNC4)c12] |
| 533 | 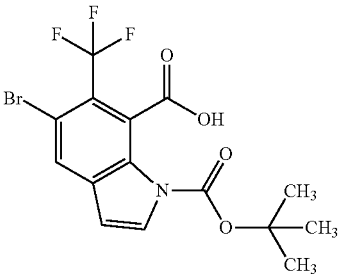 [SMILES: CC(C)(C)OC(=O)n1ccc2cc(Br)c(C(F)(F)F)c(C(=O)O)c21] |
| 534 | 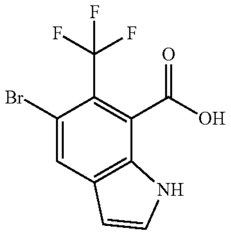 [SMILES: O=C(O)c1c(C(F)(F)F)c(Br)cc2cc[nH]c12] |
TABLE 133
| Pr | Structure |
|---|---|
| 535 | 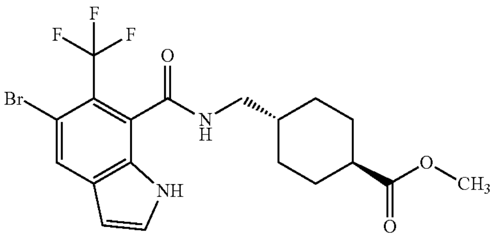 [SMILES: COC(=O)[C@H]1CC[C@H](CNC(=O)c2c(C(F)(F)F)c(Br)cc3cc[nH]c23)CC1] |

TABLE 133-continued
| Pr | Structure |
|---|---|
| 536 | 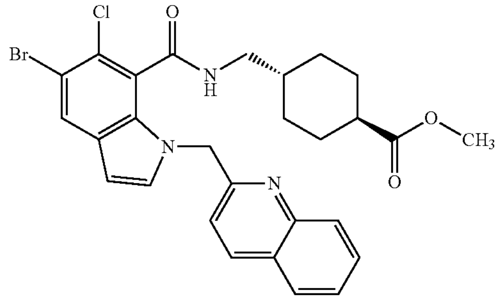 [SMILES: COC(=O)[C@H]1CC[C@H](CNC(=O)c2c(Cl)c(Br)cc3ccn(Cc4ccc5ccccc5n4)c23)CC1] |
| 537 | 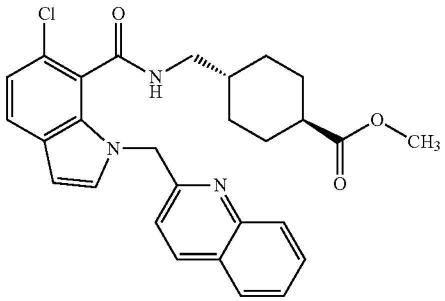 [SMILES: COC(=O)[C@H]1CC[C@H](CNC(=O)c2c(Cl)ccc3ccn(Cc4ccc5ccccc5n4)c23)CC1] |
| 538 | 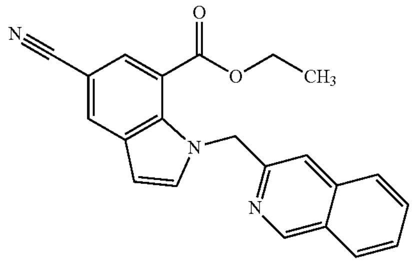 [SMILES: CCOC(=O)c1cc(C#N)cc2ccn(Cc3cc4ccccc4cn3)c12] |
TABLE 134
| Pr | Structure |
|---|---|
| 539 | 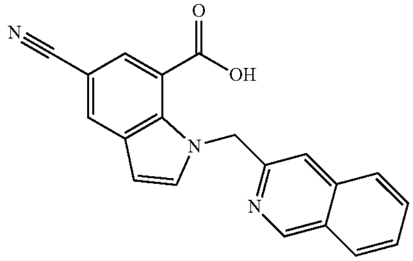 [SMILES: N#Cc1cc(C(=O)O)c2c(ccn2Cc2cc3ccccc3cn2)c1] |
| 540 | 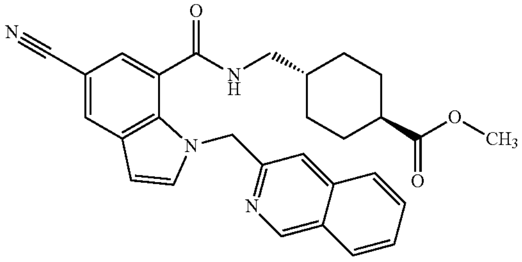 [SMILES: COC(=O)[C@H]1CC[C@H](CNC(=O)c2cc(C#N)cc3ccn(Cc4cc5ccccc5cn4)c23)CC1] |
TABLE 134-continued
| Pr | Structure |
|---|---|
| 541 | 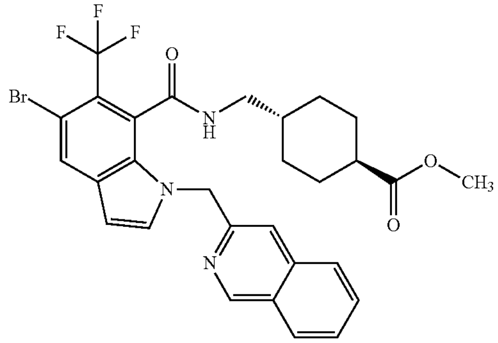 [SMILES: COC(=O)[C@H]1CC[C@H](CNC(=O)c2c(C(F)(F)F)c(Br)cc3ccn(Cc4cc5ccccc5cn4)c23)CC1] |
| 542 | 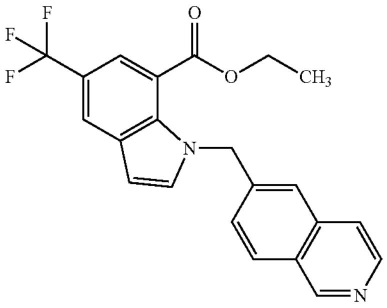 [SMILES: CCOC(=O)c1cc(C(F)(F)F)cc2ccn(Cc3ccc4cnccc4c3)c12] |
TABLE 135
| Pr | Structure |
|---|---|
| 543 | 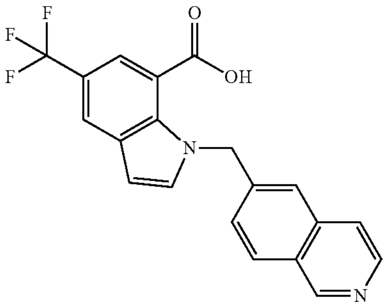 [SMILES: O=C(O)c1cc(C(F)(F)F)cc2ccn(Cc3ccc4cnccc4c3)c12] |
| 544 | 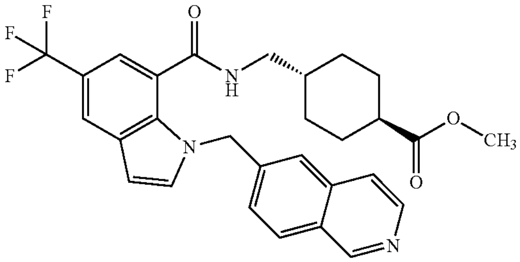 [SMILES: COC(=O)[C@H]1CC[C@H](CNC(=O)c2cc(C(F)(F)F)cc3ccn(Cc4ccc5cnccc5c4)c23)CC1] |

TABLE 135-continued
| Pr | Structure |
|---|---|
| 545 | 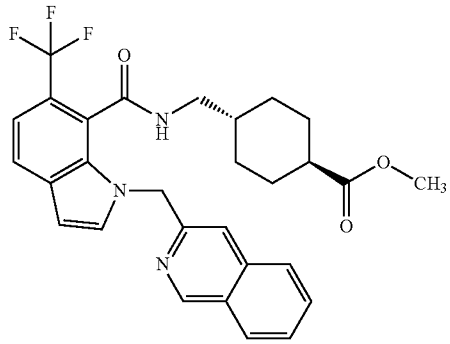 [SMILES: COC(=O)[C@H]1CC[C@H](CNC(=O)c2c(C(F)(F)F)ccc3ccn(Cc4cc5ccccc5cn4)c23)CC1] |
| 546 | 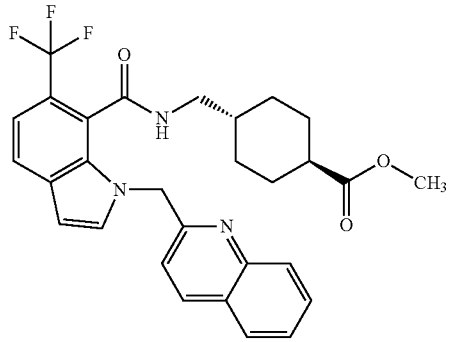 [SMILES: COC(=O)[C@H]1CC[C@H](CNC(=O)c2c(C(F)(F)F)ccc3ccn(Cc4ccc5ccccc5n4)c23)CC1] |
TABLE 136
| Pr | Structure |
|---|---|
| 547 | 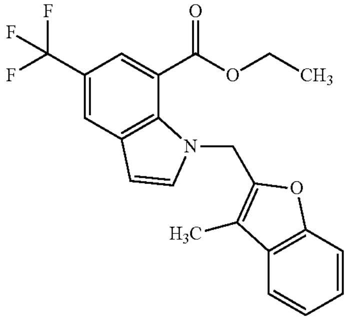 [SMILES: CCOC(=O)c1cc(C(F)(F)F)cc2ccn(Cc3oc4ccccc4c3C)c12] |
| 548 | 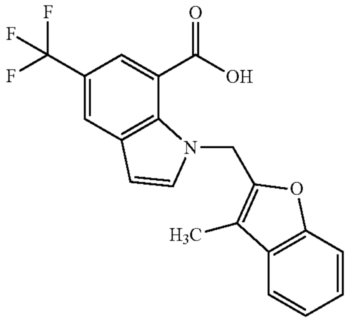 [SMILES: Cc1c(Cn2ccc3cc(C(F)(F)F)cc(C(=O)O)c32)oc2ccccc12] |
TABLE 136-continued
| Pr | Structure |
|---|---|
| 549 | 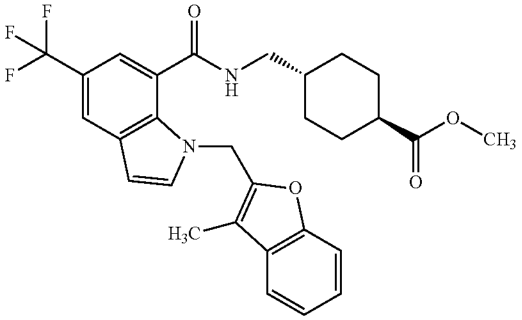 [SMILES: COC(=O)[C@H]1CC[C@H](CNC(=O)c2cc(C(F)(F)F)cc3ccn(Cc4oc5ccccc5c4C)c23)CC1] |
TABLE 137
| Ex | Structure |
|---|---|
| 1/Cl | 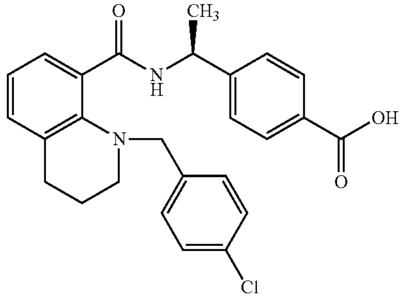 [SMILES: C[C@H](NC(=O)c1cccc2c1N(Cc1ccc(Cl)cc1)CCC2)c1ccc(C(=O)O)cc1] |
| 2 | 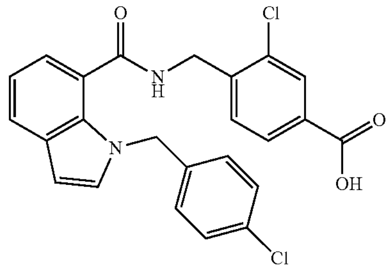 |
| 3 | 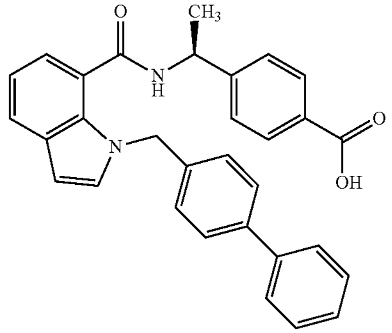 |

TABLE 137-continued
| Ex | Structure |
|---|---|
| 4 | 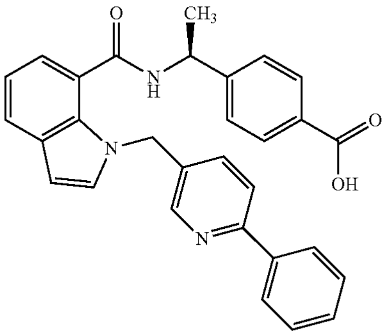 [SMILES: C[C@H](NC(=O)c1cccc2ccn(Cc3ccc(-c4ccccc4)nc3)c12)c1ccc(C(=O)O)cc1] |
TABLE 138
| Ex | Structure |
|---|---|
| 5 | 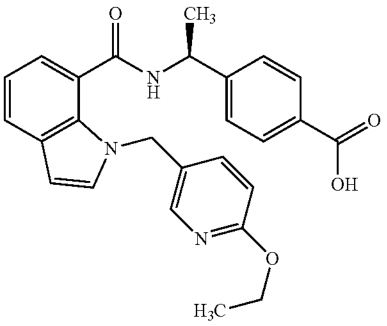 [SMILES: CCOc1ccc(Cn2ccc3cccc(C(=O)N[C@@H](C)c4ccc(C(=O)O)cc4)c32)cn1] |
| 6 | 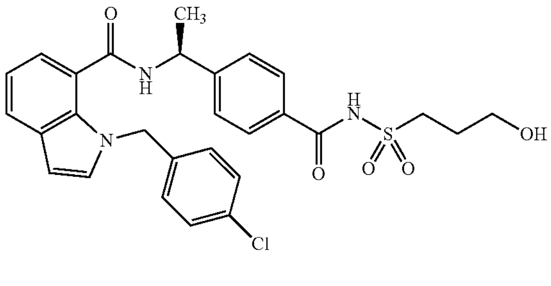 [SMILES: C[C@H](NC(=O)c1cccc2ccn(Cc3ccc(Cl)cc3)c12)c1ccc(C(=O)NS(=O)(=O)CCCO)cc1] |
| 7 | 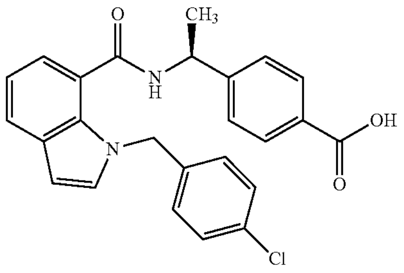 [SMILES: C[C@H](NC(=O)c1cccc2ccn(Cc3ccc(Cl)cc3)c12)c1ccc(C(=O)O)cc1] |
TABLE 138-continued
| Ex | Structure |
|---|---|
| 8 | 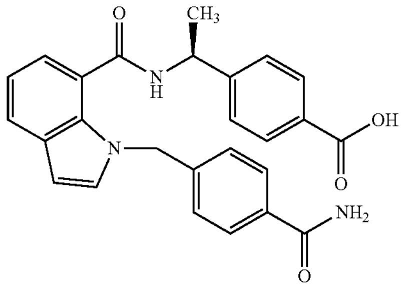 [SMILES: C[C@H](NC(=O)c1cccc2ccn(Cc3ccc(C(N)=O)cc3)c12)c1ccc(C(=O)O)cc1] |
TABLE 139
| Ex | Structure |
|---|---|
| 9 | 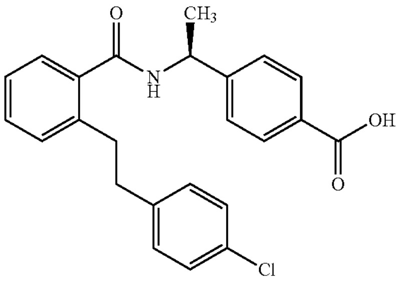 [SMILES: C[C@H](NC(=O)c1ccccc1CCc1ccc(Cl)cc1)c1ccc(C(=O)O)cc1] |
| 10 | 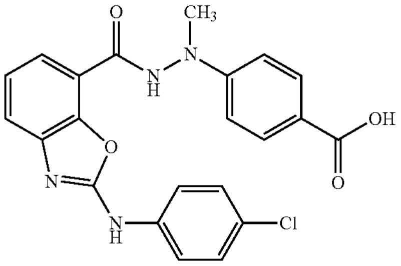 [SMILES: CN(NC(=O)c1cccc2nc(Nc3ccc(Cl)cc3)oc12)c1ccc(C(=O)O)cc1] |
| 11 | 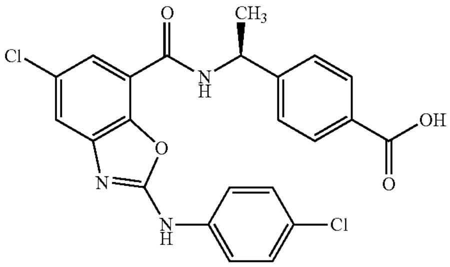 [SMILES: C[C@H](NC(=O)c1cc(Cl)cc2nc(Nc3ccc(Cl)cc3)oc12)c1ccc(C(=O)O)cc1] |
| 12 | 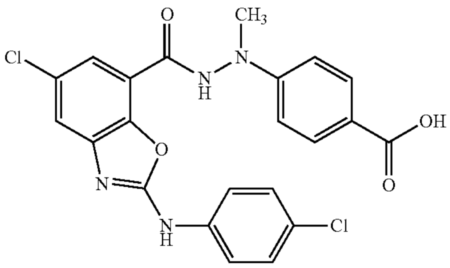 [SMILES: CN(NC(=O)c1cc(Cl)cc2nc(Nc3ccc(Cl)cc3)oc12)c1ccc(C(=O)O)cc1] |

TABLE 140
| Ex | Structure |
|---|---|
| 13 | 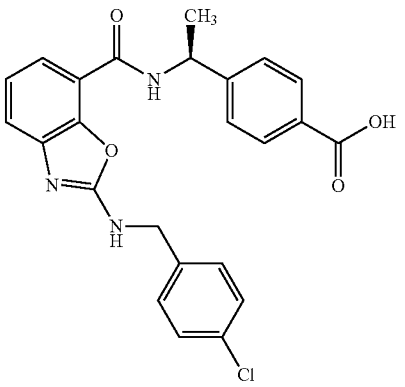 [SMILES: C[C@H](NC(=O)c1cccc2nc(NCc3ccc(Cl)cc3)oc12)c1ccc(C(=O)O)cc1] |
| 14 | 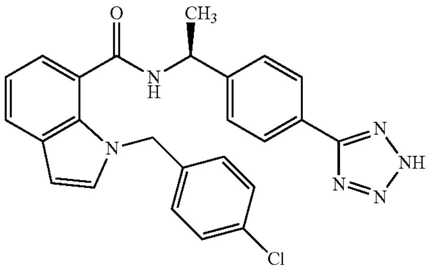 [SMILES: C[C@H](NC(=O)c1cccc2ccn(Cc3ccc(Cl)cc3)c12)c1ccc(-c2nn[nH]n2)cc1] |
| 15 | 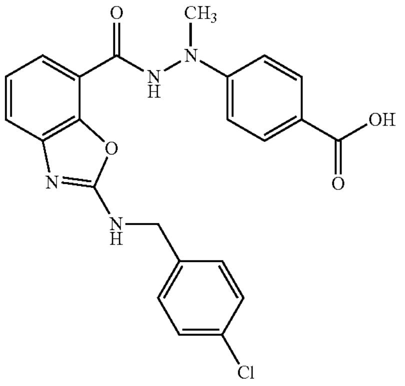 [SMILES: CN(NC(=O)c1cccc2nc(NCc3ccc(Cl)cc3)oc12)c1ccc(C(=O)O)cc1] |
| 16 | 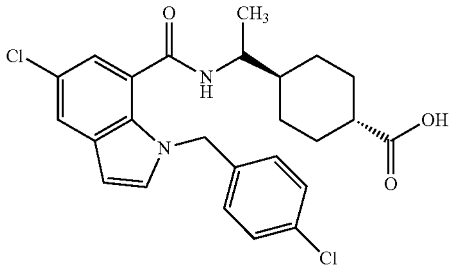 [SMILES: CC(NC(=O)c1cc(Cl)cc2ccn(Cc3ccc(Cl)cc3)c12)[C@H]1CC[C@H](C(=O)O)CC1] |
TABLE 141
| Ex | Structure |
|---|---|
| 17 | 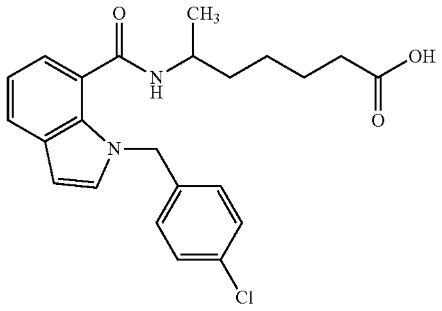 [SMILES: CC(CCCCC(=O)O)NC(=O)c1cccc2ccn(Cc3ccc(Cl)cc3)c12] |
| 18 | 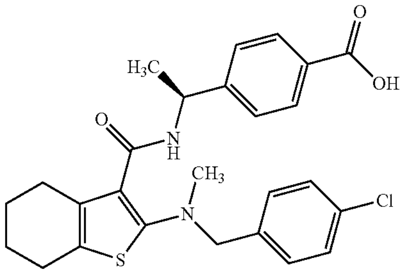 [SMILES: C[C@H](NC(=O)c1c(N(C)Cc2ccc(Cl)cc2)sc2c1CCCC2)c1ccc(C(=O)O)cc1] |
| 19 | 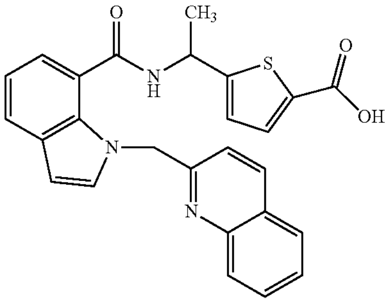 [SMILES: CC(NC(=O)c1cccc2ccn(Cc3ccc4ccccc4n3)c12)c1ccc(C(=O)O)s1] |
| 20 | 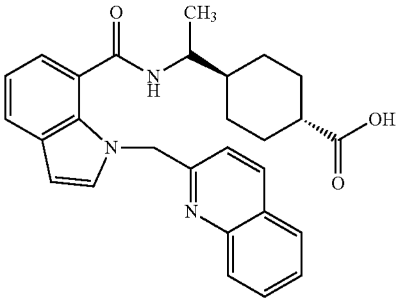 [SMILES: CC(NC(=O)c1cccc2ccn(Cc3ccc4ccccc4n3)c12)[C@H]1CC[C@H](C(=O)O)CC1] |

TABLE 142
| Ex | Structure |
|---|---|
| 21/Cl | 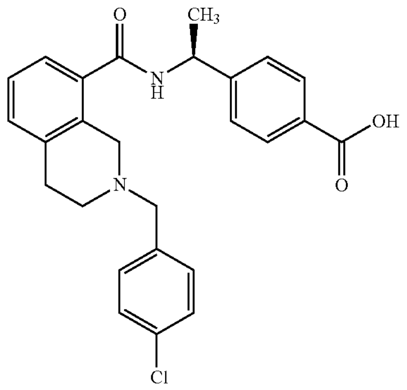 [SMILES: C[C@H](NC(=O)c1cccc2c1CN(Cc1ccc(Cl)cc1)CC2)c1ccc(C(=O)O)cc1] |
| 22 | 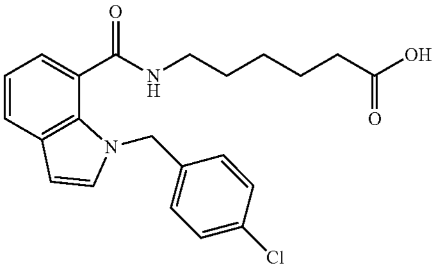 [SMILES: O=C(O)CCCCCNC(=O)c1cccc2ccn(Cc3ccc(Cl)cc3)c12] |
| 23 | 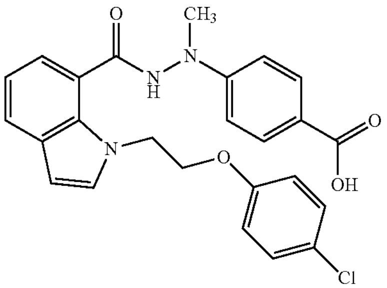 [SMILES: CN(NC(=O)c1cccc2ccn(CCOc3ccc(Cl)cc3)c12)c1ccc(C(=O)O)cc1] |
| 24 | 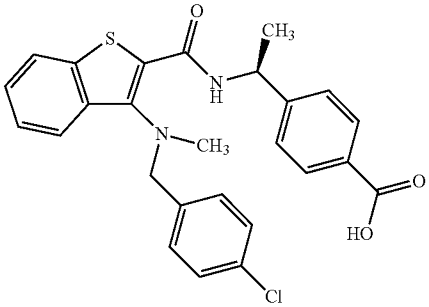 [SMILES: C[C@H](NC(=O)c1sc2ccccc2c1N(C)Cc1ccc(Cl)cc1)c1ccc(C(=O)O)cc1] |
TABLE 143
| Ex | Structure |
|---|---|
| 25 | 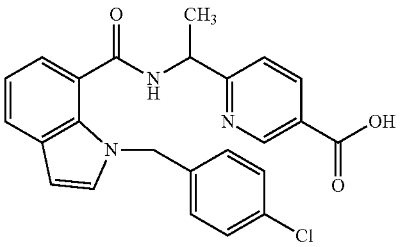 [SMILES: CC(NC(=O)c1cccc2ccn(Cc3ccc(Cl)cc3)c12)c1ccc(C(=O)O)cn1] |
| 26 | 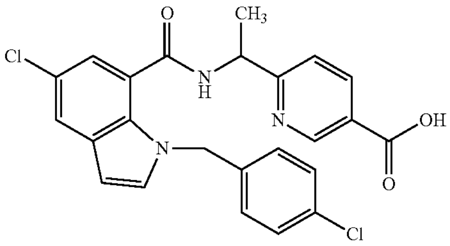 [SMILES: CC(NC(=O)c1cc(Cl)cc2ccn(Cc3ccc(Cl)cc3)c12)c1ccc(C(=O)O)cn1] |
| 27 | 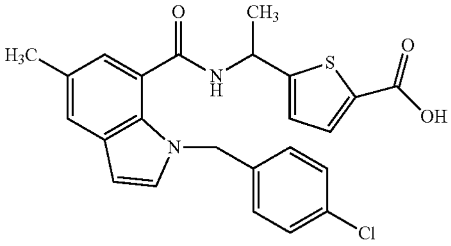 [SMILES: Cc1cc(C(=O)NC(C)c2ccc(C(=O)O)s2)c2c(ccn2Cc2ccc(Cl)cc2)c1] |
| 28 | 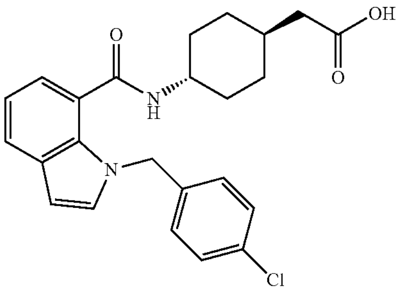 [SMILES: O=C(O)C[C@H]1CC[C@H](NC(=O)c2cccc3ccn(Cc4ccc(Cl)cc4)c23)CC1] |
TABLE 144
| Ex | Structure |
|---|---|
| 29 | 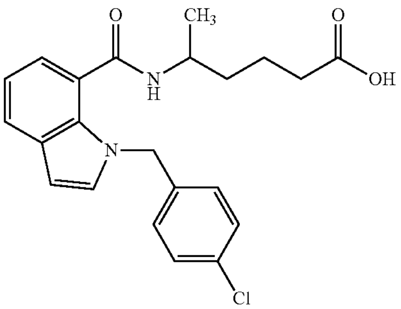 [SMILES: CC(CCCC(=O)O)NC(=O)c1cccc2ccn(Cc3ccc(Cl)cc3)c12] |

TABLE 144-continued
| Ex | Structure |
| --- | --- |
| 30 | 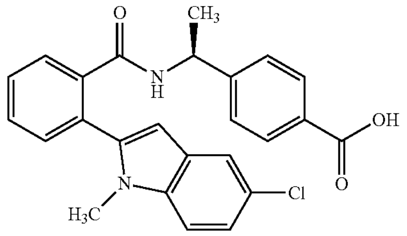 [SMILES: C[C@H](NC(=O)c1ccccc1-c1cc2cc(Cl)ccc2n1C)c1ccc(C(=O)O)cc1] |
| 31 | 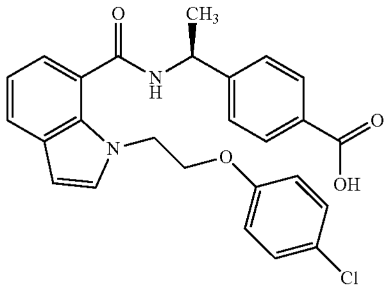 [SMILES: C[C@H](NC(=O)c1cccc2ccn(CCOc3ccc(Cl)cc3)c12)c1ccc(C(=O)O)cc1] |
| 32 | 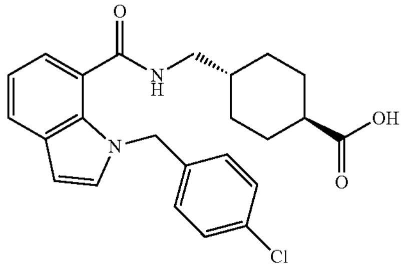 [SMILES: O=C(NC[C@H]1CC[C@H](C(=O)O)CC1)c1cccc2ccn(Cc3ccc(Cl)cc3)c12] |
TABLE 145
| Ex | Structure |
| --- | --- |
| 33 | 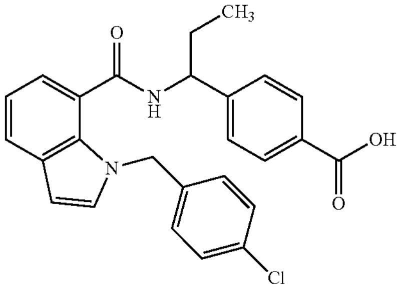 [SMILES: CCC(NC(=O)c1cccc2ccn(Cc3ccc(Cl)cc3)c12)c1ccc(C(=O)O)cc1] |
| 34 | 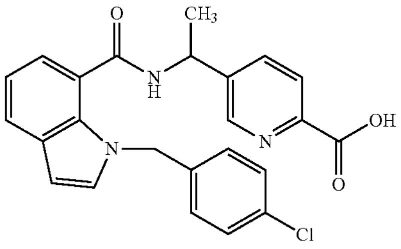 [SMILES: CC(NC(=O)c1cccc2ccn(Cc3ccc(Cl)cc3)c12)c1ccc(C(=O)O)nc1] |
TABLE 145-continued
| Ex | Structure |
| --- | --- |
| 35 | 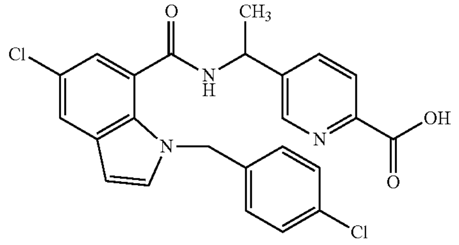 [SMILES: CC(NC(=O)c1cc(Cl)cc2ccn(Cc3ccc(Cl)cc3)c12)c1ccc(C(=O)O)nc1] |
| 36 | 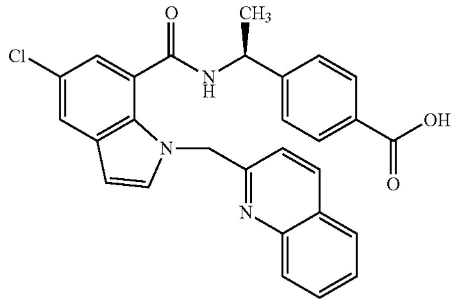 [SMILES: C[C@H](NC(=O)c1cc(Cl)cc2ccn(Cc3ccc4ccccc4n3)c12)c1ccc(C(=O)O)cc1] |
TABLE 146
| Ex | Structure |
| --- | --- |
| 37 | 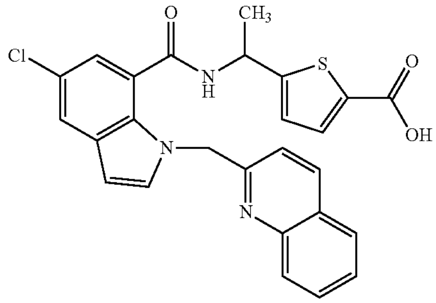 [SMILES: CC(NC(=O)c1cc(Cl)cc2ccn(Cc3ccc4ccccc4n3)c12)c1ccc(C(=O)O)s1] |
| 38 | 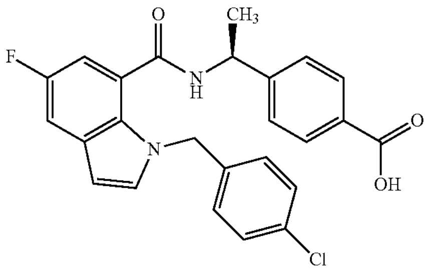 [SMILES: C[C@H](NC(=O)c1cc(F)cc2ccn(Cc3ccc(Cl)cc3)c12)c1ccc(C(=O)O)cc1] |
| 39 | 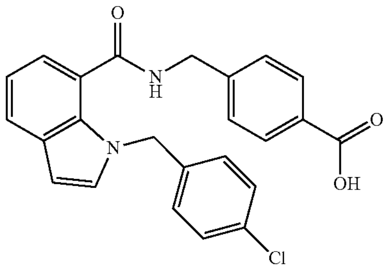 [SMILES: O=C(O)c1ccc(CNC(=O)c2cccc3ccn(Cc4ccc(Cl)cc4)c23)cc1] |

TABLE 146-continued
| Ex | Structure |
| --- | --- |
| 40 | 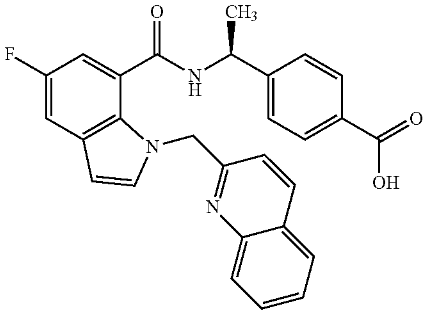 [SMILES: C[C@H](NC(=O)c1cc(F)cc2ccn(Cc3ccc4ccccc4n3)c12)c1ccc(C(=O)O)cc1] |
TABLE 147
| Ex | Structure |
| --- | --- |
| 41 | 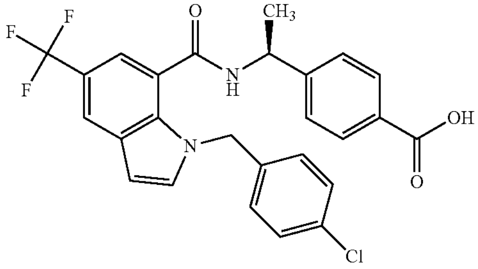 [SMILES: C[C@H](NC(=O)c1cc(C(F)(F)F)cc2ccn(Cc3ccc(Cl)cc3)c12)c1ccc(C(=O)O)cc1] |
| 42 | 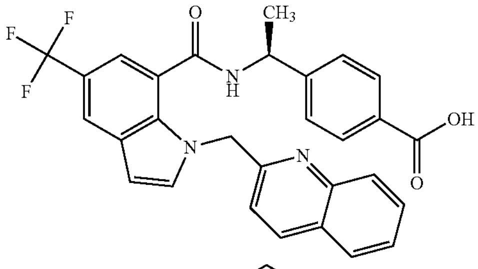 |
| 43 | 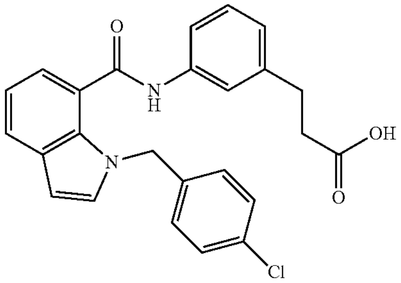 [SMILES: O=C(O)CCc1cccc(NC(=O)c2cccc3ccn(Cc4ccc(Cl)cc4)c23)c1] |
| 44 | 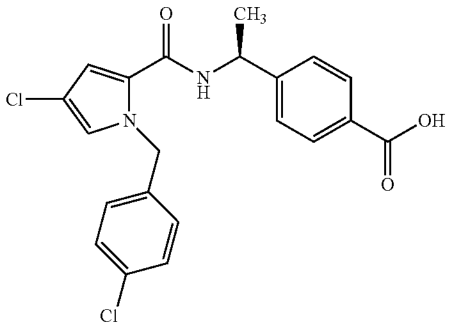 [SMILES: C[C@H](NC(=O)c1cc(Cl)cn1Cc1ccc(Cl)cc1)c1ccc(C(=O)O)cc1] |
TABLE 148
| Ex | Structure |
| --- | --- |
| 45 | 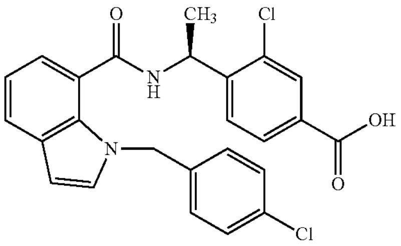 [SMILES: C[C@H](NC(=O)c1cccc2ccn(Cc3ccc(Cl)cc3)c12)c1ccc(C(=O)O)cc1Cl] |
| 46 | 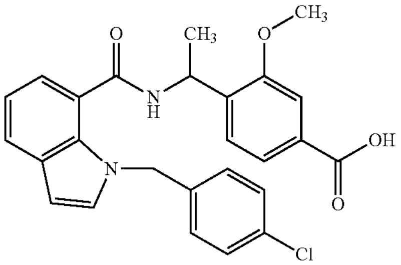 [SMILES: COc1cc(C(=O)O)ccc1C(C)NC(=O)c1cccc2ccn(Cc3ccc(Cl)cc3)c12] |
| 47 | 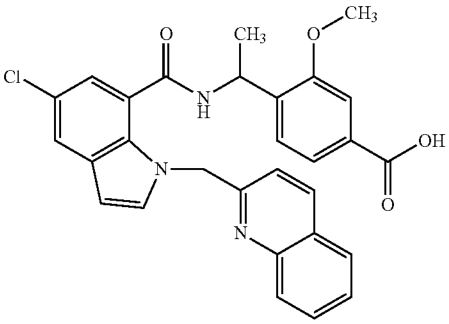 [SMILES: COc1cc(C(=O)O)ccc1C(C)NC(=O)c1cc(Cl)cc2ccn(Cc3ccc4ccccc4n3)c12] |
| 48 | 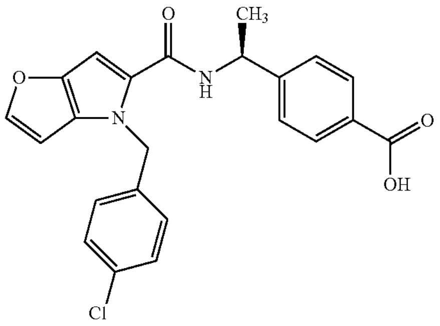 |
TABLE 149
| Ex | Structure |
| --- | --- |
| 49 | 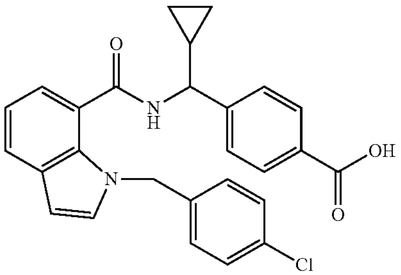 [SMILES: O=C(O)c1ccc(C(NC(=O)c2cccc3ccn(Cc4ccc(Cl)cc4)c23)C2CC2)cc1] |

TABLE 149-continued
| Ex | Structure |
| --- | --- |
| 50 | 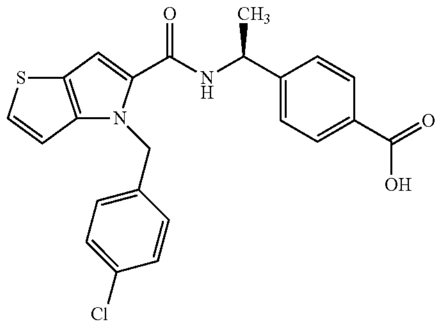 [SMILES: C[C@H](NC(=O)c1cc2sccc2n1Cc1ccc(Cl)cc1)c1ccc(C(=O)O)cc1] |
| 51 | 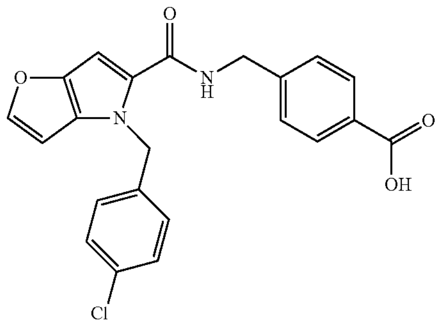 [SMILES: O=C(O)c1ccc(CNC(=O)c2cc3occc3n2Cc2ccc(Cl)cc2)cc1] |
| 52 | 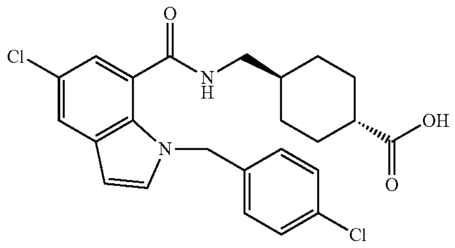 [SMILES: O=C(NC[C@H]1CC[C@H](C(=O)O)CC1)c1cc(Cl)cc2ccn(Cc3ccc(Cl)cc3)c12] |
TABLE 150
| Ex | Structure |
| --- | --- |
| 53 | 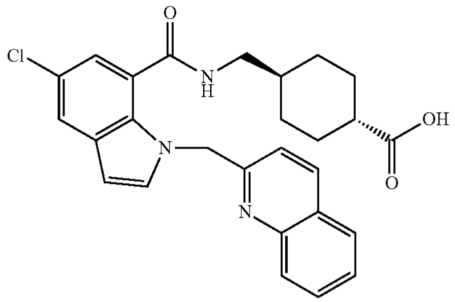 [SMILES: O=C(NC[C@H]1CC[C@H](C(=O)O)CC1)c1cc(Cl)cc2ccn(Cc3ccc4ccccc4n3)c12] |
TABLE 150-continued
| Ex | Structure |
| --- | --- |
| 54 | 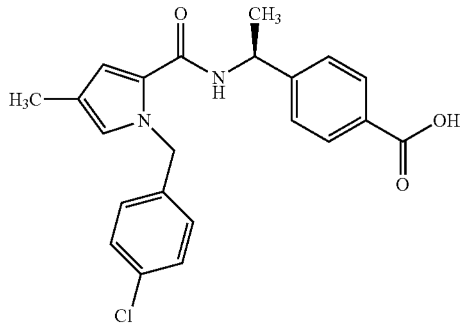 [SMILES: Cc1cc(C(=O)N[C@@H](C)c2ccc(C(=O)O)cc2)n(Cc2ccc(Cl)cc2)c1] |
| 55 | 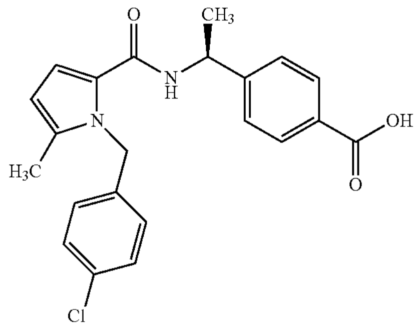 [SMILES: Cc1ccc(C(=O)N[C@@H](C)c2ccc(C(=O)O)cc2)n1Cc1ccc(Cl)cc1] |
| 56 | 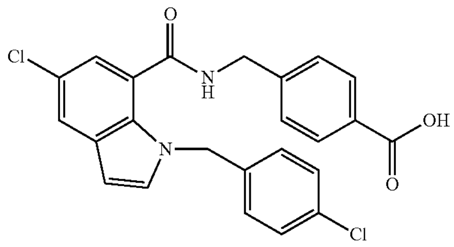 [SMILES: O=C(O)c1ccc(CNC(=O)c2cc(Cl)cc3ccn(Cc4ccc(Cl)cc4)c23)cc1] |
TABLE 151
| Ex | Structure |
| --- | --- |
| 57 | 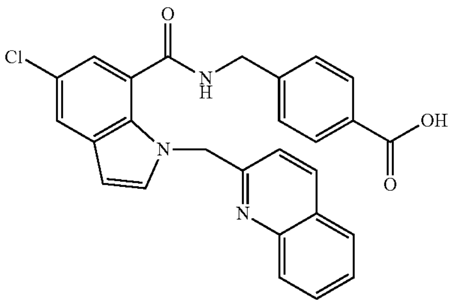 [SMILES: O=C(O)c1ccc(CNC(=O)c2cc(Cl)cc3ccn(Cc4ccc5ccccc5n4)c23)cc1] |

TABLE 151-continued
| Ex | Structure |
|---|---|
| 58 | 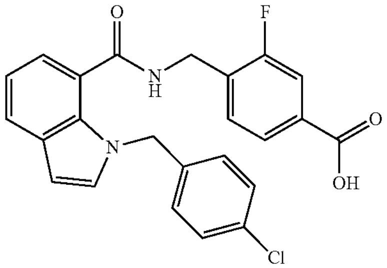 [SMILES: O=C(O)c1ccc(CNC(=O)c2cccc3ccn(Cc4ccc(Cl)cc4)c23)c(F)c1] |
| 59 | 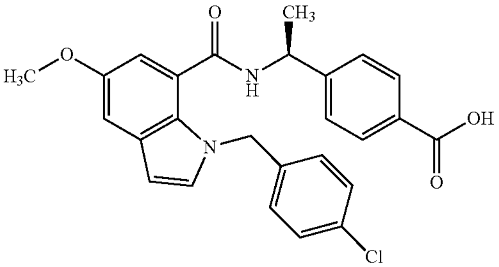 [SMILES: COc1cc(C(=O)N[C@@H](C)c2ccc(C(=O)O)cc2)c2c(ccn2Cc2ccc(Cl)cc2)c1] |
| 60 | 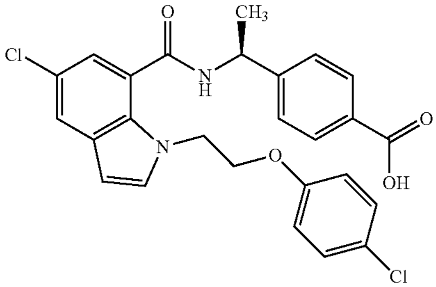 [SMILES: C[C@H](NC(=O)c1cc(Cl)cc2ccn(CCOc3ccc(Cl)cc3)c12)c1ccc(C(=O)O)cc1] |
TABLE 152
| Ex | Structure |
|---|---|
| 61 | 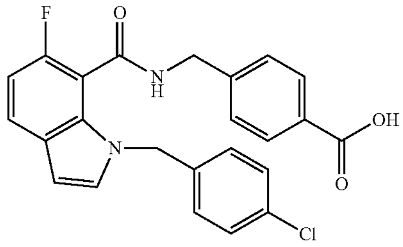 [SMILES: O=C(O)c1ccc(CNC(=O)c2c(F)ccc3ccn(Cc4ccc(Cl)cc4)c23)cc1] |
| 62 | 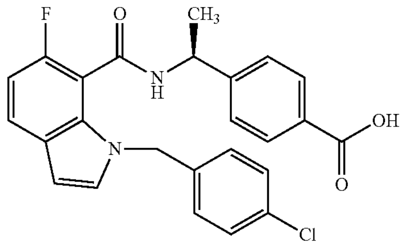 [SMILES: C[C@H](NC(=O)c1c(F)ccc2ccn(Cc3ccc(Cl)cc3)c12)c1ccc(C(=O)O)cc1] |
TABLE 152-continued
| Ex | Structure |
|---|---|
| 63 | 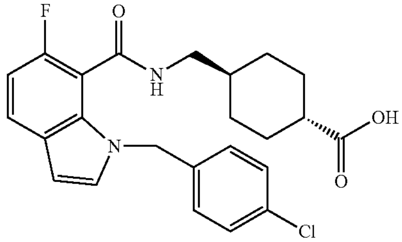 [SMILES: O=C(NC[C@H]1CC[C@H](C(=O)O)CC1)c1c(F)ccc2ccn(Cc3ccc(Cl)cc3)c12] |
| 64 | 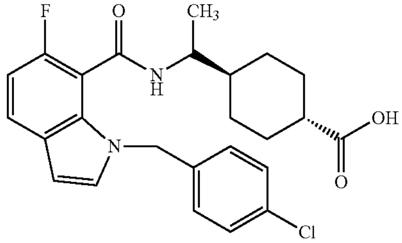 [SMILES: CC(NC(=O)c1c(F)ccc2ccn(Cc3ccc(Cl)cc3)c12)[C@H]1CC[C@H](C(=O)O)CC1] |
TABLE 153
| Ex | Structure |
|---|---|
| 65 | 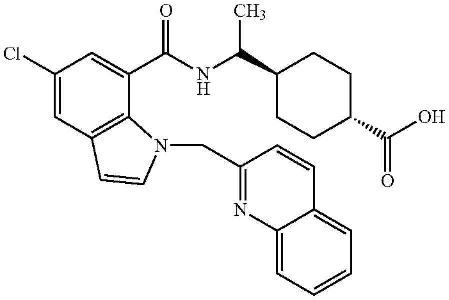 [SMILES: CC(NC(=O)c1cc(Cl)cc2ccn(Cc3ccc4ccccc4n3)c12)[C@H]1CC[C@H](C(=O)O)CC1] |
| 66 | 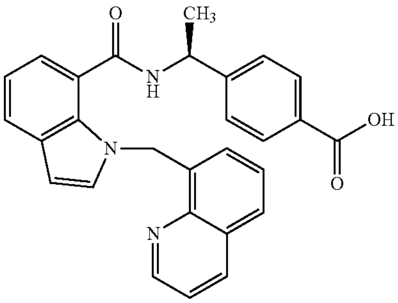 [SMILES: C[C@H](NC(=O)c1cccc2ccn(Cc3cccc4cccnc34)c12)c1ccc(C(=O)O)cc1] |
| 67 | 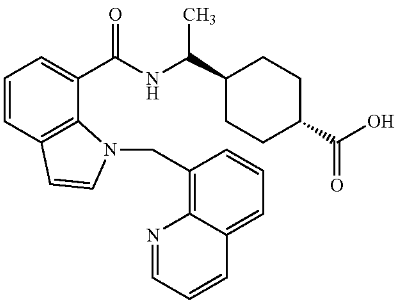 [SMILES: CC(NC(=O)c1cccc2ccn(Cc3cccc4cccnc34)c12)[C@H]1CC[C@H](C(=O)O)CC1] |

TABLE 153-continued
| Ex | Structure |
|---|---|
| 68 | 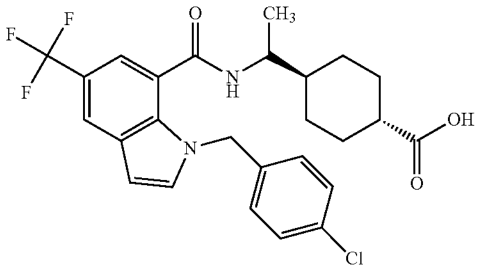 [SMILES: CC(NC(=O)c1cc(C(F)(F)F)cc2ccn(Cc3ccc(Cl)cc3)c12)[C@H]1CC[C@H](C(=O)O)CC1] |
TABLE 154
| Ex | Structure |
|---|---|
| 69 | 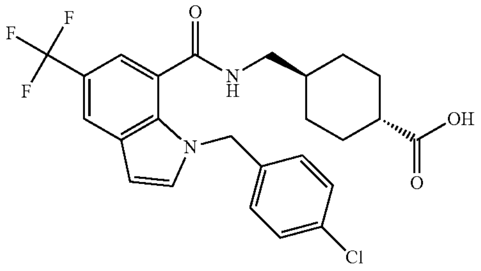 [SMILES: O=C(NC[C@H]1CC[C@H](C(=O)O)CC1)c1cc(C(F)(F)F)cc2ccn(Cc3ccc(Cl)cc3)c12] |
| 70 | 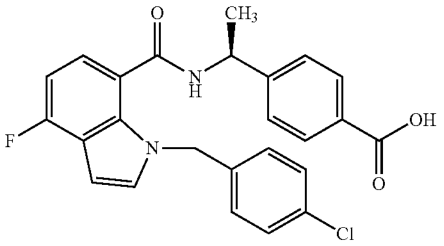 [SMILES: C[C@H](NC(=O)c1ccc(F)c2ccn(Cc3ccc(Cl)cc3)c12)c1ccc(C(=O)O)cc1] |
| 71 | 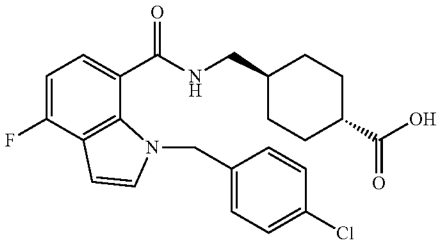 [SMILES: O=C(NC[C@H]1CC[C@H](C(=O)O)CC1)c1ccc(F)c2ccn(Cc3ccc(Cl)cc3)c12] |
| 72 | 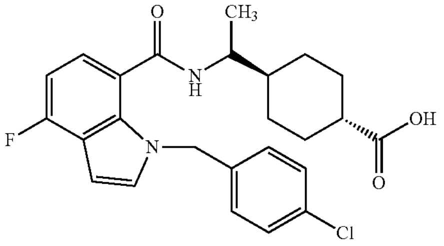 [SMILES: CC(NC(=O)c1ccc(F)c2ccn(Cc3ccc(Cl)cc3)c12)[C@H]1CC[C@H](C(=O)O)CC1] |
TABLE 155
| Ex | Structure |
|---|---|
| 73 | 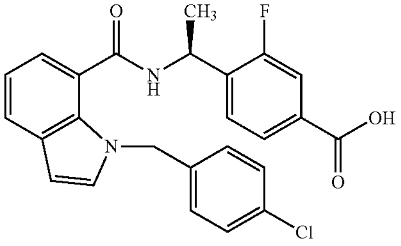 |
| 74 | 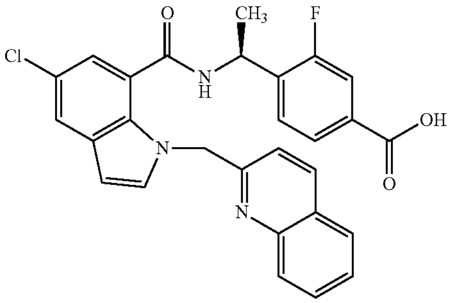 [SMILES: C[C@H](NC(=O)c1cc(Cl)cc2ccn(Cc3ccc4ccccc4n3)c12)c1ccc(C(=O)O)cc1F] |
| 75 | 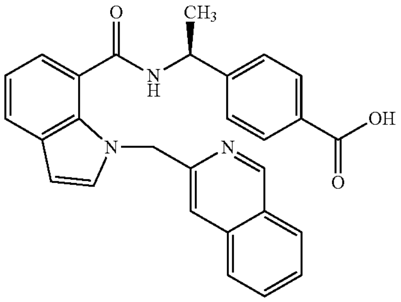 [SMILES: C[C@H](NC(=O)c1cccc2ccn(Cc3cc4ccccc4cn3)c12)c1ccc(C(=O)O)cc1] |
| 76 | 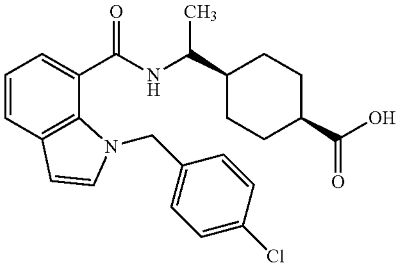 [SMILES: CC(NC(=O)c1cccc2ccn(Cc3ccc(Cl)cc3)c12)[C@H]1CC[C@@H](C(=O)O)CC1] |
TABLE 156
| Ex | Structure |
|---|---|
| 77 | 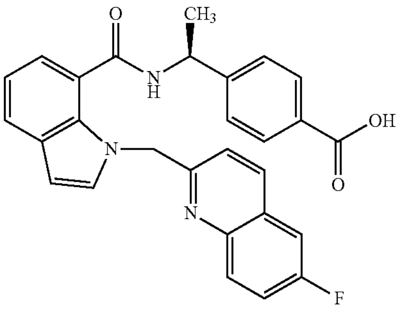 [SMILES: C[C@H](NC(=O)c1cccc2ccn(Cc3ccc4cc(F)ccc4n3)c12)c1ccc(C(=O)O)cc1] |

TABLE 156-continued
| Ex | Structure |
| --- | --- |
| 78 | 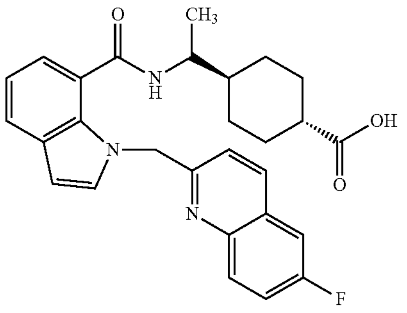 [SMILES: CC(NC(=O)c1cccc2ccn(Cc3ccc4cc(F)ccc4n3)c12)[C@H]1CC[C@H](C(=O)O)CC1] |
| 79 | 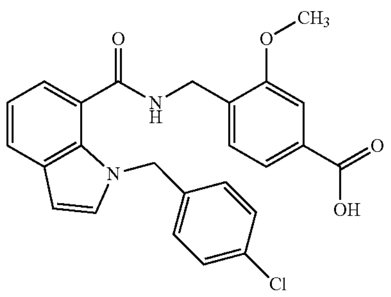 [SMILES: COc1cc(C(=O)O)ccc1CNC(=O)c1cccc2ccn(Cc3ccc(Cl)cc3)c12] |
| 80 | 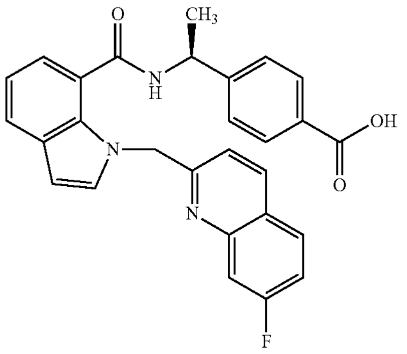 [SMILES: C[C@H](NC(=O)c1cccc2ccn(Cc3ccc4ccc(F)cc4n3)c12)c1ccc(C(=O)O)cc1] |
TABLE 157
| Ex | Structure |
| --- | --- |
| 81 | 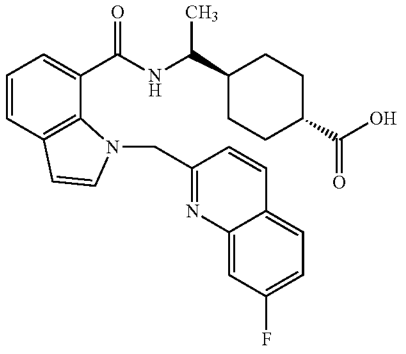 [SMILES: CC(NC(=O)c1cccc2ccn(Cc3ccc4ccc(F)cc4n3)c12)[C@H]1CC[C@H](C(=O)O)CC1] |
TABLE 157-continued
| Ex | Structure |
| --- | --- |
| 82 | 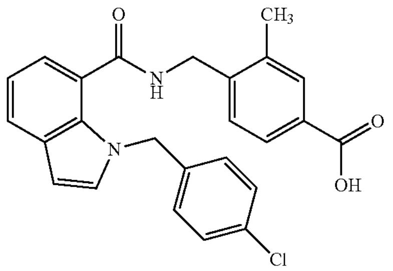 [SMILES: Cc1cc(C(=O)O)ccc1CNC(=O)c1cccc2ccn(Cc3ccc(Cl)cc3)c12] |
| 83 | 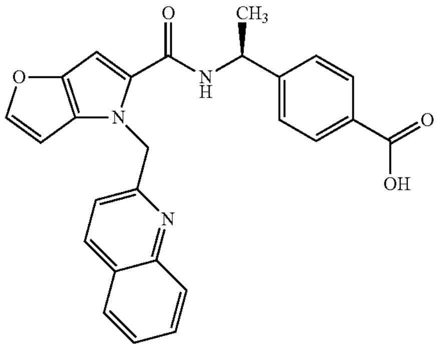 [SMILES: C[C@H](NC(=O)c1cc2occc2n1Cc1ccc2ccccc2n1)c1ccc(C(=O)O)cc1] |
| 84 | 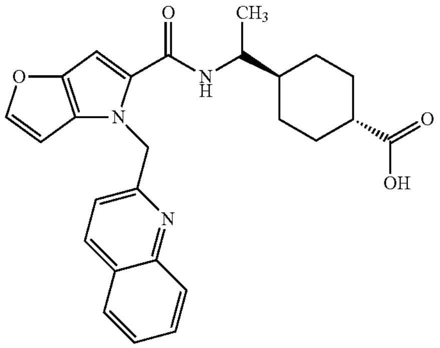 [SMILES: CC(NC(=O)c1cc2occc2n1Cc1ccc2ccccc2n1)[C@H]1CC[C@H](C(=O)O)CC1] |
TABLE 158
| Ex | Structure |
| --- | --- |
| 85 | 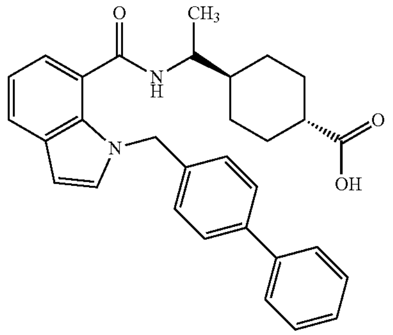 [SMILES: CC(NC(=O)c1cccc2ccn(Cc3ccc(-c4ccccc4)cc3)c12)[C@H]1CC[C@H](C(=O)O)CC1] |

TABLE 158-continued
| Ex | Structure |
|---|---|
| 86 | 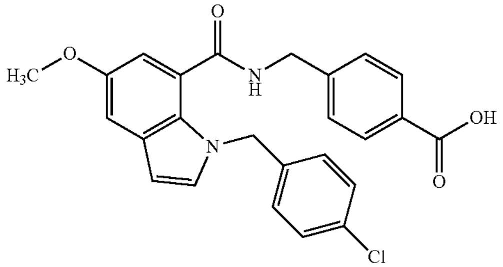 [SMILES: COc1cc(C(=O)NCc2ccc(C(=O)O)cc2)c2c(ccn2Cc2ccc(Cl)cc2)c1] |
| 87 | 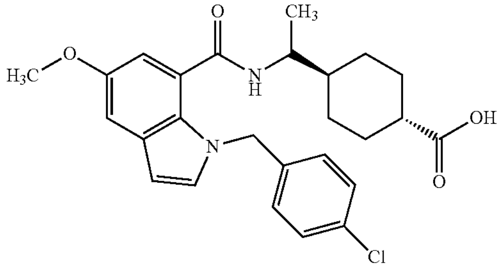 [SMILES: COc1cc(C(=O)NC(C)[C@H]2CC[C@H](C(=O)O)CC2)c2c(ccn2Cc2ccc(Cl)cc2)c1] |
| 88 | 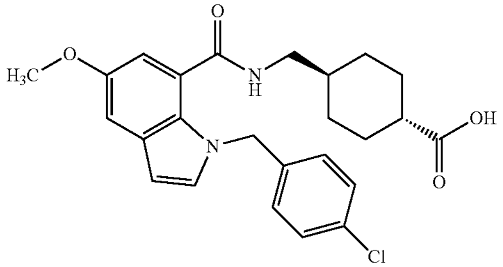 [SMILES: COc1cc(C(=O)NC[C@H]2CC[C@H](C(=O)O)CC2)c2c(ccn2Cc2ccc(Cl)cc2)c1] |
TABLE 159
| Ex | Structure |
|---|---|
| 89 | 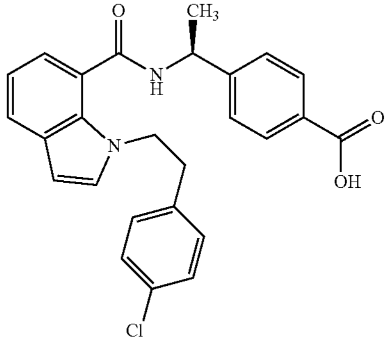 [SMILES: C[C@H](NC(=O)c1cccc2ccn(CCc3ccc(Cl)cc3)c12)c1ccc(C(=O)O)cc1] |
| 90 | 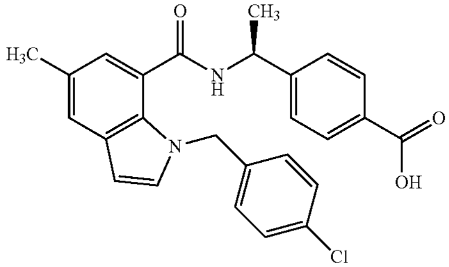 [SMILES: Cc1cc(C(=O)N[C@@H](C)c2ccc(C(=O)O)cc2)c2c(ccn2Cc2ccc(Cl)cc2)c1] |
TABLE 159-continued
| Ex | Structure |
|---|---|
| 91 | 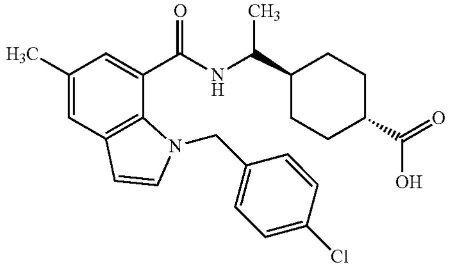 [SMILES: Cc1cc(C(=O)NC(C)[C@H]2CC[C@H](C(=O)O)CC2)c2c(ccn2Cc2ccc(Cl)cc2)c1] |
| 92 | 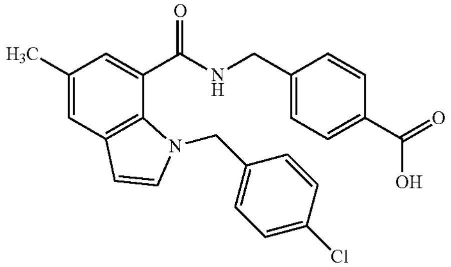 [SMILES: Cc1cc(C(=O)NCc2ccc(C(=O)O)cc2)c2c(ccn2Cc2ccc(Cl)cc2)c1] |
TABLE 160
| Ex | Structure |
|---|---|
| 93 | 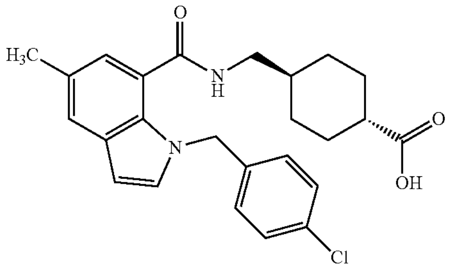 [SMILES: Cc1cc(C(=O)NC[C@H]2CC[C@H](C(=O)O)CC2)c2c(ccn2Cc2ccc(Cl)cc2)c1] |
| 94 | 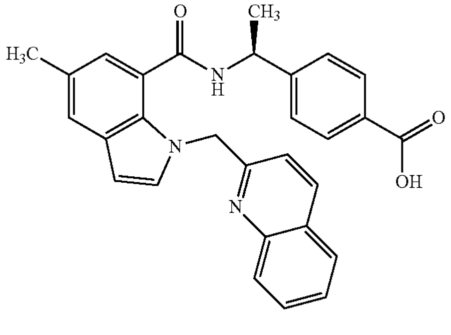 [SMILES: Cc1cc(C(=O)N[C@@H](C)c2ccc(C(=O)O)cc2)c2c(ccn2Cc2ccc3ccccc3n2)c1] |
| 95 | 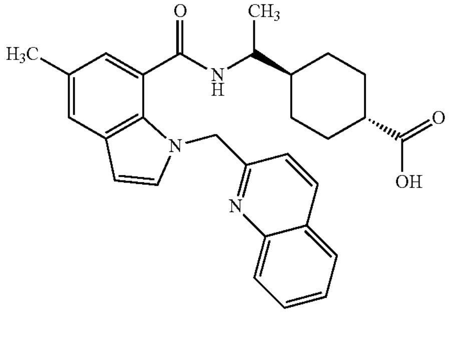 [SMILES: Cc1cc(C(=O)NC(C)[C@H]2CC[C@H](C(=O)O)CC2)c2c(ccn2Cc2ccc3ccccc3n2)c1] |

TABLE 160-continued
| Ex | Structure |
| --- | --- |
| 96 | 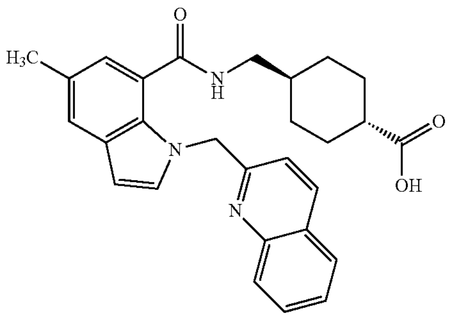 [SMILES: Cc1cc(C(=O)NC[C@H]2CC[C@H](C(=O)O)CC2)c2c(ccn2Cc2ccc3ccccc3n2)c1] |
TABLE 161
| Ex | Structure |
| --- | --- |
| 97 | 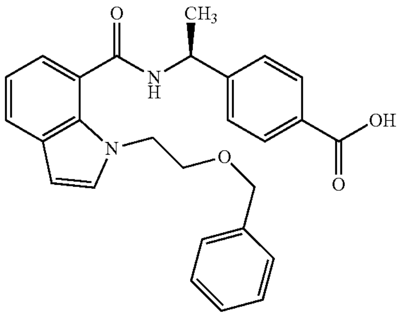 [SMILES: C[C@H](NC(=O)c1cccc2ccn(CCOCc3ccccc3)c12)c1ccc(C(=O)O)cc1] |
| 98 | 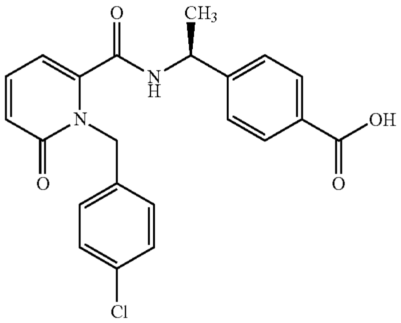 [SMILES: C[C@H](NC(=O)c1cccc(=O)n1Cc1ccc(Cl)cc1)c1ccc(C(=O)O)cc1] |
| 99 | 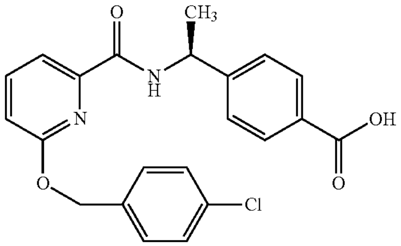 [SMILES: C[C@H](NC(=O)c1cccc(OCc2ccc(Cl)cc2)n1)c1ccc(C(=O)O)cc1] |
TABLE 161-continued
| Ex | Structure |
| --- | --- |
| 100 | 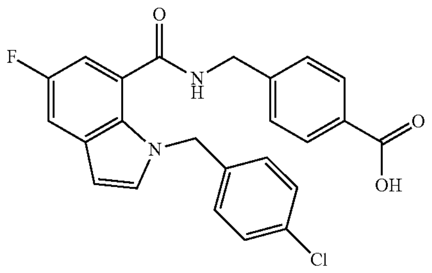 [SMILES: O=C(O)c1ccc(CNC(=O)c2cc(F)cc3ccn(Cc4ccc(Cl)cc4)c23)cc1] |
TABLE 162
| Ex | Structure |
| --- | --- |
| 101 | 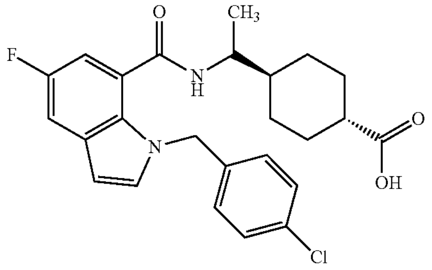 [SMILES: CC(NC(=O)c1cc(F)cc2ccn(Cc3ccc(Cl)cc3)c12)[C@H]1CC[C@H](C(=O)O)CC1] |
| 102 | 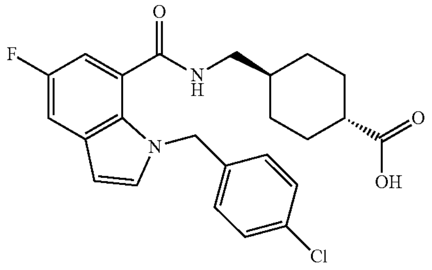 [SMILES: O=C(NC[C@H]1CC[C@H](C(=O)O)CC1)c1cc(F)cc2ccn(Cc3ccc(Cl)cc3)c12] |
| 103 | 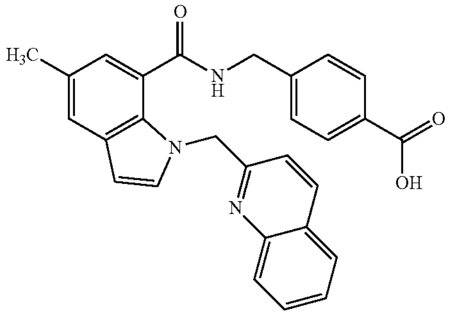 [SMILES: Cc1cc(C(=O)NCc2ccc(C(=O)O)cc2)c2c(ccn2Cc2ccc3ccccc3n2)c1] |
| 104 | 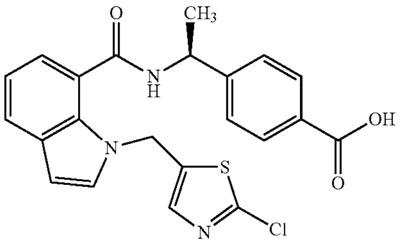 [SMILES: C[C@H](NC(=O)c1cccc2ccn(Cc3cnc(Cl)s3)c12)c1ccc(C(=O)O)cc1] |

TABLE 163
| Ex | Structure |
| --- | --- |
| 105 | 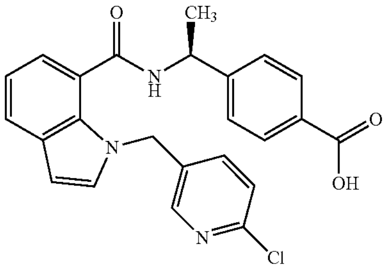 [SMILES: C[C@H](NC(=O)c1cccc2ccn(Cc3ccc(Cl)nc3)c12)c1ccc(C(=O)O)cc1] |
| 106 | 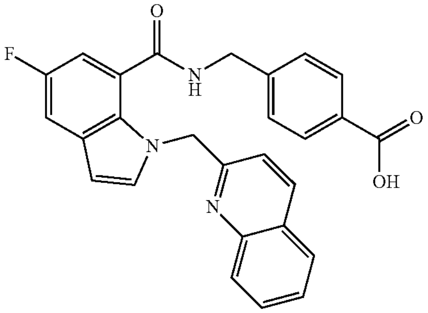 [SMILES: O=C(O)c1ccc(CNC(=O)c2cc(F)cc3ccn(Cc4ccc5ccccc5n4)c23)cc1] |
| 107 | 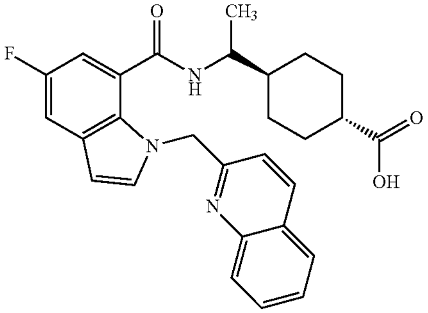 [SMILES: CC(NC(=O)c1cc(F)cc2ccn(Cc3ccc4ccccc4n3)c12)[C@H]1CC[C@H](C(=O)O)CC1] |
| 108 | 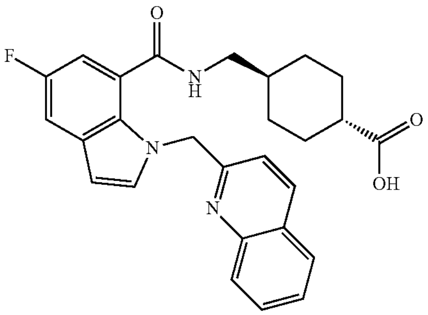 [SMILES: O=C(NC[C@H]1CC[C@H](C(=O)O)CC1)c1cc(F)cc2ccn(Cc3ccc4ccccc4n3)c12] |
TABLE 164
| Ex | Structure |
| --- | --- |
| 109 | 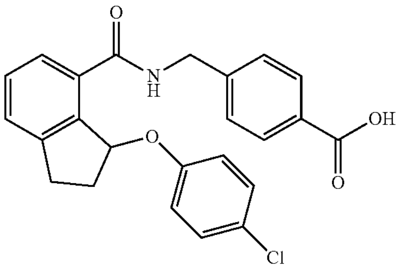 [SMILES: O=C(O)c1ccc(CNC(=O)c2cccc3c2C(Oc2ccc(Cl)cc2)CC3)cc1] |
| 110 | 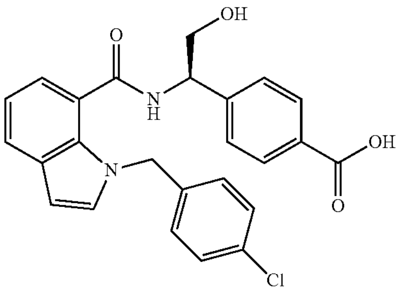 [SMILES: O=C(O)c1ccc([C@H](CO)NC(=O)c2cccc3ccn(Cc4ccc(Cl)cc4)c23)cc1] |
| 112 | 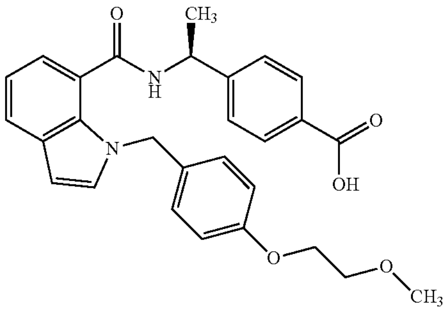 [SMILES: COCCOc1ccc(Cn2ccc3cccc(C(=O)N[C@@H](C)c4ccc(C(=O)O)cc4)c32)cc1] |
| 113 | 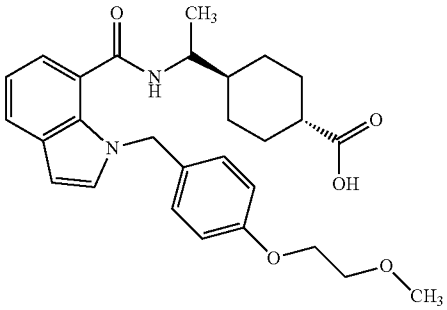 [SMILES: COCCOc1ccc(Cn2ccc3cccc(C(=O)NC(C)[C@H]4CC[C@H](C(=O)O)CC4)c32)cc1] |
TABLE 165
| Ex | Structure |
| --- | --- |
| 114 | 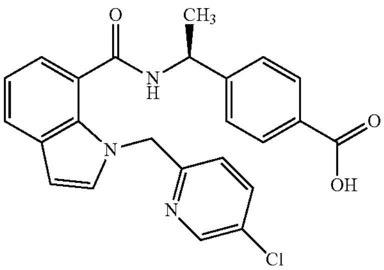 [SMILES: C[C@H](NC(=O)c1cccc2ccn(Cc3ccc(Cl)cn3)c12)c1ccc(C(=O)O)cc1] |

TABLE 165-continued
| Ex | Structure |
| --- | --- |
| 115 | 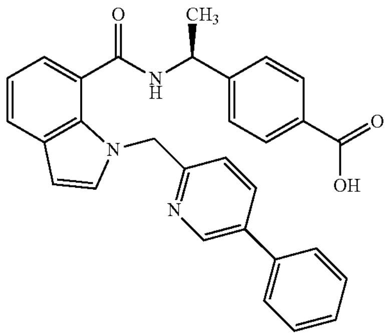 [SMILES: C[C@H](NC(=O)c1cccc2ccn(Cc3ccc(-c4ccccc4)cn3)c12)c1ccc(C(=O)O)cc1] |
| 116 | 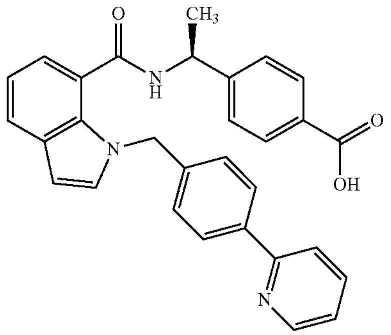 |
| 117 | 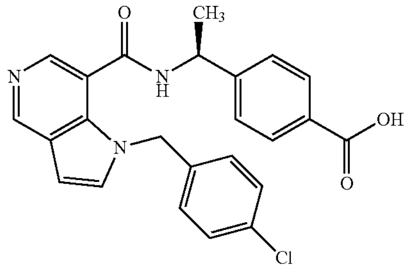 [SMILES: C[C@H](NC(=O)c1cncc2ccn(Cc3ccc(Cl)cc3)c12)c1ccc(C(=O)O)cc1] |
TABLE 166
| Ex | Structure |
| --- | --- |
| 118 | 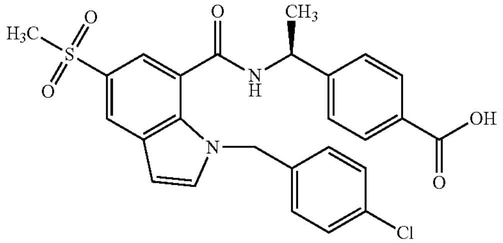 [SMILES: C[C@H](NC(=O)c1cc(S(C)(=O)=O)cc2ccn(Cc3ccc(Cl)cc3)c12)c1ccc(C(=O)O)cc1] |
TABLE 166-continued
| Ex | Structure |
| --- | --- |
| 119 | 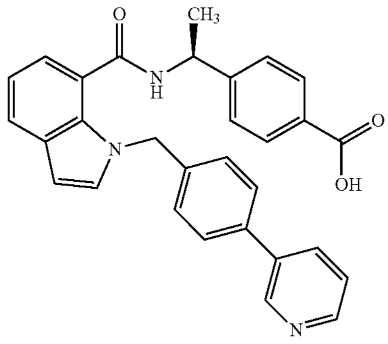 [SMILES: C[C@H](NC(=O)c1cccc2ccn(Cc3ccc(-c4cccnc4)cc3)c12)c1ccc(C(=O)O)cc1] |
| 120 | 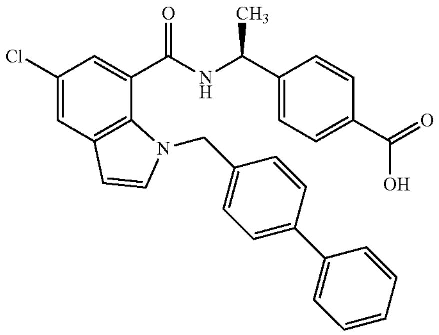 [SMILES: C[C@H](NC(=O)c1cc(Cl)cc2ccn(Cc3ccc(-c4ccccc4)cc3)c12)c1ccc(C(=O)O)cc1] |
| 121 | 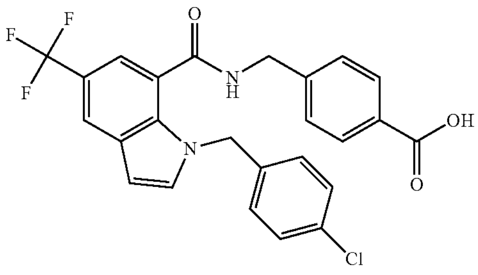 [SMILES: O=C(O)c1ccc(CNC(=O)c2cc(C(F)(F)F)cc3ccn(Cc4ccc(Cl)cc4)c23)cc1] |
TABLE 167
| Ex | Structure |
| --- | --- |
| 122 | 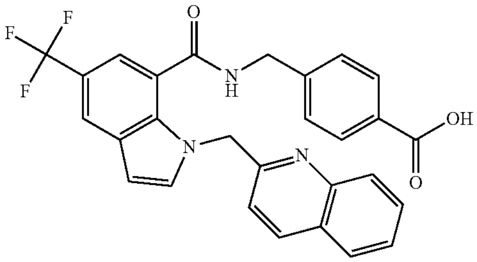 [SMILES: O=C(O)c1ccc(CNC(=O)c2cc(C(F)(F)F)cc3ccn(Cc4ccc5ccccc5n4)c23)cc1] |

TABLE 167-continued
| Ex | Structure |
|---|---|
| 123 | 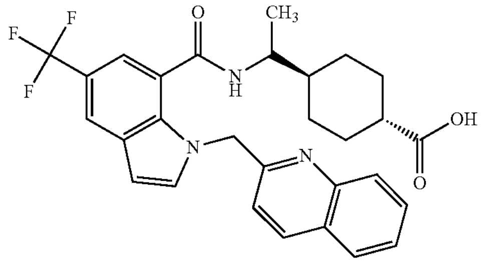 [SMILES: CC(NC(=O)c1cc(C(F)(F)F)cc2ccn(Cc3ccc4ccccc4n3)c12)[C@H]1CC[C@H](C(=O)O)CC1] |
| 124 | 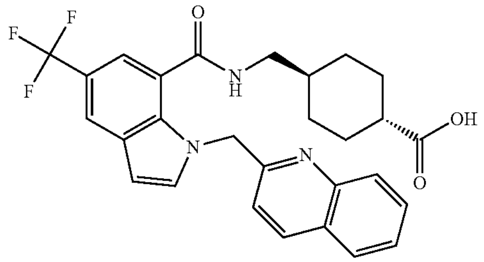 [SMILES: O=C(NC[C@H]1CC[C@H](C(=O)O)CC1)c1cc(C(F)(F)F)cc2ccn(Cc3ccc4ccccc4n3)c12] |
| 125 | 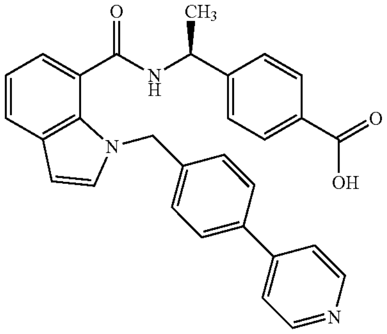 |
TABLE 168
| Ex | Structure |
|---|---|
| 126 | 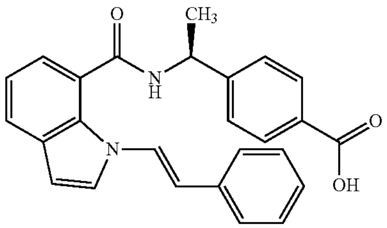 [SMILES: C[C@H](NC(=O)c1cccc2ccn(/C=C/c3ccccc3)c12)c1ccc(C(=O)O)cc1] |
| 127 | 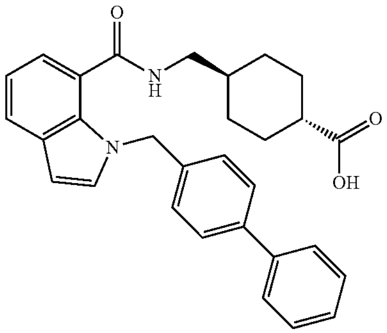 [SMILES: O=C(NC[C@H]1CC[C@H](C(=O)O)CC1)c1cccc2ccn(Cc3ccc(-c4ccccc4)cc3)c12] |
TABLE 168-continued
| Ex | Structure |
|---|---|
| 128 | 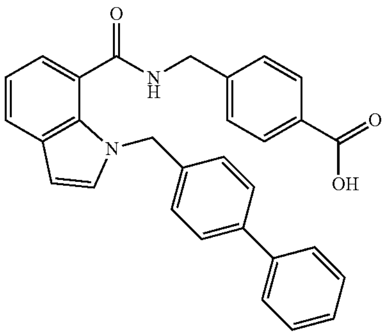 [SMILES: O=C(O)c1ccc(CNC(=O)c2cccc3ccn(Cc4ccc(-c5ccccc5)cc4)c23)cc1] |
| 129 | 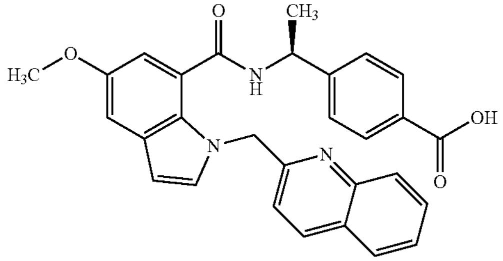 [SMILES: COc1cc(C(=O)N[C@@H](C)c2ccc(C(=O)O)cc2)c2c(ccn2Cc2ccc3ccccc3n2)c1] |
TABLE 169
| Ex | Structure |
|---|---|
| 130 | 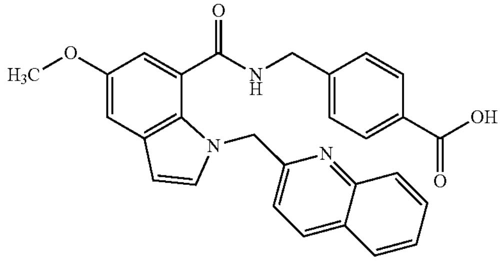 [SMILES: COc1cc(C(=O)NCc2ccc(C(=O)O)cc2)c2c(ccn2Cc2ccc3ccccc3n2)c1] |
| 131 | 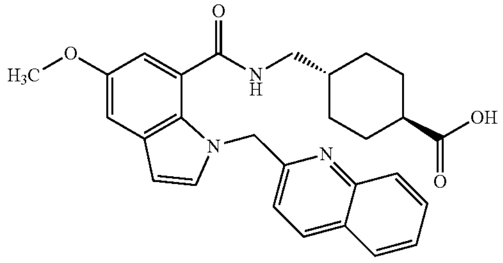 [SMILES: COc1cc(C(=O)NC[C@H]2CC[C@H](C(=O)O)CC2)c2c(ccn2Cc2ccc3ccccc3n2)c1] |
| 132 | 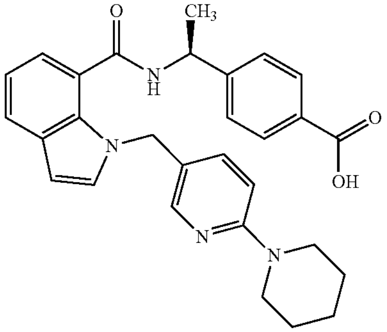 [SMILES: C[C@H](NC(=O)c1cccc2ccn(Cc3ccc(N4CCCCC4)nc3)c12)c1ccc(C(=O)O)cc1] |

TABLE 169-continued
| Ex | Structure |
|---|---|
| 133 | 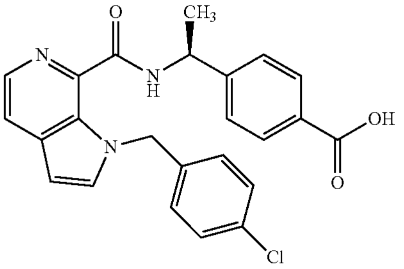 [SMILES: C[C@H](NC(=O)c1nccc2ccn(Cc3ccc(Cl)cc3)c12)c1ccc(C(=O)O)cc1] |
TABLE 170
| Ex | Structure |
|---|---|
| 134 | 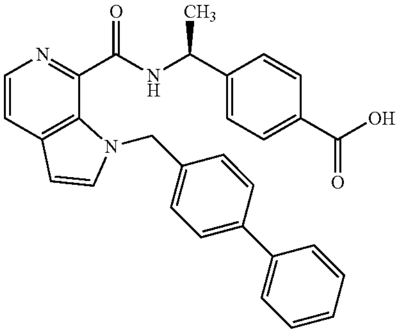 [SMILES: C[C@H](NC(=O)c1nccc2ccn(Cc3ccc(-c4ccccc4)cc3)c12)c1ccc(C(=O)O)cc1] |
| 135 | 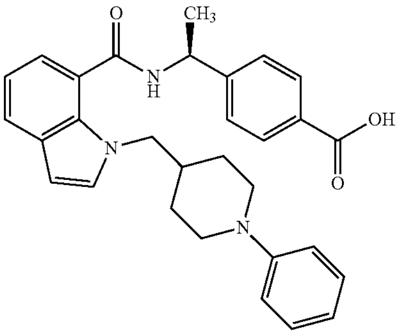 [SMILES: C[C@H](NC(=O)c1cccc2ccn(CC3CCN(c4ccccc4)CC3)c12)c1ccc(C(=O)O)cc1] |
| 136 | 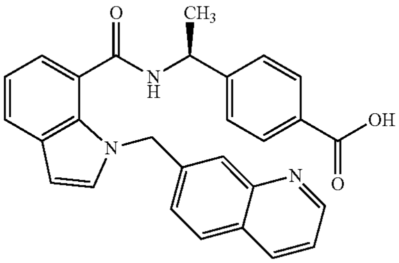 [SMILES: C[C@H](NC(=O)c1cccc2ccn(Cc3ccc4cccnc4c3)c12)c1ccc(C(=O)O)cc1] |
TABLE 170-continued
| Ex | Structure |
|---|---|
| 137 | 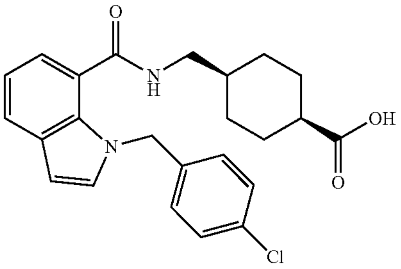 [SMILES: O=C(NC[C@H]1CC[C@@H](C(=O)O)CC1)c1cccc2ccn(Cc3ccc(Cl)cc3)c12] |
TABLE 171
| Ex | Structure |
|---|---|
| 138 | 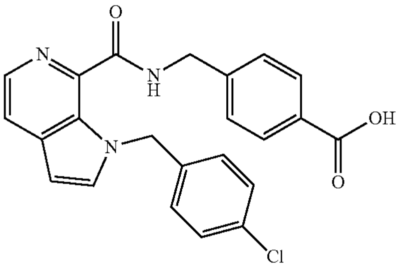 [SMILES: O=C(O)c1ccc(CNC(=O)c2nccc3ccn(Cc4ccc(Cl)cc4)c23)cc1] |
| 139 | 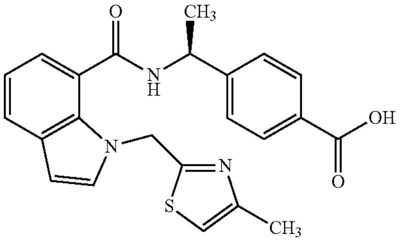 |
| 140 | 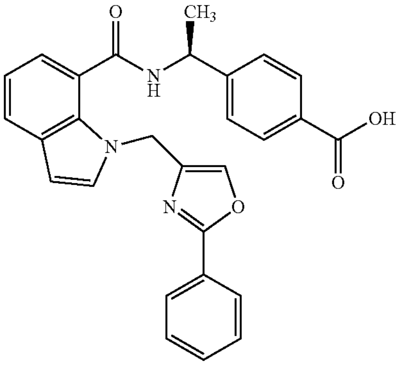 [SMILES: C[C@H](NC(=O)c1cccc2ccn(Cc3coc(-c4ccccc4)n3)c12)c1ccc(C(=O)O)cc1] |

TABLE 171-continued
| Ex | Structure |
| --- | --- |
| 141 | 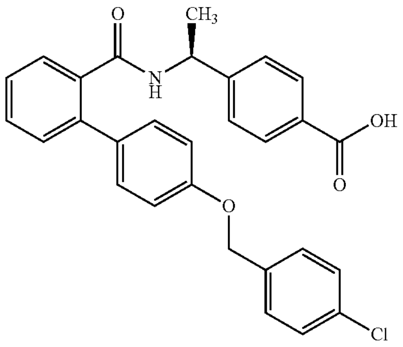 [SMILES: C[C@H](NC(=O)c1ccccc1-c1ccc(OCc2ccc(Cl)cc2)cc1)c1ccc(C(=O)O)cc1] |
TABLE 172
| Ex | Structure |
| --- | --- |
| 142 | 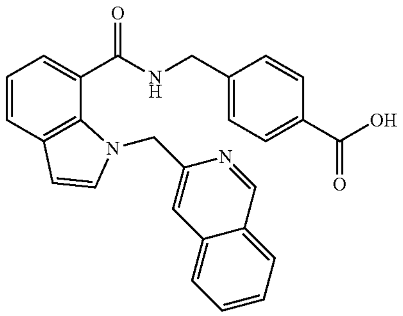 [SMILES: O=C(O)c1ccc(CNC(=O)c2cccc3ccn(Cc4cc5ccccc5cn4)c23)cc1] |
| 143 | 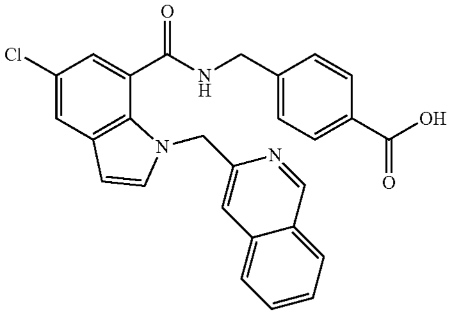 [SMILES: O=C(O)c1ccc(CNC(=O)c2cc(Cl)cc3ccn(Cc4cc5ccccc5cn4)c23)cc1] |
| 144 | 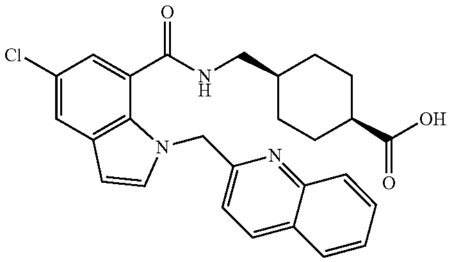 [SMILES: O=C(NC[C@H]1CC[C@@H](C(=O)O)CC1)c1cc(Cl)cc2ccn(Cc3ccc4ccccc4n3)c12] |
TABLE 172-continued
| Ex | Structure |
| --- | --- |
| 145 | 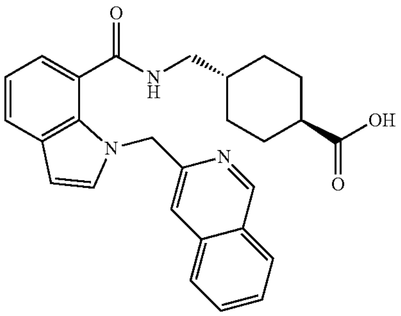 [SMILES: O=C(NC[C@H]1CC[C@H](C(=O)O)CC1)c1cccc2ccn(Cc3cc4ccccc4cn3)c12] |
TABLE 173
| Ex | Structure |
| --- | --- |
| 146 | 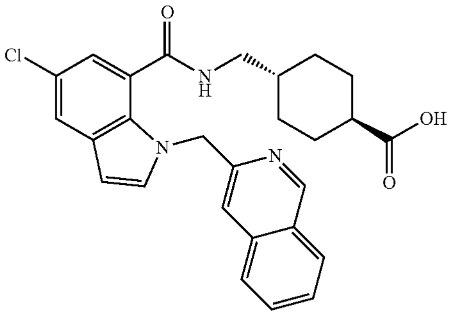 [SMILES: O=C(NC[C@H]1CC[C@H](C(=O)O)CC1)c1cc(Cl)cc2ccn(Cc3cc4ccccc4cn3)c12] |
| 147 | 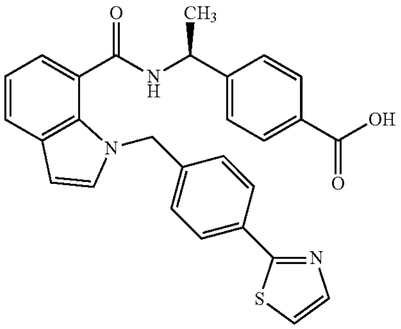 [SMILES: C[C@H](NC(=O)c1cccc2ccn(Cc3ccc(-c4nccs4)cc3)c12)c1ccc(C(=O)O)cc1] |
| 148 | 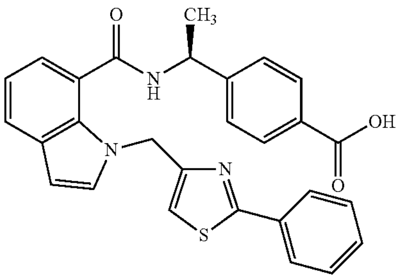 [SMILES: C[C@H](NC(=O)c1cccc2ccn(Cc3csc(-c4ccccc4)n3)c12)c1ccc(C(=O)O)cc1] |

TABLE 173-continued
| Ex | Structure |
| --- | --- |
| 149 | 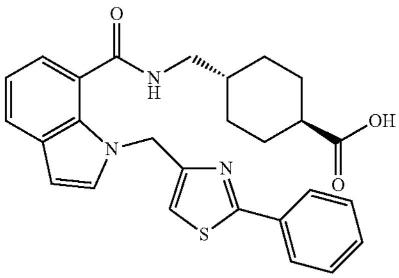 [SMILES: O=C(NC[C@H]1CC[C@H](C(=O)O)CC1)c1cccc2ccn(Cc3csc(-c4ccccc4)n3)c12] |
TABLE 174
| Ex | Structure |
| --- | --- |
| 150 | 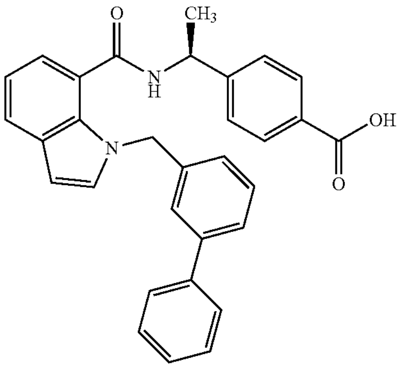 [SMILES: C[C@H](NC(=O)c1cccc2ccn(Cc3cccc(-c4ccccc4)c3)c12)c1ccc(C(=O)O)cc1] |
| 151 | 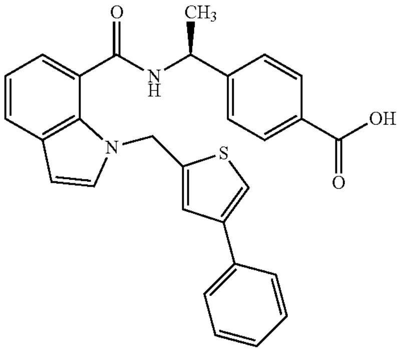 [SMILES: C[C@H](NC(=O)c1cccc2ccn(Cc3cc(-c4ccccc4)cs3)c12)c1ccc(C(=O)O)cc1] |
| 152 | 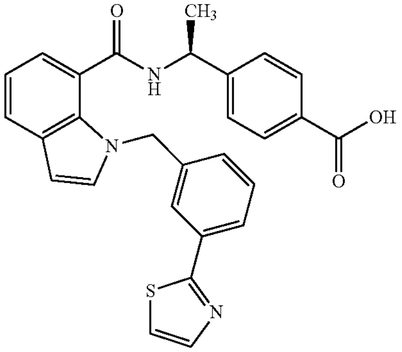 [SMILES: C[C@H](NC(=O)c1cccc2ccn(Cc3cccc(-c4nccs4)c3)c12)c1ccc(C(=O)O)cc1] |
TABLE 175
| Ex | Structure |
| --- | --- |
| 153 | 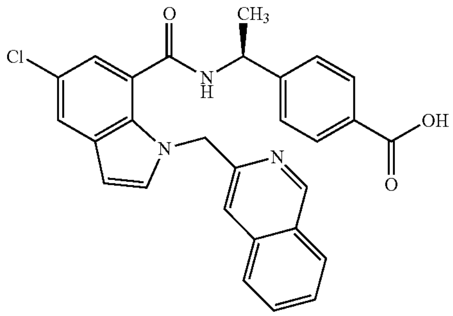 [SMILES: C[C@H](NC(=O)c1cc(Cl)cc2ccn(Cc3cc4ccccc4cn3)c12)c1ccc(C(=O)O)cc1] |
| 154 | 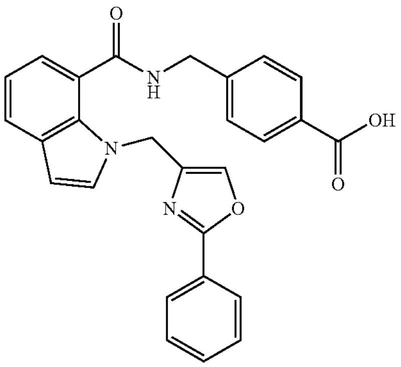 [SMILES: O=C(O)c1ccc(CNC(=O)c2cccc3ccn(Cc4coc(-c5ccccc5)n4)c23)cc1] |
| 155 | 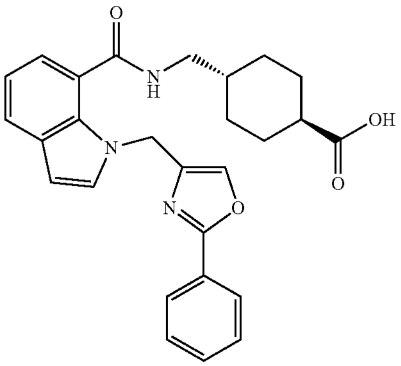 [SMILES: O=C(NC[C@H]1CC[C@H](C(=O)O)CC1)c1cccc2ccn(Cc3coc(-c4ccccc4)n3)c12] |
TABLE 176
| Ex | Structure |
| --- | --- |
| 156 | 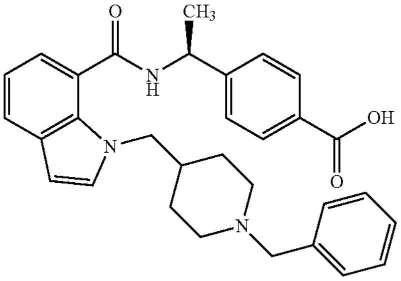 [SMILES: C[C@H](NC(=O)c1cccc2ccn(CC3CCN(Cc4ccccc4)CC3)c12)c1ccc(C(=O)O)cc1] |

TABLE 176-continued
| Ex | Structure |
|---|---|
| 157 | 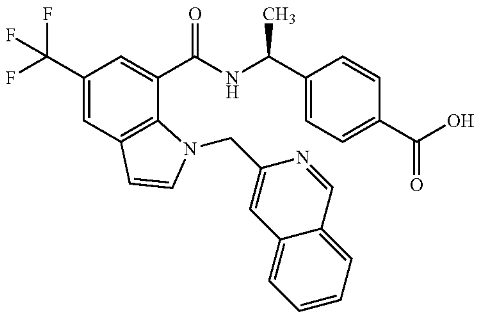 [SMILES: C[C@H](NC(=O)c1cc(C(F)(F)F)cc2ccn(Cc3cc4ccccc4cn3)c12)c1ccc(C(=O)O)cc1] |
| 158 | 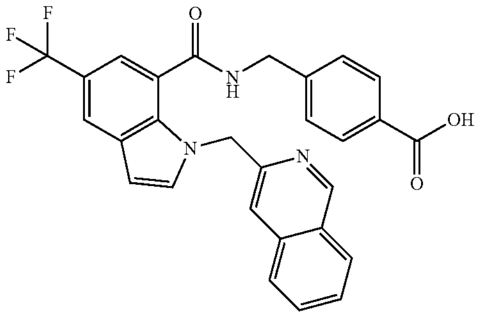 [SMILES: O=C(O)c1ccc(CNC(=O)c2cc(C(F)(F)F)cc3ccn(Cc4cc5ccccc5cn4)c23)cc1] |
| 159 | 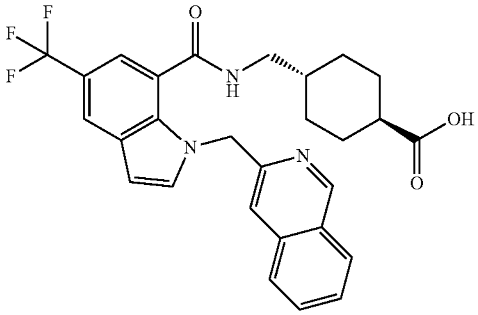 [SMILES: O=C(NC[C@H]1CC[C@H](C(=O)O)CC1)c1cc(C(F)(F)F)cc2ccn(Cc3cc4ccccc4cn3)c12] |
TABLE 177
| Ex | Structure |
|---|---|
| 160 | 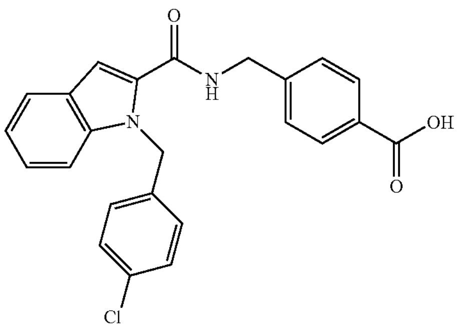 [SMILES: O=C(O)c1ccc(CNC(=O)c2cc3ccccc3n2Cc2ccc(Cl)cc2)cc1] |
TABLE 177-continued
| Ex | Structure |
|---|---|
| 161 | 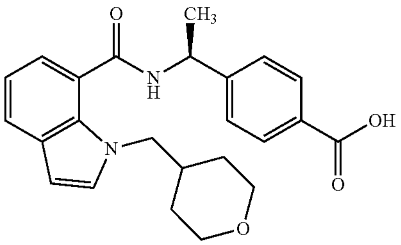 [SMILES: C[C@H](NC(=O)c1cccc2ccn(CC3CCOCC3)c12)c1ccc(C(=O)O)cc1] |
| 162 | 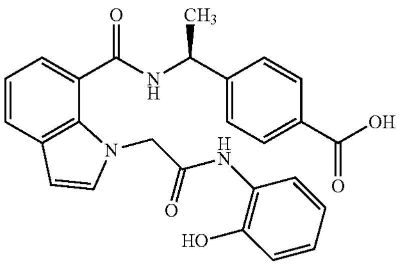 [SMILES: C[C@H](NC(=O)c1cccc2ccn(CC(=O)Nc3ccccc3O)c12)c1ccc(C(=O)O)cc1] |
| 163 | 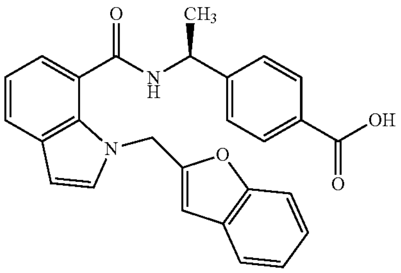 [SMILES: C[C@H](NC(=O)c1cccc2ccn(Cc3cc4ccccc4o3)c12)c1ccc(C(=O)O)cc1] |
TABLE 178
| Ex | Structure |
|---|---|
| 164 | 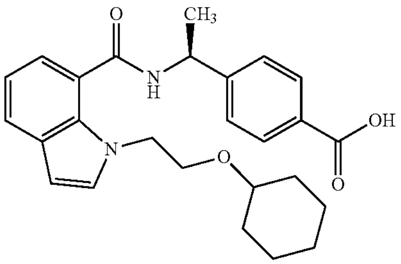 [SMILES: C[C@H](NC(=O)c1cccc2ccn(CCOC3CCCCC3)c12)c1ccc(C(=O)O)cc1] |
| 165 | 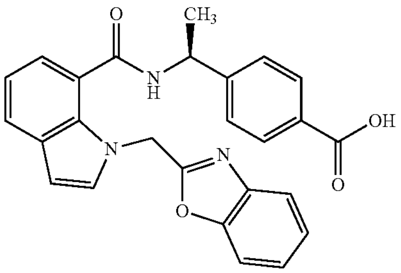 [SMILES: C[C@H](NC(=O)c1cccc2ccn(Cc3nc4ccccc4o3)c12)c1ccc(C(=O)O)cc1] |

TABLE 178-continued
| Ex | Structure |
|---|---|
| 166 | 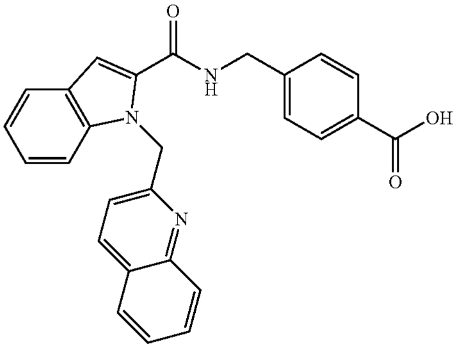 [SMILES: O=C(O)c1ccc(CNC(=O)c2cc3ccccc3n2Cc2ccc3ccccc3n2)cc1] |
| 167 | 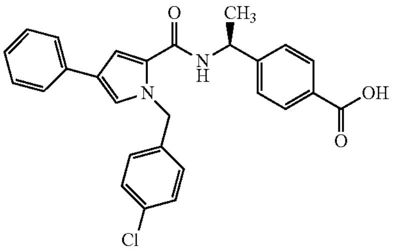 [SMILES: C[C@H](NC(=O)c1cc(-c2ccccc2)cn1Cc1ccc(Cl)cc1)c1ccc(C(=O)O)cc1] |
TABLE 179
| Ex | Structure |
|---|---|
| 168 | 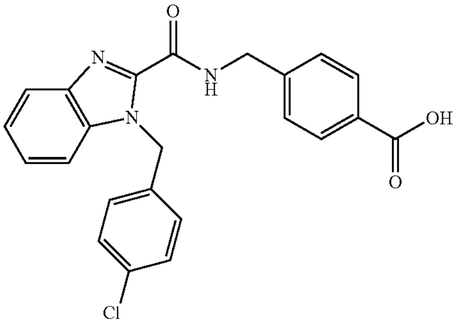 [SMILES: O=C(O)c1ccc(CNC(=O)c2nc3ccccc3n2Cc2ccc(Cl)cc2)cc1] |
| 169 | 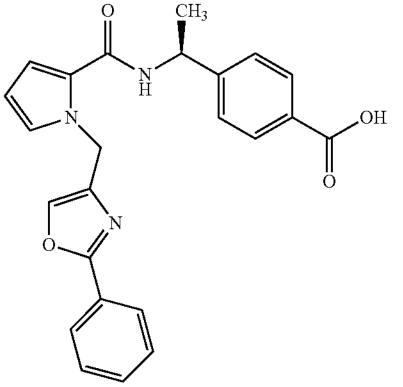 [SMILES: C[C@H](NC(=O)c1cccn1Cc1coc(-c2ccccc2)n1)c1ccc(C(=O)O)cc1] |
TABLE 179-continued
| Ex | Structure |
|---|---|
| 170 | 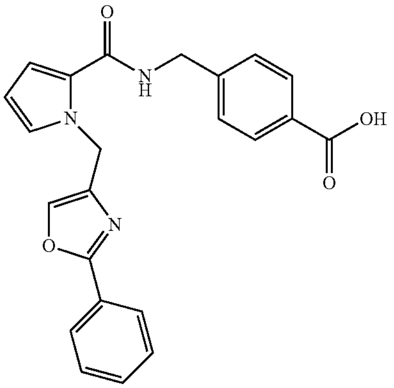 [SMILES: O=C(O)c1ccc(CNC(=O)c2cccn2Cc2coc(-c3ccccc3)n2)cc1] |
TABLE 180
| Ex | Structure |
|---|---|
| 171 | 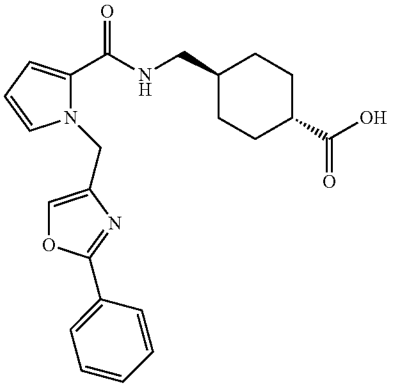 [SMILES: O=C(NC[C@H]1CC[C@H](C(=O)O)CC1)c1cccn1Cc1coc(-c2ccccc2)n1] |
| 172 | 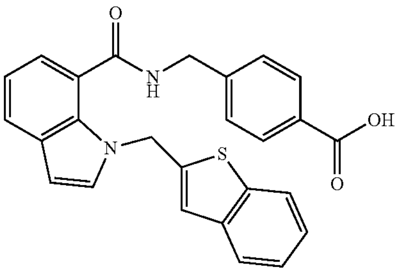 [SMILES: O=C(O)c1ccc(CNC(=O)c2cccc3ccn(Cc4cc5ccccc5s4)c23)cc1] |
| 173 | 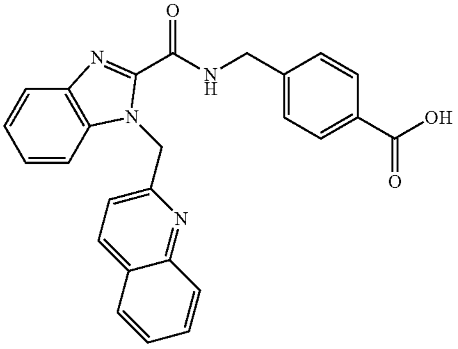 [SMILES: O=C(O)c1ccc(CNC(=O)c2nc3ccccc3n2Cc2ccc3ccccc3n2)cc1] |

TABLE 181
| Ex | Structure |
| --- | --- |
| 174 | 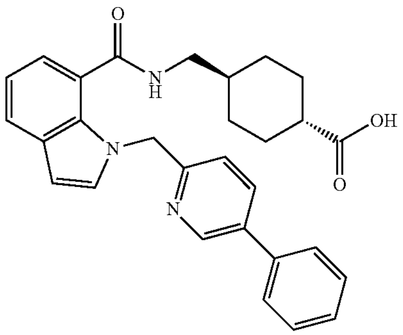 [SMILES: O=C(NC[C@H]1CC[C@H](C(=O)O)CC1)c1cccc2ccn(Cc3ccc(-c4ccccc4)cn3)c12] |
| 175 | 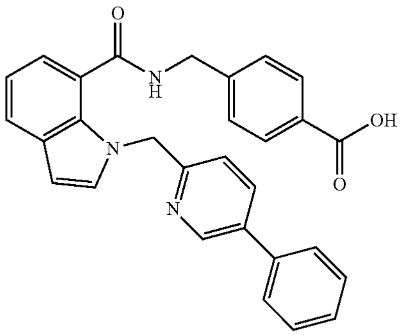 [SMILES: O=C(O)c1ccc(CNC(=O)c2cccc3ccn(Cc4ccc(-c5ccccc5)cn4)c23)cc1] |
| 176 | 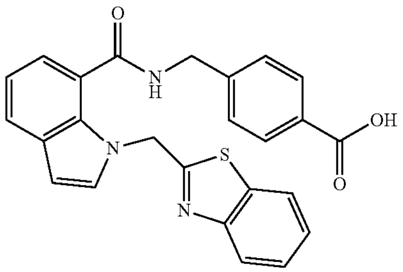 [SMILES: O=C(O)c1ccc(CNC(=O)c2cccc3ccn(Cc4nc5ccccc5s4)c23)cc1] |
TABLE 182
| Ex | Structure |
| --- | --- |
| 177 | 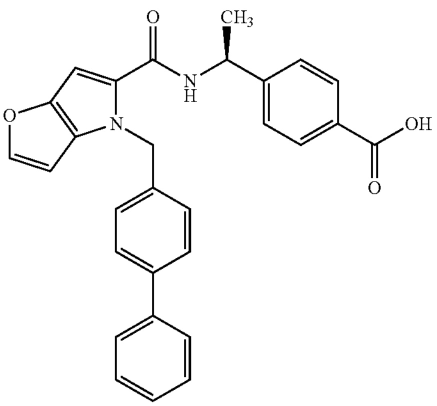 [SMILES: C[C@H](NC(=O)c1cc2occc2n1Cc1ccc(-c2ccccc2)cc1)c1ccc(C(=O)O)cc1] |
TABLE 182-continued
| Ex | Structure |
| --- | --- |
| 178 | 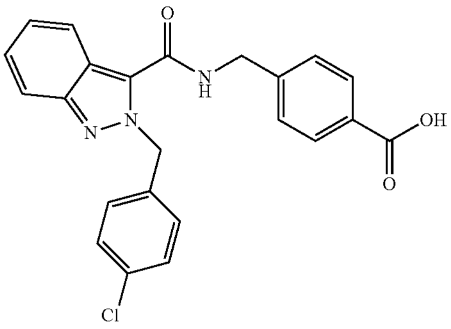 [SMILES: O=C(O)c1ccc(CNC(=O)c2c3ccccc3nn2Cc2ccc(Cl)cc2)cc1] |
| 179 | 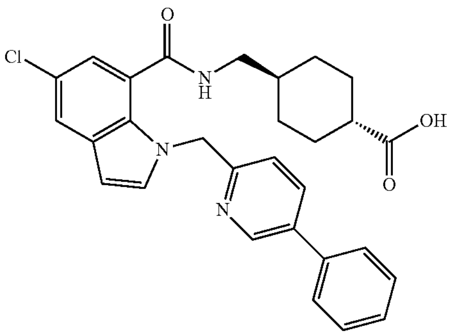 [SMILES: O=C(NC[C@H]1CC[C@H](C(=O)O)CC1)c1cc(Cl)cc2ccn(Cc3ccc(-c4ccccc4)cn3)c12] |
TABLE 183
| Ex | Structure |
| --- | --- |
| 180 | 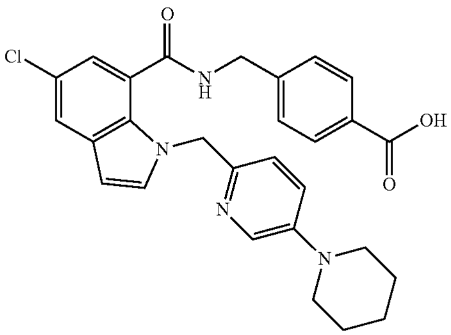 [SMILES: O=C(O)c1ccc(CNC(=O)c2cc(Cl)cc3ccn(Cc4ccc(N5CCCCC5)cn4)c23)cc1] |
| 181 | 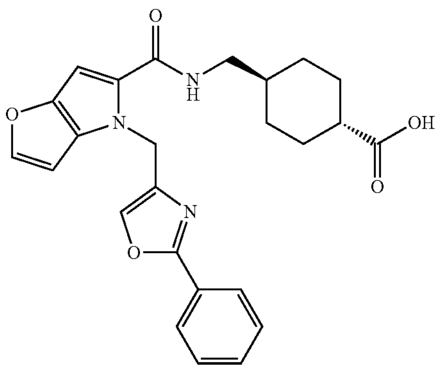 [SMILES: O=C(NC[C@H]1CC[C@H](C(=O)O)CC1)c1cc2occc2n1Cc1coc(-c2ccccc2)n1] |

TABLE 183-continued
| Ex | Structure |
| --- | --- |
| 182 | 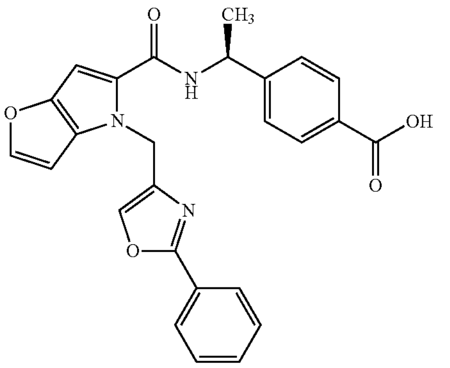 [SMILES: C[C@H](NC(=O)c1cc2occc2n1Cc1coc(-c2ccccc2)n1)c1ccc(C(=O)O)cc1] |
TABLE 184
| Ex | Structure |
| --- | --- |
| 183 | 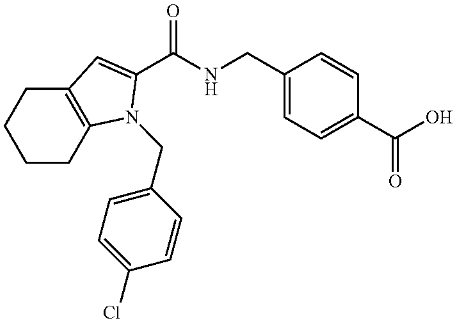 [SMILES: O=C(O)c1ccc(CNC(=O)c2cc3c(n2Cc2ccc(Cl)cc2)CCCC3)cc1] |
| 184 | 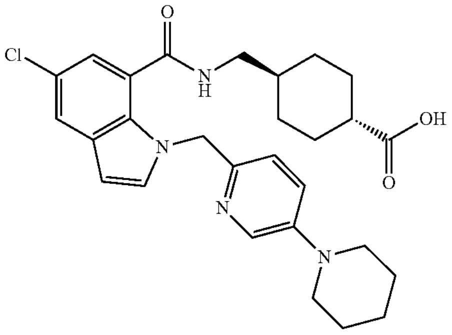 [SMILES: O=C(NC[C@H]1CC[C@H](C(=O)O)CC1)c1cc(Cl)cc2ccn(Cc3ccc(N4CCCCC4)cn3)c12] |
| 185/Cl | 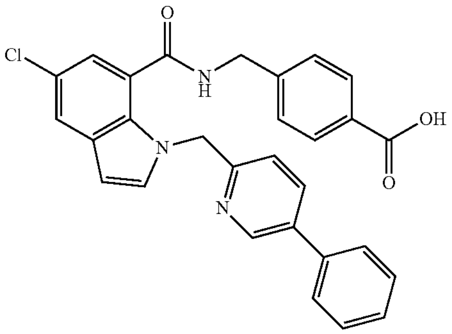 [SMILES: O=C(O)c1ccc(CNC(=O)c2cc(Cl)cc3ccn(Cc4ccc(-c5ccccc5)cn4)c23)cc1] |
TABLE 185
| Ex | Structure |
| --- | --- |
| 186 | 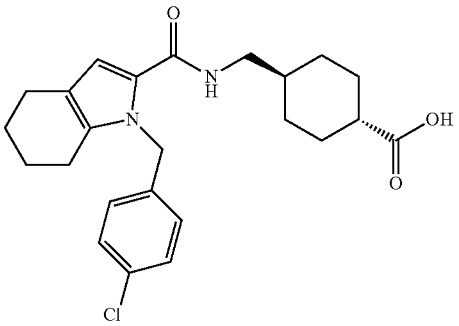 [SMILES: O=C(NC[C@H]1CC[C@H](C(=O)O)CC1)c1cc2c(n1Cc1ccc(Cl)cc1)CCCC2] |
| 187 | 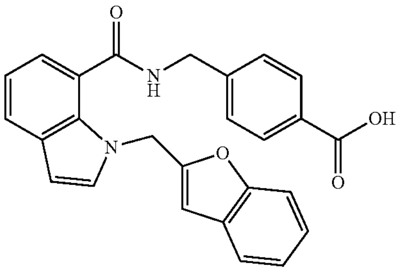 [SMILES: O=C(O)c1ccc(CNC(=O)c2cccc3ccn(Cc4cc5ccccc5o4)c23)cc1] |
| 188 | 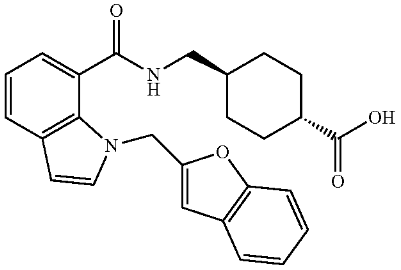 [SMILES: O=C(NC[C@H]1CC[C@H](C(=O)O)CC1)c1cccc2ccn(Cc3cc4ccccc4o3)c12] |
| 189 | 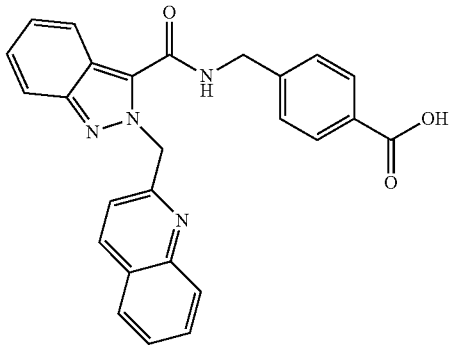 [SMILES: O=C(O)c1ccc(CNC(=O)c2c3ccccc3nn2Cc2ccc3ccccc3n2)cc1] |

TABLE 186
| Ex | Structure |
|---|---|
| 190 | 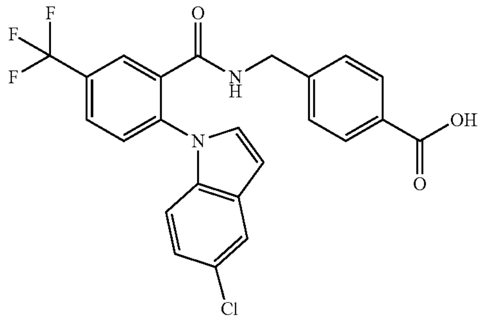 [SMILES: O=C(O)c1ccc(CNC(=O)c2cc(C(F)(F)F)ccc2-n2ccc3cc(Cl)ccc32)cc1] |
| 191 | 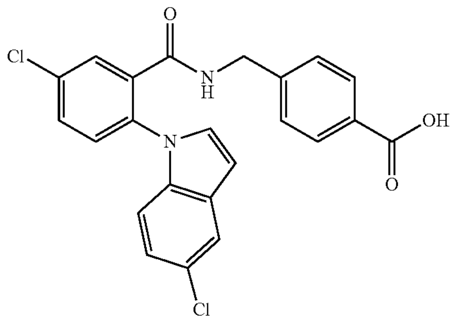 [SMILES: O=C(O)c1ccc(CNC(=O)c2cc(Cl)ccc2-n2ccc3cc(Cl)ccc32)cc1] |
| 192 | 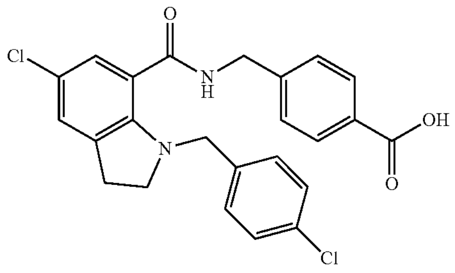 [SMILES: O=C(O)c1ccc(CNC(=O)c2cc(Cl)cc3c2N(Cc2ccc(Cl)cc2)CC3)cc1] |
| 193 | 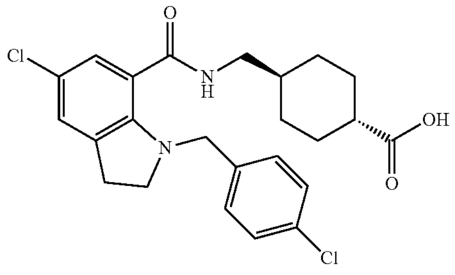 [SMILES: O=C(NC[C@H]1CC[C@H](C(=O)O)CC1)c1cc(Cl)cc2c1N(Cc1ccc(Cl)cc1)CC2] |
TABLE 187
| Ex | Structure |
|---|---|
| 194 | 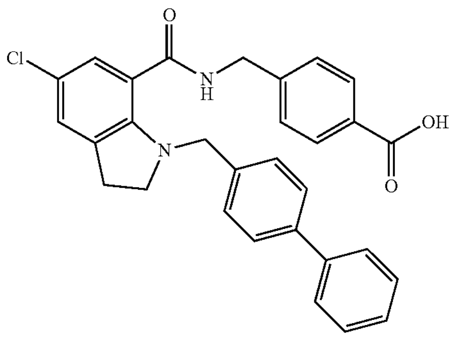 [SMILES: O=C(O)c1ccc(CNC(=O)c2cc(Cl)cc3c2N(Cc2ccc(-c4ccccc4)cc2)CC3)cc1] |
| 195 | 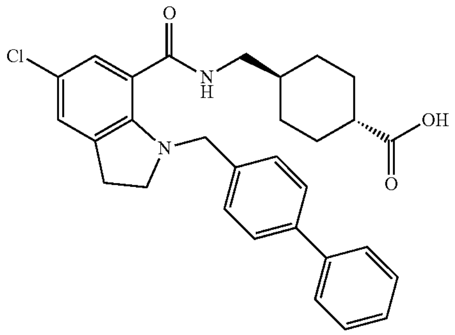 [SMILES: O=C(NC[C@H]1CC[C@H](C(=O)O)CC1)c1cc(Cl)cc2c1N(Cc1ccc(-c3ccccc3)cc1)CC2] |
| 196 | 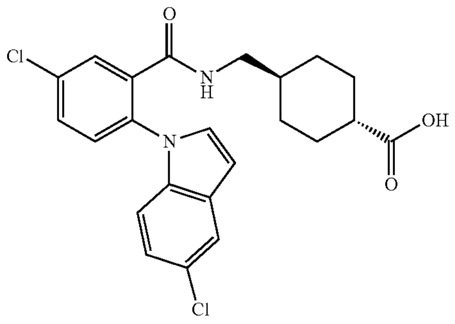 [SMILES: O=C(NC[C@H]1CC[C@H](C(=O)O)CC1)c1cc(Cl)ccc1-n1ccc2cc(Cl)ccc21] |
TABLE 188
| Ex | Structure |
|---|---|
| 197 | 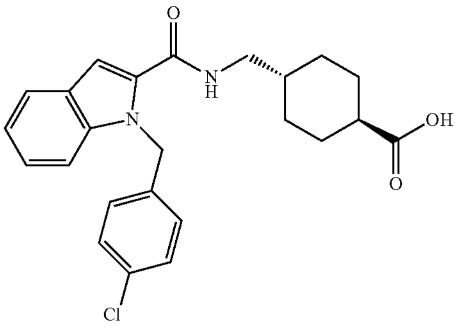 [SMILES: O=C(NC[C@H]1CC[C@H](C(=O)O)CC1)c1cc2ccccc2n1Cc1ccc(Cl)cc1] |

TABLE 188-continued
| Ex | Structure |
| --- | --- |
| 198 | 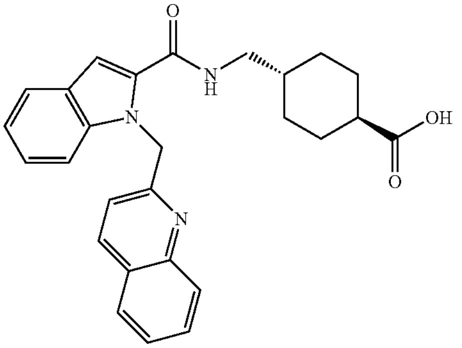 [SMILES: O=C(NC[C@H]1CC[C@H](C(=O)O)CC1)c1cc2ccccc2n1Cc1ccc2ccccc2n1] |
| 199 | 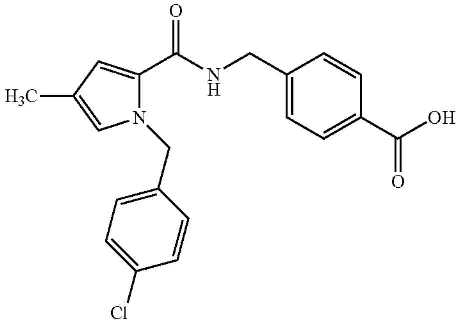 [SMILES: Cc1cc(C(=O)NCc2ccc(C(=O)O)cc2)n(Cc2ccc(Cl)cc2)c1] |
TABLE 189
| Ex | Structure |
| --- | --- |
| 200 | 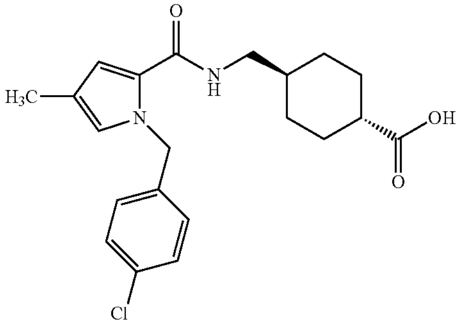 [SMILES: Cc1cc(C(=O)NC[C@H]2CC[C@H](C(=O)O)CC2)n(Cc2ccc(Cl)cc2)c1] |
| 201 | 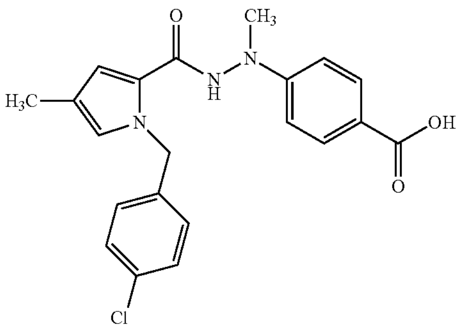 [SMILES: Cc1cc(C(=O)NN(C)c2ccc(C(=O)O)cc2)n(Cc2ccc(Cl)cc2)c1] |
TABLE 189-continued
| Ex | Structure |
| --- | --- |
| 202 | 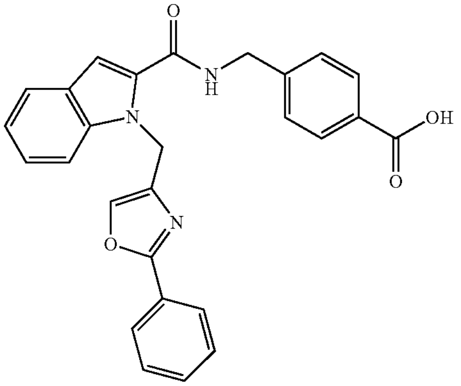 [SMILES: O=C(O)c1ccc(CNC(=O)c2cc3ccccc3n2Cc2coc(-c3ccccc3)n2)cc1] |
TABLE 190
| Ex | Structure |
| --- | --- |
| 203 | 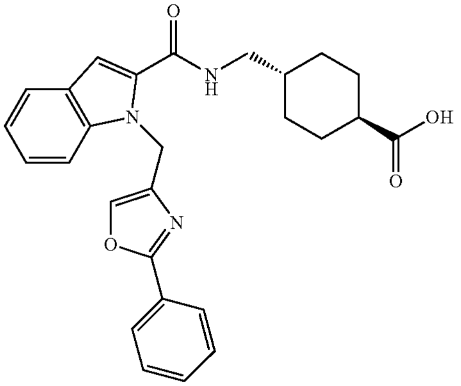 [SMILES: O=C(NC[C@H]1CC[C@H](C(=O)O)CC1)c1cc2ccccc2n1Cc1coc(-c2ccccc2)n1] |
| 204 | 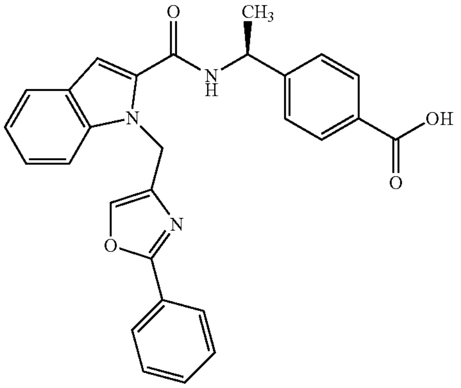 [SMILES: C[C@H](NC(=O)c1cc2ccccc2n1Cc1coc(-c2ccccc2)n1)c1ccc(C(=O)O)cc1] |

TABLE 190-continued
| Ex | Structure |
|---|---|
| 205 | 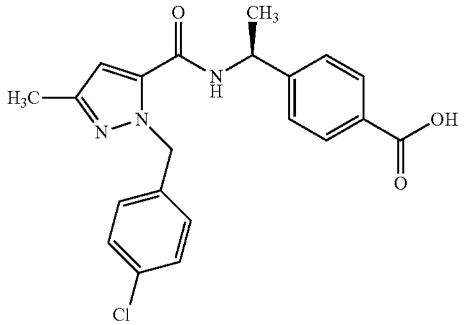 |
TABLE 191
| Ex | Structure |
|---|---|
| 206 | 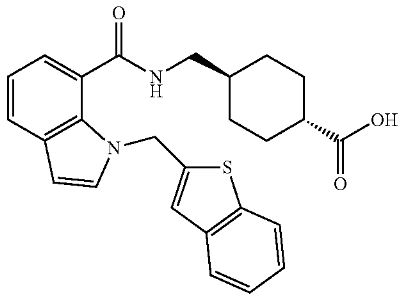 [SMILES: O=C(NC[C@H]1CC[C@H](C(=O)O)CC1)c1cccc2ccn(Cc3cc4ccccc4s3)c12] |
| 207 | 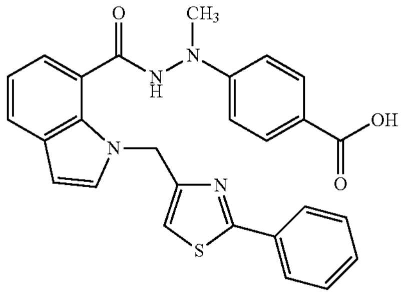 [SMILES: CN(NC(=O)c1cccc2ccn(Cc3csc(-c4ccccc4)n3)c12)c1ccc(C(=O)O)cc1] |
| 208 | 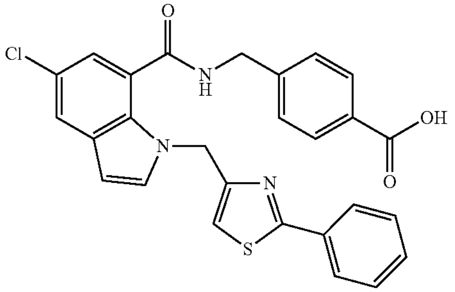 [SMILES: O=C(O)c1ccc(CNC(=O)c2cc(Cl)cc3ccn(Cc4csc(-c5ccccc5)n4)c23)cc1] |
TABLE 191-continued
| Ex | Structure |
|---|---|
| 209 | 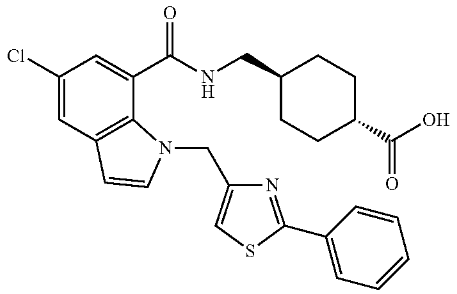 [SMILES: O=C(NC[C@H]1CC[C@H](C(=O)O)CC1)c1cc(Cl)cc2ccn(Cc3csc(-c4ccccc4)n3)c12] |
TABLE 192
| Ex | Structure |
|---|---|
| 210 | 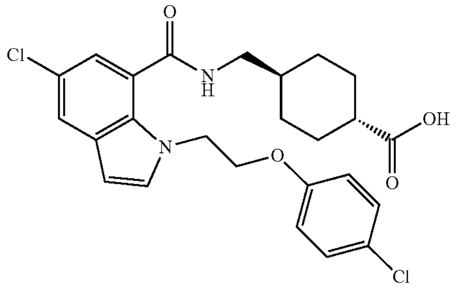 [SMILES: O=C(NC[C@H]1CC[C@H](C(=O)O)CC1)c1cc(Cl)cc2ccn(CCOc3ccc(Cl)cc3)c12] |
| 211 | 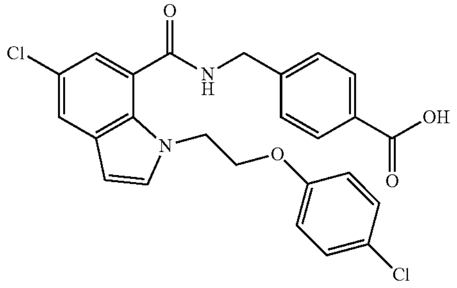 [SMILES: O=C(O)c1ccc(CNC(=O)c2cc(Cl)cc3ccn(CCOc4ccc(Cl)cc4)c23)cc1] |
| 212 | 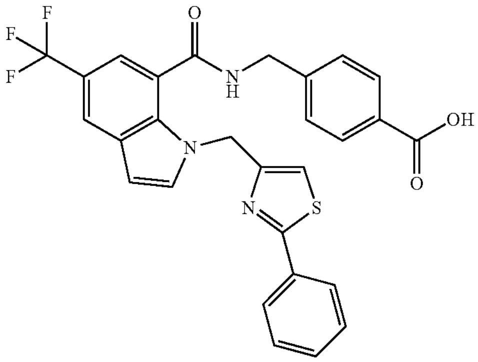 [SMILES: O=C(O)c1ccc(CNC(=O)c2cc(C(F)(F)F)cc3ccn(Cc4csc(-c5ccccc5)n4)c23)cc1] |

TABLE 193
| Ex | Structure |
|---|---|
| 213 | 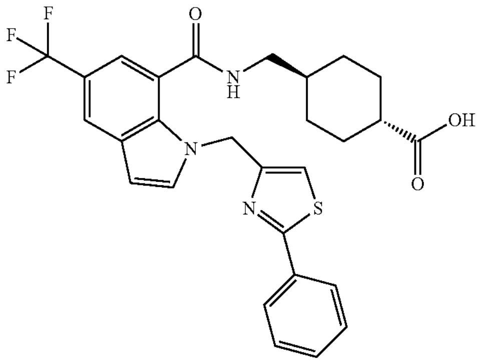 [SMILES: O=C(NC[C@H]1CC[C@H](C(=O)O)CC1)c1cc(C(F)(F)F)cc2ccn(Cc3csc(-c4ccccc4)n3)c12] |
| 214 | 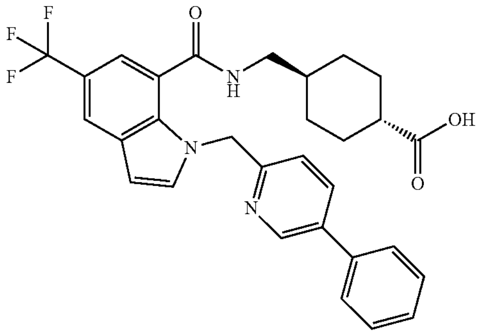 [SMILES: O=C(NC[C@H]1CC[C@H](C(=O)O)CC1)c1cc(C(F)(F)F)cc2ccn(Cc3ccc(-c4ccccc4)cn3)c12] |
| 215 | 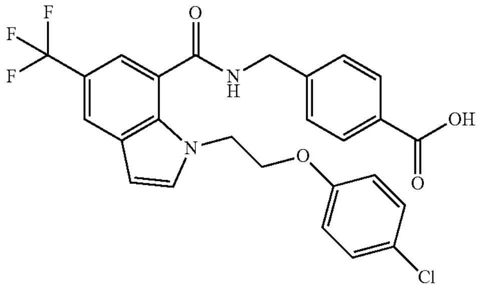 [SMILES: O=C(O)c1ccc(CNC(=O)c2cc(C(F)(F)F)cc3ccn(CCOc4ccc(Cl)cc4)c23)cc1] |
| 216 | 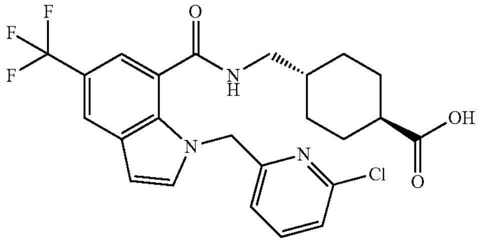 [SMILES: O=C(NC[C@H]1CC[C@H](C(=O)O)CC1)c1cc(C(F)(F)F)cc2ccn(Cc3cccc(Cl)n3)c12] |
TABLE 194
| Ex | Structure |
|---|---|
| 217 | 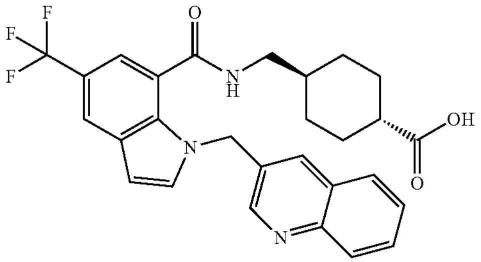 [SMILES: O=C(NC[C@H]1CC[C@H](C(=O)O)CC1)c1cc(C(F)(F)F)cc2ccn(Cc3cnc4ccccc4c3)c12] |
| 218 | 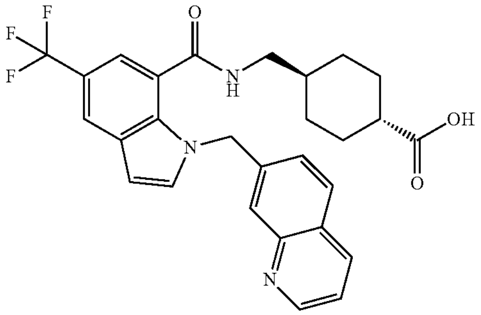 [SMILES: O=C(NC[C@H]1CC[C@H](C(=O)O)CC1)c1cc(C(F)(F)F)cc2ccn(Cc3ccc4cccnc4c3)c12] |
| 219 | 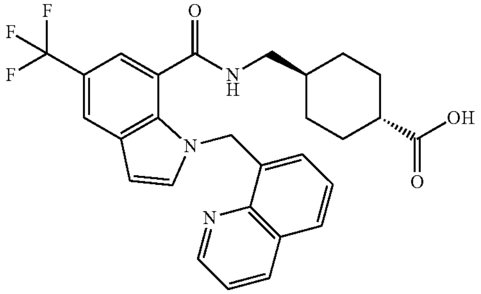 [SMILES: O=C(NC[C@H]1CC[C@H](C(=O)O)CC1)c1cc(C(F)(F)F)cc2ccn(Cc3cccc4cccnc34)c12] |
| 220 | 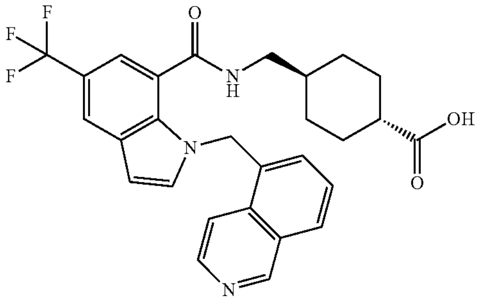 [SMILES: O=C(NC[C@H]1CC[C@H](C(=O)O)CC1)c1cc(C(F)(F)F)cc2ccn(Cc3cccc4cnccc34)c12] |

TABLE 195
| Ex | Structure |
| --- | --- |
| 221 | 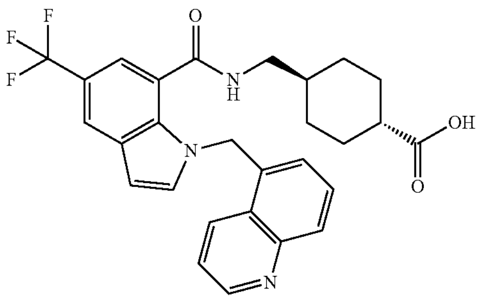 |
| 222 | 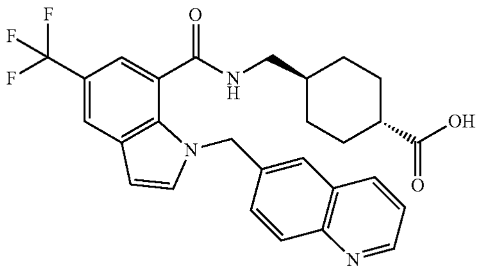 [SMILES: O=C(NC[C@H]1CC[C@H](C(=O)O)CC1)c1cc(C(F)(F)F)cc2ccn(Cc3ccc4ncccc4c3)c12] |
| 223 | 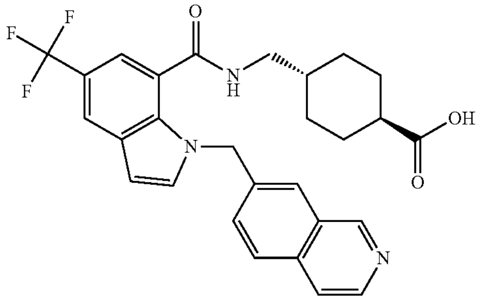 [SMILES: O=C(NC[C@H]1CC[C@H](C(=O)O)CC1)c1cc(C(F)(F)F)cc2ccn(Cc3ccc4ccncc4c3)c12] |
| 224 | 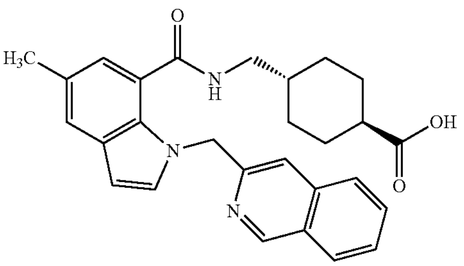 [SMILES: Cc1cc(C(=O)NC[C@H]2CC[C@H](C(=O)O)CC2)c2c(ccn2Cc2cc3ccccc3cn2)c1] |
TABLE 196
| Ex | Structure |
| --- | --- |
| 225 | 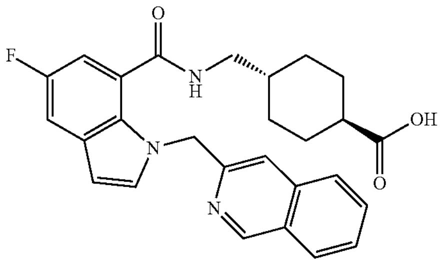 [SMILES: O=C(NC[C@H]1CC[C@H](C(=O)O)CC1)c1cc(F)cc2ccn(Cc3cc4ccccc4cn3)c12] |
TABLE 196-continued
| Ex | Structure |
| --- | --- |
| 226 | 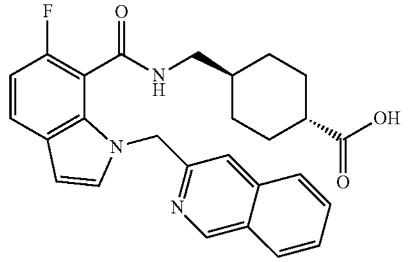 [SMILES: O=C(NC[C@H]1CC[C@H](C(=O)O)CC1)c1c(F)ccc2ccn(Cc3cc4ccccc4cn3)c12] |
| 227 | 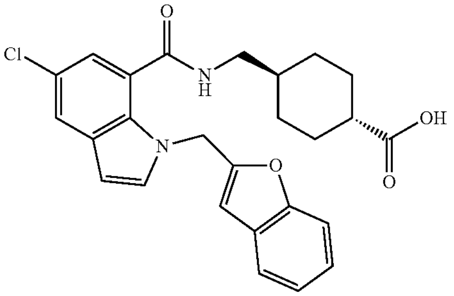 [SMILES: O=C(NC[C@H]1CC[C@H](C(=O)O)CC1)c1cc(Cl)cc2ccn(Cc3cc4ccccc4o3)c12] |
| 228 | 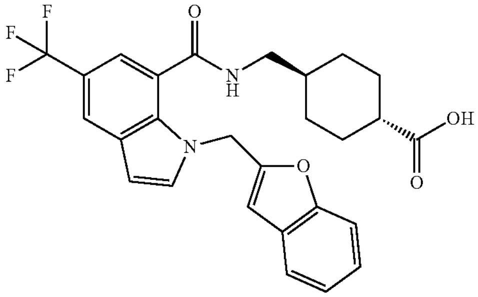 [SMILES: O=C(NC[C@H]1CC[C@H](C(=O)O)CC1)c1cc(C(F)(F)F)cc2ccn(Cc3cc4ccccc4o3)c12] |
TABLE 197
| Ex | Structure |
| --- | --- |
| 229 | 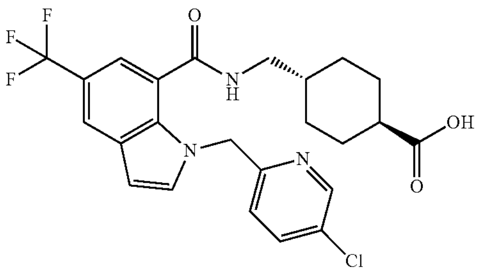 [SMILES: O=C(NC[C@H]1CC[C@H](C(=O)O)CC1)c1cc(C(F)(F)F)cc2ccn(Cc3ccc(Cl)cn3)c12] |
| 230 | 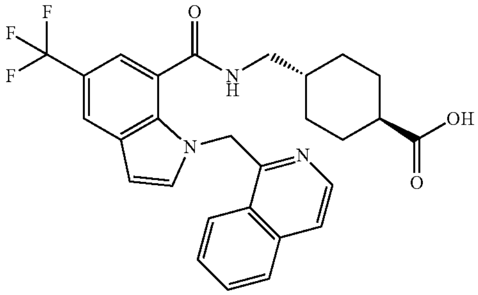 [SMILES: O=C(NC[C@H]1CC[C@H](C(=O)O)CC1)c1cc(C(F)(F)F)cc2ccn(Cc3nccc4ccccc34)c12] |

TABLE 197-continued
| Ex | Structure |
| --- | --- |
| 231 | 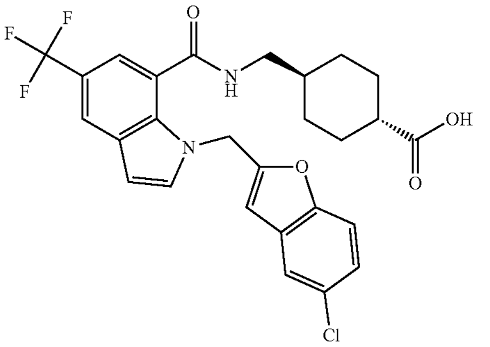 [SMILES: O=C(NC[C@H]1CC[C@H](C(=O)O)CC1)c1cc(C(F)(F)F)cc2ccn(Cc3cc4cc(Cl)ccc4o3)c12] |
| 232 | 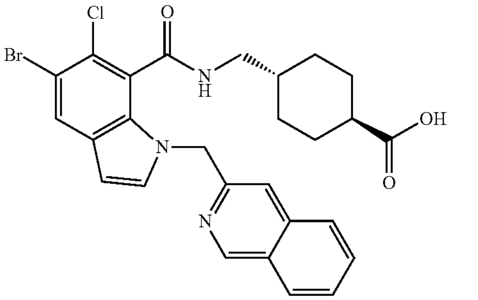 [SMILES: O=C(NC[C@H]1CC[C@H](C(=O)O)CC1)c1c(Cl)c(Br)cc2ccn(Cc3cc4ccccc4cn3)c12] |
TABLE 198
| Ex | Structure |
| --- | --- |
| 233 | 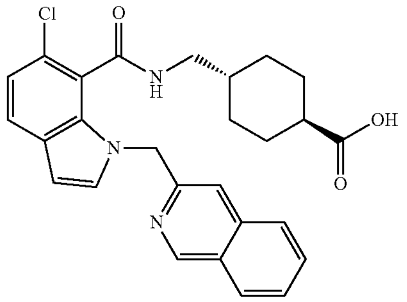 [SMILES: O=C(NC[C@H]1CC[C@H](C(=O)O)CC1)c1c(Cl)ccc2ccn(Cc3cc4ccccc4cn3)c12] |
| 234 | 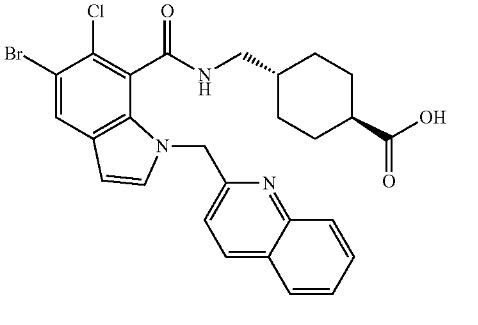 [SMILES: O=C(NC[C@H]1CC[C@H](C(=O)O)CC1)c1c(Cl)c(Br)cc2ccn(Cc3ccc4ccccc4n3)c12] |
TABLE 198-continued
| Ex | Structure |
| --- | --- |
| 235 | 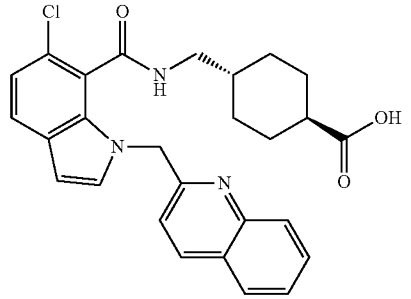 [SMILES: O=C(NC[C@H]1CC[C@H](C(=O)O)CC1)c1c(Cl)ccc2ccn(Cc3ccc4ccccc4n3)c12] |
| 236 | 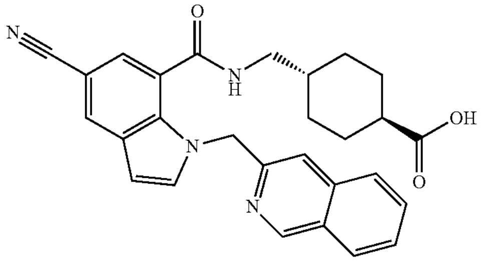 [SMILES: N#Cc1cc(C(=O)NC[C@H]2CC[C@H](C(=O)O)CC2)c2c(ccn2Cc2cc3ccccc3cn2)c1] |
TABLE 199
| Ex | Structure |
| --- | --- |
| 237 | 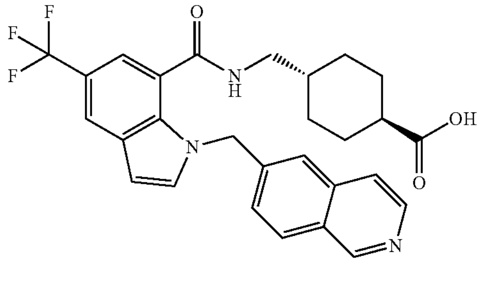 [SMILES: O=C(NC[C@H]1CC[C@H](C(=O)O)CC1)c1cc(C(F)(F)F)cc2ccn(Cc3ccc4cnccc4c3)c12] |
| 238 | 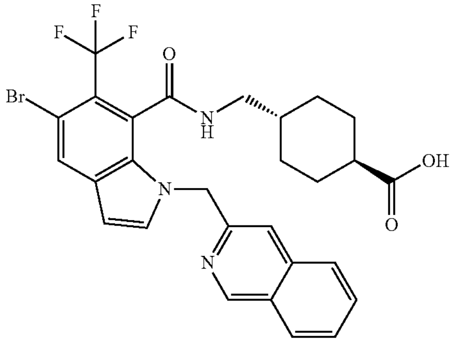 [SMILES: O=C(NC[C@H]1CC[C@H](C(=O)O)CC1)c1c(C(F)(F)F)c(Br)cc2ccn(Cc3cc4ccccc4cn3)c12] |

TABLE 199-continued

| Ex | Structure |
|---|---|
| 239 | 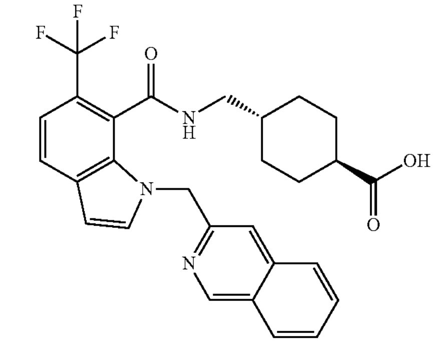 [SMILES: O=C(NC[C@H]1CC[C@H](C(=O)O)CC1)c1c(C(F)(F)F)ccc2ccn(Cc3cc4ccccc4cn3)c12] |

TABLE 200

| Ex | Structure |
|---|---|
| 240 | 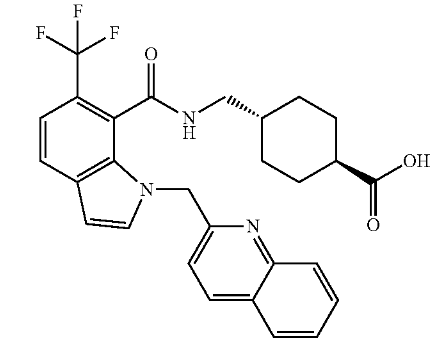 [SMILES: O=C(NC[C@H]1CC[C@H](C(=O)O)CC1)c1c(C(F)(F)F)ccc2ccn(Cc3ccc4ccccc4n3)c12] |
| 241 | 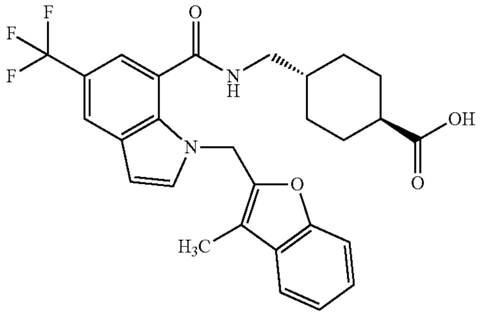 [SMILES: Cc1c(Cn2ccc3cc(C(F)(F)F)cc(C(=O)NC[C@H]4CC[C@H](C(=O)O)CC4)c32)oc2ccccc12] |

TABLE 201

| Pr | Syn | Data |
|---|---|---|
| 1 | Pr 1 | ESI+: 224 |
| 2 | Pr 2 | CI+: 226 |
| 3/Cl | Pr 3 | FAB+: 200 |
| 4 | Pr 4 | ESI+: 330 |
| 5 | Pr 5 | ESI+: 303 |
| 6 | Pr 6 | ESI+: 456 |
| 7 | Pr 7 | ESI+: 463 |
| 9/Cl | Pr 9 | ESI+: 186 |
| 10 | Pr 10 | FAB+: 238 |
| 11 | Pr 11 | ESI+: 373 |
| 12 | Pr 12 | ESI+: 497 |
| 13 | Pr 13 | ESI+: 314 |
| 14 | Pr 14 | ESI+: 302 |
| 15 | Pr 15 | ESI+: 272 |
| 16 | Pr 16 | ESI+: 180 |
| 17 | Pr 17 | ESI+: 272 |

TABLE 201-continued

| Pr | Syn | Data |
|---|---|---|
| 19/Cl | Pr 19 | ESI+: 194 |
| 20 | Pr 20 | ESI+: 182 |
| 21 | Pr 21 | ESI+: 207 |
| 23 | Pr 23 | ESI+: 267 |
| 24 | Pr 24 | ESI+: 237 |
| 25 | Pr 25 | ESI+: 289 |
| 27 | Pr 27 | ESI+: 256 |
| 30/Cl | Pr 30 | ESI+: 210 |
| 31/Cl | Pr 31 | ESI−: 198 |
| 32 | Pr 32 | ESI+: 276 |
| 34 | Pr 34 | ESI−: 190 |
| 35/Cl | Pr 35 | ESI+: 224 |
| 36 | Pr 36 | ESI+: 240 |
| 37/Cl | Pr 37 | FAB+: 180 |
| 38 | Pr 38 | ESI+: 489 |
| 39 | Pr 39 | ESI+: 227 |
| 40 | Pr 40 | ESI+: 190 |
| 41a | Pr 41a | ESI+: 278 |
| 41b | Pr 41b | ESI+: 278 |
| 42 | Pr 42 | ESI+: 254 |
| 43 | Pr 43 | ESI+: 296 |
| 44 | Pr 44 | ESI+: 392 |
| 46 | Pr 46 | ESI+: 297 |
| 47 | Pr 47 | EI: 315, 317 |
| 48 | Pr 48 | ESI+: 177 |
| 49 | Pr 49 | ESI+: 596 |
| 50 | Pr 50 | ESI+: 343 |
| 51 | Pr 51 | EI: 431 |
| 52 | Pr 52 | ESI−: 262 |
| 53 | Pr 53 | EI: 341 |
| 54 | Pr 54 | ESI−: 326 |
| 55 | Pr 55 | ESI+: 350 |
| 56 | Pr 56 | ESI+: 343 |
| 57 | Pr 57 | ESI+: 349 |
| 60/Cl | Pr 60 | ESI+: 420 |
| 61 | Pr 61 | ESI+: 510 |
| 62 | Pr 62 | ESI−: 309 |
| 63 | Pr 63 | ESI+: 434 |
| 64/Cl | Pr 64 | ESI+: 226 |
| 65 | Pr 65 | ESI+: 398 |
| 66 | Pr 66 | EI: 320 |
| 67 | Pr 67 | ESI−: 338 |
| 68 | Pr 68 | ESI+: 399 |
| 69 | Pr 38 | ESI+: 447 |
| 71 | Pr 54 | ESI+: 286 |
| 72 | Pr 54 | ESI+: 289 |
| 73 | Pr 53 | ESI+: 300 |
| 74 | Pr 54 | ESI+: 286 |
| 75 | Pr 53 | ESI+: 317 |
| 76 | Pr 54 | ESI+: 303 |
| 77 | Pr 7 | ESI+: 422 |
| 78 | Pr 54 | ESI+: 302 |
| 79 | Pr 53 | ESI+: 348 |
| 80 | Pr 54 | ESI+: 320 |
| 81 | Pr 38 | ESI+: 451 |
| 82 | Pr 5 | ESI+: 351 |

TABLE 202

| Pr | Syn | Data |
|---|---|---|
| 83 | Pr 54 | ESI+: 323 |
| 84 | Pr 7 | ESI+: 484 |
| 85 | Pr 38 | ESI+: 485 |
| 86 | Pr 5 | ESI+: 317 |
| 87 | Pr 54 | ESI+: 303 |
| 88 | Pr 38 | ESI+: 464 |
| 89 | Pr 38 | ESI+: 465 |
| 90 | Pr 38 | ESI+: 487 |
| 91 | Pr 7 | ESI+: 441 |
| 92 | Pr 4 | ESI+: 316 |
| 93 | Pr 54 | FAB+: 302 |
| 94 | Pr 38 | ESI+: 330 |
| 95 | Pr 7 | ESI+: 463 |
| 96 | Pr 7 | ESI+: 484 |

TABLE 202-continued

| Pr | Syn | Data |
|---|---|---|
| 97 | Pr 7 | ESI+: 470 |
| 98 | Pr 7 | ESI+: 413 |
| 99 | Pr 54 | ESI+: 316 |
| 100 | Pr 11 | ESI+: 369 |
| 101 | Pr 38 | ESI+: 477 |
| 102 | Pr 38 | ESI+: 492 |
| 103 | Pr 53 | ESI+: 365 |
| 104 | Pr 54 | ESI+: 337 |
| 105 | Pr 12 | ESI+: 493 |
| 106 | Pr 54 | ESI+: 300 |
| 107 | Pr 7 | FAB+: 427 |
| 108 | Pr 21 | ESI+: 221 |
| 109 | Pr 38 | ESI+: 439 |
| 110 | Pr 7 | ESI+: 462 |
| 111 | Pr 7 | ESI+: 496 |
| 112 | Pr 7 | ESI+: 481 |
| 114 | Pr 7 | FAB+: 447 |
| 115 | Pr 38 | ESI+: 439 |
| 116 | Pr 1 | EI: 257 |
| 117 | Pr 1 | EI: 207 |
| 118 | Pr 38 | ESI+: 461 |
| 120 | Pr 53 | EI: 331 |
| 121/Cl | Pr 3 | ESI+: 181 |
| 122 | Pr 54 | FAB−: 302 |
| 123 | Pr 38 | ESI+: 465 |
| 124 | Pr 38 | FAB+: 433 |
| 125 | Pr 7 | ESI+: 448 |
| 126 | Pr 7 | ESI+: 482 |
| 127 | Pr 53 | FAB+: 349 |
| 128 | Pr 7 | ESI+: 498 |
| 129 | Pr 7 | ESI+: 518 |
| 130 | Pr 54 | FAB+: 321 |
| 131 | Pr 38 | FAB+: 482 |
| 132 | Pr 53 | FAB+: 399 |
| 134 | Pr 53 | ESI+: 278 |
| 135 | Pr 53 | ESI+: 278 |
| 136 | Pr 54 | FAB+: 371 |
| 137 | Pr 54 | ESI−: 248 |
| 138 | Pr 54 | ESI+: 250 |
| 139 | Pr 7 | ESI+: 532 |
| 140 | Pr 7 | ESI+: 515 |
| 141 | Pr 7 | ESI+: 447 |
| 143 | Pr 38 | ESI+: 431 |
| 144 | Pr 38 | ESI+: 437 |
| 145 | Pr 7 | ESI+: 481 |
| 146 | Pr 7 | ESI+: 477 |
| 147 | Pr 7 | ESI+: 528 |
| 148 | Pr 40 | EI: 168 |
| 149 | Pr 7 | ESI+: 473 |
| 150 | Pr 38 | ESI+: 423 |
| 151 | Pr 25 | EI: 245 |
| 152 | Pr 54 | ESI+: 292 |
| 153 | Pr 40 | ESI+: 208 |
| 154 | Pr 38 | FAB+: 453 |
| 155 | Pr 1 | ESI+: 220 |
| 156 | Pr 40 | ESI+: 344 |
| 157 | Pr 38 | ESI+: 411 |
| 158 | Pr 38 | ESI+: 411 |

TABLE 203

| Pr | Syn | Data |
|---|---|---|
| 159 | Pr 7 | ESI+: 473 |
| 160 | Pr 7 | ESI−: 488 |
| 161/Cl | Pr 35 | FAB+: 184 |
| 162 | Pr 53 | CI+: 378 |
| 163 | Pr 54 | ESI−: 314 |
| 164 | Pr 38 | ESI+: 451 |
| 165 | Pr 38 | ESI+: 477 |
| 166 | Pr 7 | ESI+: 467 |
| 167 | Pr 7 | ESI+: 484 |
| 168 | Pr 40 | ESI+: 208 |
| 169 | Pr 54 | EI: 349 |
| 170 | Pr 38 | ESI+: 511 |

TABLE 203-continued

| Pr | Syn | Data |
|---|---|---|
| 171 | Pr 38 | ESI+: 463 |
| 172 | Pr 53 | ESI+: 332 |
| 173 | Pr 53 | ACPI+: 317 |
| 174 | Pr 54 | ESI+: 304 |
| 175 | Pr 54 | ESI+: 303 |
| 176 | Pr 7 | ESI+: 451 |
| 177 | Pr 7 | ESI+: 465 |
| 178 | Pr 7 | ESI+: 457 |
| 179 | Pr 7 | ESI+: 471 |
| 180 | Pr 7 | ESI+: 504 |
| 181 | Pr 7 | ESI+: 464 |
| 182 | Pr 7 | ESI+: 470 |
| 183 | Pr 53 | ESI+: 332 |
| 184 | Pr 54 | ESI+: 304 |
| 185 | Pr 7 | FAB+: 521 |
| 186 | Pr 7 | FAB+: 507 |
| 187/Cl | Pr 31 | ESI+: 184 |
| 188/Cl | Pr 27 | ESI+: 198 |
| 189 | Pr 53 | EI: 341 |
| 190 | Pr 7 | ESI+: 465 |
| 191 | Pr 7 | ESI+: 457 |
| 192 | Pr 7 | ESI+: 471 |
| 193 | Pr 38 | FAB+: 447 |
| 194 | Pr 54 | ESI+: 328 |
| 195 | Pr 53 | ESI+: 307 |
| 196 | Pr 53 | ESI+: 344 |
| 197 | Pr 54 | ESI+: 293 |
| 198 | Pr 38 | ESI+: 454 |
| 199 | Pr 38 | ESI+: 460 |
| 200 | Pr 38 | ESI+: 495 |
| 201 | Pr 53 | ESI+: 317 |
| 202 | Pr 54 | ESI+: 303 |
| 203 | Pr 7 | ESI+: 465 |
| 204 | Pr 7 | ESI−: 514 |
| 205 | Pr 53 | ESI+: 335 |
| 206 | Pr 54 | ESI+: 321 |
| 207 | Pr 53 | ESI+: 335 |
| 208 | Pr 54 | ESI+: 321 |
| 209 | Pr 53 | EI: 313 |
| 210 | Pr 8 | ESI+: 242 |
| 211/Cl | Pr 3 | ESI+: 228 |
| 212 | Pr 38 | ESI+: 495 |
| 213 | Pr 7 | ESI+: 464 |
| 214 | Pr 7 | APCI+: 482 |
| 215 | Pr 7 | APCI+: 488 |
| 216 | Pr 7 | APCI+: 482 |
| 217 | Pr 38 | ESI+: 463 |
| 218 | Pr 7 | APCI+: 488 |
| 219 | Pr 38 | ESI+: 483 |
| 220 | Pr 38 | ESI+: 469 |
| 222 | Pr 53 | ESI+: 331 |
| 223 | Pr 54 | ESI+: 317 |
| 225 | Pr 53 | ESI+: 301 |
| 226 | Pr 54 | ESI+: 287 |
| 227 | Pr 54 | FAB−: 298 |
| 228 | Pr 38 | ESI+: 461 |
| 229 | Pr 38 | ESI+: 467 |
| 230 | Pr 38 | ESI+: 447 |
| 231 | Pr 38 | ESI+: 453 |
| 232 | Pr 53 | ESI+: 310 |

TABLE 204

| Pr | Syn | Data |
|---|---|---|
| 233 | Pr 54 | ESI+: 296 |
| 234 | Pr 38 | ESI+: 461 |
| 235 | Pr 38 | ESI+: 478 |
| 236 | Pr 38 | ESI+: 484 |
| 237 | Pr 38 | ESI+: 470 |
| 238 | Pr 38 | ESI+: 464 |
| 239 | Pr 53 | ESI+: 307 |
| 240 | Pr 41a | ESI−: 262 |
| 241 | Pr 41b | ESI−: 262 |
| 242 | Pr 38 | ESI+: 457 |

TABLE 204-continued

| Pr | Syn | Data |
|---|---|---|
| 243 | Pr 54 | ESI+: 293 |
| 244 | Pr 38 | ESI+: 451 |
| 245 | Pr 38 | ESI+: 471 |
| 246 | Pr 38 | ESI+: 457 |
| 247 | Pr 7 | ESI+: 454 |
| 248 | Pr 7 | ESI+: 425 |
| 249 | Pr 7 | ESI+: 425 |
| 250 | Pr 38 | ESI+: 448 |
| 251 | Pr 38 | ESI+: 468 |
| 252 | Pr 38 | ESI+: 488 |
| 253 | Pr 38 | ESI+: 474 |
| 254/Cl | Pr 43 | ESI+: 196 |
| 256 | Pr 7 | ESI+: 463 |
| 257 | Pr 56 | ESI+: 343 |
| 261 | Pr 54 | ESI+: 329 |
| 262 | Pr 38 | ESI+: 490 |
| 263 | Pr 38 | ESI+: 490 |
| 266 | Pr 53 | EI: 300 |
| 268 | Pr 7 | ESI+: 493 |
| 269 | Pr 54 | ESI+: 287 |
| 270 | Pr 38 | ESI+: 448 |
| 271 | Pr 53 | EI: 389 |
| 272 | Pr 53 | ESI+: 301 |
| 273 | Pr 54 | ESI+: 287 |
| 274 | Pr 54 | ESI−: 360 |
| 275 | Pr 38 | ESI+: 523 |
| 276 | Pr 38 | ESI+: 448 |
| 277 | Pr 54 | ESI+: 329 |
| 278 | Pr 38 | ESI+: 490 |
| 279 | Pr 53 | ESI+: 378 |
| 280 | Pr 54 | ESI+: 364 |
| 281 | Pr 38 | ESI+: 425 |
| 282 | Pr 38 | ESI+: 475 |
| 283 | Pr 38 | ESI+: 481 |
| 284 | Pr 7 | ESI+: 525 |
| 285 | Pr 7 | FAB+: 501 |
| 286 | Pr 7 | ESI+: 518 |
| 287 | Pr 7 | ESI+: 538 |
| 288 | Pr 7 | APCI/ESI+: 524 |
| 289 | Pr 53 | ESI+: 347 |
| 290 | Pr 54 | ESI+: 333 |
| 291 | Pr 38 | ESI+: 494 |
| 292 | Pr 38 | ESI+: 480 |
| 293 | Pr 38 | ESI+: 486 |
| 294 | Pr 54 | ESI+: 336 |
| 295 | Pr 38 | ESI+: 497 |
| 296 | Pr 54 | ESI+: 329 |
| 297 | Pr 53 | ESI+: 317 |
| 298 | Pr 54 | ESI+: 303 |
| 299 | Pr 53 | ESI+: 301 |
| 300 | Pr 38 | ESI+: 464 |
| 301 | Pr 54 | ESI+: 335 |
| 302 | Pr 38 | ESI+: 448 |
| 303 | Pr 38 | ESI+: 434 |
| 304 | Pr 54 | ESI+: 287 |
| 305 | Pr 7 | ESI+: 496 |
| 306 | Pr 38 | ESI+: 490 |
| 307 | Pr 53 | ESI+: 287 |
| 308 | Pr 7 | FAB+: 439 |
| 309 | Pr 54 | ESI+: 273 |
| 310 | Pr 53 | EI: 348 |
| 311 | Pr 56 | ESI+: 349 |

TABLE 205

| Pr | Syn | Data |
|---|---|---|
| 312 | Pr 53 | ESI+: 333 |
| 313 | Pr 7 | ESI+: 434 |
| 314 | Pr 54 | ESI+: 319 |
| 315 | Pr 54 | ESI+: 335 |
| 316 | Pr 38 | ESI+: 496 |
| 317 | Pr 38 | ESI+: 488 |
| 318 | Pr 54 | ESI+: 335 |
| 319 | Pr 38 | ESI+: 496 |

TABLE 205-continued

| Pr | Syn | Data |
|---|---|---|
| 320 | Pr 44 | ESI+: 392 |
| 321 | Pr 7 | ESI+: 480 |
| 322 | Pr 50 | EI: 348 |
| 323 | Pr 53 | EI: 347 |
| 324 | Pr 38 | ESI+: 489 |
| 325 | Pr 54 | ESI+: 334 |
| 326 | Pr 38 | ESI+: 495 |
| 327 | Pr 54 | ESI+: 335 |
| 328 | Pr 38 | ESI+: 496 |
| 331 | Pr 4 | EI: 352 |
| 333 | Pr 53 | ESI+: 365 |
| 334 | Pr 54 | ESI+: 339 |
| 335 | Pr 54 | ESI+: 337 |
| 336 | Pr 7 | ESI+: 520 |
| 337 | Pr 7 | FAB+: 490 |
| 338 | Pr 7 | FAB+: 500 |
| 339 | Pr 7 | EI: 450 |
| 340 | Pr 7 | ESI+: 484 |
| 341 | Pr 53 | ESI+: 274 |
| 342 | Pr 7 | ESI+: 456 |
| 343 | Pr 7 | ESI+: 490 |
| 344 | Pr 7 | ESI+: 498 |
| 345 | Pr 7 | ESI+: 466 |
| 346 | Pr 7 | ESI+: 472 |
| 347 | Pr 54 | EI: 259 |
| 348 | Pr 38 | FAB+: 421 |
| 349 | Pr 53 | ESI+: 307 |
| 350 | Pr 38 | ESI+: 472 |
| 351 | Pr 53 | EI: 305 |
| 352 | Pr 54 | ESI+: 292 |
| 353 | Pr 53 | ESI+: 399 |
| 354 | Pr 53 | ESI+: 345 |
| 355 | Pr 54 | ESI+: 371 |
| 356 | Pr 38 | ESI+: 453 |
| 357 | Pr 7 | ESI+: 532 |
| 358 | Pr 7 | ESI+: 518 |
| 359 | Pr 7 | ESI+: 524 |
| 360 | Pr 53 | EI: 301 |
| 361 | Pr 54 | ESI+: 288 |
| 362 | Pr 38 | ESI+: 449 |
| 363 | Pr 54 | ESI+: 293 |
| 364 | Pr 38 | ESI+: 454 |
| 366 | Pr 54 | ESI+: 331 |
| 368 | Pr 53 | ESI+: 331 |
| 369 | Pr 54 | ESI+: 303 |
| 370 | Pr 7 | ESI+: 433 |
| 371 | Ex 4 | ESI+: 329 |
| 372 | Pr 7 | ESI+: 450 |
| 373 | Pr 38 | ESI+: 476 |
| 374 | Pr 38 | ESI+: 482 |
| 375 | Pr 53 | ESI+: 332 |
| 376 | Pr 53 | ESI+: 323 |
| 377 | Pr 53 | ESI+: 283 |
| 378 | Pr 38 | ESI+: 473 |
| 379 | Pr 54 | ESI+: 269 |
| 380 | Pr 7 | ESI+: 310 |
| 381 | Pr 53 | EI: 321 |
| 382 | Pr 54 | ESI+: 318 |
| 383 | Pr 38 | ESI+: 479 |
| 384 | Pr 54 | ESI+: 309 |
| 385 | Pr 38 | ESI+: 456 |
| 386 | Pr 38 | ESI+: 430 |
| 387 | Pr 38 | ESI+: 416 |
| 388 | Pr 38 | ESI+: 422 |

TABLE 206

| Pr | Syn | Data |
|---|---|---|
| 389 | Pr 54 | FAB−: 306 |
| 390 | Pr 38 | ESI+: 455 |
| 391 | Pr 63 | ESI+: 451 |
| 392 | Pr 53 | EI: 392 |
| 393 | Pr 53 | ESI+: 301 |
| 395 | Pr 54 | ESI+: 287 |

TABLE 206-continued

| Pr | Syn | Data |
|---|---|---|
| 396 | Pr 54 | ESI+: 370 |
| 397 | Pr 53 | ESI+: 323 |
| 398 | Ex 4 | ESI+: 363 |
| 399 | Pr 38 | ESI+: 517 |
| 400 | Pr 7 | ESI+: 434 |
| 401 | Pr 38 | ESI+: 523 |
| 402 | Pr 38 | ESI+: 510 |
| 403 | Pr 54 | ESI+: 309 |
| 404 | Pr 38 | ESI+: 516 |
| 405 | Pr 38 | ESI+: 470 |
| 406 | Pr 38 | ESI+: 462 |
| 407 | Pr 53 | ESI+: 304 |
| 408 | Pr 53 | EI: 349 |
| 409 | Pr 54 | ESI+: 290 |
| 410 | Pr 38 | FAB+: 445 |
| 411 | Pr 7 | ESI+: 437 |
| 412 | Pr 7 | ESI+: 443 |
| 413 | Pr 38 | FAB+: 439 |
| 414 | Pr 53 | EI: 391 |
| 415 | Pr 54 | ESI+: 322 |
| 416 | Pr 38 | ESI+: 469 |
| 417 | Pr 38 | ESI+: 475 |
| 418 | Pr 66 | EI: 286 |
| 419 | Pr 67 | ESI−: 304 |
| 420 | Pr 54 | FAB−: 362 |
| 421 | Pr 38 | ESI+: 511 |
| 422 | Pr 38 | ESI+: 517 |
| 423 | Pr 53 | ESI+: 318 |
| 424 | Pr 54 | ESI+: 304 |
| 425 | Pr 7 | ESI+: 451 |
| 426 | Pr 7 | FAB+: 487 |
| 427 | Pr 7 | FAB+: 453 |
| 428 | Pr 38 | ESI+: 412 |
| 429 | Pr 7 | ESI+: 459 |
| 430 | Pr 38 | ESI+: 403 |
| 431 | Pr 38 | ESI+: 397 |
| 432 | Pr 53 | ESI+: 347 |
| 433 | Pr 54 | ESI+: 319 |
| 434 | Pr 7 | ESI+: 439 |
| 435 | Pr 7 | ESI+: 456 |
| 436 | Pr 7 | ESI+: 466 |
| 437 | Pr 7 | ESI+: 472 |
| 438 | Pr 7 | ESI+: 480 |
| 439 | Pr 7 | ESI+: 412 |
| 440 | Pr 38 | ESI+: 461 |
| 441 | Pr 38 | ESI+: 497 |
| 442 | Pr 53 | ESI+: 397 |
| 443 | Pr 38 | ESI+: 516 |
| 444 | Pr 38 | FAB+: 503 |
| 445 | Pr 54 | ESI+: 369 |
| 446 | Pr 38 | ESI+: 522 |
| 447 | Pr 38 | FAB+: 497 |
| 448 | Pr 53 | APCI/ESI+: 431 |
| 449 | Pr 53 | APCI/ESI+: 425 |
| 450 | Pr 54 | APCI/ESI+: 403 |
| 451 | Pr 54 | APCI/ESI+: 397 |
| 452 | Pr 38 | APCI/ESI+: 550 |
| 453 | Pr 38 | APCI/ESI+: 556 |
| 454 | Pr 38 | APCI/ESI+: 550 |
| 455 | Pr 53 | APCI/ESI+: 412 |
| 456 | Pr 54 | APCI/ESI+: 384 |
| 457 | Pr 7 | APCI/ESI+: 531 |
| 458 | Pr 32 | ESI+: 371 |
| 459 | Pr 53 | ESI+: 383 |
| 460 | Pr 53 | ESI+: 399 |
| 461 | Pr 54 | ESI+: 355 |

TABLE 207

| Pr | Syn | Data |
|---|---|---|
| 462 | Pr 54 | ESI+: 371 |
| 463 | Pr 7 | ESI+: 508 |
| 464 | Pr 53 | ESI+: 383 |
| 465 | Pr 7 | ESI+: 524 |

TABLE 207-continued

| Pr | Syn | Data |
|---|---|---|
| 466 | Pr 53 | APCI/ESI+: 399 |
| 467 | Pr 54 | APCI/ESI+: 371 |
| 468 | Pr 7 | APCI/ESI+: 524 |
| 469 | Pr 7 | ESI+: 524 |
| 470 | Pr 32 | ESI+: 371 |
| 471 | Pr 7 | ESI+: 524 |
| 472 | Pr 53 | ESI+: 399 |
| 473 | Pr 53 | ESI+: 399 |
| 474 | Pr 53 | ESI+: 399 |
| 475 | Pr 54 | ESI+: 371 |
| 476 | Pr 54 | ESI+: 371 |
| 477 | Pr 7 | ESI+: 524 |
| 478 | Pr 7 | ESI+: 524 |
| 479 | Pr 53 | ESI+: 503 |
| 480 | Pr 33 | ESI+: 403 |
| 481 | Pr 53 | APCI/ESI+: 349 |
| 482 | Pr 53 | ESI+: 335 |
| 483 | Pr 53 | ESI+: 331 |
| 484 | Pr 54 | APCI/ESI+: 321 |
| 485 | Pr 54 | ESI+: 317 |
| 486 | Pr 53 | APCI/ESI+: 354 |
| 487 | Pr 53 | APCI/ESI+: 388 |
| 488 | Pr 54 | ESI+: 321 |
| 489 | Pr 38 | APCI/ESI+: 474 |
| 490 | Pr 54 | ESI+: 371 |
| 491 | Pr 7 | ESI+: 524 |
| 492 | Pr 7 | ESI+: 470 |
| 493 | Pr 7 | ESI+: 474 |
| 494 | Pr 54 | ESI+: 371 |
| 495 | Pr 54 | APCI/ESI+: 326 |
| 496 | Pr 54 | APCI/ESI−: 358 |
| 497 | Pr 7 | APCI/ESI+: 479 |
| 498 | Pr 7 | APCI/ESI+: 513 |
| 499 | Pr 54 | ESI+: 355 |
| 500 | Pr 7 | ESI+: 508 |
| 501 | Pr 7 | ESI+: 524 |
| 502 | Pr 53 | ESI+: 422 |
| 503 | Pr 54 | FAB−: 392 |
| 504 | Pr 7 | ESI+: 547 |
| 505 | Pr 505 | EI: 345 |
| 506 | Pr 506 | ESI+: 298 |
| 507 | Pr 507 | FAB+: 358 |
| 508 | Pr 508 | FAB−: 372 |
| 509 | Pr 509 | FAB−: 272 |
| 510 | Pr 510 | EI: 253 |
| 511 | Pr 511 | APCI/ESI+: 293 |
| 512 | Pr 512 | APCI/ESI+: 221 |
| 513 | Pr 513 | FAB+: 392 |
| 514 | Pr 514 | APCI/ESI+: 223 |
| 515 | Pr 515 | ESI+: 490 |
| 516 | Pr 516 | ESI+: 383 |
| 517 | Pr 511 | EI: 315 |
| 518 | Pr 512 | ESI+: 244 |
| 519 | Pr 514 | EI: 243 |
| 520 | Pr 46 | FAB+: 343 |
| 521 | Pr 25 | FAB+: 421 |
| 522 | Pr 505 | EI: 379 |
| 523 | Pr 511 | EI: 349 |
| 524 | Pr 512 | EI: 277 |
| 525 | Pr 514 | EI: 277 |
| 526 | Pr 46 | FAB+: 377 |
| 527 | Pr 7 | ESI+: 427 |
| 528 | Pr 53 | ESI+: 568 |
| 529 | Pr 53 | FAB−: 501 |
| 530 | Pr 34 | APCI/ESI−: 185 |
| 531 | Pr 1 | APCI/ESI+: 215 |
| 532 | Pr 33 | APCI/ESI+: 403 |
| 533 | Pr 508 | FAB+: 408 |
| 534 | Pr 509 | EI: 307 |
| 536 | Pr 53 | ESI+: 568 |

TABLE 208

| Pr | Syn | Data |
|---|---|---|
| 537 | Pr 515 | ESI+: 490 |
| 538 | Pr 53 | APCI/ESI+: 356 |
| 539 | Pr 54 | APCI/ESI+: 328 |
| 540 | Pr 7 | APCI/ESI+: 481 |
| 541 | Pr 53 | ESI+: 602 |
| 542 | Pr 68 | APCI/ESI+: 399 |
| 543 | Pr 54 | APCI/ESI+: 371 |

TABLE 208-continued

| Pr | Syn | Data |
|---|---|---|
| 544 | Pr 7 | APCI/ESI+: 524 |
| 545 | Pr 53 | ESI+: 524 |
| 546 | Pr 53 | ESI+: 524 |
| 547 | Pr 53 | ESI−: 400 |
| 548 | Pr 54 | ESI−: 372 |
| 549 | Pr 7 | ESI+: 527 |

TABLE 209

| Pr | Syn | Data |
|---|---|---|
| 8 | Pr 8 | NMR-C: 8.42-8.31 (1H, brs), 3.68 (3H, s), 2.33-2.23 (1H, m), 2.19-2.02 (3H, m), 1.97-1.89 (2H, m), 1.86 (3H, s), 1.58-1.25 (4H, m) |
| 18 | Pr 18 | NMR-D: 7.97-7.93 (1H, m), 7.76-7.70 (1H, m), 7.67-7.62 (1H, m), 7.59 (1H, d, J = 2.1 Hz), 7.55-7.52 (1H, m), 7.51 (1H, d, J = 8.7 Hz), 7.18 (1H, dd, J = 2.1, 8.7 Hz), 6.37 (1H, s), 3.60 (3H, s), 3.47 (3H, s) |
| 22 | Pr 22 | NMR-C: 7.55 (1H, dd, J = 7.7, 1.5 Hz), 7.47 (1H, d, J = 1.5 Hz), 7.26 (1H, s), 7.17 (1H, d, J = 7.7 Hz), 4.36 (2H, q, J = 7.1 Hz), 4.10 (2H, q, J = 7.1 Hz), 2.27 (3H, s), 1.44 (3H, t, J = 7.1 Hz), 1.39 (3H, t, J = 7.1 Hz) |
| 26 | Pr 26 | NMR-C: 7.30 (2H, d, J = 8.5 Hz), 7.06 (2H, d, J = 8.5 Hz), 7.02 (1H, d, J = 2.0 Hz), 6.85 (1H, d, J = 2.0 Hz), 5.45 (2H, s) |
| 28 | Pr 28 | NMR-C: 7.68-7.64 (1H, ddd, J = 1.5, 1.5, 7.8 Hz), 7.55-7.52 (1H, t, J = 1.5 Hz), 7.44 (1H, d, J = 7.8 Hz), 5.19-5.08 (1H, m), 3.92 (3H, s), 3.92 (3H, s), 2.53 (1H, brs), 1.52-1.47 (3H, m) |
| 29 | Pr 29 | NMR-C: 7.49-7.41 (2H, m), 7.25-7.15 (2H, m), 4.98 (1H, brs), 4.02 (1H, brs), 1.41 (9H, s), 1.10-0.97 (1H, m), 0.64-0.50 (2H, m), 0.46-0.28 (2H, m) |
| 33/Cl | Pr 33 | NMR-D: 8.80 (2H, brs), 8.05-7.97 (2H, m), 7.76-7.66 (2H, m), 3.87 (3H, s), 3.74-3.64 (1H, m), 1.37-1.23 (1H, m), 0.74-0.58 (2H, m), 0.56-0.35 (2H, m) |
| 45 | Pr 45 | NMR-C: 7.45-6.88 (7H, m), 5.75-5.5 (1H, m), 3.36-3.21 (1H, m), 3.05-2.94 (1H, m), 2.45-2.23 (2H, m) |
| 58 | Pr 58 | NMR-D: 7.90 (1H, d, J = 1.7 Hz), 7.71-7.62 (3H, m), 7.46-7.37 (2H, m), 7.34-7.26 (1H, m), 5.06 (2H, s) |
| 59 | Pr 59 | NMR-C: 7.56-7.47 (2H, m), 7.40-7.25 (5H, m), 7.25-7.16 (2H, m), 7.13-7.06 (2H, m), 5.55 (2H, s), 3.80 (3H, m) |
| 70 | Pr 53 | NMR-C: 7.71 (1H, d, J = 8.0 Hz), 7.39 (1H, s), 7.31 (2H, d, J = 4.3 Hz), 7.26-7.11 (3H, m), 6.98 (2H, d, J = 8.0 Hz), 5.80 (2H, s), 4.32 (2H, q, J = 7.1 Hz), 1.36 (3H, t, J = 7.1 Hz). |
| 113 | Pr 54 | NMR-D: 7.94 (1H, dd, J = 1, 8 Hz), 7.68 (1H, dt, J = 1, 8 Hz), 7.64-7.57 (2H, m), 7.52-7.57 (2H, m), 7.16 (1H, dd, J = 2, 9 Hz), 6.38 (1H, s), 3.48 (3H, s) |
| 119 | Pr 53 | NMR-D: 8.27 (1H, s), 7.85 (1H, d, J = 3.2 Hz), 7.64 (1H, d, J = 1.5 Hz), 7.31 (2H, d, J = 8.8 Hz), 6.89 (1H, d, J = 3.2 Hz), 6.78 (2H, d, J = 8.8 Hz), 5.65 (2H, s), 4.19 (2H, q, J = 7.0 Hz), 1.15 (3H, t, J = 7.0 Hz) |
| 133 | Pr 54 | NMR-D: 13.42 (1H, brs), 8.27-8.19 (1H, m), 7.82 (1H, d, J = 3.4 Hz), 7.77-7.67 (1H, m), 7.31 (2H, d, J = 8.8 Hz), 6.91-6.82 (3H, m), 5.74 (2H, s) |

TABLE 210

| Pr | Syn | Data |
|---|---|---|
| 142 | Pr 16 | NMR-C: 8.04-7.97 (2H, m), 7.45-7.35 (2H, m), 5.12 (1H, brs), 4.10 (1H, brs), 3.91 (3H, s), 1.41 (9H, s), 1.13-1.00 (1H, m), 0.66-0.50 (2H, m), 0.49-0.32 (2H, m) |
| 255 | Pr 20 | NMR-C: 7.37-7.31 (1H, m), 7.22-7.08 (2H, m), 5.33 (1H, dd, J = 2.8, 7.0 Hz), 3.28-3.15 (1H, m), 2.94-2.82 (1H, m), 2.47-2.21 (2H, m), 2.17-2.06 (1H, m) |
| 258 | Pr 34 | NMR-C: 7.98-7.94 (1H, m), 7.58-7.54 (1H, m), 7.47-7.42 (1H, m), 7.26-7.21 (2H, m), 6.92-6.86 (2H, m), 6.26 (1H, dd, J = 1.8, 5.7 Hz), 3.28-3.16 (1H, m), 3.01-2.90 (1H, m), 2.42-2.26 (2H, m) |
| 259 | Pr 7 | NMR-C: 7.84-7.73 (3H, m), 7.50-7.41 (2H, m), 7.24-7.08 (5H, m), 6.67-6.59 (2H, m), 5.81-5.75 (1H, m), 4.67 (1H, dd, J = 6.5, 14.5 Hz), 4.32 (1H, dd, J = 4.6, 14.5 Hz), 3.94 (3H, s), 3.23-3.11 (1H, m), 2.98-2.87 (1H, m), 2.32-2.20 (2H, m) |

TABLE 210-continued

| Pr | Syn | Data |
|---|---|---|
| 260 | Pr 53 | NMR-D: 7.81 (1H, d, J = 7.2 Hz), 7.62 (1H, d, J = 3.4 Hz), 7.40 (1H, d, J = 7.2 Hz), 7.07 (1H, t, J = 7.2 Hz), 6.81-6.71 (4H, m), 6.65 (1H, d, J = 3.4 Hz), 5.49 (2H, s), 4.01-3.96 (2H, m), 3.75 (3H, s), 3.62-3.57 (2H, m), 3.39-3.25 (3H, m) |
| 264 | Pr 54 | NMR-D: 7.77 (1H, d, J = 7.6 Hz), 7.57 (1H, d, J = 2.9 Hz), 7.47 (1H, d, J = 7.6 Hz), 7.06 (1H, t, J = 7.6 Hz), 6.84 (2H, d, J = 8.5 Hz), 6.77 (2H, d, J = 8.5 Hz), 6.62 (1H, d, J = 2.9 Hz), 5.91 (2H, s), 4.01-3.96 (2H, m), 3.61-3.56 (2H, m), 3.26 (3H, s) |
| 267 | Pr 7 | NMR-D: 8.91 (1H, d, J = 8.3 Hz), 7.90 (2H, d, J = 8.3 Hz), 7.68 (1H, d, J = 6.9 Hz), 7.51 (2H, d, J = 8.3 Hz), 7.47 (1H, d, J = 3.2 Hz), 7.20 (1H, d, J = 6.9 Hz), 7.06 (1H, d, J = 6.9 Hz), 6.78 (2H, d, J = 8.8 Hz), 6.69 (2H, d, J = 8.8 Hz), 6.57 (1H, d, J = 3.2 Hz), 5.43-5.31 (2H, m), 5.21-5.11 (1H, m), 4.01-3.94 (2H, m), 3.85 (3H, s), 3.63-3.57 (2H, m), 3.27 (3H, s), 1.34 (3H, d, J = 6.8 Hz) |
| 329 | Pr 53 | NMR-D: 7.74-7.78 (1H, m), 7.54-7.48 (1H, m), 7.43 (1H, d, J = 2.9 Hz), 7.10 (1H, t, J = 7.6 Hz), 6.57 (1H, d, J = 2.9 Hz), 4.23 (2H, d, J = 7.4 Hz), 3.96-3.79 (5H, m), 2.63-2.41 (2H, m), 1.72-1.57 (1H, m), 1.37 (9H, s), 1.23-1.14 (2H, m), 1.06-0.92 (2H, m) |
| 330 | Pr 53 | NMR-C: 7.32-7.25 (2H, m), 7.10-7.04 (2H, m), 6.98-6.96 (1H, m), 6.87-6.83 (1H, m), 5.47 (2H, s), 3.77 (3H, s) |
| 332 | Pr 54 | NMR-D: 7.78-7.73 (1H, m), 7.55-7.49 (1H, m), 7.41 (1H, d, J = 3.2 Hz), 7.07 (1H, t, J = 7.8 Hz), 6.54 (1H, d, J = 3.2 Hz), 4.32 (2H, d, J = 7.3 Hz), 3.96-3.77 (2H, m), 2.64-2.38 (2H, m), 1.82-1.67 (1H, m), 1.37 (9H, s), 1.27-1.14 (2H, m), 1.08-0.93 (2H, m) |

TABLE 211

| Pr | Syn | Data |
|---|---|---|
| 367 | Pr 54 | NMR-D: 12.4-12.3 (1H, brs), 7.77 (1H, d, J = 2.2 Hz), 7.59 (2H, d, J = 7.7 Hz), 7.42-7.31 (5H, m), 7.27 (1H, d, J = 1.7 Hz), 7.21-7.13 (2H, m), 5.57 (2H, s) |
| 394 | Pr 54 | NMR-D: 13.3-13.1 (1H, brs), 8.55 (1H, d, J = 2.4 Hz), 7.92 (1H, dd, J = 8.4, 2.4 Hz), 7.87 (1H, d, J = 2.3 Hz), 7.66 (1H, d, J = 3.3 Hz), 7.43 (1H, d, J = 2.3 Hz), 6.66 (1H, d, J = 3.3 Hz), 6.60 (1H, d, J = 8.4 Hz), 5.77 (2H, s) |
| 535 | Pr 7 | NMR-C: 9.22-9.00 (1H, brs), 7.99 (1H, s), 7.39-7.34 (1H, m), 6.56-6.50 (1H, m), 5.96-5.85 (1H, m), 3.84 (3H, s), 3.40-3.29 (2H, m), 2.31-2.18 (1H, m), 2.08-1.95 (2H, m), 1.92-1.79 (2H, m), 1.67-1.53 (1H, m), 1.52-1.35 (2H, m), 1.11-0.94 (2H, m) |

TABLE 212

| Ex | Syn | Data |
|---|---|---|
| 1/Cl | Ex 1 | ESI+: 449 |
| 2 | Ex 2 | FAB−: 451 |
| 3 | Ex 3 | FAB−: 473 |
| 4 | Ex 4 | ESI+: 476 |
| 5 | Ex 5 | ESI+: 444 |
| 6 | Ex 6 | FAB+: 554 |
| 7 | Ex 3 | ESI+: 433 |
| 8 | Ex 3 | ESI+: 442 |
| 9 | Ex 3 | ESI+: 408 |
| 10 | Ex 3 | ESI+: 437 |
| 11 | Ex 3 | ESI−: 468 |
| 12 | Ex 3 | ESI+: 471 |
| 13 | Ex 3 | ESI+: 450 |
| 14 | Pr 38 | ESI+: 457 |
| 15 | Ex 3 | FAB+: 451 |
| 16 | Ex 3 | ESI+: 473 |
| 17 | Ex 3 | ESI+: 413 |
| 18 | Ex 3 | ESI+: 483 |
| 19 | Ex 3 | ESI+: 456 |
| 20 | Ex 3 | ESI+: 456 |
| 21/Cl | Ex 3 | ESI+: 449 |
| 22 | Ex 3 | FAB+: 399 |

TABLE 212-continued

| Ex | Syn | Data |
|---|---|---|
| 23 | Ex 3 | ESI+: 464 |
| 24 | Ex 3 | ESI+: 479 |
| 25 | Ex 3 | ESI+: 434 |
| 26 | Ex 3 | ESI+: 468 |
| 27 | Ex 3 | ESI+: 453 |
| 28 | Ex 3 | ESI+: 425 |
| 29 | Ex 3 | FAB+: 399 |
| 30 | Ex 3 | FAB+: 433 |
| 31 | Ex 3 | ESI+: 463 |
| 32 | Ex 3 | ESI+: 425 |
| 33 | Ex 3 | ESI+: 447 |
| 34 | Ex 3 | ESI+: 434 |
| 35 | Ex 3 | ESI+: 468 |
| 36 | Ex 3 | ESI+: 484 |
| 37 | Ex 3 | ESI+: 490 |
| 38 | Ex 3 | FAB+: 451 |
| 39 | Ex 3 | FAB+: 419 |
| 40 | Ex 3 | FAB+: 468 |
| 41 | Ex 3 | ESI+: 501 |
| 42 | Ex 3 | ESI+: 518 |
| 43 | Ex 3 | ESI+: 433 |
| 44 | Ex 3 | ESI+: 417 |
| 45 | Ex 3 | ESI+: 467 |
| 46 | Ex 3 | ESI+: 463 |
| 47 | Ex 3 | ESI+: 514 |
| 48 | Ex 3 | FAB−: 421 |
| 49 | Ex 3 | ESI+: 459 |
| 50 | Ex 3 | ESI+: 439 |
| 51 | Ex 3 | FAB+: 409 |
| 52 | Ex 3 | ESI+: 459 |
| 53 | Ex 3 | ACPI+: 476 |
| 54 | Ex 3 | ESI+: 397 |
| 55 | Ex 3 | ESI+: 397 |
| 56 | Ex 3 | ESI+: 453 |
| 57 | Ex 3 | ESI+: 470 |
| 58 | Ex 3 | ESI+: 437 |
| 59 | Ex 3 | ESI+: 463 |
| 60 | Ex 3 | FAB+: 497 |
| 61 | Ex 3 | ESI+: 437 |
| 62 | Ex 3 | ESI+: 451 |
| 63 | Ex 3 | ESI+: 443 |
| 64 | Ex 3 | ESI+: 457 |

TABLE 212-continued

| Ex | Syn | Data |
|---|---|---|
| 65 | Ex 3 | ESI+: 490 |
| 66 | Ex 3 | ESI+: 450 |
| 67 | Ex 3 | ESI−: 454 |
| 68 | Ex 3 | FAB+: 507 |
| 69 | Ex 3 | FAB+: 493 |
| 70 | Ex 3 | ESI+: 451 |
| 71 | Ex 3 | ESI+: 443 |
| 72 | Ex 3 | ESI+: 457 |
| 73 | Ex 3 | ESI+: 451 |
| 74 | Ex 3 | ESI+: 502 |
| 75 | Ex 3 | ESI+: 450 |
| 76 | Ex 3 | ESI+: 439 |
| 77 | Ex 3 | APCI+: 468 |
| 78 | Ex 3 | APCI+: 474 |
| 79 | Ex 3 | FAB+: 449 |
| 80 | Ex 3 | APCI+: 468 |
| 81 | Ex 3 | APCI+: 474 |
| 82 | Ex 3 | FAB+: 433 |

TABLE 213

| Ex | Syn | Data |
|---|---|---|
| 83 | Ex 3 | FAB+: 440 |
| 84 | Ex 3 | FAB+: 446 |
| 85 | Ex 3 | FAB+: 481 |
| 86 | Ex 3 | ESI+: 449 |
| 87 | Ex 3 | ESI+: 469 |
| 88 | Ex 3 | ESI+: 455 |
| 89 | Ex 3 | ESI+: 447 |
| 90 | Ex 3 | ESI+: 447 |
| 91 | Ex 3 | ESI+: 453 |
| 92 | Ex 3 | ESI+: 433 |
| 93 | Ex 3 | ESI+: 439 |
| 94 | Ex 3 | ESI+: 464 |
| 95 | Ex 3 | ESI+: 470 |
| 96 | Ex 3 | ESI+: 456 |
| 97 | Ex 3 | ESI+: 443 |
| 98 | Ex 3 | ESI+: 411 |
| 99 | Ex 3 | ESI+: 411 |
| 100 | Ex 3 | ESI−: 435 |
| 101 | Ex 3 | ESI+: 457 |
| 102 | Ex 3 | ESI+: 443 |
| 103 | Ex 3 | ESI+: 450 |
| 104 | Ex 3 | ESI+: 440 |
| 105 | Ex 3 | FAB+: 434 |
| 106 | Ex 3 | ESI+: 454 |
| 107 | Ex 3 | ESI+: 474 |
| 108 | Ex 3 | ESI+: 460 |
| 109 | Ex 3 | ESI+: 422 |
| 110 | Ex 3 | ESI+: 449 |
| 112 | Ex 3 | ESI+: 473 |
| 113 | Ex 3 | ESI+: 479 |
| 114 | Ex 3 | ESI+: 434 |
| 115 | Ex 4 | ESI+: 476 |
| 116 | Ex 3 | ESI+: 476 |
| 117 | Ex 3 | ESI+: 434 |
| 118 | Ex 3 | ESI+: 511 |
| 119 | Ex 3 | ESI+: 476 |
| 120 | Ex 3 | ESI+: 509 |
| 121 | Ex 3 | FAB+: 487 |
| 122 | Ex 3 | FAB+: 504 |
| 123 | Ex 3 | FAB+: 524 |
| 124 | Ex 3 | FAB+: 510 |
| 125 | Ex 3 | ESI+: 476 |
| 126 | Ex 3 | ESI+: 411 |
| 127 | Ex 3 | ESI+: 467 |
| 128 | Ex 3 | FAB+: 461 |
| 129 | Ex 3 | ESI+: 480 |
| 130 | Ex 3 | ESI+: 466 |
| 131 | Ex 3 | ESI+: 472 |
| 132 | Ex 3 | ESI+: 483 |
| 133 | Ex 3 | ESI+: 434 |
| 134 | Ex 3 | ESI+: 476 |
| 135 | Ex 3 | ESI+: 482 |

TABLE 213-continued

| Ex | Syn | Data |
|---|---|---|
| 136 | Ex 3 | ESI+: 450 |
| 137 | Ex 3 | FAB+: 425 |
| 138 | Ex 3 | FAB+: 420 |
| 139 | Ex 3 | ESI+: 420 |
| 140 | Ex 3 | ESI+: 466 |
| 141 | Ex 3 | ESI+: 486 |
| 142 | Ex 3 | ESI+: 436 |
| 143 | Ex 3 | ESI+: 470 |
| 144 | Ex 3 | FAB+: 476 |
| 145 | Ex 3 | FAB+: 442 |
| 146 | Ex 3 | FAB+: 476 |
| 147 | Ex 3 | ESI+: 482 |
| 148 | Ex 3 | ESI+: 482 |
| 149 | Ex 3 | ESI+: 474 |
| 150 | Ex 3 | ESI+: 475 |
| 151 | Ex 3 | ESI+: 481 |
| 152 | Ex 3 | ESI+: 482 |
| 153 | Ex 3 | FAB+: 484 |
| 154 | Ex 3 | FAB+: 452 |
| 155 | Ex 3 | FAB+: 458 |
| 156 | Ex 3 | ESI+: 496 |
| 157 | Ex 3 | ESI+: 518 |
| 158 | Ex 3 | ESI+: 504 |
| 159 | Ex 3 | ESI+: 510 |
| 160 | Ex 3 | FAB+: 419 |
| 161 | Ex 3 | ESI+: 407 |
| 162 | Ex 3 | ESI+: 458 |
| 163 | Ex 3 | ESI+: 439 |
| 164 | Ex 3 | ESI+: 435 |
| 165 | Ex 3 | ESI+: 440 |

TABLE 214

| Ex | Syn | Data |
|---|---|---|
| 166 | Ex 3 | ESI+: 436 |
| 167 | Ex 3 | ESI+: 459 |
| 168 | Ex 3 | ESI+: 420 |
| 169 | Ex 3 | ESI+: 416 |
| 170 | Ex 3 | ESI+: 402 |
| 171 | Ex 3 | ESI+: 408 |
| 172 | Ex 3 | ESI+: 441 |
| 173 | Ex 3 | ESI+: 437 |
| 174 | Ex 3 | ESI+: 468 |
| 175 | Ex 3 | ESI+: 462 |
| 176 | Ex 3 | ESI+: 442 |
| 177 | Ex 3 | ESI+: 465 |
| 178 | Ex 3 | ESI+: 420 |
| 179 | Ex 3 | ESI+: 502 |
| 180 | Ex 3 | ESI+: 503 |
| 181 | Ex 3 | ESI+: 448 |
| 182 | Ex 3 | ESI+: 456 |
| 183 | Ex 3 | ESI+: 423 |
| 184 | Ex 3 | ESI+: 509 |
| 185/Cl | Ex 1 | ESI+: 496 |
| 186 | Ex 3 | ESI+: 429 |
| 187 | Ex 3 | ESI+: 425 |
| 188 | Ex 3 | ESI+: 431 |
| 189 | Ex 3 | ESI+: 437 |
| 190 | Ex 3 | FAB+: 473 |
| 191 | Ex 3 | FAB+: 439 |
| 192 | Ex 3 | ESI+: 455 |
| 193 | Ex 3 | ESI+: 461 |
| 194 | Ex 3 | ESI+: 497 |
| 195 | Ex 3 | ESI+: 503 |
| 196 | Ex 3 | ESI+: 445 |
| 197 | Ex 3 | ESI+: 425 |
| 198 | Ex 3 | ESI+: 442 |
| 199 | Ex 3 | ESI+: 383 |
| 200 | Ex 3 | ESI+: 389 |
| 201 | Ex 3 | ESI+: 398 |
| 202 | Ex 3 | ESI+: 452 |
| 203 | Ex 3 | ESI+: 458 |
| 204 | Ex 3 | FAB+: 466 |
| 205 | Ex 3 | FAB+: 398 |

TABLE 214-continued

| Ex | Syn | Data |
|---|---|---|
| 206 | Ex 3 | ESI+: 447 |
| 207 | Ex 3 | ESI+: 483 |
| 208 | Ex 3 | ESI+: 502 |
| 209 | Ex 3 | ESI+: 508 |
| 210 | Ex 3 | ESI+: 489 |
| 211 | Ex 3 | ESI+: 483 |
| 212 | Ex 3 | ESI+: 536 |
| 213 | Ex 3 | ESI+: 542 |
| 214 | Ex 3 | APCI/ESI+: 536 |
| 215 | Ex 3 | APCI/ESI+: 517 |
| 216 | Ex 3 | ESI+: 494 |
| 217 | Ex 3 | APCI/ESI+: 510 |
| 218 | Ex 3 | ESI+: 510 |
| 219 | Ex 3 | ESI+: 510 |
| 220 | Ex 3 | ESI+: 510 |
| 221 | Ex 3 | ESI+: 510 |
| 222 | Ex 3 | ESI+: 510 |
| 223 | Ex 3 | ESI+: 510 |
| 224 | Ex 3 | ESI+: 456 |

TABLE 214-continued

| Ex | Syn | Data |
|---|---|---|
| 225 | Ex 3 | ESI+: 460 |
| 226 | Ex 3 | APCI/ESI+: 460 |
| 227 | Ex 3 | APCI/ESI+: 465 |
| 228 | Ex 3 | APCI/ESI+: 499 |
| 229 | Ex 3 | ESI+: 494 |
| 230 | Ex 3 | ESI+: 510 |
| 231 | Ex 3 | ESI+: 533 |
| 232 | Ex 3 | ESI+: 554 |
| 233 | Ex 3 | ESI+: 476 |
| 234 | Ex 3 | ESI+: 554 |
| 235 | Ex 3 | ESI+: 476 |
| 236 | Ex 3 | APCI/ESI+: 467 |
| 237 | Ex 3 | APCI/ESI+: 510 |
| 238 | Ex 3 | ESI+: 588 |
| 239 | Ex 3 | ESI+: 510 |
| 240 | Ex 3 | ESI+: 510 |
| 241 | Ex 3 | ESI+: 513 |

TABLE 215

| Ex | Syn | Data |
|---|---|---|
| 3 | Ex 3 | NMR-D: 12.9-12.8 (1H, brs), 8.88 (1H, d, J = 7.9 Hz), 7.88 (2H, d, J = 8.4 Hz), 7.73-7.68 (1H, m), 7.59-7.52 (3H, m), 7.49 (2H, d, J = 8.4 Hz), 7.45-7.38 (4H, m), 7.36-7.29 (1H, m), 7.24-7.19 (1H, m), 7.08 (1H, dd, J = 7.4, 7.4 Hz), 6.91 (2H, d, J = 8.2 Hz), 6.63 (1H, d, J = 3.1 Hz), 5.60-5.48 (2H, m), 5.20-5.10 (1H, m), 1.28 (3H, d, J = 7.1 Hz) |
| 4 | Ex 4 | NMR-D: 8.91 (1H, d, J = 7.8 Hz), 8.17 (1H, d, J = 2.1 Hz), 8.02-7.95 (2H, m), 7.87 (2H, d, J = 8.3 Hz), 7.75-7.67 (2H, m), 7.62 (1H, d, J = 3.1 Hz), 7.50-7.36 (5H, m), 7.27-7.18 (2H, m), 7.10 (1H, dd, J = 7.6, 7.6 Hz), 6.65 (1H, d, J = 3.3 Hz), 5.67-5.49 (2H, m), 5.18-5.07 (1H, m), 1.27 (3H, d, J = 7.0 Hz) |
| 6 | Ex 6 | NMR-D: 12.06-11.94 (1H, brs), 8.83 (1H, d, J = 7.8 Hz), 7.88 (2H, d, J = 8.4 Hz), 7.70 (1H, d, J = 7.8 Hz), 7.53 (1H, d, J = 3.2 Hz), 7.47 (2H, d, J = 8.4 Hz), 7.23-7.15 (3H, m), 7.12-7.05 (1H, m), 6.78 (2H, d, J = 8.4 Hz), 6.62 (1H, d, J = 3.2 Hz), 5.52 (1H, d, J = 18.0 Hz), 5.46 (1H, d, J = 18.0 Hz), 5.11-5.00 (1H, m), 4.75-4.62 (1H, br), 3.62-3.41 (4H, m), 1.90-1.78 (2H, m), 1.25 (3H, d, J = 7.1 Hz) |
| 23 | Ex 3 | NMR-D: 12.4-12.3 (1H, brs), 10.9 (1H, s), 7.80 (2H, d, J = 8.9 Hz), 7.76-7.73 (1H, m), 7.52-7.46 (2H, m), 7.29-7.24 (2H, m), 7.15 (1H, dd, J = 7.4, 7.4 Hz), 6.98 (2H, d, J = 8.9 Hz), 6.92-6.87 (2H, m), 6.60 (1H, d, J = 3.2 Hz), 4.68 (2H, t, J = 5.2 Hz), 4.21 (2H, t, J = 5.2 Hz), 3.31 (3H, s) |
| 53 | Ex 3 | NMR-D: 12.0-11.8 (1H, brs), 8.31-8.25 (1H, m), 8.19 (1H, d, J = 8.5 Hz), 7.92-7.85 (2H, m), 7.78 (1H, d, J = 2.1 Hz), 7.73-7.67 (1H, m), 7.65 (1H, d, J = 3.3 Hz), 7.56-7.49 (1H, m), 7.10 (1H, d, J = 2.1 Hz), 6.69-6.62 (2H, m), 5.84 (2H, s), 2.78 (2H, t, J = 6.2 Hz), 1.96-1.84 (1H, m), 1.67-1.56 (2H, m), 1.48-1.35 (2H, m), 1.14-0.87 (3H, m), 0.72-0.57 (2H, m) |
| 54 | Ex 3 | NMR-D: 12.9-12.7 (1H, brs), 8.32 (1H, d, J = 8.1 Hz), 7.87 (2H, d, J = 8.3 Hz), 7.39 (2H, d, J = 8.3 Hz), 7.29 (2H, d, J = 8.5 Hz), 7.05 (2H, d, J = 8.5 Hz), 6.83 (1H, s), 6.79 (1H, s), 5.47-5.36 (2H, m), 5.11-5.01 (2H, m), 2.01 (3H, s), 1.41 (2H, d, J = 7.0 Hz) |
| 57 | Ex 3 | NMR-D: 12.9-12.7 (1H, brs), 8.98-8.90 (1H, m), 8.18 (1H, d, J = 8.6 Hz), 7.93-7.86 (2H, m), 7.81 (1H, d, J = 2.1 Hz), 7.75-7.62 (4H, m), 7.59-7.53 (1H, m), 7.20 (1H, d, J = 2.1 Hz), 7.13 (2H, d, J = 8.2 Hz), 6.72 (1H, d, J = 8.4 Hz), 6.67 (1H, d, J = 3.2 Hz), 5.83 (2H, s), 4.25 (2H, d, J = 5.7 Hz) mp: 243-244 (dec) |

TABLE 216

| Ex | Syn | Data |
|---|---|---|
| 96 | Ex 3 | NMR-D: 11.9-11.8 (1H, brs), 8.17-8.10 (2H, m), 7.91 (1H, d, J = 8.4 Hz), 7.87 (1H, d, J = 7.8 Hz), 7.73-7.67 (1H, m), 7.55-7.45 (3H, m), 6.97-6.93 (1H, m), 6.58-6.50 (2H, m), 5.81 (2H, s), 2.84-2.76 (2H, m), 2.39 (3H, s), |

TABLE 216-continued

| Ex | Syn | Data |
|---|---|---|
| | | 1.95-1.84 (1H, m), 1.65-1.54 (2H, m), 1.47-1.38 (2H, m), 1.19-0.87 (3H, m), 0.73-0.56 (2H, m) mp: 244-245 (dec) |
| 115 | Ex 4 | NMR-D: 13.1-12.6 (1H, brs), 8.84 (1H, d, J = 7.9 Hz), 8.72 (1H, d, J = 2.1 Hz), 7.86-7.78 (3H, m), 7.76-7.70 (1H, m), 7.63 (2H, d, J = 7.4 Hz), 7.54-7.35 (6H, m), 7.24-7.18 (1H, m), 7.13-7.06 (1H, m), 6.64 (1H, d, J = 3.1 Hz), 6.57 (1H, d, J = 8.2 Hz), 5.72-5.58 (2H, m), 5.12-5.01 (1H, m), 1.21 (3H, d, J = 7.1 Hz) |
| 124 | Ex 3 | NMR-D: 12.0-11.8 (1H, brs), 8.41-8.34 (1H, m), 8.21 (1H, d, J = 8.5 Hz), 8.13 (1H, s), 7.92-7.83 (2H, m), 7.76 (1H, d, J = 3.2 Hz), 7.73-7.76 (1H, m), 7.56-7.49 (1H, m), 7.37-7.31 (1H, m), 6.85 (1H, d, J = 3.2 Hz), 6.73 (1H, d, J = 8.5 Hz), 5.91 (2H, s), 2.88-2.76 (2H, m), 1.96-1.82 (1H, m), 1.67-1.53 (2H, m), 1.48-1.34 (2H, m), 1.16-1.02 (1H, m), 1.02-0.85 (2H, m), 0.74-0.57 (2H, m) mp: 242 (dec) |
| 132 | Ex 3 | NMR-D: 12.9-12.7 (1H, brs), 8.97 (1H, d, J = 7.9 Hz), 7.90 (2H, d, J = 8.3 Hz), 7.73-7.65 (2H, m), 7.54-7.48 (3H, m), 7.24-7.18 (1H, m), 7.09-6.98 (2H, m), 6.57 (1H, d, J = 3.1 Hz), 6.56-6.49 (1H, m), 5.39-5.14 (3H, m), 3.46-3.36 (4H, m), 1.59-1.43 (6H, m), 1.39 (3H, d, J = 7.0 Hz) |
| 137 | Ex 3 | NMR-D: 12.1-11.9 (1H, brs), 8.31-8.22 (1H, m), 7.71-7.64 (1H, m), 7.52 (1H, d, J = 3.1 Hz), 7.27 (2H, d, J = 8.5 Hz), 7.16-7.09 (1H, m), 7.05 (1H, t, J = 7.5 Hz), 6.86 (2H, d, J = 8.5 Hz), 6.61 (1H, d, J = 3.1 Hz), 5.56 (2H, s), 3.06-2.94 (2H, m), 2.44-2.37 (1H, m), 1.90-1.76 (2H, m), 1.57-1.33 (5H, m), 1.21-1.06 (2H, m) |
| 140 | Ex 3 | NMR-D: 12.85-12.75 (1H, br), 9.03 (1H, d, J = 7.9 Hz), 7.91-7.83 (3H, m), 7.68 (1H, d, J = 7.9 Hz), 7.53 (2H, d, J = 8.3 Hz), 7.51-7.43 (6H, m), 7.26 (1H, d, J = 7.5 Hz), 7.11-7.05 (1H, m), 6.57 (1H, d, J = 3.4 Hz), 5.46 (1H, d, J = 15.7 Hz), 5.39 (1H, d, J = 15.7 Hz), 5.27-5.17 (1H, m), 1.38 (3H, d, J = 7.0 Hz) |
| 143 | Ex 3 | NMR-D: 12.85-12.77 (1H, brs), 9.17 (1H, s), 8.99-8.93 (1H, m), 8.06 (1H, d, J = 7.7 Hz), 7.79 (1H, d, J = 2.3 Hz), 7.77-7.59 (6H, m), 7.21-7.16 (3H, m), 7.05 (1H, s), 6.65 (1H, d, J = 3.3 Hz), 5.79 (2H, s), 4.36-4.30 (2H, m) |

TABLE 217

| Ex | Syn | Data |
|---|---|---|
| 146 | Ex 3 | NMR-D: 11.92 (1H, s), 9.20 (1H, s), 8.36-8.27 (1H, m), 8.05 (1H, d, J = 8.4 Hz), 7.77 (1H, d, J = 2.0 Hz), 7.75-7.66 (2H, m), 7.65 (1H, d, J = 3.1 Hz), 7.63-7.56 (1H, m), 7.08 (1H, d, J = 2.0 Hz), 6.96 (1H, s), 6.64 (1H, d, J = 3.1 Hz), 5.80 (2H, s), 2.90-2.82 (2H, m), 2.00-1.90 (1H, m), 1.71-1.62 (2H, m), 1.50-1.41 (2H, m), 1.20-0.94 (3H, m), 0.76-0.62 (2H, m) mp: 221 |
| 149 | Ex 3 | NMR-D: 11.9 (1H, s), 8.38-8.31 (1H, m), 7.89-7.82 (2H, m), 7.68 (1H, dd, J = 7.7, 1.2 Hz), 7.53 (1H, d, J = 3.0 Hz), 7.49-7.41 (3H, m), 7.19-7.15 (1H, m), 7.09-7.03 (1H, m), 6.81 (1H, s), 6.60 (1H, d, J = 3.0 Hz), 5.71 (2H, s), 3.05-2.97 (2H, m), 2.06-1.95 (1H, m), 1.82-1.62 (4H, m), 1.42-1.06 (3H, m), 0.92-0.77 (2H, m) |
| 155 | Ex 3 | NMR-D: 11.98-11.88 (1H, brs), 8.48-8.41 (1H, m), 7.92-7.84 (2H, m), 7.66 (1H, dd, J = 1.0, 7.9 Hz), 7.63 (1H, s), 7.52-7.44 (4H, m), 7.18 (1H, dd, J = 1.0, 7.9 Hz), 7.08-7.02 (1H, m), 6.57 (1H, d, J = 3.4 Hz), 5.52 (2H, s), 3.13-3.05 (2H, m), 2.11-2.00 (1H, m), 1.85-1.70 (4H, m), 1.51-1.38 (1H, m), 1.25-1.10 (2H, m), 0.98-0.84 (2H, m). |
| 159 | Ex 3 | NMR-D: 11.97-11.90 (1H, brs), 9.20 (1H, s), 8.45-8.39 (1H, m), 8.14-8.11 (1H, brs), 8.05 (1H, d, J = 8.2 Hz), 7.78-7.57 (4H, m), 7.33 (1H, s), 7.03 (1H, s), 6.83 (1H, d, J = 3.2 Hz), 5.87 (2H, s), 2.93-2.86 (2H, m), 2.00-1.89 (1H, m), 1.70-1.62 (2H, m), 1.50-1.42 (2H, m), 1.20-0.92 (3H, m), 0.77-0.66 (2H, m) mp: 260 |
| 164 | Ex 3 | NMR-D: 12.9-12.8 (1H, brs), 9.14 (1H, d, J = 8.1 Hz), 7.93 (2H, d, J = 8.3 Hz), 7.66-7.61 (1H, m), 7.57 (2H, d, J = 8.3 Hz), 7.28 (1H, d, J = 3.3 Hz), 7.21-7.15 (1H, m), 7.09-7.01 (1H, m), 6.47 (1H, d, J = 3.3 Hz), 5.28-5.15 (1H, m), 4.29-4.06 (2H, m), 3.29-3.13 (2H, m), 2.96-2.84 (1H, m), 1.61-0.94 (13H, m) |

TABLE 217-continued

| Ex | Syn | Data |
|---|---|---|
| 169 | Ex 3 | NMR-D: 12.9-12.7 (1H, brs), 8.47 (1H, d, J = 8.2 Hz), 7.93-7.85 (5H, m), 7.74 (1H, s), 7.54-7.49 (2H, m), 7.47 (1H, s), 7.45 (1H, s), 7.10-7.06 (1H, m), 6.95-6.90 (1H, m), 6.10-6.06 (1H, m), 5.47 (2H, s), 5.18-5.09 (1H, m), 1.45 (3H, d, J = 7.1 Hz) |
| 174 | Ex 3 | NMR-D: 11.9 (1H, s), 8.74 (1H, d, J = 2.3 Hz), 8.29-8.22 (1H, m), 7.89 (1H, dd, J = 8.1, 2.4 Hz), 7.73-7.59 (3H, m), 7.52 (1H, d, J = 3.3 Hz), 7.49-7.34 (3H, m), 7.17-7.02 (2H, m), 6.63 (1H, d, J = 3.3 Hz), 6.56 (1H, d, J = 8.1 Hz), 5.72 (2H, s), 2.96-2.87 (2H, m), 2.09-1.97 (1H, m), 1.81-1.52 (4H, m), 1.37-1.04 (3H, m), 0.90-0.73 (2H, m) |

TABLE 218

| Ex | Syn | Data |
|---|---|---|
| 182 | Ex 3 | NMR-D: 12.9-12.8 (1H, brs), 8.51 (1H, d, J = 7.8 Hz), 7.93-7.83 (5H, m), 7.70 (1H, d, J = 2.1 Hz), 7.56-7.42 (5H, m), 6.99 (1H, s), 6.72-6.69 (1H, m), 5.59 (2H, s), 5.24-5.09 (1H, m), 1.48 (3H, d, J = 7.1 Hz) |
| 187 | Ex 3 | NMR-D: 12.9-12.8 (1H, brs), 9.15-9.08 (1H, m), 7.82 (2H, d, J = 8.3 Hz), 7.74-7.69 (1H, m), 7.57 (1H, d, J = 3.3 Hz), 7.48-7.39 (4H, m), 7.34-7.30 (1H, m), 7.24-7.06 (3H, m), 6.62 (1H, d, J = 3.3 Hz), 6.22 (1H, s), 5.76 (2H, s), 4.54 (2H, d, J = 6.0 Hz) |
| 188 | Ex 3 | NMR-D: 12.0-11.9 (1H, brs), 8.50-8.41 (1H, m), 7.72-7.66 (1H, m), 7.56 (1H, d, J = 3.4 Hz), 7.51-7.46 (1H, m), 7.42 (1H, d, J = 8.2 Hz), 7.24-7.03 (4H, m), 6.61 (1H, d, J = 3.0 Hz), 6.35 (1H, s), 5.78 (2H, s), 3.13-3.06 (2H, m), 2.12-2.01 (1H, m), 1.85-1.68 (4H, m), 1.50-1.36 (1H, m), 1.25-1.09 (2H, m), 0.99-0.84 (2H, m) |
| 201 | Ex 3 | NMR-D: 12.3 (1H, s), 10.3 (1H, s), 7.74 (2H, d, J = 8.8 Hz), 7.35 (2H, d, J = 8.4 Hz), 7.09 (2H, d, J = 8.4 Hz), 6.98 (1H, s), 6.77 (1H, s), 6.68 (2H, d, J = 8.8 Hz), 5.43 (2H, s), 3.17 (3H, s), 2.04 (3H, s) |
| 202 | Ex 3 | NMR-D: 12.94-12.78 (1H, brs), 9.28-9.18 (1H, m), 7.94-7.87 (3H, m), 7.86-7.80 (2H, m), 7.73 (1H, d, J = 8.4 Hz), 7.66 (1H, d, J = 7.8 Hz), 7.53-7.43 (5H, m), 7.32-7.25 (1H, m), 7.19 (1H, s), 7.14-7.09 (1H, m), 5.81 (2H, s), 4.58 (2H, d, J = 6.0 Hz). |
| 204 | Ex 3 | NMR-D: 12.93-12.76 (1H, brs), 9.05 (1H, d, J = 8.1 Hz), 7.90 (2H, d, J = 8.1 Hz), 7.86-7.78 (3H, m), 7.71 (1H, d, J = 8.6 Hz), 7.66 (1H, d, J = 7.8 Hz), 7.55 (2H, d, J = 8.1 Hz), 7.51-7.44 (3H, m), 7.31-7.25 (1H, m), 7.23 (1H, s), 7.14-7.08 (1H, m), 5.75 (1H, d, J = 15.7 Hz), 5.71 (1H, d, J = 15.7 Hz), 5.29-5.19 (1H, m), 1.52 (3H, d, J = 7.0 Hz). |
| 206 | Ex 3 | NMR-D: 12.0-11.9 (1H, brs), 8.40 (1H, t, J = 5.6 Hz), 7.77 (1H, d, J = 7.8 Hz), 7.68 (2H, dd, J = 6.9, 6.9 Hz), 7.58 (1H, d, J = 3.1 Hz), 7.33-7.15 (3H, m), 7.08-7.01 (1H, m), 6.95 (1H, s), 6.63 (1H, d, J = 3.1 Hz), 5.89 (2H, s), 3.14-3.03 (2H, m), 2.13-1.99 (1H, m), 1.86-1.64 (4H, m), 1.49-1.33 (1H, m), 1.25-0.82 (4H, m) |
| 207 | Ex 3 | NMR-D: 12.3-12.2 (1H, brs), 10.8 (1H, s), 7.93-7.87 (2H, m), 7.83-7.80 (1H, m), 7.69 (2H, d, J = 8.9 Hz), 7.56 (1H, d, J = 3.1 Hz), 7.54-7.50 (1H, m), 7.49-7.44 (3H, m), 7.22-7.16 (1H, m), 6.83 (2H, d, J = 8.9 Hz), 6.79 (1H, s), 6.67 (1H, d, J = 3.3 Hz), 5.75 (2H, s), 3.08 (3H, s) |

TABLE 219

| Ex | Syn | Data |
|---|---|---|
| 208 | Ex 3 | NMR-D: 12.9-12.7 (1H, brs), 9.16 (1H, t, J = 5.9 Hz), 7.90-7.79 (4H, m), 7.78 (1H, d, J = 2.2 Hz), 7.64 (1H, d, J = 3.1 Hz), 7.49-7.42 (3H, m), 7.37 (2H, d, J = 8.2 Hz), 7.26 (1H, d, J = 2.2 Hz), 6.89 (1H, s), 6.61 (1H, d, J = 3.4 Hz), 5.67 (2H, s), 4.46 (2H, d, J = 5.9 Hz) |
| 209 | Ex 3 | NMR-D: 12.0-11.8 (1H, brs), 8.48 (1H, t, J = 5.6 Hz), 7.91-7.80 (2H, m), 7.75 (1H, d, J = 2.0 Hz), 7.63 (1H, d, J = 3.2 Hz), 7.50-7.40 (3H, m), 7.14 (1H, d, J = 2.0 Hz), 6.84 (1H, s), 6.61 (1H, d, J = 3.2 Hz), 5.70 (2H, s), 3.04-2.94 (2H, m), 2.08-1.90 (1H, m), 1.82-1.57 (4H, m), 1.41-1.03 (3H, m), 0.90-0.73 (2H, m)<br>mp: 237 |

TABLE 219-continued

| Ex | Syn | Data |
|---|---|---|
| 210 | Ex 3 | NMR-D: 12.1-11.9 (1H, brs), 8.77 (1H, t, J = 5.6 Hz), 7.71 (1H, d, J = 2.1 Hz), 7.51 (1H, d, J = 3.3 Hz), 7.30-7.22 (2H, m), 7.14 (1H, d, J = 2.1 Hz), 6.89-6.81 (2H, m), 6.53 (1H, d, J = 3.3 Hz), 4.62 (2H, t, J = 5.3 Hz), 4.15 (2H, t, J = 5.3 Hz), 3.14-3.06 (2H, m), 2.19-2.04 (1H, m), 1.95-1.73 (4H, m), 1.60-1.43 (1H, m), 1.34-1.14 (2H, m), 1.04-0.88 (2H, m) |
| 211 | Ex 3 | NMR-D: 13.0-12.8 (1H, brs), 9.37 (1H, t, J = 6.0 Hz), 7.93 (2H, d, J = 8.3 Hz), 7.73 (1H, d, J = 2.0 Hz), 7.56-7.46 (3H, m), 7.27-7.19 (3H, m), 6.73-6.65 (2H, m), 6.53 (1H, d, J = 3.1 Hz), 4.61-4.50 (4H, m), 3.91 (2H, t, J = 5.1 Hz) |
| 212 | Ex 3 | NMR-D: 9.26 (1H, t, J = 5.9 Hz), 8.13 (1H, s), 7.87-7.79 (4H, m), 7.75 (1H, d, J = 3.3 Hz), 7.54-7.50 (1H, m), 7.48-7.42 (3H, m), 7.38 (2H, d, J = 8.2 Hz), 6.93 (1H, s), 6.81 (1H, d, J = 3.2 Hz), 5.73 (2H, s), 4.50 (2H, d, J = 5.8 Hz)<br>mp: 248 |
| 213 | Ex 3 | NMR-D: 12.0-11.7 (1H, brs), 8.57 (1H, t, J = 5.5 Hz), 8.10 (1H, s), 7.90-7.82 (2H, m), 7.74 (1H, d, J = 3.3 Hz), 7.49-7.42 (3H, m), 7.40 (1H, s), 6.89 (1H, s), 6.81 (1H, d, J = 3.1 Hz), 5.76 (2H, s), 3.03 (2H, t, J = 6.2 Hz), 2.05-1.93 (1H, m), 1.82-1.71 (2H, m), 1.71-1.60 (2H, m), 1.43-1.29 (1H, m), 1.20-1.04 (2H, m), 0.91-0.77 (2H, m)<br>mp: 241 |
| 214 | Ex 3 | NMR-D: 12.07-11.83 (1H, brs), 8.72 (1H, d, J = 2.1 Hz), 8.46 (1H, t, J = 5.5 Hz), 8.12 (1H, s), 7.97-7.90 (1H, m), 7.72 (1H, d, J = 3.1 Hz), 7.63 (2H, d, J = 7.2 Hz), 7.50-7.42 (2H, m), 7.42-7.33 (2H, m), 6.82 (1H, d, J = 3.1 Hz), 6.72 (1H, d, J = 8.2 Hz), 5.77 (2H, s), 2.98-2.89 (2H, m), 2.07-1.96 (1H, m), 1.79-1.69 (2H, m), 1.63-1.51 (2H, m), 1.36-1.22 (1H, m), 1.17-1.04 (2H, m), 0.88-0.73 (2H, m)<br>mp: 235 (dec) |

TABLE 220

| Ex | Syn | Data |
|---|---|---|
| 215 | Ex 3 | NMR-D: 9.42 (1H, t, J = 6.0 Hz), 8.07 (1H, s), 7.92 (2H, d, J = 8.2 Hz), 7.60 (1H, d, J = 3.2 Hz), 7.54-7.45 (3H, m), 7.21 (2H, d, J = 9.0 Hz), 6.72 (1H, d, J = 3.2 Hz), 6.69 (2H, d, J = 9.0 Hz), 4.66-4.50 (4H, m), 3.92 (2H, t, J = 5.0 Hz)<br>mp: 208-210 |
| 216 | Ex 3 | NMR-D: 12.2-11.7 (1H, brs), 8.51-8.40 (1H, m), 8.13 (1H, s), 7.75-7.64 (2H, m), 7.37 (1H, s), 7.34 (1H, d, J = 7.8 Hz), 6.83 (1H, d, J = 3.1 Hz), 6.45 (1H, d, J = 7.8 Hz), 5.71 (2H, s), 3.02-2.85 (2H, m), 2.14-1.98 (1H, m), 1.91-1.78 (2H, m), 1.67-1.51 (2H, m), 1.36-1.10 (3H, m), 0.92-0.73 (2H, m) |
| 217 | Ex 3 | NMR-D: 12.1-11.7 (1H, brs), 8.53 (1H, d, J = 2.0 Hz), 8.43 (1H, t, J = 5.3 Hz), 8.14 (1H, s), 7.95 (1H, d, J = 8.4 Hz), 7.85 (1H, d, J = 3.2 Hz), 7.81 (1H, d, J = 8.1 Hz), 7.73-7.65 (2H, m), 7.57-7.51 (1H, m), 7.35 (1H, s), 6.87 (1H, d, J = 3.2 Hz), 5.86 (2H, s), 2.92 (2H, t, J = 6.0 Hz), 2.04-1.92 (1H, m), 1.79-1.64 (2H, m), 1.58-1.44 (2H, m), 1.26-0.98 (3H, m), 0.82-0.66 (2H, m) |
| 218 | Ex 3 | NMR-D: 12.3-11.5 (1H, brs), 8.91-8.80 (1H, m), 8.45-8.34 (2H, m), 8.15 (1H, s), 7.92 (1H, d, J = 8.5 Hz), 7.81 (1H, d, J = 3.1 Hz), 7.58-7.48 (1H, m), 7.36 (1H, s), 7.30 (1H, d, J = 8.7 Hz), 7.24 (1H, s), 6.88 (1H, d, J = 3.1 Hz), 5.89 (2H, s), 2.95-2.81 (2H, m), 2.00-1.87 (1H, m), 1.72-1.60 (2H, m), 1.51-1.38 (2H, m), 1.16-0.92 (3H, m), 0.77-0.60 (2H, m) |
| 219 | Ex 3 | NMR-D: 12.4-11.4 (1H, brs), 9.04-8.97 (1H, m), 8.46-8.31 (2H, m), 8.14 (1H, s), 7.83 (1H, d, J = 8.0 Hz), 7.70 (1H, d, J = 3.1 Hz), 7.60 (1H, dd, J = 4.2, 8.3 Hz), 7.42-7.28 (2H, m), 6.85 (1H, d, J = 3.1 Hz), 6.36 (1H, d, J = 7.0 Hz), 6.27 (2H, s), 2.70-2.59 (2H, m), 1.88-1.76 (1H, m), 1.63-1.47 (2H, m), 1.33-1.21 (2H, m), 0.98-0.76 (3H, m), 0.58-0.42 (2H, m) |
| 220 | Ex 3 | NMR-D: 9.64 (1H, s), 8.72 (1H, d, J = 6.4 Hz), 8.39-8.27 (2H, m), 8.25-8.14 (2H, m), 7.70 (1H, d, J = 3.2 Hz), 7.65-7.57 (1H, m), 7.39-7.35 (1H, m), 6.90 (1H, d, J = 3.2 Hz), 6.60 (1H, d, J = 7.1 Hz), 6.21 (2H, s), 2.57-2.50 (2H, m), 1.90-1.79 (1H, m), 1.65-1.54 (2H, m), 1.31-1.18 (2H, m), 0.96-0.78 (3H, m), 0.56-0.40 (2H, m) |

TABLE 220-continued

| Ex | Syn | Data |
|---|---|---|
| 221 | Ex 3 | NMR-D: 9.07 (1H, d, J = 3.5 Hz), 8.82 (1H, d, J = 8.8 Hz), 8.37-8.29 (1H, m), 8.18 (1H, s), 7.98 (1H, d, J = 8.5 Hz), 7.85-7.78 (1H, m), 7.69 (1H, d, J = 3.1 Hz), 7.65-7.58 (1H, m), 7.39-7.36 (1H, m), 6.89 (1H, d, J = 3.1 Hz), 6.32 (1H, d, J = 7.1 Hz), 6.23 (2H, s), 2.55-2.50 (2H, m), 1.92-1.74 (1H, m), 1.65-1.51 (2H, m), 1.27-1.15 (2H, m), 0.95-0.75 (3H, m), 0.56-0.36 (2H, m) |

TABLE 221

| Ex | Syn | Data |
|---|---|---|
| 222 | Ex 3 | NMR-D: 12.6-11.2 (1H, brs), 8.93-8.85 (1H, m), 8.42-8.35 (1H, m), 8.32 (1H, d, J = 9.5 Hz), 8.14 (1H, s), 7.93 (1H, d, J = 8.7 Hz), 7.80 (1H, d, J = 3.2 Hz), 7.55 (1H, dd, J = 4.3, 8.3 Hz), 7.43 (1H, s), 7.39-7.30 (2H, m), 6.86 (1H, d, J = 3.2 Hz), 5.85 (2H, s), 2.95-2.81 (2H, m), 2.01-1.91 (1H, m), 1.76-1.64 (2H, m), 1.56-1.42 (2H, m), 1.21-1.09 (1H, m), 1.09-0.95 (2H, m), 0.81-0.66 (2H, m) |
| 223 | Ex 3 | NMR-D: 12.0-11.7 (1H, brs), 9.13 (1H, s), 8.44 (1H, d, J = 5.7 Hz), 8.41-8.34 (1H, m), 8.16-8.11 (1H, m), 7.86 (1H, d, J = 8.6 Hz), 7.81 (1H, d, J = 3.2 Hz), 7.75 (1H, d, J = 5.7 Hz), 7.49 (1H, s), 7.39-7.31 (2H, m), 6.86 (1H, d, J = 3.2 Hz), 5.84 (2H, s), 2.94-2.84 (2H, m), 2.02-1.90 (1H, m), 1.75-1.63 (2H, m), 1.55-1.44 (2H, m), 1.21-0.95 (3H, m), 0.80-0.65 (2H, m) |
| 224 | Ex 3 | NMR-D: 12.0-11.8 (1H, brs), 9.20 (1H, s), 8.20-8.11 (1H, m), 8.04 (1H, d, J = 8.1 Hz), 7.69-7.65 (2H, m), 7.61-7.56 (1H, m), 7.51-7.45 (2H, m), 6.96-6.93 (1H, m), 6.88 (1H, s), 6.54 (1H, d, J = 3.1 Hz), 5.78 (2H, s), 2.92-2.82 (2H, m), 2.38 (3H, s), 1.98-1.88 (1H, m), 1.73-1.60 (2H, m), 1.53-1.40 (2H, m), 1.20-1.08 (1H, m), 1.08-0.93 (2H, m), 0.80-0.60 (2H, m)<br>mp: 251-252 (dec) |
| 225 | Ex 3 | NMR-D: 12.2-11.5 (1H, brs), 9.22 (1H, s), 8.30-8.21 (1H, m), 8.06 (1H, d, J = 8.1 Hz), 7.76-7.56 (4H, m), 7.50 (1H, dd, J = 2.6, 9.3 Hz), 6.97 (1H, s), 6.94 (1H, dd, J = 2.6, 9.3 Hz), 6.64 (1H, d, J = 3.1 Hz), 5.80 (2H, s), 2.91-2.81 (2H, m), 2.02-1.89 (1H, m), 1.74-1.60 (2H, m), 1.55-1.40 (2H, m), 1.20-0.94 (3H, m), 0.79-0.61 (2H, m)<br>mp: 233 |
| 226 | Ex 3 | NMR-D: 12.1-11.7 (1H, brs), 9.25 (1H, s), 8.45-8.37 (1H, m), 8.08 (1H, d, J = 8.1 Hz), 7.77-7.58 (4H, m), 7.51 (1H, d, J = 3.2 Hz), 7.03 (1H, s), 6.95 (1H, dd, J = 8.7, 10 Hz), 6.64 (1H, d, J = 3.2 Hz), 5.66 (2H, s), 2.86-2.77 (2H, m), 2.02-1.90 (1H, m), 1.74-1.63 (2H, m), 1.57-1.46 (2H, m), 1.19-0.95 (3H, m), 0.80-0.64 (2H, m)<br>mp: 197 |
| 227 | Ex 3 | NMR-D: 8.59 (1H, t, J = 5.6 Hz), 7.75 (1H, d, J = 2.1 Hz), 7.64 (1H, d, J = 3.2 Hz), 7.52-7.46 (1H, m), 7.45-7.39 (1H, m), 7.25-7.12 (3H, m), 6.61 (1H, d, J = 3.2 Hz), 6.39-6.34 (1H, m), 5.77 (2H, s), 3.13-3.03 (2H, m), 2.08-1.96 (1H, m), 1.84-1.65 (4H, m), 1.48-1.33 (1H, m), 1.22-1.11 (2H, m), 0.96-0.81 (2H, m)<br>mp: 228-230 |

TABLE 222

| Ex | Syn | Data |
|---|---|---|
| 228 | Ex 3 | NMR-D: 12.1-11.8 (1H, brs), 8.70 (1H, t, J = 5.5 Hz), 8.14-8.09 (1H, m), 7.76 (1H, d, J = 3.3 Hz), 7.53-7.47 (1H, m), 7.46-7.39 (2H, m), 7.26-7.13 (2H, m), 6.81 (1H, d, J = 3.2 Hz), 6.42-6.37 (1H, m), 5.84 (2H, s), 3.16-3.06 (2H, m), 2.10-1.99 (1H, m), 1.83-1.64 (4H, m), 1.48-1.33 (1H, m), 1.22-1.07 (2H, m), 0.98-0.83 (2H, m)<br>mp: 209 |
| 229 | Ex 3 | NMR-D: 12.2-11.7 (1H, brs), 8.49-8.36 (2H, m), 8.14-8.07 (1H, m), 7.79 (1H, dd, J = 2.5, 8.4 Hz), 7.69 (1H, d, J = 3.2 Hz), 7.37-7.33 (1H, m), 6.81 (1H, d, J = 3.2 Hz), 6.65 (1H, d, J = 8.5 Hz), 5.73 (2H, s), 2.97-2.83 (2H, m), 2.13-2.00 (1H, m), 1.89-1.78 (2H, m), 1.64-1.51 (2H, m), 1.34-1.10 (3H, m), 0.91-0.73 (2H, m)<br>mp: 224-226 (dec) |

TABLE 222-continued

| Ex | Syn | Data |
|---|---|---|
| 230 | Ex 3 | NMR-D: 12.3-11.4 (1H, brs), 8.32-8.28 (1H, m), 8.27-8.22 (1H, m), 8.13-8.06 (2H, m), 8.00-7.93 (1H, m), 7.84-7.72 (2H, m), 7.66 (1H, d, J = 5.6 Hz), 7.62 (1H, d, J = 3.2 Hz), 7.34-7.29 (1H, m), 6.78 (1H, d, J = 3.2 Hz), 6.38 (2H, s), 2.49-2.41 (2H, m), 1.88-1.73 (1H, m), 1.60-1.48 (2H, m), 1.27-1.13 (2H, m), 0.92-0.71 (3H, m), 0.51-0.34 (2H, m) |
| 231 | Ex 3 | NMR-D: 8.71-8.60 (1H, m), 8.14-8.10 (1H, m), 7.75 (1H, d, J = 3.3 Hz), 7.58 (1H, d, J = 2.1 Hz), 7.48 (1H, d, J = 8.8 Hz), 7.45-7.42 (1H, m), 7.24 (1H, dd, J = 2.2, 8.8 Hz), 6.82 (1H, d, J = 3.3 Hz), 6.35-6.32 (1H, m), 5.85 (2H, s), 3.11-3.00 (2H, m), 2.06-1.94 (1H, m), 1.84-1.59 (4H, m), 1.44-1.29 (1H, m), 1.19-1.03 (2H, m), 0.95-0.77 (2H, m)<br>mp: 211-213 |
| 232 | Ex 3 | NMR-D: 12.0-11.8 (1H, brs), 9.26 (1H, s), 8.51-8.40 (1H, m), 8.13-8.05 (2H, m), 7.79-7.55 (4H, m), 6.97 (1H, s), 6.67 (1H, d, J = 3.2 Hz), 5.71-5.51 (2H, m), 3.13-2.95 (1H, m), 2.47-2.35 (1H, m), 2.03-1.80 (1H, m), 1.75-1.36 (4H, m), 1.13-0.90 (3H, m), 0.82-0.58 (2H, m) |
| 233 | Ex 3 | NMR-D: 12.2-11.7 (1H, brs), 9.31 (1H, s), 8.53-8.41 (1H, m), 8.14 (1H, d, J = 8.0 Hz), 7.83-7.52 (5H, m), 7.17 (1H, d, J = 8.5 Hz), 7.05 (1H, s), 6.72 (1H, d, J = 3.2 Hz), 5.78-5.56 (2H, brs), 3.21-2.76 (2H, brs), 2.08-1.95 (1H, m), 1.87-1.47 (4H, m), 1.21-1.00 (3H, m), 0.89-0.68 (2H, m) |

TABLE 223

| Ex | Syn | Data |
|---|---|---|
| 234 | Ex 3 | NMR-D: 12.0-11.8 (1H, brs), 8.48-8.40 (1H, m), 8.23 (1H, d, J = 8.6 Hz), 8.09 (1H, s), 7.97-7.90 (2H, m), 7.78-7.70 (1H, m), 7.62 (1H, d, J = 3.2 Hz), 7.59-7.52 (1H, m), 6.71 (1H, d, J = 8.6 Hz), 6.68 (1H, d, J = 3.2 Hz), 5.66 (2H, s), 3.08-2.89 (1H, brs), 2.48-2.34 (1H, brs), 2.01-1.88 (1H, m), 1.79-1.30 (4H, m), 1.13-0.91 (3H, m), 0.84-0.56 (2H, brs) |
| 235 | Ex 3 | NMR-D: 12.1-11.7 (1H, brs), 8.43-8.35 (1H, m), 8.23 (1H, d, J = 8.6 Hz), 8.00-7.88 (2H, m), 7.79-7.49 (4H, m), 7.14 (1H, d, J = 8.5 Hz), 6.73 (1H, d, J = 8.6 Hz), 6.69 (1H, d, J = 3.2 Hz), 5.67 (2H, s), 3.14-2.34 (2H, brs), 2.04-1.88 (1H, m), 1.80-1.40 (4H, m), 1.18-0.95 (3H, m), 0.83-0.60 (2H, m) |
| 236 | Ex 3 | NMR-D: 12.5-11.8 (1H, brs), 9.18 (1H, s), 8.38-8.32 (1H, m), 8.25 (1H, d, J = 1.6 Hz), 8.05 (1H, d, J = 7.5 Hz), 7.77 (1H, d, J = 3.2 Hz), 7.75 (1H, s), 7.73-7.67 (1H, m), 7.64-7.58 (1H, m), 7.43 (1H, d, J = 1.6 Hz), 7.08 (1H, s), 6.81 (1H, d, J = 3.2 Hz), 5.86 (2H, s), 2.94-2.82 (2H, m), 2.01-1.90 (1H, m), 1.74-1.61 (2H, m), 1.55-1.43 (2H, m), 1.21-0.94 (3H, m), 0.80-0.62 (2H, m) |
| 237 | Ex 3 | NMR-D: 11.95-11.84 (1H, brs), 9.22 (1H, s), 8.42 (1H, d, J = 5.7 Hz), 8.40-8.34 (1H, m), 8.16-8.12 (1H, m), 8.00 (1H, d, J = 8.5 Hz), 7.80 (1H, d, J = 3.2 Hz), 7.64 (1H, d, J = 5.8 Hz), 7.37-7.33 (1H, m), 7.29 (1H, s), 7.26-7.23 (1H, m), 6.88 (1H, d, J = 3.2 Hz), 5.86 (2H, s), 2.95-2.82 (2H, m), 2.01-1.88 (1H, m), 1.72-1.61 (2H, m), 1.52-1.41 (2H, m), 1.21-0.94 (3H, m), 0.78-0.63 (2H, m) |

TABLE 224
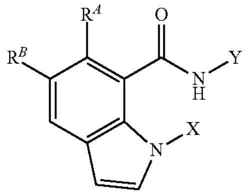
| No | $R^A$ | $R^B$ | X | Y |
|---|---|---|---|---|
| 1 | H | $CH_3$ | 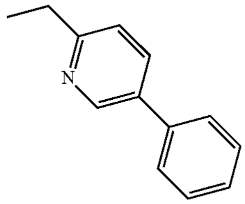 | 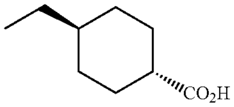 |
| 2 | H | $CH_3$ | 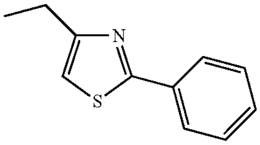 | 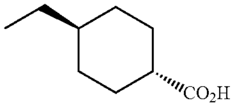 |
| 3 | H | $CH_3$ | 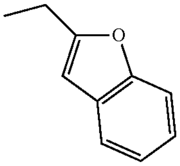 | 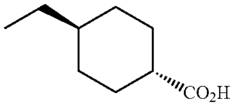 |
| 4 | H | $CH_3$ | 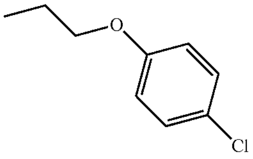 | 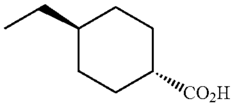 |
| 5 | H | $CH_3$ | 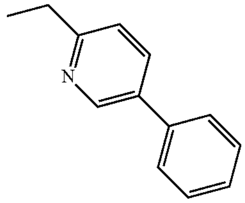 | 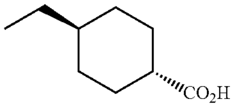 |
| 6 | H | $CH_3$ | 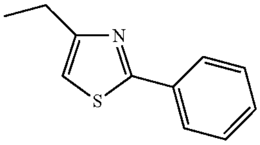 | 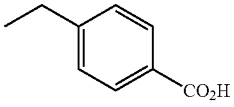 |
| 7 | H | $CH_3$ | 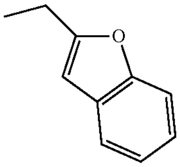 | 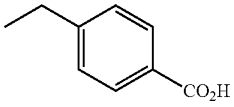 |

TABLE 224-continued
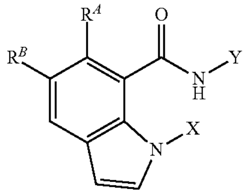
| No | $R^A$ | $R^B$ | X | Y |
|---|---|---|---|---|
| 8 | H | $CH_3$ | 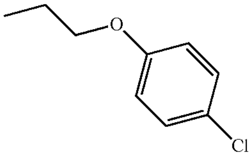 | 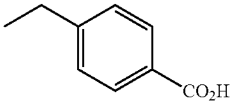 |
TABLE 225
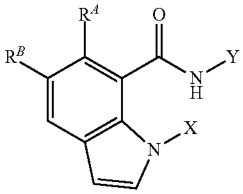
| No | $R^A$ | $R^B$ | X | Y |
|---|---|---|---|---|
| 9 | H | F | 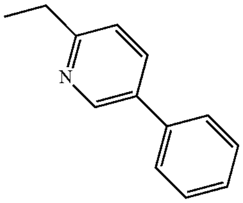 | 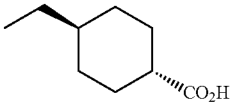 |
| 10 | H | F | 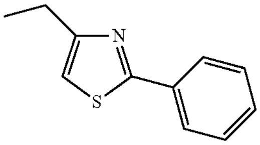 | 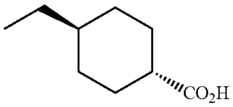 |
| 11 | H | F | 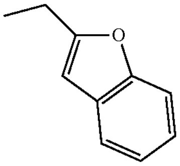 | 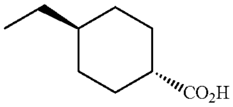 |
| 12 | H | F | 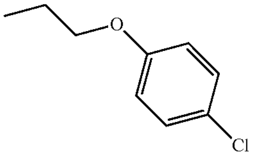 | 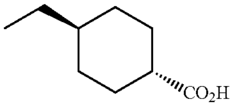 |

TABLE 225-continued
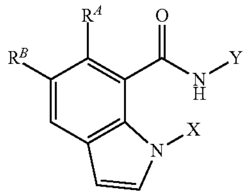
| No | $R^A$ | $R^B$ | X | Y |
| --- | --- | --- | --- | --- |
| 13 | H | F | 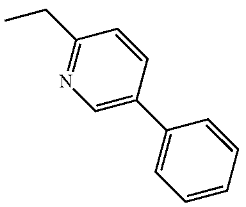 | 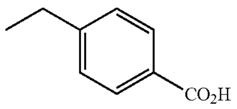 |
| 14 | H | F | 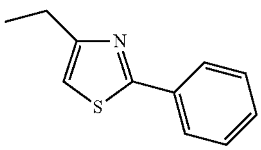 | 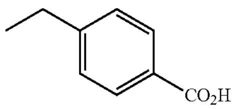 |
| 15 | H | F | 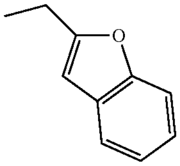 | 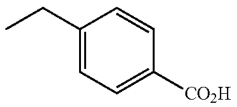 |
| 16 | H | F | 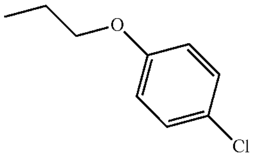 | 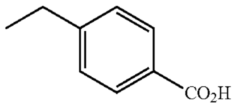 |
TABLE 226
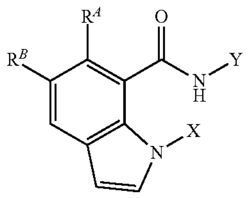
| No | $R^A$ | $R^B$ | X | Y |
| --- | --- | --- | --- | --- |
| 17 | H | CN | 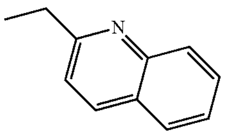 | 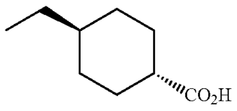 |

TABLE 226-continued
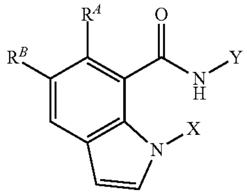
| No | $R^A$ | $R^B$ | X | Y |
| --- | --- | --- | --- | --- |
| 18 | H | CN | 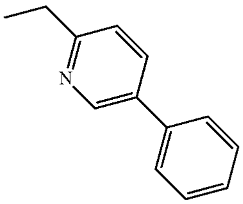 | 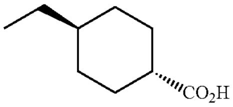 |
| 19 | H | CN | 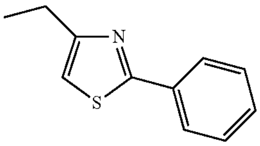 | 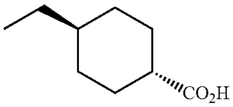 |
| 20 | H | CN | 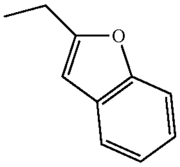 | 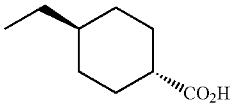 |
| 21 | H | CN | 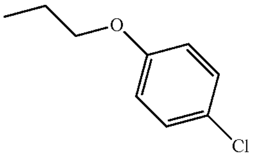 | 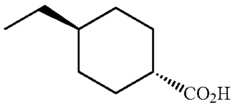 |
| 22 | H | CN | 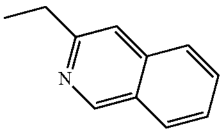 | 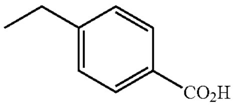 |
| 23 | H | CN | 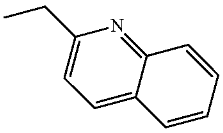 | 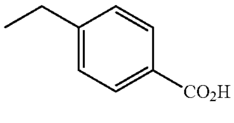 |
| 24 | H | CN | 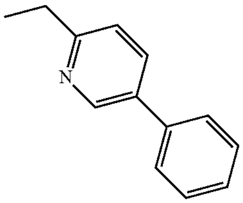 | 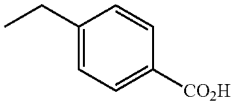 |

TABLE 227
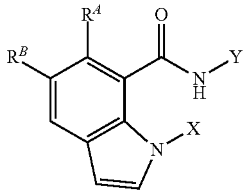
| No | $R^A$ | $R^B$ | X | Y |
| --- | --- | --- | --- | --- |
| 25 | H | CN | 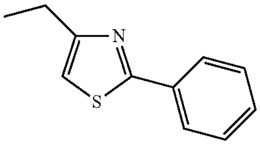 | 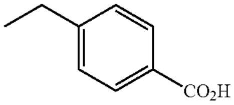 |
| 26 | H | CN | 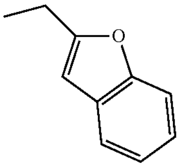 | 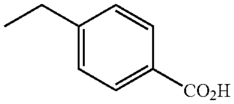 |
| 27 | H | CN | 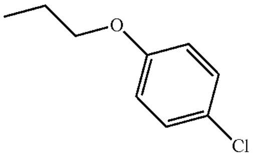 | 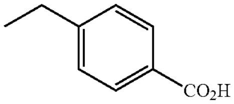 |
| 28 | F | H | 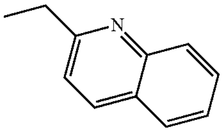 | 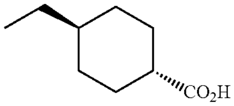 |
| 29 | F | H | 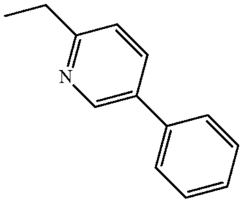 | 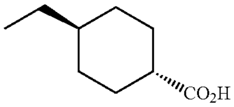 |
| 30 | F | H | 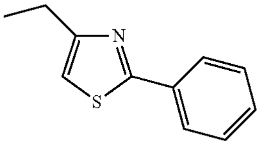 | 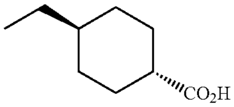 |
| 31 | F | H | 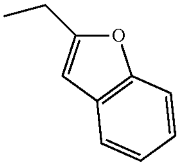 | 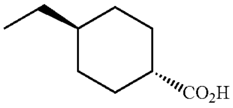 |
| 32 | F | H | 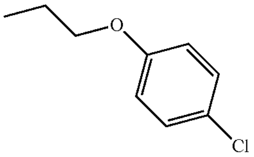 | 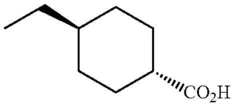 |

TABLE 228
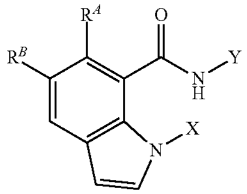
| No | $R^A$ | $R^B$ | X | Y |
|---|---|---|---|---|
| 33 | F | H | 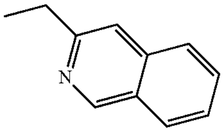 | 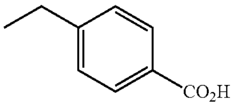 |
| 34 | F | H | 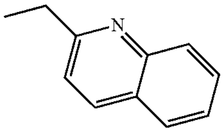 | 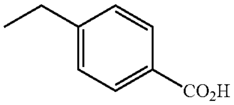 |
| 35 | F | H | 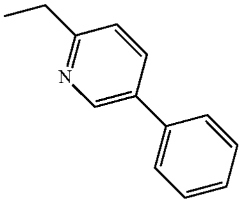 | 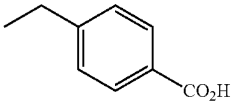 |
| 36 | F | H | 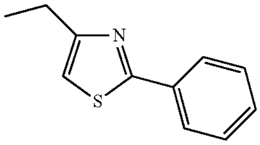 | 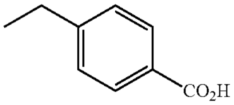 |
| 37 | F | H | 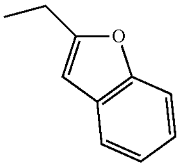 | 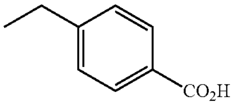 |
| 38 | F | H | 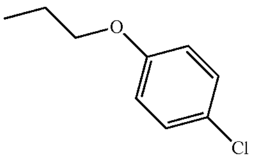 | 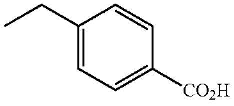 |
| 39 | $CF_3$ | Br | 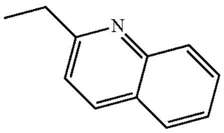 | 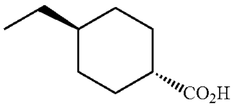 |

INDUSTRIAL APPLICABILITY

The compound of the formula (I) or a salt thereof has an EP4 receptor antagonistic activity, and can be used as an active ingredient of a pharmaceutical composition for preventing and/or treating chronic renal failure and/or diabetic nephropathy.

SEQUENCE LISTING FREE TEXT

The following sequence numeral list <400> has a description of nucleotide sequence of rat EP4 (Sequence Number 1).

The invention claimed is:

1. A compound of the formula (I) or a salt thereof:

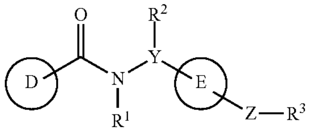

(I)

SEQUENCE LISTING

<160> NUMBER OF SEQ ID NOS: 1

<210> SEQ ID NO 1
<211> LENGTH: 1501
<212> TYPE: DNA
<213> ORGANISM: Rattus sp.

<400> SEQUENCE: 1
aagctgtgta ctactgacca ccatcatgtc catccccgga gtcaacgcgt ccttctcctc 60
cactccggag aggttgaaca gcccagtgac cattcccgca gtgatgttta tcttcggggt 120
ggtgggcaac ctggtggcca tcgtagtatt gtgcaagtcg cgcaaggagc agaaggagac 180
taccttttac actctggtat gtgggctggc tgtcactgac ctactgggca cattgttggt 240
aagcccagtg accatcgcca catacatgaa gggccagtgg cccggagacc aggcattgtg 300
tgactacagc accttcatcc tacttttctt cggcctgtcg ggtctcagca tcatctgtgc 360
catgagcatt gagcgctacc tggccatcaa ccacgcctac ttctacagcc actacgtgga 420
caagcggctg gccggtctca cgctcttcgc cgtctatgca tctaacgtgc tcttctgcgc 480
actgcccaac atgggcctgg gtaggtccga gcggcagtac ccggggacct ggtgcttcat 540
cgactggacc accaacgtaa cggcctacgc cgccttctct tacatgtacg cgggcttcag 600
ttccttcctc atcctcgcca ccgtgctctg caatgtgctg gtgtgcggcg cgctgctccg 660
catgctccgc cagttcatgc gccgcacctc gctgggcacg gagcagcacc acgcggccgc 720
tgcagcagcg gtggcttcgg tggcctgtcg gggtcacgcg gccgcctccc cagccctgca 780
gcgcctcagt gactttcgcc gccgcaggag cttccggcgc atcgcgggtg cagagatcca 840
gatggtcatc ttactcatcg ccacctctct ggtggtgctc atctgctcca ttccgctcgt 900
ggtgcgagtg ttcatcaacc agttatatca gccaagtgtg gtgaaagaca tcagcagaaa 960
cccggatttg caggccatca gaattgcttc tgtgaacccc atcctggacc cttggatcta 1020
catccttctt cggaagactg tgctcagtaa agccatagaa aagatcaagt gcctcttctg 1080
ccgcattggt ggttctggca gagacggttc agcacagcac tgctcagaga gtcggaggac 1140
atcttctgcc atgtctggcc actcccgctc cttcctctcg cgggagttga gggagatcag 1200
cagcacctct cacaccctcc tatacctgcc agacctaact gaaagcagcc tcggaggcaa 1260
gaatttgctt ccaggtacgc atggcatggg cctgacccaa gcagacacca cctcgctgag 1320
aactttgcga atttcagaga cctcagactc ctcccagggc caggactctg agagtgtctt 1380
gttggtggat gaggttagtg ggagccagag agaggagcct gcctctaagg ggaactctct 1440
gcaagtcacg ttccccagtg aaacgctgaa attatctgaa aaatgtatat agtagcttaa 1500 a 1501 wherein ring D is a group of the formula (II),

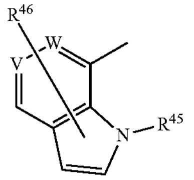

(II)

$R^{45}$ is —$X^1$—$B^5$, $R^{46}$ is —H, halogen, $C_{1-6}$ alkyl which may be substituted with one or more halogens, or —O—$C_{1-6}$ alkyl, V and W are CH, $X^1$ is methylene, $B^5$ represents (i) a bicyclic hetero ring which may be substituted with one or more groups selected from the group consisting of halogen and $C_{1-6}$ alkyl, or (ii) monocyclic aryl, a monocyclic hetero ring, or $C_{3-10}$ monocyclic cycloalkyl, each of which is substituted with the same or different 1 to 5 groups selected from $R^5$, $R^5$ is selected from the group consisting of halogen, —OH, —O—($C_{1-6}$ alkyl), —O—($C_{1-6}$ alkylene)-O—($C_{1-6}$ alkyl), aryl which may be substituted, a hetero ring which may be substituted, ($C_{1-6}$ alkylene)-aryl, ($C_{1-6}$ alkylene)-hetero ring, —O—($C_{1-6}$ alkylene)-aryl, and —O—($C_{1-6}$ alkylene)-hetero ring, ring E is cyclohexane-1,4-diyl, $R^1$ and $R^2$ are both H, Y is CH, Z is a bond, and $R^3$ is —$CO_2$H.

2. The compound or a salt thereof, as described in claim 1, which is trans-4-[({[5-methyl-1-(quinolin-2-ylmethyl)-1H-indol-7-yl]carbonyl}amino)methyl]cyclohexane carboxylic acid, trans-4-[({[5-fluoro-1-(quinolin-2-ylmethyl)-1H-indol-7-yl]carbonyl}amino)methyl]cyclohexane carboxylic acid, trans-4-[({[1-(quinolin-2-ylmethyl)-5-(trifluoromethyl)-1H-indol-7-yl]carbonyl}amino)methyl]cyclohexane carboxylic acid, trans-4-[({[5-chloro-1-(isoquinolin-3-ylmethyl)-1H-indol-7-yl]carbonyl}amino)methyl]cyclohexane carboxylic acid, trans-4-[({[1-(isoquinolin-3-ylmethyl)-5-(trifluoromethyl)-1H-indol-7-yl]carbonyl}amino)methyl]cyclohexane carboxylic acid, trans-4-{[({5-chloro-1-[(2-phenyl-1,3-thiazol-4-yl)methyl]-1H-indol-7-yl}carbonyl)amino]methyl}cyclohexane carboxylic acid, trans-4-{[({1-[(2-phenyl-1,3-thiazol-4-yl)methyl]-5-(trifluoromethyl)-1H-indol-7-yl}carbonyl)amino]methyl}cyclohexane carboxylic acid, trans-4-{[({1-[(5-phenylpyridin-2-yl)methyl]-5-(trifluoromethyl)-1H-indol-7-yl}carbonyl)amino]methyl}cyclohexane carboxylic acid, trans-4-[({[1-(isoquinolin-3-ylmethyl)-5-methyl-1H-indol-7-yl]carbonyl}amino)methyl]cyclohexane carboxylic acid, trans-4-[({[5-fluoro-1-(isoquinolin-3-ylmethyl)-1H-indol-7-yl]carbonyl}amino)methyl]cyclohexane carboxylic acid, trans-4-[({[6-fluoro-1-(isoquinolin-3-ylmethyl)-1H-indol-7-yl]carbonyl}amino)methyl]cyclohexane carboxylic acid, trans-4-[({[1-(1-benzofuran-2-ylmethyl)-5-chloro-1H-indol-7-yl]carbonyl}amino)methyl]cyclohexane carboxylic acid, trans-4-[({[1-(1-benzofuran-2-ylmethyl)-5-(trifluoromethyl)-1H-indol-7-yl]carbonyl}amino)methyl]cyclohexane carboxylic acid, or trans-4-{[({1-[(5-chloro-1-benzofuran-2-yl)methyl]-5-(trifluoromethyl)-1H-indol-7-yl}carbonyl)amino]methyl}cyclohexane carboxylic acid, or a salt thereof.

3. A pharmaceutical composition comprising the compound or a salt thereof as described in claim 1 and a pharmaceutically acceptable excipient.

4. A method for treating chronic renal failure or diabetic nephropathy, comprising administering an effective amount of a compound or a salt thereof as described in claim 1 to a subject in need thereof.

5. The compound or a salt thereof as described in claim 1, wherein $B^5$ is quinolyl, isoquinolyl, benzofuryl, or benzothienyl, each of which may be substituted with one or more groups selected from the group consisting of fluoro, chloro, and methyl.

6. The compound or a salt thereof as described in claim 1, wherein $B^5$ is a monocyclic hetero ring which is substituted with 1 to 5 groups selected from $R^5$, and $R^5$ is aryl.

7. The compound or a salt thereof, as described in claim 1, which is trans-4-[({[1-(quinolin-2-ylmethyl)-5-(trifluoromethyl)-1H-indol-7-yl]carbonyl}amino)methyl]cyclohexane carboxylic acid or a salt thereof.

8. The compound or a salt thereof, as described in claim 1, which is trans-4-[({[1-(isoquinolin-3-ylmethyl)-5-(trifluoromethyl)-1H-indol-7-yl]carbonyl}amino)methyl]cyclohexane carboxylic acid or a salt thereof.

9. The compound or a salt thereof, as described in claim 1, which is trans-4-[({[5-fluoro-1-(isoquinolin-3-ylmethyl)-1H-indol-7-yl]carbonyl}amino)methyl]cyclohexane carboxylic acid or a salt thereof.

10. The compound or a salt thereof, as described in claim 1, wherein $B^5$ is quinolyl which may be substituted with one or more fluorine atoms.

* * * * *